US012318635B2

(12) United States Patent
Rousso et al.

(10) Patent No.: US 12,318,635 B2
(45) Date of Patent: Jun. 3, 2025

(54) APPARATUS AND METHOD FOR TREATING KIDNEYS

(71) Applicant: MDSG Innovation Ltd., Rehovot (IL)

(72) Inventors: Benny Rousso, Rishon-LeZion (IL); Naama Winetraub, Holon (IL); Boaz Rippin, Beit Yehoshua (IL); Lior Eshel, Rishon-LeZion (IL); Assaf Erell, Ramat-Gan (IL); Rodny Zarini, Doar-Na Shimshon (IL)

(73) Assignee: MDSG Innovation Ltd., Rehovot (IL)

( * ) Notice: Subject to any disclaimer, the term of this patent is extended or adjusted under 35 U.S.C. 154(b) by 840 days.

(21) Appl. No.: 17/282,390

(22) PCT Filed: Oct. 3, 2019

(86) PCT No.: PCT/IL2019/051085
§ 371 (c)(1),
(2) Date: Apr. 2, 2021

(87) PCT Pub. No.: WO2020/070748
PCT Pub. Date: Apr. 9, 2020

(65) Prior Publication Data
US 2021/0346725 A1 Nov. 11, 2021

Related U.S. Application Data

(60) Provisional application No. 62/740,535, filed on Oct. 3, 2018.

(51) Int. Cl.
*A61N 7/00* (2006.01)

(52) U.S. Cl.
CPC ........ *A61N 7/00* (2013.01); *A61N 2007/0004* (2013.01); *A61N 2007/0078* (2013.01)

(58) Field of Classification Search
CPC .............. A61N 7/00; A61N 2007/0004; A61N 2007/0078
See application file for complete search history.

(56) References Cited

U.S. PATENT DOCUMENTS

| 5,558,092 | A | 9/1996 | Unger et al. |
| 6,941,172 | B2 | 9/2005 | Nachum |
| 8,382,689 | B2 | 2/2013 | Sliwa et al. |
| 8,414,494 | B2 | 4/2013 | Vaezy et al. |

(Continued)

FOREIGN PATENT DOCUMENTS

| JP | 2006-192181 | 7/2006 |
| WO | WO 2018/071908 | 4/2018 |
| WO | WO 2020/070748 | 4/2020 |

OTHER PUBLICATIONS

Supplementary European Search Report and the European Search Opinion Dated Jun. 27, 2022 From the European Patent Office Re. Application No. 19869708.8. (10 Pages).

(Continued)

*Primary Examiner* — Jason M Ip

(57) ABSTRACT

The present invention relates to means and methods for modifying renal function in a subject, comprising selecting a patient requiring an increment in renal function; emitting a quantity of ultrasound radiation, enough to provide an increment in renal function, to at least one part of a kidney for a period of time from about 1 hours to about 30 days.

17 Claims, 71 Drawing Sheets

(56) References Cited

U.S. PATENT DOCUMENTS

| | | | |
|---|---|---|---|
| 9,072,879 | B2 | 7/2015 | Yang |
| 2002/0123702 | A1 | 9/2002 | Cho |
| 2009/0112098 | A1 | 4/2009 | Vaezy et al. |
| 2011/0092781 | A1* | 4/2011 | Gertner .................. A61B 5/055 600/407 |
| 2011/0208095 | A1 | 8/2011 | Jolesz et al. |
| 2012/0010502 | A1 | 1/2012 | Yang et al. |
| 2012/0065501 | A1 | 3/2012 | Dae et al. |
| 2012/0215106 | A1 | 8/2012 | Sverdlik et al. |
| 2015/0080926 | A1 | 3/2015 | Emery |
| 2016/0038753 | A1 | 2/2016 | Chornenky et al. |
| 2016/0059044 | A1 | 3/2016 | Gertner |
| 2016/0113699 | A1 | 4/2016 | Sverdlik et al. |
| 2016/0136462 | A1 | 5/2016 | Lewis, Jr. et al. |
| 2016/0287909 | A1* | 10/2016 | Maxwell .................. A61N 7/00 |
| 2016/0332003 | A1* | 11/2016 | Dae .......................... A61B 8/08 |
| 2017/0245874 | A1* | 8/2017 | Bailey .................... A61B 8/085 |
| 2018/0161002 | A1 | 6/2018 | Alford et al. |

OTHER PUBLICATIONS

Notice of Reason(s) for Rejection Dated Jan. 4, 2022 From the Japan Patent Office Re. Application No. 2021-538486 and Its Translation Into English. (8 Pages).

Disposition of Dismissal of Procedure Dated Oct. 18, 2022 From the Japan Patent Office Re. Application No. 2021-538486 and Its Translation Into English. (8 Pages).

International Preliminary Report on Patentability Dated Apr. 15, 2021 From the International Bureau of WIPO Re. Application No. PCT/IL2019/051085. (9 Pages).

International Search Report and the Written Opinion Dated Mar. 11, 2020 From the International Searching Authority Re. Application No. PCT/IL2019/051085. (15 Pages).

Invitation to Pay Additional Fees Dated Jan. 15, 2020 From the International Searching Authority Re. Application No. PCT/IL2019/051085. (2 Pages).

Fischer et al. "Renal Ultrafiltration Changes Induced by Focused US", Radiology, 253(3): 697-705, Dec. 2009.

Gigliotti et al. "Ultrasound Modulates the Splenic Neurimmune Axis in Attenuating AKI", Journal of the American Society of Nephrology, 26(10): 2470-2481, Published Online Feb. 2, 2015.

Gigliotti et al. "Ultrasound Prevents Renal Ischemia-Reperfusion Injury by Stimulating the Splenic Cholinergic Anti-Inflammatory Pathway", Journal of the American Society of Nephrology, 24(9): 1451-1460, Published Online Aug. 1, 2013.

Hougardy et al. "Ultrasonic Stimulation of the Cholinergic Anti-Inflammatory Pathway for Renal Protection", Journal of the American Society of Nephrology, 24(9): 1339-1341, Published Online Aug. 1, 2013.

Johns "Nonthermal Effects of Therapeutic Ultrasound: The Frequency Resonance Hypothesis", Journal of Athletic Training, 37(3): 293-299, Jul.-Sep. 2002.

Kerschan-Schindl et al. "Whole-Body Vibration Exercise Leads to Alterations in Muscle Blood Volume", Clinical Physiology, 21(3): 377-382, May 2001.

Koga et al. "Mild Electrical Stimulation and Heat Shock Ameliorates Progressive Proteinuria and Renal Inflammation in Mouse Model of Alport Syndrome", Plos One, 7(8): 1c43852-1-c43852-11, Published Online Aug. 24, 2012.

Li et al. "Renal Interstitial Permeability Changes Induced by Microblubble-Enhanced Diagnostic Ultrasound", Journal of Drug Targeting, 21(5): 507-514, Published Online Apr. 29, 2013.

Mcdannold et al. "Blood-Brain Barrier Disruption Induced by Focused Ultrasound and Circulating Preformed Microbubbles Appears to be Characterized by the Mechanical Index", Ultrasound in Medicine and Biology, 34(5): 834-840, May 2008.

Mele et al. "Changing Paradigms in Cranio-Facial Regeneration: Current and New Strategies for the Activation of Endogenous Stem Cells", Frontiers in Psychology, 7(62): 1-13, Published Online Feb. 24, 2016.

Miloradovic et al. "Vibroacustic Microvibrations enhance Kndney Blood Supply, Gloerular Filtration and Glutathione Peroxidase Activity in Spontaneously Hypertensive Rats", General Physiology and Biophysics, 34(1): 89-94, Published Online Nov. 14, 2014.

Sato et al. "Low-Intensity Pulsed Ultrasound Rescues Insufficient Salivary Secretion in Autoimmune Sialadenitis", Arthritis Research & Therapy, 17(1): 278-1-278-12, Published Online Oct. 7, 2015.

Singh et al. "Low-Frequency, Loe-Intensity Ultrasound as A Potential Novel Treatment for Type 2 Diabetes", 2017 IEEE International Ultrasonic Symposium, IUS 2017, Washington, D.C., USA, Sep. 6-9, 2017, Abstract, Sep. 6, 2017.

Varani et al. "Effect of Low Frequency Electromagnetic Fields on A2A Adenosine Receptors in Human Neutrophils", British Journal of Pharmacology, 136(1): 57-66, May 2002.

Vincent et al. "Adenosine 2A Receptors in Acute Kidney Injury", Acta Physiologica, 214(3): 303-310, Jul. 2015.

Yang et al. "Focused Ultrasound-Modulated Glomerular Ultrafiltration Assessed by Functional Changes in Renal Arteries", Plos One, 8(1): e54034-1-e54034-6, Published Online Jan. 10, 2013.

Yang et al. "Low-Intensity Ultrasound-Induced Anti-Inflammatory Effects Are Mediated by Several New Mechanisms Including Gene Induction, Immunosuppressor Cell Promotion, and Enhancement of Exosome Biogenesis and Docking", Frontiers in Physiology, 8: 818-1-818-23, Published Online Oct. 23, 2017.

* cited by examiner

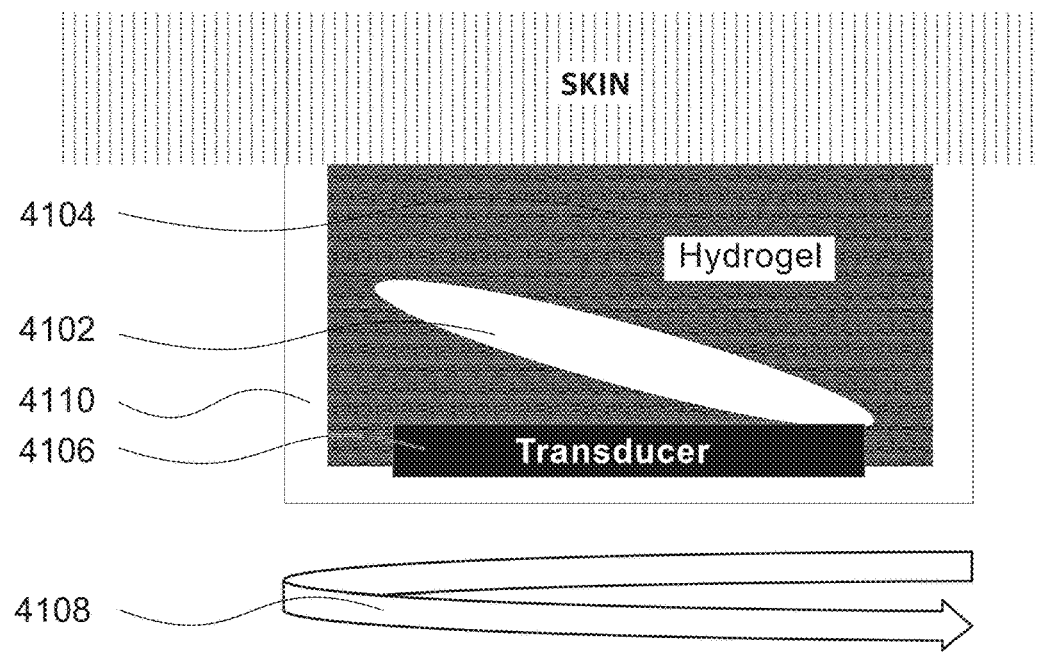
Figure 41
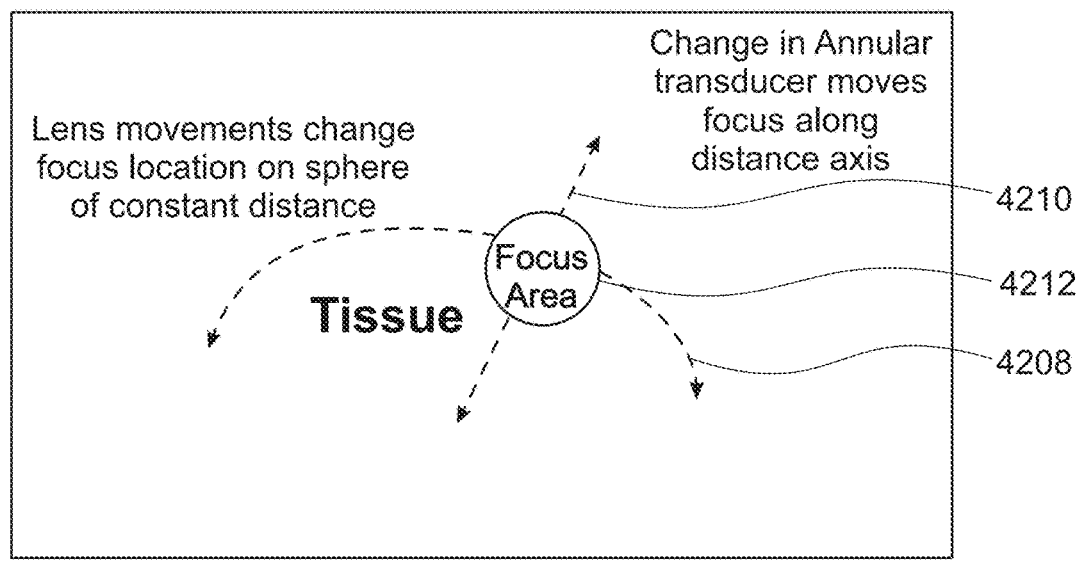
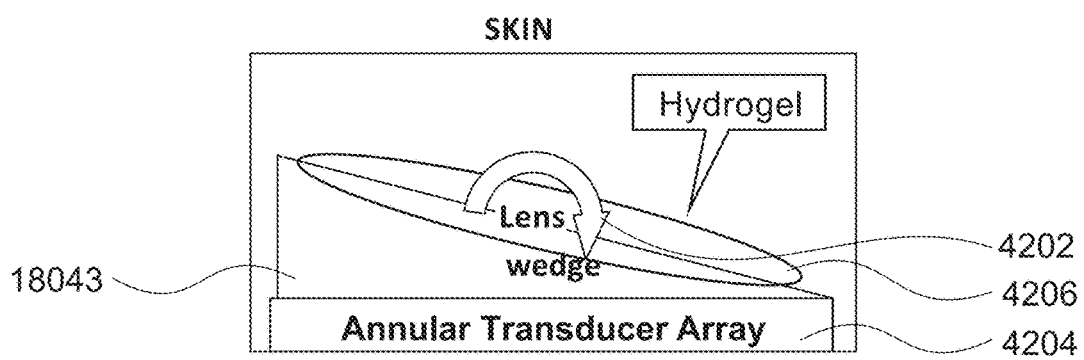
Figure 42

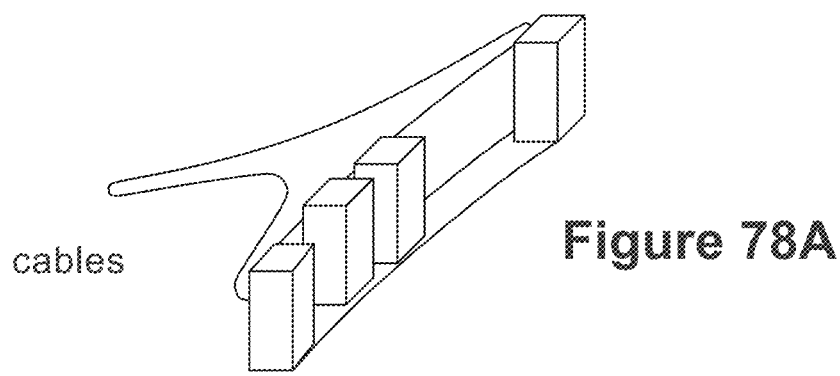
Figure 78A
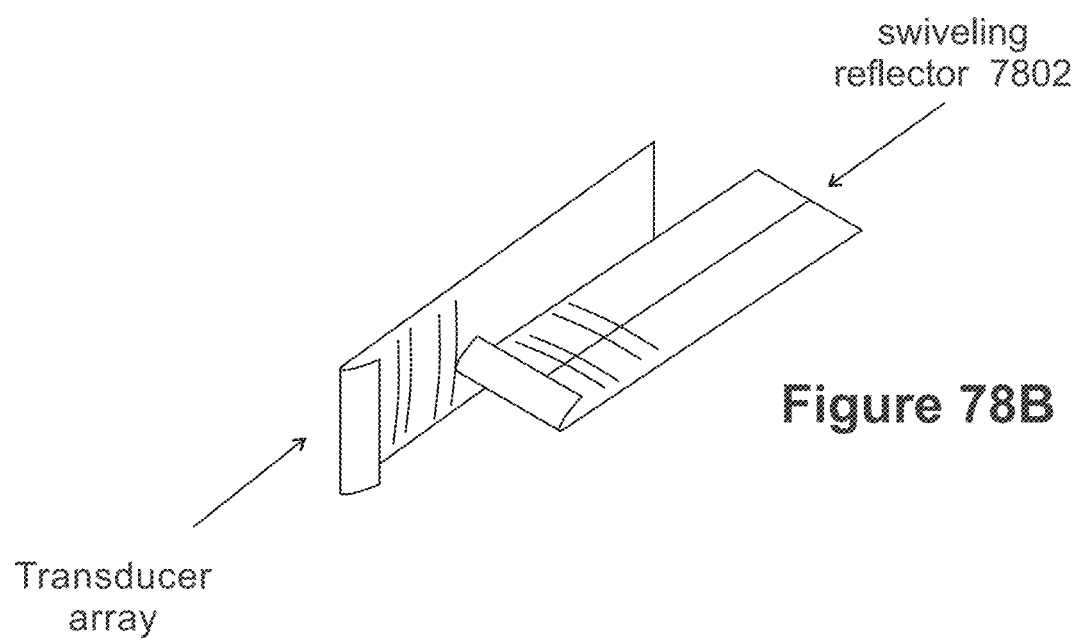
Figure 78B
Figure 78C
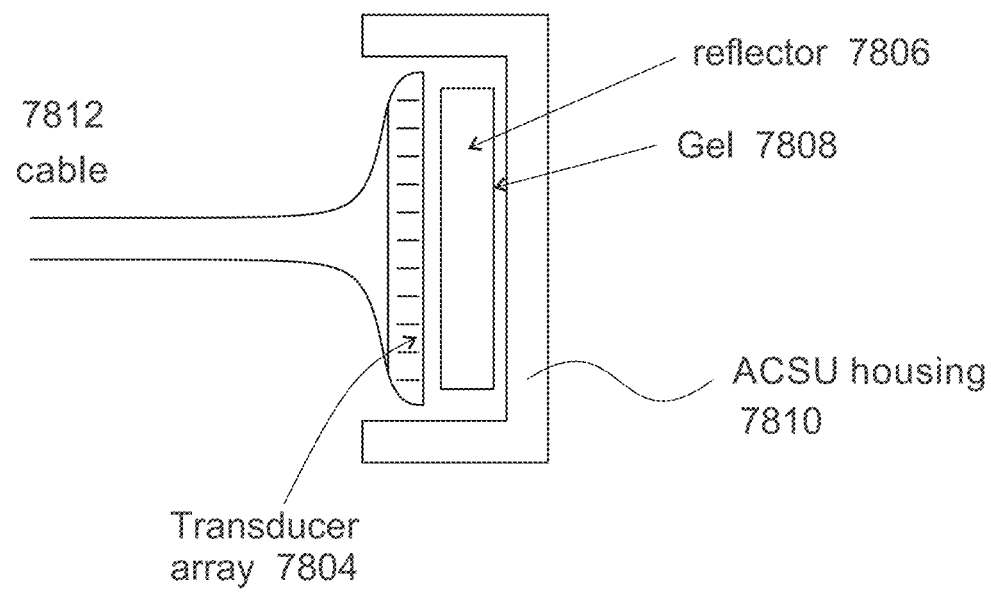

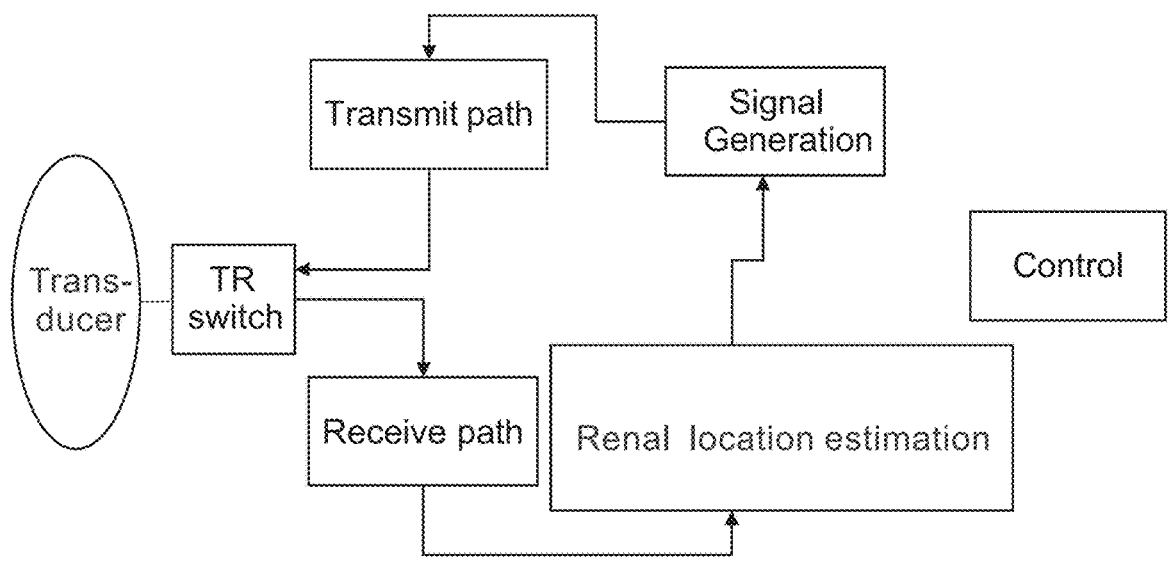
Figure 94
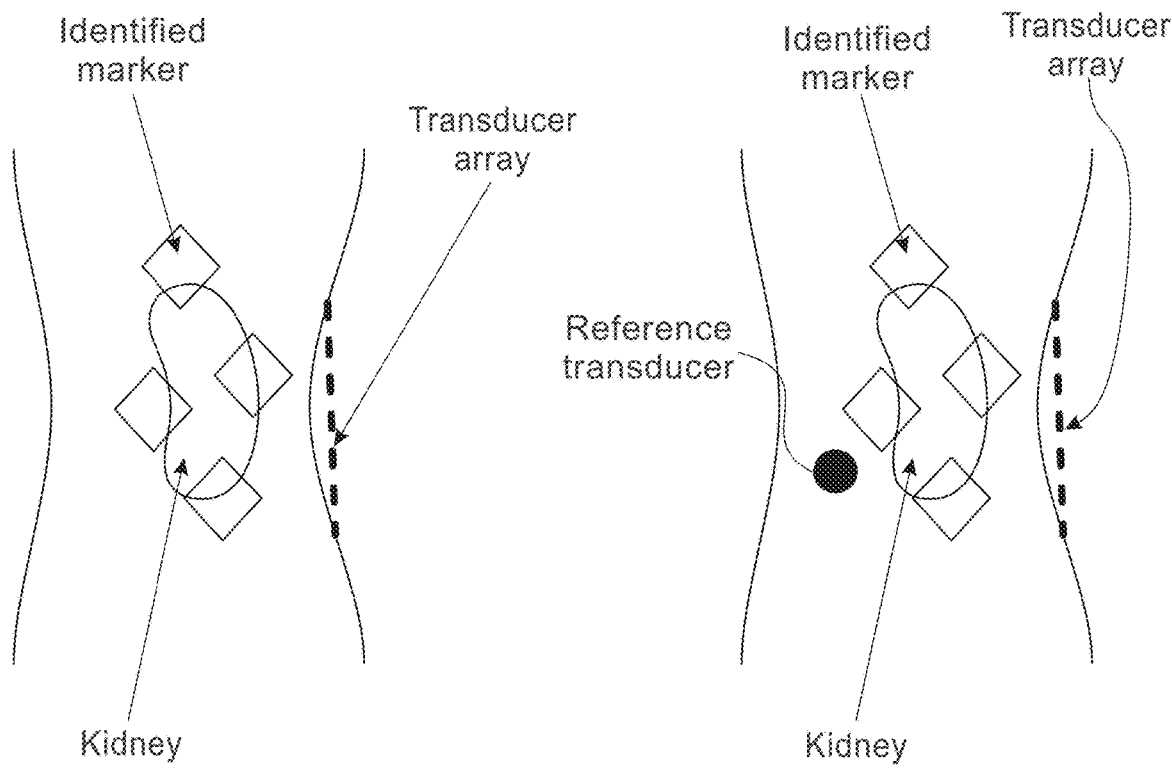
Figure 95 | Figure 96

APPARATUS AND METHOD FOR TREATING KIDNEYS

RELATED APPLICATIONS

This application is a National Phase of PCT Patent Application No. PCT/IL2019/051085 having International filing date of Oct. 3, 2019, which claims the benefit of priority under 35 USC § 119(e) of U.S. Provisional Patent Application No. 62/740,535 filed on Oct. 3, 2018. The contents of the above applications are all incorporated by reference as if fully set forth herein in their entirety.

FIELD AND BACKGROUND

The present invention, in some embodiments thereof, relates to apparatuses and methods for treating kidneys and, more particularly, but not exclusively, to ultrasonic apparatuses and methods for treating kidneys.

The kidneys include a complex collection of microstructures that co-function, which include, among others, the nephron as a whole, and sub-components such as glomeruli, Bowmen capsule, tubule, loop of Henle, collection duct, blood vessels and capillaries, nephrons, etc. The kidneys' Glomerulus, is a network of small blood vessels (e.g., capillaries)—that acts as a barrier between blood and urine, and performs the first filtration stage of blood, by mechanisms of diffusion and osmosis. In some of patients with renal disorders, the renal filtration process is impaired causing a variety of illnesses. The kidney has a role also in balancing and regulating body fluids volume and pressure, as well as maintaining proper fluids and electrolytes balance. Improper processes might cause a variety of undesired conditions, including, for example, fluids accumulation or loss, hyper or hypo tension, bleeding or proteins leakage, electrolyte imbalance, and other. The quality of renal filtration is commonly estimated by the Glomerular Filtration Rate GFR measure or similar estimates. Additionally, the collection duct system of the kidney includes tubule and ducts, which participate and control electrolytes and fluid balance, by reabsorption and excretion. Various clinical conditions and disorders are categorized as pre-renal, intrinsic and post-renal, depending on the stage in the filtration and reuptake processes they relate to. Some of the function or disorders are associated with blood flow (From the heart and through the renal artery and capillaries), blood pulsatility, and pressure gradients, whether systemically or locally. Some of the function or disorders are associated with the various control and feedback mechanisms of the kidney—whether of homeostasis, or concentration balances, hormonal feedback or of neuronal feedback. Some of the function or disorders are associated with the tubular structure, tubular damage, tubular regeneration, epithelial cells detaching from tubular wall, protein casts formation. Some of the function or disorders are associated with infection of other nephron-toxic conditions. Among the post-renal disorders, some are associated with blockade, kidney stones formation and infection. Some disorders are related to sepsis, to toxins affecting the kidney, to allergies and inflammatory processes, to proteins accumulated in the glomerular region or the tubular region, to sclerosis of the capillaries and to endothelial damage.

In most cases, treatment of chronic kidney disorders is based on reduction of risk factors for chronic conditions (e.g. reduction of glucose, lipids, sodium, etc.) and in maintaining volume, blood pressure and cardiac output, but not in pathways that recover the kidney itself. The use of diuretics and ACE-inhibitors affect kidney function, but normally in the context of balancing the cardiovascular system and not for the purpose of recovery of the kidney itself.

Historically, ultrasound was used for imaging tissue at very low intensities and short duration. Alternatively, it was used for treatment such as physiological treatment by tissue heating (diathermy) or by very high intensities for achieving tissue ablation (by High Intensity Focused Ultrasound, HIFU) or breaking kidney stones (lithotripsy). These therapies achieve damage to the tissue and the stones and are associated with generation of high degree of thermal damage and cavitation damage, at the focused target area, but often also to some extent in the vicinity—in surrounding healthy tissue of the kidney and neighboring organs. While ultrasound is being used to treat a disorder, it is usually associated with major side effects that reduce to some extent the kidney function. All these imaging techniques and treatment techniques are commonly used for short term, in procedures that span over several minutes.

Several published studies have explored potential impact of ultrasound on tissue, and an important extensive summary of such potential aspects was published in "Potential Adverse Ultrasound-related Biological Effects: A Critical Review", Anesthesiology 112011, Vol. 115, 1109-1124. Some studies (e.g. "Vibroacustic microvibrations enhance kidney blood supply, glomerular filtration and glutathione peroxidase activity in spontaneously hypertensive rats", Gen. Physiol. Biophys. (2015), 34, 89-94) looked at microvibrations at frequencies of a few Hz (e.g. 7 Hz or 30 Hz) and up to several KHz (e.g. 4.5 KHz) to observe changes, but these are possibly less likely to have meaningful effect on renal system in clinical use due to one or more of the following or other reasons: limit on power to avoid the disturbing sound that is produced, and predominantly due to the non-specific nature of the energy in this frequency range to any target tissue or mechanism, and lack of ability to focus any such energy on a desired target region (the wavelength is far greater than any possible focusing on a desired region), thus could be prone to side effects on other tissue, safety aspects or alternatively too low energy to obtain any clinically meaningful benefit. Some studies (e.g. "Renal Ultrafiltration Changes Induced by Focused US", Radiology, Volume 253: Number 3—December 2009) attempted to use higher frequencies, in the range of about 260 KHz and focused ultrasound, however, they required addition of contrast agent (microbubbles) to observe any effect—and with that become non useful for clinical applications, both because the use of microbubbles is invasive and complex and irrelevant for chronic use, and because this type of frequency and microbubbles generate cavitation, which has negative safety implication on the tissue.

U.S. Pat. No. 8,382,672B2 discloses "devices, systems, and methods treatment of patients can be used to help mitigate injury to the kidneys by applying cyclical mechanical pressure energy at low intensities. The energy often be selectively directed from non-invasive transducers disposed outside the patients. The energy will typically comprise low frequency ultrasound energy, shock wave energy, or the like, and may induce the generation and/or release of nitric oxide, thereby enhancing perfusion and ameliorating tissue damage. Superimposed micro and macro duty cycles may help avoid thermal and other injury to tissues of the patient during treatment. Bilateral treatments are facilitated by a support structure that orients at least one transducer toward each kidney".

Patent application US20110152986A1 discloses "a therapeutic device for relieving an affected organ or part of the body comprises a mass of material such as beeswax which in use is capable of maintaining a temperature range of 36 to 38 degrees Celsius at the affected part of the body when retained on the skin near the affected part. The invention also extends to articles of apparel containing such a therapeutic device".

SUMMARY

According to an aspect of some embodiments of the present invention there is provided method for modifying renal function, comprising: selecting a patient requiring an increment in renal function; emitting a quantity of ultrasound radiation, enough to provide an increment in renal function, to at least one part of a kidney for a period of time from about 1 hours to about 30 days.

According to some embodiments of the invention, said patient is a patient with a chronic condition.

According to some embodiments of the invention, said patient is a patient with an acute condition.

According to some embodiments of the invention, said ultrasound radiation is characterized by having a frequency above 3 MHz, optionally from about 3 MHz to about 15 MHz, and a duration from about 0.2 μsec to about 10 μsec.

According to some embodiments of the invention, said ultrasound radiation is characterized by individual emissions having an amplitude above 1 MPa.

According to some embodiments of the invention, said ultrasound radiation is characterized by a pulse repetition rate from about 0.1 kHz to about 30 kHz.

According to some embodiments of the invention, said emitting ultrasound radiation comprises emitting said ultrasound radiation between ribs.

According to some embodiments of the invention, said emitting ultrasound radiation comprises emitting said ultrasound radiation over a large area of skin.

According to some embodiments of the invention, further comprising positioning an ultrasound emission device in one or more locations selected from the group consisting of back, sides, under thorax and over thorax.

According to some embodiments of the invention, said ultrasound radiation is characterized by having high frequency and short duration.

According to some embodiments of the invention, further comprising achieving renal function modification while avoiding inducing thermal or cavitation adverse effects.

According to some embodiments of the invention, further comprising not using ultrasound contrast agent or any other injected material that modifies its characteristics when exposed to ultrasonic radiations.

According to some embodiments of the invention, further comprising avoiding skin irritation and/or ulcers/injuries and/or skin rashes.

According to some embodiments of the invention, further comprising monitoring cavitation at multiple interface locations to manage ultrasound power distribution.

According to some embodiments of the invention, further comprising providing evenly pressure distribution over a plurality of transducers elements contact area in order to increase patient ease of use and reduce risk of decubitus ulcers.

According to an aspect of some embodiments of the present invention there is provided method for preventing acute kidney dysfunction in a patient, comprising: selecting a patient at risk to develop symptoms caused by acute kidney dysfunction; emitting a quantity of ultrasound radiation to at least one part of a kidney, for a duration sufficient to reduce said symptoms by at least 10%; when comparing with untreated population with similar risks of developing acute kidney dysfunction.

According to some embodiments of the invention, said reduction includes shortening the healing time from acute kidney dysfunction.

According to some embodiments of the invention, said reduction includes reducing a residual damage in the patient.

According to some embodiments of the invention, said reduction includes reducing the risk to develop symptoms caused by acute kidney dysfunction in a population.

According to some embodiments of the invention, said reduction includes reducing the severity of the symptoms of acute kidney dysfunction once developed.

According to some embodiments of the invention, said acute kidney dysfunction is Acute Kidney Injury (AKI).

According to some embodiments of the invention, said acute kidney dysfunction is defined by elevation of serum Cr by 100% relative to baseline.

According to some embodiments of the invention, said acute kidney dysfunction is defined by elevation of serum Cr by 200% relative to baseline.

According to some embodiments of the invention, said reduction is calculated on a window spanning from day 1 to day 3 of when acute kidney dysfunction might happen and wherein said reduction comprises a mathematical reduction in an average displacement of a biomarker from a baseline value.

According to some embodiments of the invention, further comprising achieving renal function modification while avoiding inducing thermal or cavitation adverse effects.

According to an aspect of some embodiments of the present invention there is provided disposable acoustic coupler, comprising: an encasement comprising at least one acoustically transparent material; at least one interface for coupling at least one transducer element so said at least one transducer element is in contact with said at least one acoustically transparent material; at least one interface to form contact of the skin with said disposable acoustic coupler; and at least one circuitry incorporated in said encasement; where said encasement and said at least one acoustically transparent material are configured to enable transfer of acoustic energy from said transducer element across the coupling material to the skin; and wherein said circuitry is used for monitoring the status of said disposable acoustic coupler.

According to some embodiments of the invention, said at least one acoustically transparent material is in alignment with said at least one transducer element.

According to some embodiments of the invention, said disposable acoustic coupler comprises a silicone layer material.

According to some embodiments of the invention, said disposable acoustic coupler comprises an adhesive to said skin and an adhesive to a Transducer Subunit (TSU).

According to some embodiments of the invention, said adhesive is hypoallergenic and enables vapor and oxygen permeability.

According to some embodiments of the invention, further comprising a vacuum mechanism to achieve a highly efficient ultrasonic transmission from said TSU to said skin.

According to some embodiments of the invention, further comprising at least one sensor.

According to some embodiments of the invention, wherein said at least one sensor requires skin contact.

According to some embodiments of the invention, said at least one sensor is configured to detect at least one selected from the group consisting of:
a. overheating of device;
b. acoustic coupling to skin;
c. strain;
d. electrical resistance;
e. any combination thereof.

According to some embodiments of the invention, said at least one sensor is configured to detect at least one selected from the group consisting of:
a. overheating of skin and tissue;
b. cavitation;
c. skin level blood perfusion;
d. skin temperature;
e. humidity;
f. pressure; and
g. any combination thereof.

According to some embodiments of the invention, said at least one sensor is included in a disposable sensor portion.

According to some embodiments of the invention, said at least one sensor is configured to provide feedback on treatment parameters.

According to some embodiments of the invention, comprising a disposable belt or cushion or wearable garment and mechanism to attach and adjust said disposable acoustic coupler to the patient.

According to an aspect of some embodiments of the present invention there is provided a system for modifying renal function, comprising: a plurality of rigid transducer elements; an acoustic coupling in direct communication with said plurality of rigid transducer elements and configured to achieve acoustic coupling between said plurality of rigid transducer elements and skin of a patient; where said plurality of rigid transducer elements and said acoustic coupling comprise a material covering said plurality of rigid transducers; said units are aligned to each other according to said material; and where said plurality of rigid transducer elements and said acoustic coupling comprise a flexible material interconnecting said plurality of rigid transducers; said units are aligned to each other according to said flexible material.

According to some embodiments of the invention, further comprising at least one Transducer Subunit (TSU), at least one Acoustic Coupling Subunit (ACSU), at least one Power Subunit (PSU), at least one Electrical Subunit (ESU) and at least one User Interface Subunit (UI).

According to an aspect of some embodiments of the present invention there is provided a method for treating symptoms of heart failure with acute decompensation in a patient, comprising: selecting a patient with heart failure with acute decompensation in need for diuresis for reducing excessive fluids accumulation in the body; emitting a quantity of ultrasound radiation to at least one part of a kidney, for a duration sufficient to increase daily clearance rate of excessive fluids by at least 10%.

According to some embodiments of the invention, further comprising achieving renal function modification while avoiding inducing thermal or cavitation adverse effects.

According to an aspect of some embodiments of the present invention there is provided method for treating symptoms of heart failure in a patient, comprising: selecting a patient suffering from symptoms of heart failure; emitting a quantity of ultrasound radiation at least one part of a kidney, for a duration sufficient to reduce said symptoms by at least 10%.

According to some embodiments of the invention, further comprising achieving renal function modification while avoiding inducing thermal or cavitation adverse effects.

According to an aspect of some embodiments of the present invention there is provided an apparatus for treating a kidney configured to deliver ultrasonic radiation to at least one kidney following at least one protocol to perform a suitable waveform and power and duration causing said ultrasonic radiation to positively affect kidney function, wherein the delivery of ultrasonic radiation covers a large volumetric area.

According to an aspect of some embodiments of the present invention there is provided an apparatus for treating a kidney configured to deliver ultrasonic radiation to at least one kidney following at least one protocol to perform a suitable waveform and power and duration causing said ultrasonic radiation to positively affect kidney function, wherein the apparatus comprises a disposable acoustic coupler.

According to an aspect of some embodiments of the present invention there is provided an apparatus for treating a kidney configured to deliver ultrasonic radiation to at least one kidney following at least one protocol to perform a suitable waveform and power and duration causing said ultrasonic radiation to positively affect kidney function, wherein the apparatus comprises at least one tracking mechanism.

According to an aspect of some embodiments of the present invention there is provided an apparatus for treating a kidney configured to deliver ultrasonic radiation to at least one kidney following at least one protocol to perform a suitable waveform and power and duration causing said ultrasonic radiation to positively affect kidney function, wherein the apparatus comprises a plurality of independent transducers. Optionally, the apparatus comprises a plurality of independent transducer arrays.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product.

Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as radiation control, might be expected to use completely different methods, e.g., making use of expert knowledge and/or the pattern recognition capabilities of the human brain, which would be vastly more efficient than manually going through the steps of the methods described herein.

The scope of the present invention includes embodiments described in the articles and patent publications cited in the Background of the Invention of this application. Any embodiment, technique and apparatus described in one or more of such references are combined with the techniques and apparatus described herein, and form an exemplary embodiment of the present invention.

All values, durations, frequencies, amplitudes, doses and dose ranges given in this application are for a typical adult human having a typical body mass of between about 50 and about 90 kg. For children, or underweight or overweight adults, the values may be used as described (e.g. frequencies, durations) or may be adjusted (e.g. doses and power—for as long as within safe ranges and limits on the ultrasound signal intensity, Mechanical Index (MI) and Thermal Index for soft tissue (TIS) values, and possibly frequencies—if needed to adapt for depth of tissue) appropriately, as known by those skilled in the art.

It will be appreciated by persons skilled in the art that the present invention is not limited to what has been particularly shown and described hereinabove. Rather, the scope of the present invention includes both combinations and sub-combinations of the various features, parameters, described hereinabove, as well as variations and modifications thereof that are not in the prior art, which would occur to persons skilled in the art upon reading the foregoing description.

Similarly, each of the energy parameters, probe structure, beam forming, mechanical structures and mechanisms, algorithms, decision processes, circuits, treatment protocols, triggering events for initiating treatment, sensors, transducers, duration of treatments, location of treatment, feedback mechanisms, clinical conditions, clinical risk factors, measured parameters, clinical endpoints, methods, devices and/or others that are described in any of the sections, paragraphs, drawings, experiments, results and/or background may be combined with others that are described in any one or more of the other sections, paragraphs, drawings, experiments, results and/or background, and form an exemplary embodiment of the present invention.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 41 is a schematic representation of an exemplary way to achieve beam revolution, according to come embodiments of the present invention;

FIG. 42 is a schematic representation of a system comprising lens, according to come embodiments of the present invention;

FIGS. 78A-C are schematic representations of the use of a reflector for a low height design, according to come embodiments of the present invention;

FIG. 94 is a schematic representation of an architecture of a system comprising kidney location estimation using ultrasound, according to come embodiments of the present invention;

FIG. 95 is a schematic representation of the transducer array at the waist, and 4 identified markers over the left kidney, according to come embodiments of the present invention;

FIG. 96 is a schematic representation of a system with a reference transducer, according to come embodiments of the present invention;

FIG. 102 is a schematic representation of a transducer mat, according to come embodiments of the present invention;

FIG. 103 is a schematic representation of a transducer mat, according to come embodiments of the present invention;

FIG. 104 is a schematic representation of a braiding that limits the movement of the window, according to come embodiments of the present invention;

FIG. 105 is a schematic representation of an example of an adhesive patch on the disposable material, according to come embodiments of the present invention;

FIG. 106 is a schematic representation of the use of strain sensors, according to come embodiments of the present invention;

FIG. 107 is a schematic representation of the use of pressure sensors, according to come embodiments of the present invention;

FIG. 108 is a schematic representation of a system, according to come embodiments of the present invention;

FIG. 109 is a schematic representation of the transducer matched with the acoustically transparent material, according to come embodiments of the present invention;

FIG. 110 is a schematic representation of the transducer shaped spherically to push the air bubbles and extra acoustically transparent material away from the transducer center to the inter-transducer area, according to come embodiments of the present invention;

FIG. 111 is a schematic representation of a method for connecting the transducer to the acoustically transparent window, according to come embodiments of the present invention;

Figure 112A:
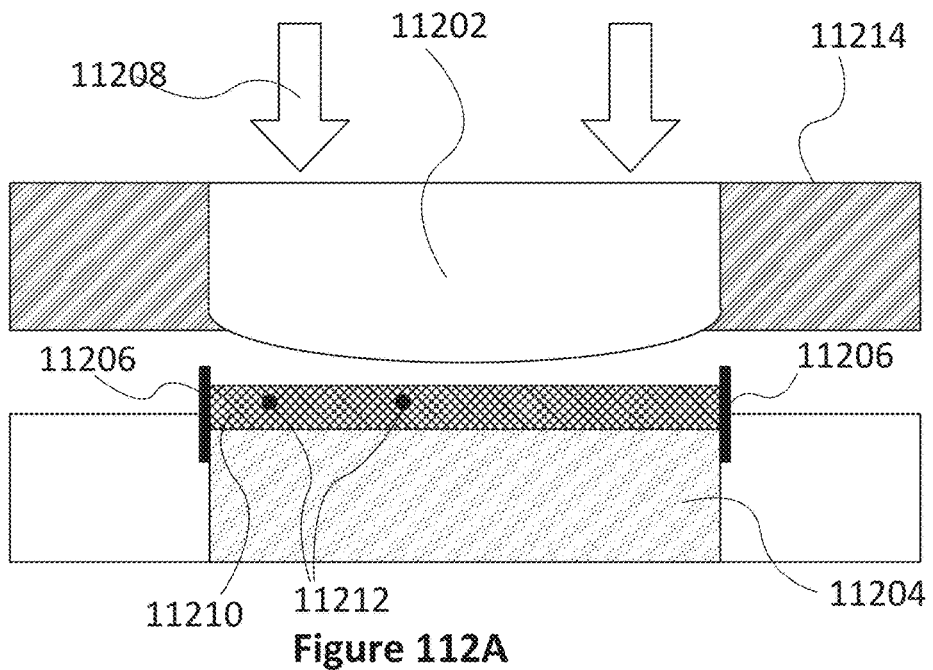
Figure 112B:
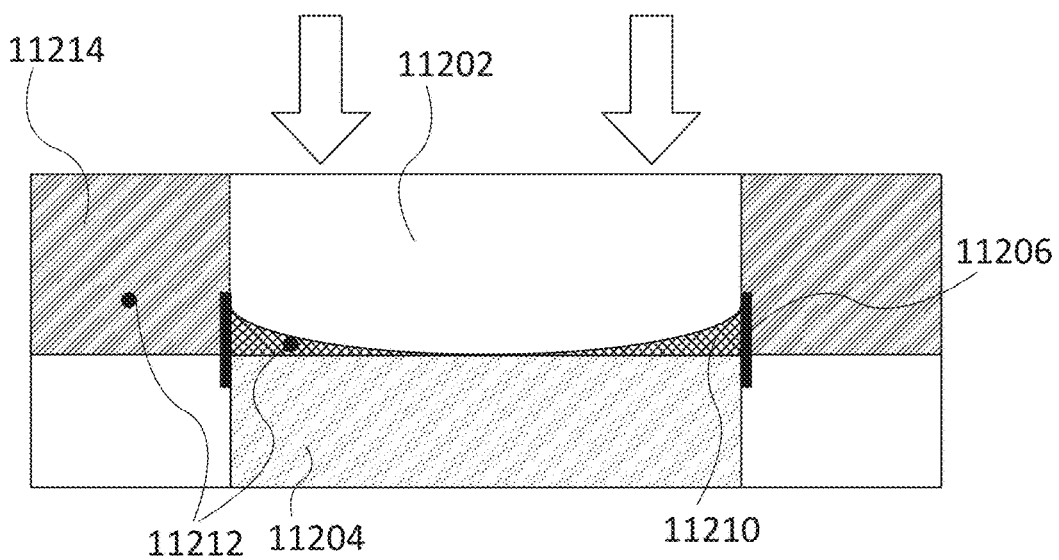
Figure 113:
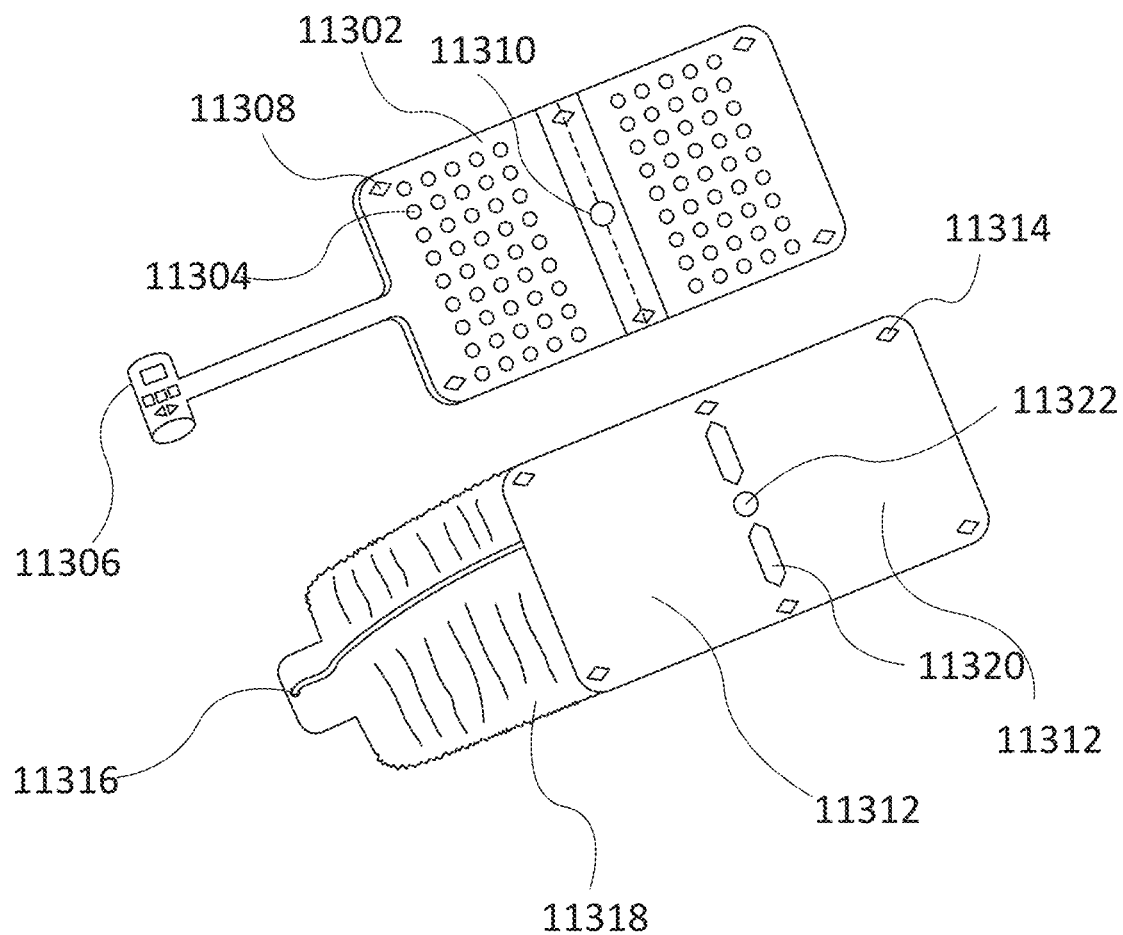
Figure 114:
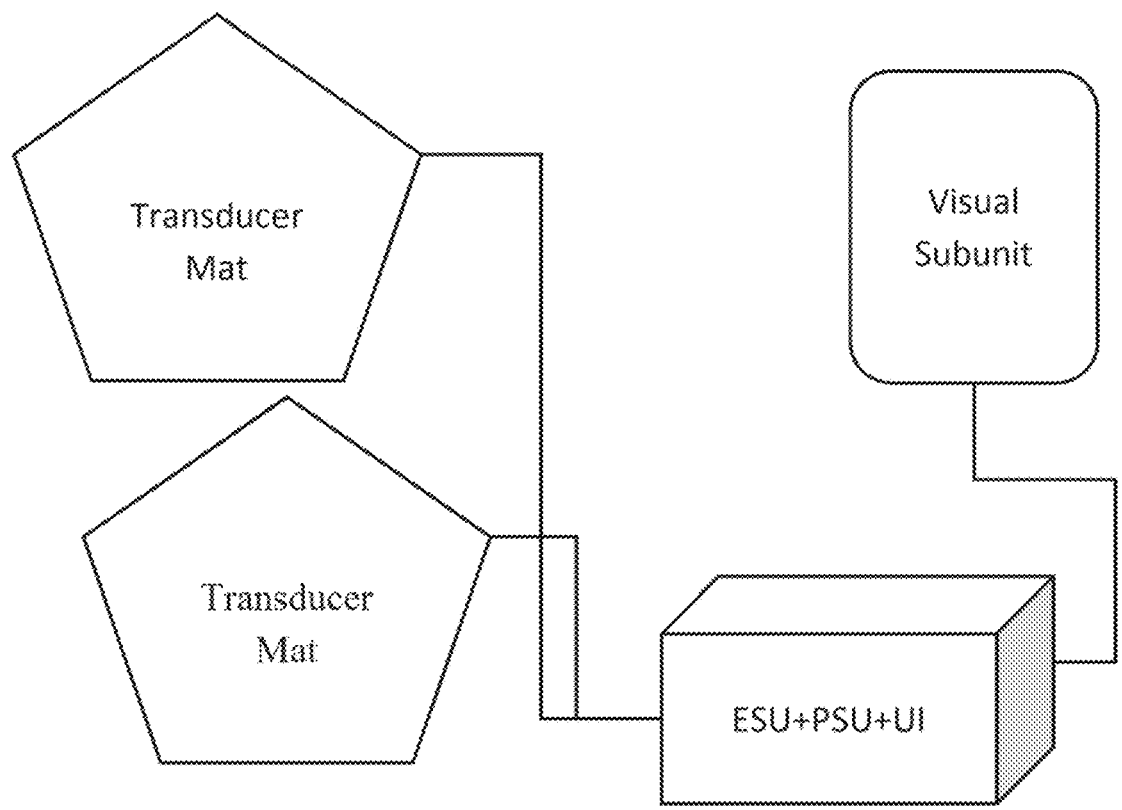
Figure 115:
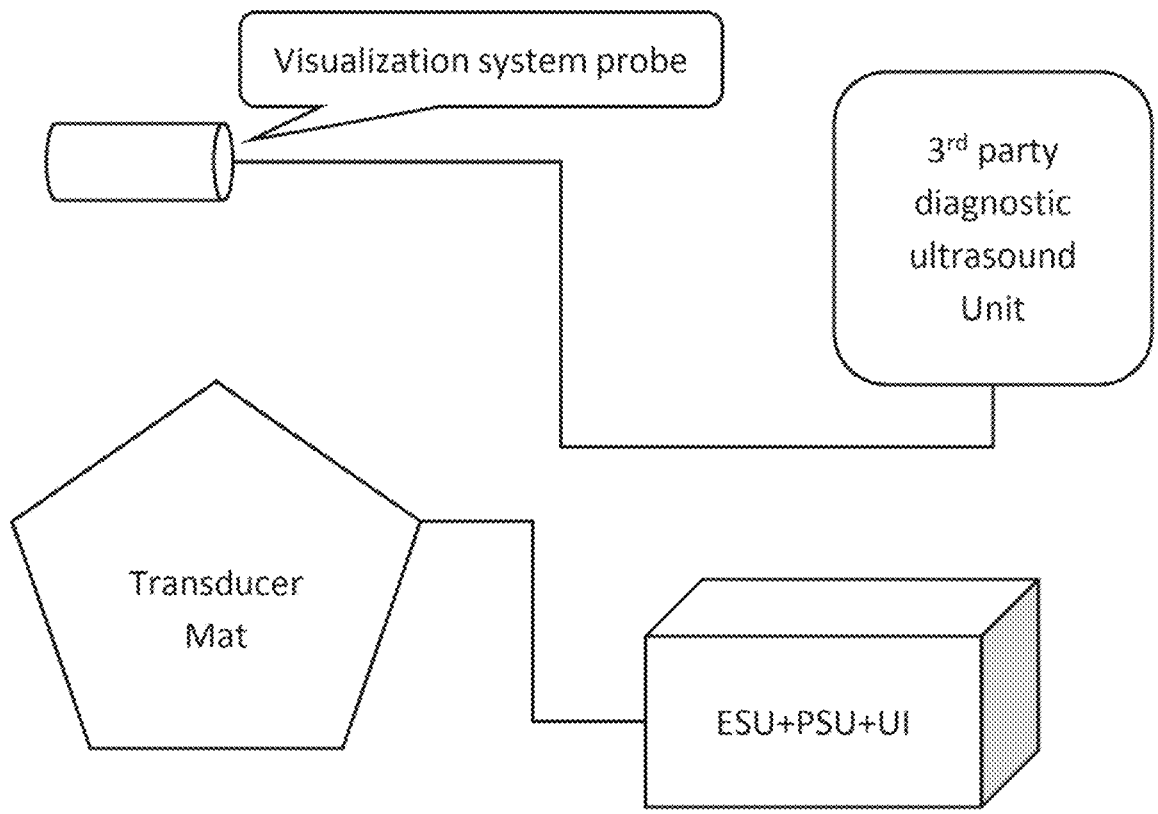
Figure 116:
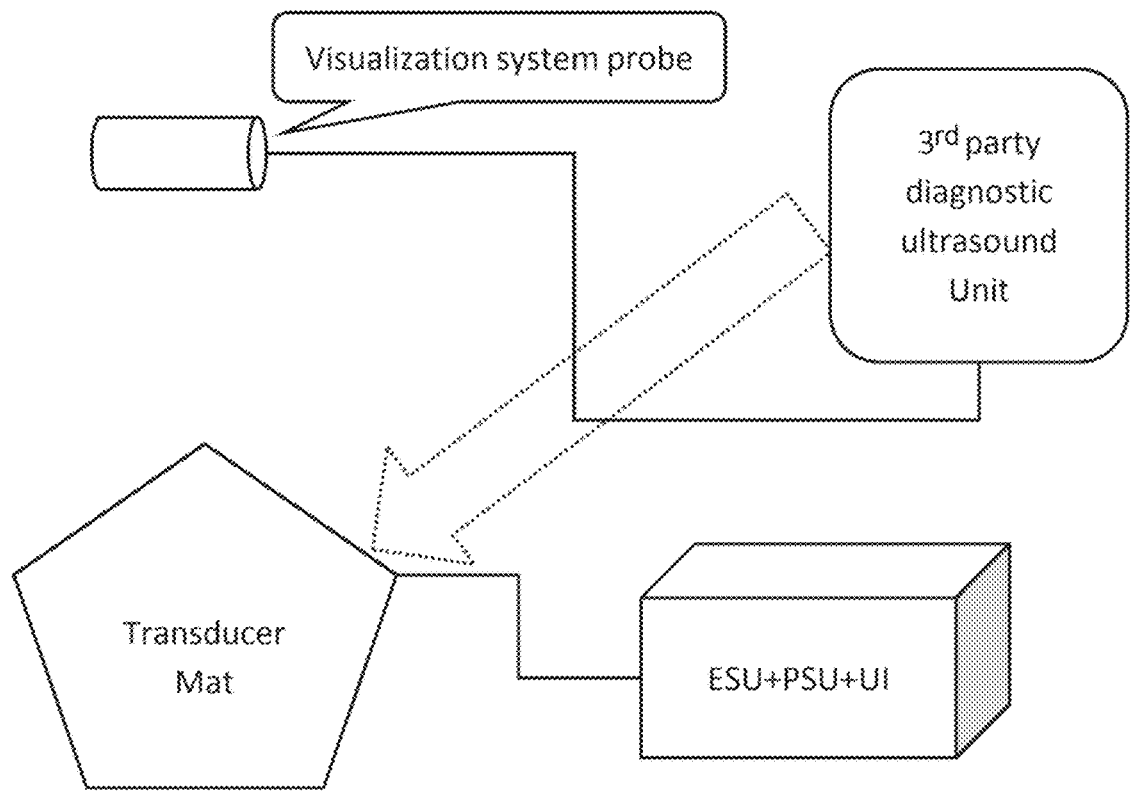
Figure 117:
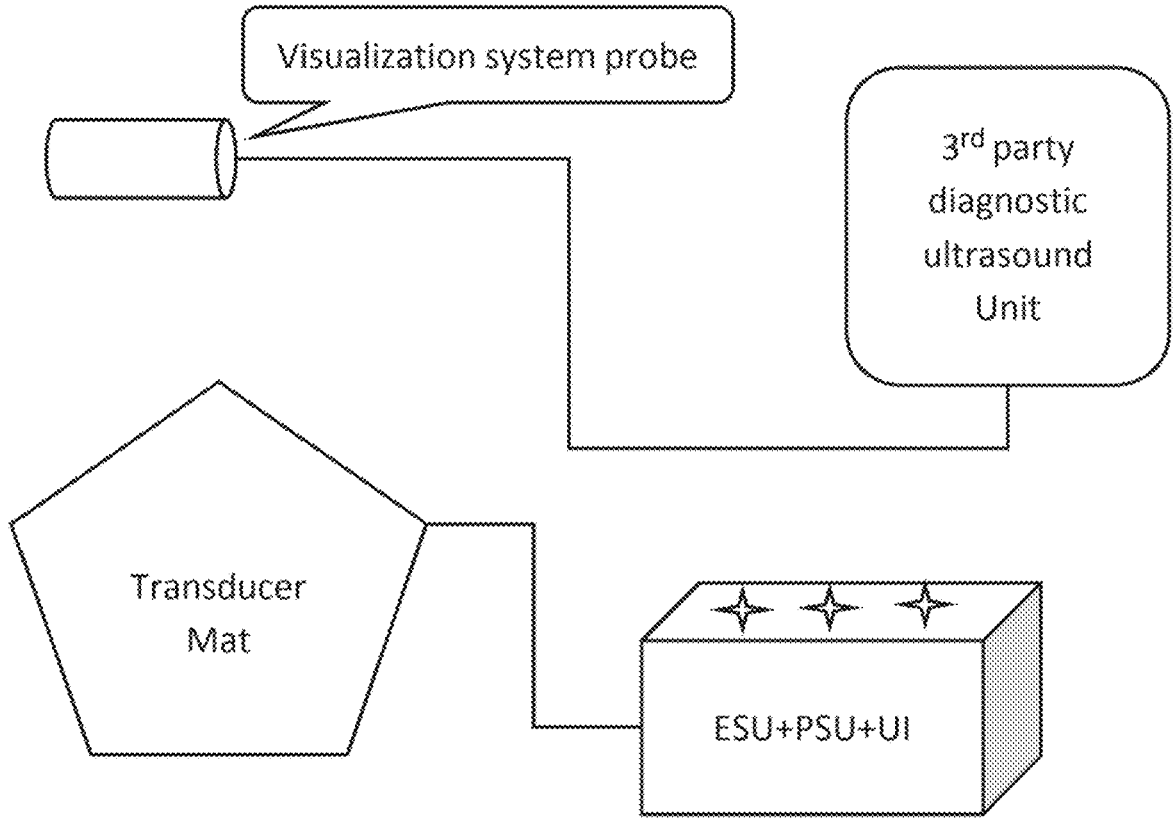
Figure 118:
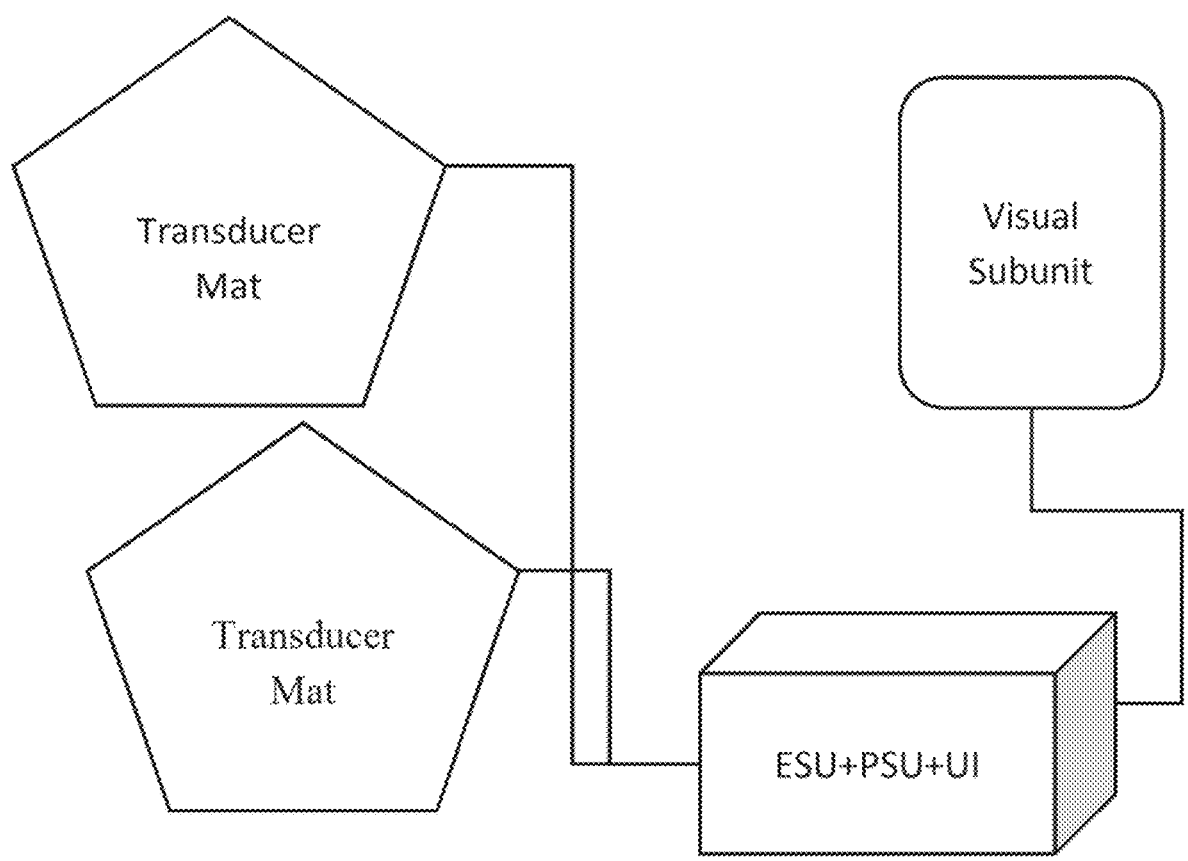
Figure 119A:
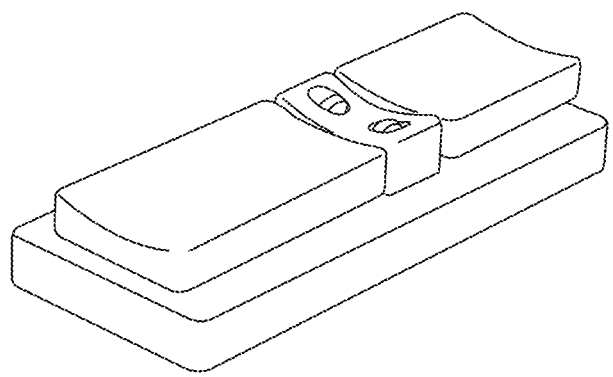
Figure 119B:
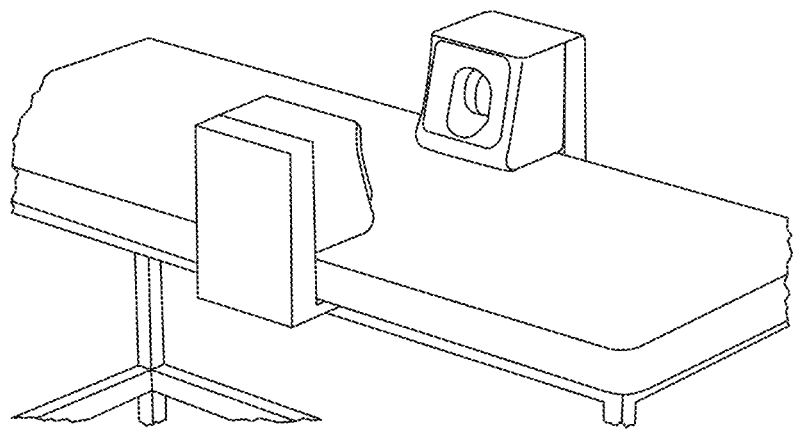
Figure 119C:
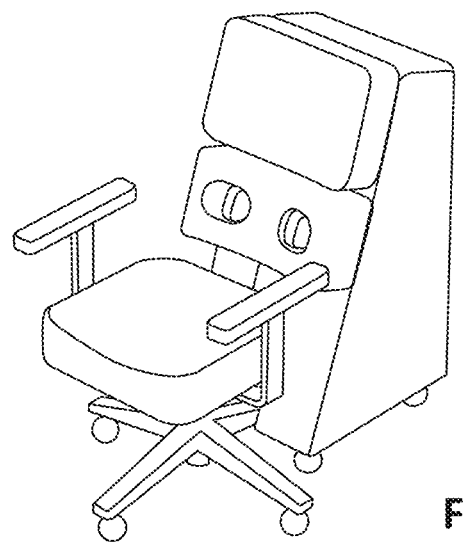
Figure 120:
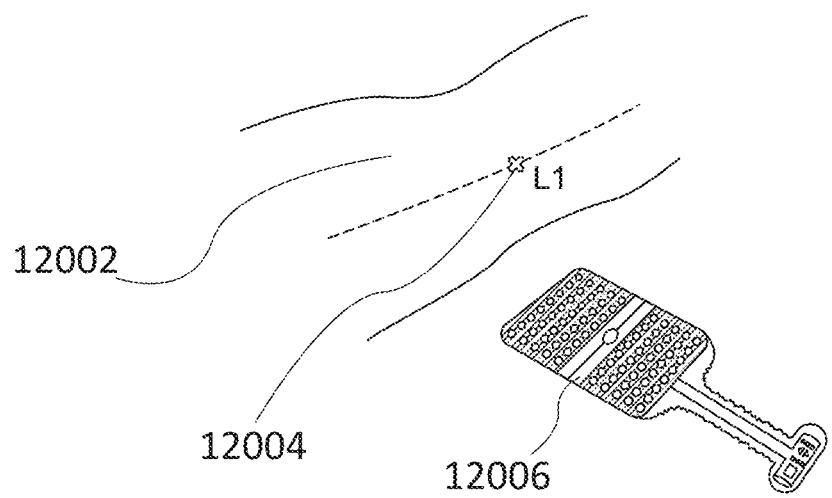
Figure 121:
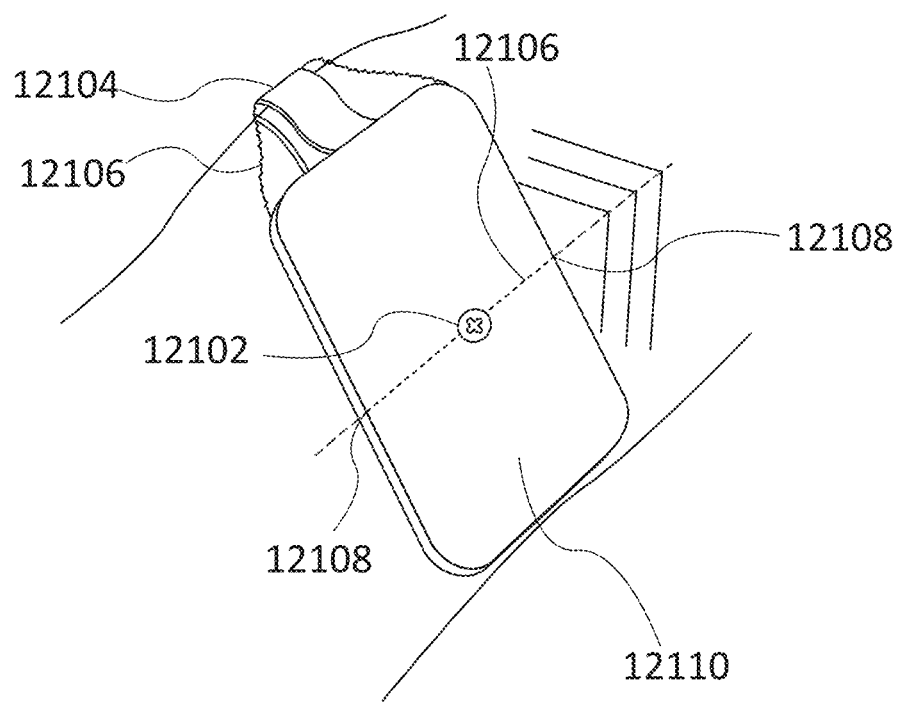
Figure 122:
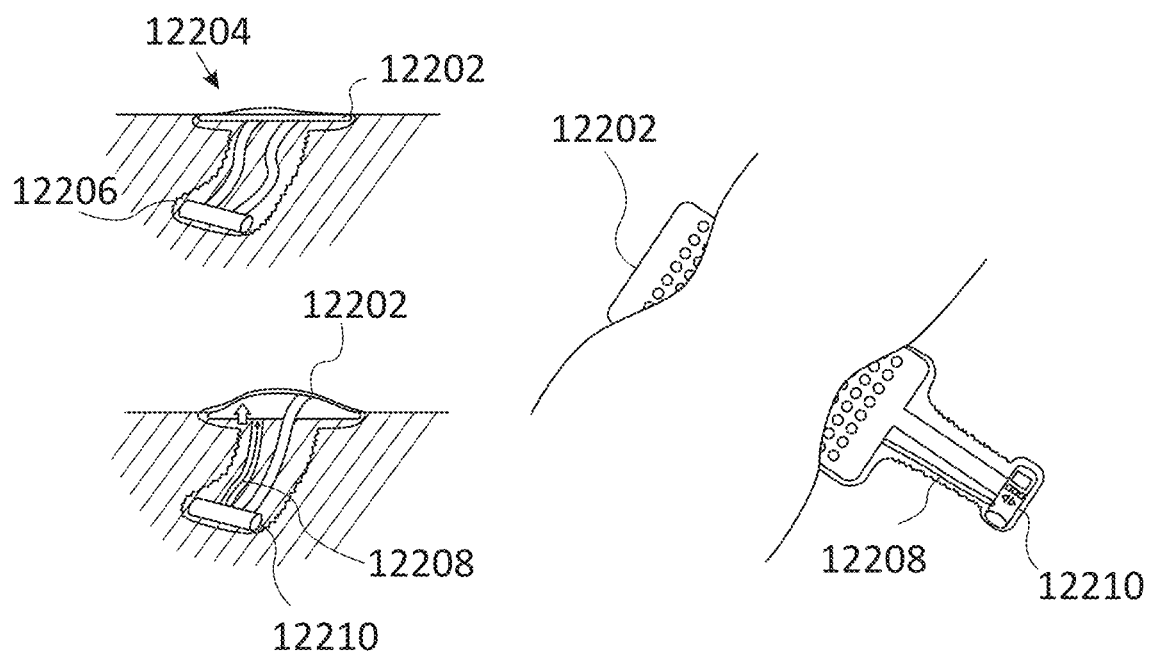
Figure 123:
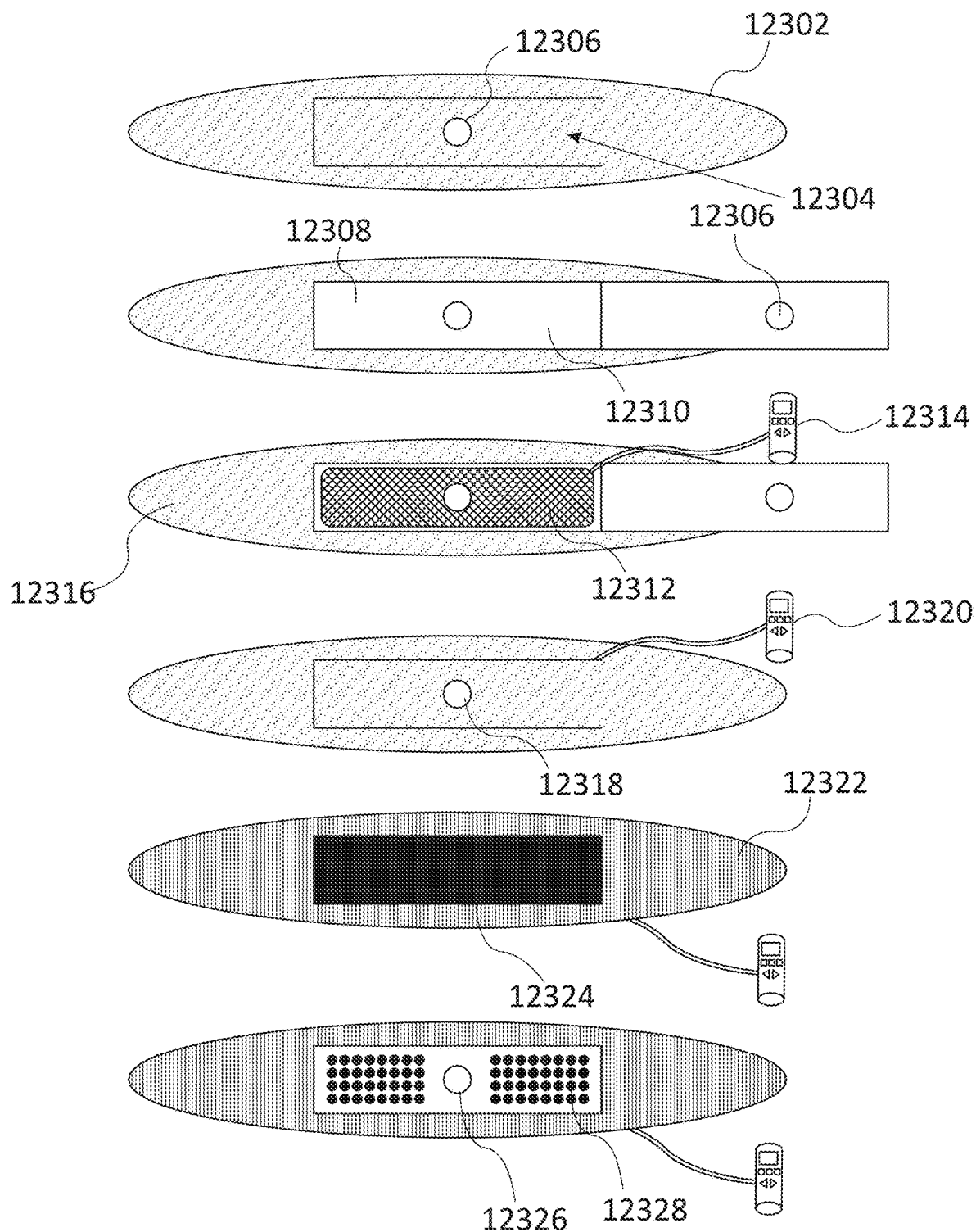
Figure 124A:
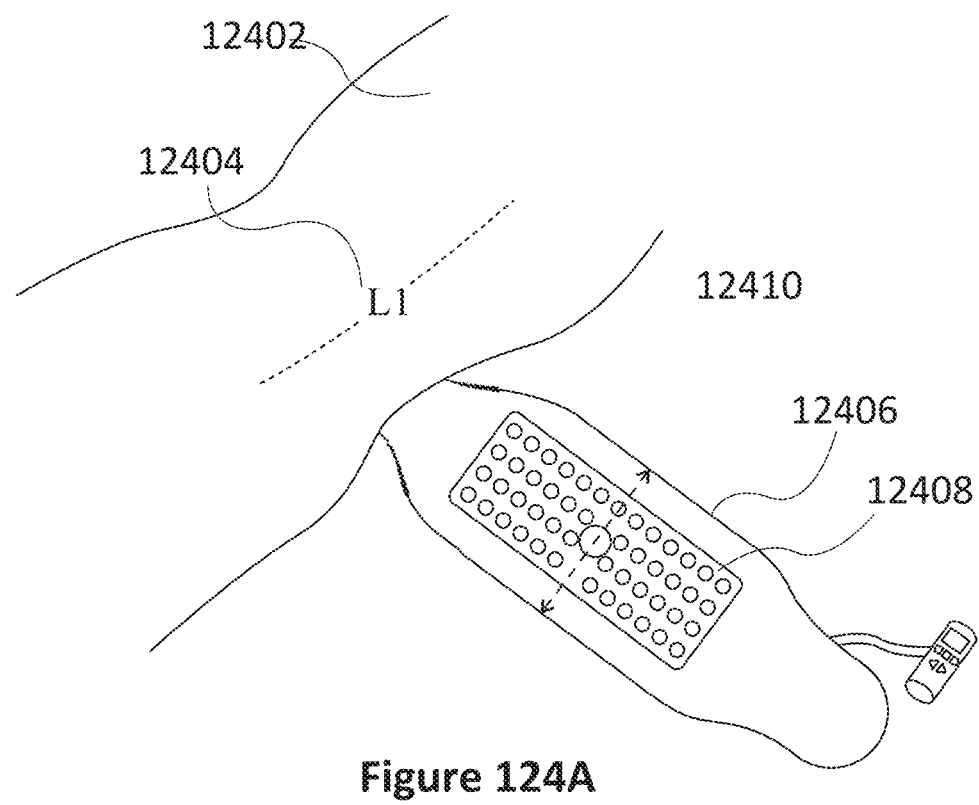
Figure 124B:
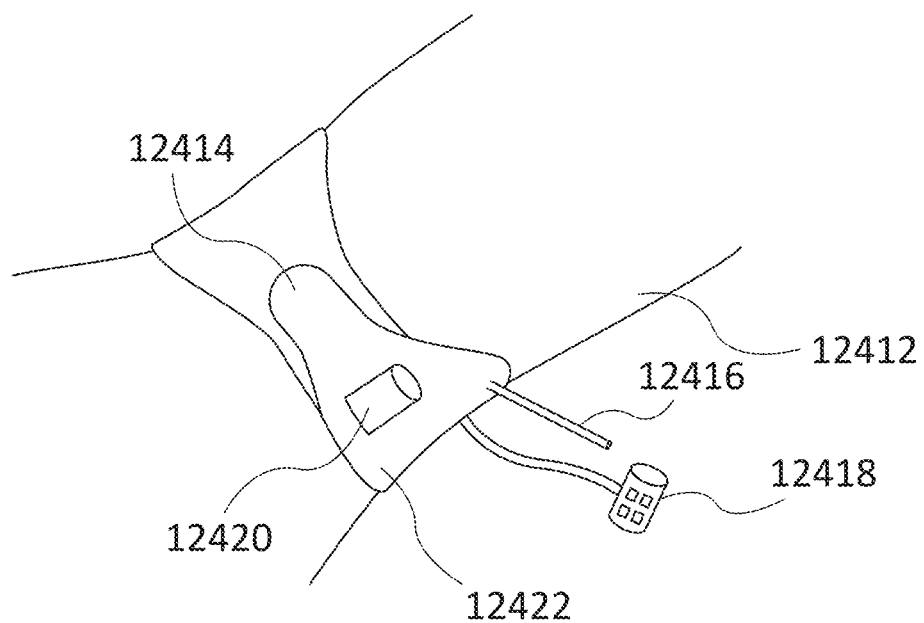

FIGS. 112A-B are schematic representations of the transducer and the window connected using an adhesive, according to come embodiments of the present invention;

FIG. 113 is a schematic representation of a multi-use device, according to come embodiments of the present invention;

FIG. 114 is a schematic representation of a system with a visual interface, according to come embodiments of the present invention;

FIG. 115 is a schematic representation of a big portion of the abdomen exposed to ultrasound, according to come embodiments of the present invention;

FIG. 116 is a schematic representation of the use of a third party Ultrasound visualization system to locate the kidneys, according to come embodiments of the present invention;

FIG. 117 is a schematic representation of how simple interface with arrows, colored LEDs efficiently direct the practitioner with the placement, according to come embodiments of the present invention;

FIG. 118 is a schematic representation of how the system has the ability to show visual interface, according to come embodiments of the present invention;

FIGS. 119A-C are exemplary devices built for back access and is embedded in a bed mattress, side access, designed as a bed top; and back access, embedded in a chair, accordingly, according to come embodiments of the present invention;

FIG. 120 is a schematic representation of the first part of the procedure, according to come embodiments of the present invention;

FIG. 121 is a schematic representation of applying the device to the patient in back cushion version, according to come embodiments of the present invention;

FIG. 122 is a schematic representation of placing the patient in the supine position, according to come embodiments of the present invention;

FIG. 123 is a schematic representation of the description of the application procedure for the back belt version, according to come embodiments of the present invention; and FIGS. 124A-B are schematic representations of the method for preparing a patient, according to come embodiments of the present invention.

DESCRIPTION OF SPECIFIC EMBODIMENTS OF THE INVENTION

The present invention, in some embodiments thereof, relates to apparatuses and methods for treating kidneys and, more particularly, but not exclusively, to ultrasonic apparatuses and methods for treating kidneys and to coupling to the body ultrasonic signals for kidney treatment for prolonged periods of time.

Overview

An aspect of some embodiments of the present invention relates to providing a system for modifying renal function by emitting ultra sound radiation to the kidneys, which does not require specialized trained user to operate it.

An aspect of some embodiments of the present invention relates to providing a system for modifying renal function by emitting ultra sound radiation to the kidneys, which does not require the user to move the system to achieve the modification of the renal function.

An aspect of some embodiments of the present invention relates to providing a system for modifying renal function by emitting ultra sound radiation to the kidneys, which does not require interface equipment to verify the effectiveness of the treatment.

In some embodiments, the emission covers a large volumetric area. In some embodiments, the large volumetric coverage allows the system to treat the kidney without the need of knowing the specific location of the kidney. In some embodiments, individual emissions are in the amplitude of about 1 MPa, optionally about 2 MPa, optionally about 3 MPa, optionally higher or lower values of MPa.

In some embodiments, the treatment achieving renal function modification does not induce thermal or cavitation side effects.

In some embodiments, the renal function modification do not require the use of ultrasound contrast agent or any other injected material that modifies its characteristics when exposed to ultrasonic vibrations In some embodiments, the system comprises a single transducer. In some embodiments, the system comprises a plurality of independent transducers. Optionally, the system comprises a plurality of independent transducer arrays. In some embodiments, the system comprises mechanical means to move transducers. In some embodiments, the system employs beam forming for modifying renal function. In some embodiments, the bean forming is formed by a 1D array, 2D array, annular array, circle array, or any combination thereof.

In some embodiments, the system transmits the ultrasonic signal using a temporal and spatial pattern. In some embodiments, the pattern is predefined and/or tuned and/or adaptive. In some embodiments, the adaptive pattern is modified by incoming data from sensors. In some embodiments, the adaptive pattern is modified by inputs from other systems. In some embodiments, the pattern is modified from data from previous activation.

A broad aspect of some embodiments of the present invention relates to controlling the transducer location and the transducer orientation (determined by, for example, posture, skin, equipment limitations) to provide the angle needed to irradiate the desired location (e.g. the kidney).

An aspect of some embodiments of the present invention relates to providing a system for modifying renal function by emitting ultra sound radiation to the kidneys, which is comfortable to the patient and allows long-term use of the system by the patient.

An aspect of some embodiments of the present invention relates to providing a system for modifying renal function by emitting ultra sound radiation to the kidneys, which allows for almost continuous use over a period of 24 h, optionally a period of 48 h, optionally a period of 72 h, optionally higher or lower values of hours, without significant interference to the treatment that a patient receives while hospitalized, and/or without significant interference to the mobility of the patient, his well-being and common activities (or similar overseen situations).

In some embodiments, the system comprises a disposable acoustic coupler with liquid replenishment mechanisms.

In some embodiments, the disposable acoustic coupler comprises a hydrogel material.

In some embodiments, the disposable acoustic coupler comprises a silicone layer material.

In some embodiments, the disposable acoustic coupler comprises an adhesive to the skin.

In some embodiments, the disposable acoustic coupler comprises an adhesive to the transducer.

In some embodiments, the disposable acoustic coupler comprises a vacuum mechanism to achieve a highly efficient ultrasonic transmission from the transducers to the skin.

In some embodiments, the disposable acoustic coupler comprises a repositionable adhesive, allowing for adjustment of the system to the patient after initial application, without causing significant pain to the patient in the process.

In some embodiments, the disposable acoustic coupler comprises a switchable adhesive to the skin. In some embodiments, a switchable adhesive is an adhesive that has at least two states: strong adhesion and weak adhesion, and a mechanism allowing for a transition from the former to the latter. In some embodiments, this allows for proper adhesion during treatment together with patient friendly low-pain removal of the disposable interface from the skin when not needed.

In some embodiments, the disposable acoustic coupler comprises a hydrophilic membrane.

In some embodiments, the disposable acoustic coupler provides extra pressure by mechanical means, a pump, device elasticity, the patient's mass, and any combination thereof.

In some embodiments, a sensor activates the pump. In some embodiments, the disposable acoustic coupler enables relative movement between transducer and/or lens and/or reflector and/or skin.

In some embodiments, the disposable acoustic coupler does not cause skin irritation and/or ulcers/injuries and/or skin rashes.

In some embodiments, the disposable acoustic coupler provides even pressure distribution over the transducers contact area in order to increase patient ease of use and reduce risk of decubitus ulcers. In some embodiments, when the pressure is spread evenly over a large area the peak pressure at any given point may be reduced, thus reducing the probability to pressure related skin damage. In some embodiments, the pressure is spread over an area of 150 mm by 200 mm, optionally over an area of 250 mm by 300 mm, optionally over an area of 350 mm by 500 mm, optionally higher or lower area values. In some embodiments, the pressure applied to a single area is higher than an area of a circle having 50 mm diameter, optionally a circle having 75 mm diameter, optionally a circle having 100 mm diameter, optionally higher or lower area values.

In some embodiments, the system provides a dynamic pressure distribution (pressure changing over time and location) over the transducers contact area in order to ease of use and reduce risk of decubitus ulcers, optimizing both ultrasound (US) dosage and contact pressure per contact spot.

In some embodiments, the system monitors cavitation (for instance at the skin interface) at multiple interface locations to manage US power distribution to reduce risk of damage from cavitation In some embodiments, micro air bubbles are pushed to the non-active areas between the transducers, at the interface between the transducers and skin, to increase system efficiency and reduce the risk of damage from cavitation.

In some embodiments, adhesion and/or glue are not used with the disposable acoustic coupler when not necessary.

In some embodiments, the disposable acoustic coupler functions as an acoustic lens.

In some embodiments, the disposable acoustic coupler functions as a modifiable acoustic lens.

In some embodiments, the disposable acoustic coupler is incorporated in non-sticker garments, such as belts, corsets, and/or other garments for long term wearing and light pressure.

In some embodiments, such belts, corsets, and/or other garments for long term wearing and light pressure, incorporate elements for pressure management such as pressure sensors, contact sensors, air or fluid pumps and valves.

In some embodiments, a disposable bag containing acoustically transparent liquid is placed between the patient's skin and the ultrasound emitting device. In some embodiments, this bag provides the following functions:

a. Filling the volume between the transducer mat and the patient skin and adjusting for human body structure variability;
b. Evenly hydrostatically distributing the pressure applied to the body. In some embodiments, excess fluid exits the bag through a dedicated valve to adjust the pressure to a desired value;
c. Replenishing the patient's skin with moisture over the prolonged periods of time that the treatment is active;
d. Avoiding the generation of air bubbles at the interface between the transducer and the skin, since the bag is preloaded with the acoustically transparent material.

In some embodiments, physiological sensors detect urine output. In some embodiments, this is done, by exemplary ultrasonic sensors, measuring fluid content of the bladder. Optionally, by exemplary ultrasonic sensors, measuring fluid content of the bottom part of the lung, using ultrasonic sensors at both sides of the thoracic spine. Optionally, by exemplary sensors, measuring heart activity such as EKG, impedance, acoustic sensors, radar. In some embodiments, total patient weight is measured using weight sensors embedded in the patient bed. In some embodiments, total patient weight is one of the target goals of increased urine output treatment using the exemplary system.

In some embodiments, urine biomarkers and electrolytes are monitored and their measurements are fed to the system.

In some embodiments, skin texture is used to detect patient fluid balance and provide system feedback.

In some embodiments, for the treatment of high blood pressure, the blood pressure of the patient is monitored as feedback to the system.

In some embodiments, the disposable acoustic coupler is incorporated into furniture.

In some embodiments, stickers are used with the disposable acoustic coupler when the patient requires movement.

In some embodiments, the disposable acoustic coupler with a sticker is flat, lightweight, cheap, and any combination thereof.

In some embodiments, the disposable acoustic coupler with a sticker is hypoallergenic, enables vapor and oxygen permeability and any combination thereof.

In some embodiments, the disposable acoustic coupler comprises at least one sensor. In some embodiments, the sensor requires skin contact.

In some embodiments, the sensor detects overheating of device and/or overheating of skin and tissue and/or cavitation and/or acoustic coupling to skin and/or strain and/or electrical resistance and/or pressure and/or skin level blood perfusion and/or skin temperature and/or humidity, in relation to the patient that is coupled to the system and/or reflected ultrasonic signal.

An aspect of some embodiments of the present invention relates to providing a system for modifying renal function by emitting ultra sound radiation to the kidneys, which is a low cost system.

In some embodiments, the system comprises a disposable low-cost acoustic coupler.

In some embodiments, the system comprises a disposable low-cost belt or cushion or wearable garment and mechanism to attach and adjust the unit to the patient.

In some embodiments, the system comprises a disposable low-cost sensor portion such as textile based pressure sensors and textile based strain sensors. In some embodiments, these sensors provide feedback on treatment related parameters such as the contact pressure near the transducer and the transducer relative position and orientation, allowing for efficient therapeutic use.

An aspect of some embodiments of the present invention relates to providing a system for modifying renal function by emitting ultra sound radiation to the kidneys, which comprises a safety mechanisms and power efficiency mechanisms.

In some embodiments, the system comprises at least one tracking mechanism.

In some embodiments, the tracking mechanism tracks the kidney location. In some embodiments, the tracking mechanism tracks the hemodynamic cycle of the kidney.

In some embodiments, the tracking mechanism tracks the kidney location by detecting rib cage location, for example, ribs 12, 11, 10 and spine.

In some embodiments, the tracking mechanism tracks the kidney location by detecting renal artery location, for example Doppler detection of the blood flow in the artery.

In some embodiments, the tracking is performed by ultrasound sensors, ultrasound Doppler sensors, breathing tracking sensors, and any combination thereof.

In some embodiments, the tracked location of the kidney is used to direct the emission of the ultra sound radiation towards the kidney, by controlling emission location, and timing.

In some embodiments, the tracked location of the kidney is used to verify system initial application and changes thereafter.

In some embodiments, the tracked location of the kidney is used to verify system re-application between distinct applications. In some embodiments, a potential advantage of such automatic verification is that it provides a significant cost saving to the medical caretaker since it will relieve the nurse from re-applying the unit to the patient between distinct applications. In some embodiments, a nurse is called only if the automatic self-verification of the system has alerted that the new application of the system is non-satisfactory. In some applications, such as the chronic patient home use, there is no trained medical professional on location, and the kidney location verification may be key to the effectiveness of the system.

In some embodiments, the tracked hemodynamic cycle of the kidney is used to reduce and/or modify and/or increase the emission of the ultra sound radiation towards the kidney.

An aspect of some embodiments of the present invention relates to providing a system for modifying renal function by emitting ultra sound radiation to the kidneys, which irradiates the kidneys while avoiding irradiating the ribs or the lungs or the spine or a plurality of them.

In some embodiments, the system comprises a plurality of independent transducers. In some embodiments, the plurality of independent transducers are small transducers or small transducer arrays. In some embodiments, the plurality of independent transducers or plurality of independent transducer arrays radiate between the ribs.

In some embodiments, the system comprises at least one tracking mechanism.

In some embodiments, the tracking mechanism tracks the ribs location. In some embodiments, the tracking mechanism tracks the plurality of independent transducers. In some embodiments, the tracking mechanism tracks the plurality of independent transducers in relation to the ribs.

In some embodiments, the system comprises at least one sensor. In some embodiments, the sensors are ultrasound sensors and/or ultrasound Doppler sensors and/or breathing tracking sensors and/or movement sensors and or hemodynamic sensors.

In some embodiments, the system measures the ultrasound reflection.

In some embodiments, the system measures the ultrasonic impedance.

An aspect of some embodiments of the present invention relates to ultrasound systems that enable procedure initialization without requiring a trained medical caretaker (e.g. use of a trained US technician) and/or guarantee that satisfactory ultrasound emissions arrive at the desired locations without the need of a human operator to move the device (except perhaps, for the initialization) and/or guarantee that satisfactory ultrasound emissions arrive at the desired locations without the need of a human operator to verify this using some type of interface—visual or other.

In some embodiments, the system enables a large volumetric coverage, so specific relative location of kidney is not important. In some embodiments, the system provides enough focus during ultrasound transmission of individual bursts such that required amplitude (about 1 MPa or 3 MPa or 10 MPa) is achieved. In some embodiments, the design limits ultrasonic exposure to safe levels, avoids heating and keeps the mechanical index below safety threshold. In some embodiments, to achieve this by using a temporal/spatial design, the system uses either a single transducer, multiple independent transducers, multiple independent transducer arrays, mechanical movement (various options listed, including revolving transducer, revolving lens), beam forming (including 1D array, 2D array, Annular array, circle array), or a combination thereof.

In some embodiments, multiple transducers are active simultaneously without multi-transducer focus. In some embodiments, the near field beam structure generates high pressure values in various locations within the superimposed combined ultrasonic beam, enabling treatment in those volume segments. In some embodiments, such a system enables treatment of large bodied patients, where the signal may be highly attenuated between the transducers on the skin and the kidneys.

In some embodiments, the system provides the ability to overcome difference between transducer location and orientation (e.g. determined by posture, skin, and furniture) and angle to desired kidney location. In some embodiments, the system transmits the ultrasonic signal with a temporal/spatial pattern to achieve the technical goals. In some embodiments, the temporal/spatial pattern is predefined to achieve goals, initially tuned, adaptive using sensed data, learnt from previous applications.

In some embodiments, the potential advantage is to provide a system that does not require human professional in the loop making the procedure significantly cheaper. In some embodiments, the potential advantage is to provide a system that does not require human specialist at initialization making the procedure significantly cheaper and available. In some embodiments, the potential advantage is to provide a system that does not require special ultrasound equipment during initialization making the procedure significantly cheaper and available.

An aspect of some embodiments of the present invention relates to ultrasound systems that provide a comfortable interface to the patient to guarantee compliance and/or provide a comfortable mechanism to allow the patient to perform various activities (such as take breaks, move, take a shower) while continuing the treatment or stop and resume the treatment, minimizing human intervention, to guarantee compliance.

In some embodiments, the system comprises a disposable acoustic coupler that conforms to the following technical requirements: water that is displaced or absorbed from skin will be replenished by use of hydrogel materials, a hydrophilic membrane, using a mechanical construction or pump, or the patient's mass to ensure extra pressure, sensor activated pump, enabling relative movement (if needed) between transducer, lens, reflector, skin. In some embodiments, the disposable acoustic coupler avoids skin irritation, ulcers/injuries, skin rashes, stickers and glue if glue is non-comfortable.

In some embodiments, the system comprises the use of: non-sticker garments such as designed belt/corset/other garments for long term wearing and light pressure; embedding the system into furniture, providing solutions to various cases such as bed rest, on bed device, armchair attached device.

In some embodiments, the system comprises the use of a combination of an active anti-decubitus ulcers apparatus and ultrasound measurements and transmission to provide both therapeutic ultrasound and avoid lengthy and damaging contact pressure on the skin. In some embodiments, the system comprises the use of a combination of a passive anti-decubitus ulcers pressure distribution apparatus that provides ultrasound transmissivity together with ultrasound measurements to provide both therapeutic ultrasound and avoid lengthy and damaging contact pressure on the skin.

In some embodiments, the system comprises disposable sensors that require skin contact to: detect overheating of device, detect overheating of skin and tissue, detect cavitation, detect acoustic coupling to skin, detect that the patient is coupled to the system and/or measure reflected ultrasonic signal.

Alternatively, in some embodiments, when necessary and/or advantageous, the system comprises the use of stickers when a sticker is more practical for daily use (for instance for a walking patient, patient performing sport, when device needs to be concealed). In some embodiments, the sticker is flat, lightweight and/or cost effective.

In some embodiments, the potential advantage is to provide a system that ensures patient is long term comfortable. In some embodiments, the potential advantage is to provide a system that enables adjustment to people preferences. In some embodiments, the potential advantage is to provide a system that enables a wearable solution—light weight, concealable under clothes, does not interfere with normal activities like sitting—to allow patients to continue with normal activity. In some embodiments, the potential advantage is to provide a system that ensures low cost per treatment.

An aspect of some embodiments of the present invention relates to ultrasound systems that, since the system is used by a single patient for many hours, is a low cost system and/or since the equipment is in contact with the patient's skin, the system comprises a low cost disposable component to guarantee patient's safety and low cost per treatment.

In some embodiments, the system comprises transducer technology with relaxed requirements compared to diagnostic transducer design. In some embodiments, the system comprises a disposable transducer. In some embodiments, the system requires a reduced to non-necessary receive sensitivity and resolution. In some embodiments, the system comprises disposable sensors that require skin contact to: detect overheating of device, detect overheating of skin and tissue, detect cavitation, detect acoustic coupling to skin, detect that the patient is coupled to the system and/or measure reflected ultrasonic signal.

In some embodiments, the system comprises disposable sensors that require skin contact to detect that the transducers are placed in the right location (guaranteeing that the target organs shall receive the treatment) and right orientation, and are well coupled to the skin.

In some embodiments, the potential advantage is to provide a system that is characterized by a simple design and reduced costs.

An aspect of some embodiments of the present invention relates to ultrasound systems that improves safety and/or power efficiency (by reducing exposure on non-kidney tissue, by tracking kidney location) or increase efficacy (by aligning treatment with hemodynamic cycle).

In some embodiments, the system tracks the location of the kidney. In some embodiments, the signal may be directed to the kidney and not to other tissues. In some embodiments, this has an effect on: increased safety, increased power efficiency, increased efficacy and/or reduction of treatment time per day and thus improved compliance. In some embodiments, tracking is performed with various sensors, for example, ultrasound sensors, ultrasound Doppler sensors, sensors that track breathing (pressure, accelerometers, EMG, Oxygen saturation).

In some embodiments, the system tracks hemodynamics in the kidney. In some embodiments, this has an effect on: improve efficacy, reduce treatment time and thus improve power efficiency, efficacy and/or compliance. In some embodiments, tracking is performed with various sensors, for example, ultrasound Doppler sensors, ECG, pressure.

An aspect of some embodiments of the present invention relates to ultrasound systems, which have access to the kidney below the ribs, which require complex beam steering that may increase overall system cost and power consumption.

In some embodiments, the system comprises multiple small transducers that can transmit between the ribs and avoid rib exposure. In some embodiments, the system comprises multiple small transducer arrays that are electronically steered to transmit the ultrasonic beam to reach the kidney between the ribs and reduce rib exposure. In some embodiments, the system transmits between the ribs by: tracking relative location of ribs and transducers, utilizing adaptive measurement of US reflection, utilizing model building for when and where to transmit the beam towards the kidney avoiding the beam, utilizing direct modeling, utilizing Kalman filtering, utilizing learning algorithms and/or utilizing sensors such as: US sensors, Doppler US sensors.

In some embodiments, the potential advantage is to provide a system that emits at a shorter distance and/or comprises a simpler design for direct access between ribs. In some embodiments, the potential advantage is to provide a system that avoids transmission of ultrasound directly onto the ribs, which would reflect these signals and not let them reach the kidney.

In some embodiments, the signal frequency, intensity, duration and amplitude are such that rib exposure is not a safety concern or only a marginal concern, allowing for simple and low cost treatment from locations over the rib cage.

An aspect of some embodiments of the present invention relates to prevention of development of AKI symptoms in patients at risk to develop AKI.

In some embodiments, patients in risk of developing AKI or showing AKI symptoms are treated with ultrasound radiation prior to the development of AKI and/or prior to showing AKI symptoms. In some embodiments, sufficient ultrasound treatment reduces the symptoms or the risk of developing AKI by at least 10%, optionally by at least 20%, optionally by at least 50%, optionally higher or lower % values. In some embodiments, the percentage is calculated on a window spanning from day 1 to day 5, optionally from day 1 to day 7, optionally from day 3 to day 7, optionally at higher or lower intervals of days, of when AKI might happen and wherein said reduction comprises a mathematical reduction in an average displacement of a biomarker from a baseline value. In some embodiments, the displacement is of about 10%, optionally of about 30%, optionally of about 50%, optionally higher or lower % values.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary System Type 1

In some embodiments, the exemplary system type 1 comprises one or more transducers attached to the body of the patient. In some embodiments, the one or more transducers are attached to the body of the patient by sticker and/or belt and/or corset, and/or a vest, with one or more disposable acoustic gel pockets. In some embodiments, the exemplary system type 1 comprises a power and signal sub-unit which generates an electrical signal for the transducers, optionally one transducer or transducer array at a time. In some embodiments, the one or more transducers do not require to move to work. In some embodiments, the system does not require to sense internal organs in order to correctly deliver the treatment. In some embodiments, the exemplary system type 1 is adapted to spread ultrasound energy in the abdomen, covering the target tissue as well as other tissues.

Figure 1:
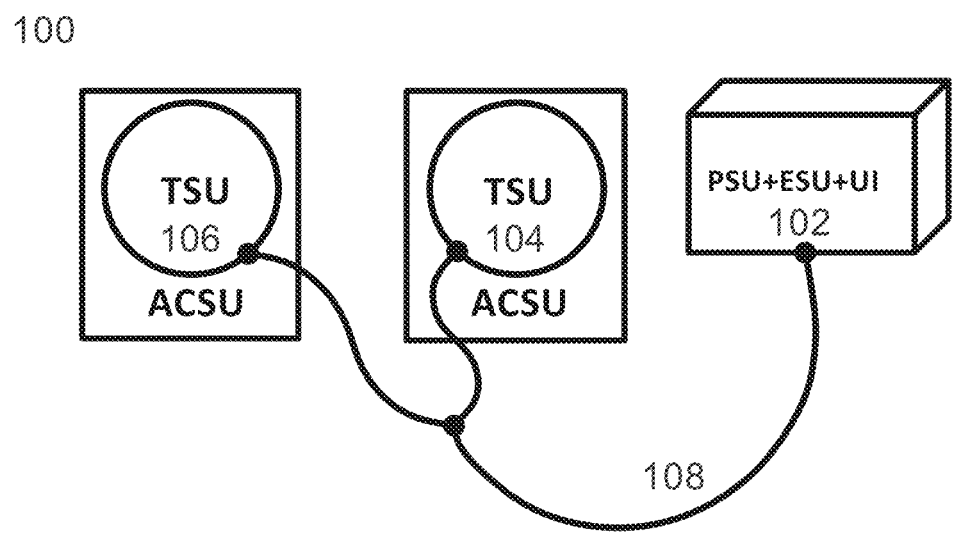
FIG. 1 is a schematic representation of an exemplary configuration of an exemplary system type 1, according to come embodiments of the present invention.

In some embodiments, the exemplary system type 1 comprises a Transducer Subunit (TSU), an Acoustic Coupling Subunit (ACSU), a Power Subunit (PSU), an Electrical Subunit (ESU) and a User Interface Subunit (UI). Referring now to FIG. 1, showing a schematic representation of an exemplary configuration of an exemplary system type 1 100 with three of the subunits packaged together—the PSU, ESU and UI 102, and two copies 104 and 106 each of the TSU and ACSU—one pair for the left kidney and one pair for the right kidney. In some embodiments, the units are connected via cables 108 and/or directly attach one to the next.

Exemplary Type 1 System Subunits

Transducer Sub-Unit

In some embodiments, the transducer sub-unit includes one or more transducers. In some embodiments, the transducers convert electrical signal to ultrasound signal. In some embodiments, the transducers are coupled to the body using acoustic gel, or silicone gel or an adhesive, which is part of the acoustic coupling subunit.

Transducer Parameters:

| Parameter | Value | Comment |
| --- | --- | --- |
| Low frequency | 0.5 MHz | |
| High Frequency | 15 MHz | |
| Diameter | 0.1-25 mm | |
| Peak pressure | 15 MPa | On surface |

Acoustic Coupling Sub-Unit

In some embodiments, the sub-unit is designed to achieve long term acoustic coupling between the transducer and the skin. In some embodiments, the unit is disposable. In some embodiments, the unit may be integrated with the transducer subunit.

| Parameter | Value | Comment |
| --- | --- | --- |
| Operational time from start | 1-10 hours | Time that acoustic coupling is guaranteed. |
| Operational time from start | 1-72 hours | Time that acoustic coupling is guaranteed. |

Power Subunit

In some embodiments, the power subunit holds the energy reservoir of the system.

| Parameter | Value | Comment |
| --- | --- | --- |
| Operational lifetime of power unit | 1-10 hours | when not connected to main |
| Power | 0.5 W | |

Electrical Subunit

In some embodiments, the electrical subunit contains the main control function of the system and well as the generation of the electrical signal to the transducer.

| Parameter | Value |
| --- | --- |
| Pulse frequency range | 0.5-15 MHz |
| Pulse duration | 0.2-10 microseconds |
| Pulse repetition rate | 0.1-30 kHz |

User Interface Subunit

In some embodiments, the subunit enables the operation and activation off the device. It provides an indication for proper functioning

| Parameter | Value | Comment |
| --- | --- | --- |
| On Off switch | Available | |
| Activate/Pause switch | Optional | |
| Proper function indication | Available | Light/screen |

Examples of the Transducer Subunit

In some embodiments, in the System type 1, the therapeutic ultrasound is generated in a transducer subunit. In some embodiments, the design of the transducer subunit is as follows:

Single Pulse Width and Duration, Spectral Content

Figure 2:
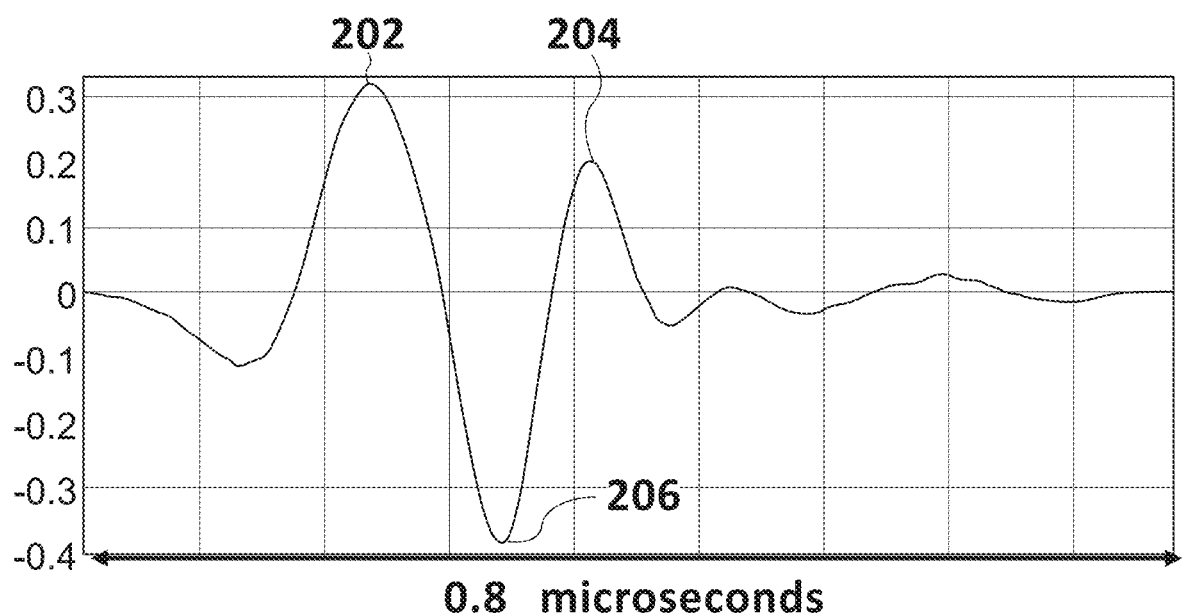
FIG. 2 is an exemplary graph of a pressure signal measured from the system, according to come embodiments of the present invention.

Referring now to FIG. 2 showing an exemplary graph of a pressure signal measured from the system. The pulse duration is about 0.8 microseconds. In some embodiments, it may contain two positive pressure peaks (compression) (202, 204) and a single negative (rarefaction) peak 206.

Figure 3:
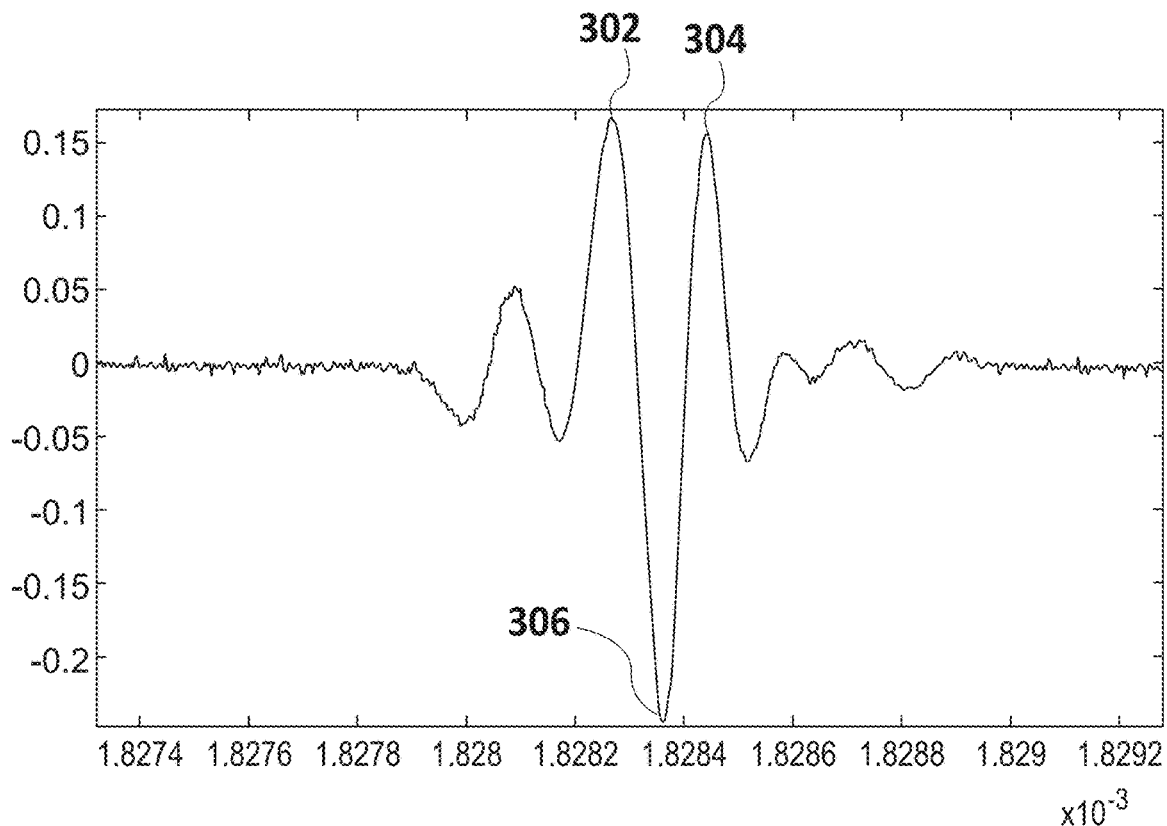
FIG. 3 is an exemplary graph of a pressure signal measured from the system, according to come embodiments of the present invention.

Referring now to FIG. 3 showing another exemplary graph of a pressure signal measured from the system. It can be seen in the figure the positive peaks 302 and 304. In this example, they have the same compression amplitude. The negative peak 306 is the rarefaction pressure peak. The spectral content of the signal is wideband and contains signal in the frequency range of 1-10 MHz, optionally higher or lower values of MHz.

Figure 4:
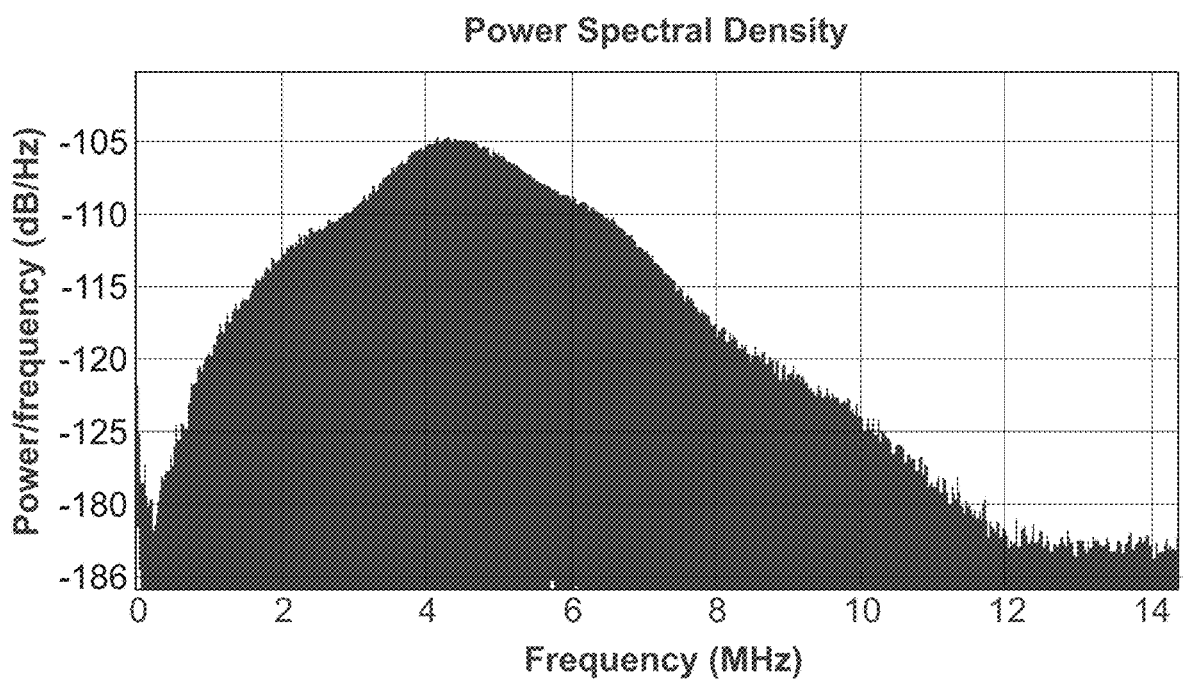
FIG. 4 is an exemplary signal pulse spectral content, according to come embodiments of the present invention.

Referring now to FIG. 4 showing an exemplary signal pulse spectral content. Since the treatment pulse is short, the spectral content of the therapeutic signal is relatively wide, in the order of a number of MHz. This is much different from physiotherapy ultrasonic systems that operate with constant wave signal (which is thus very narrow band) or pulsed ultrasonic systems where the duration of the ultrasonic pulse is of the order of milliseconds. For these systems the spectral band is thus of the order of a KHz. The signal bandwidth is also a much wider than signals from other therapeutic systems, such as those used for bone healing which have bandwidths up to 10 KHz, optionally higher or lower values of KHz. This therapeutic device signal has thus two to four orders of magnitude wider bandwidth than the corresponding therapeutic devices, applying a potentially unique treatment modality.

Exemplary Transducer Subunit Containing a Single Transducer

In some embodiments, the transducer subunit contains a single transducer. In some embodiments, the single transducer converts electrical signal to ultrasound signal. In some embodiments, once the transducer subunit is placed properly against the patient's skin, then the unit may operate. In some embodiments, there may be limitations with regard to the placement of this transducer subunit on the patient's skin; optionally there may not be such limitations. In some embodiments, an example of a possible limitation is not to place the transducer over a bone, such as the rib or the spine.

Figure 5:
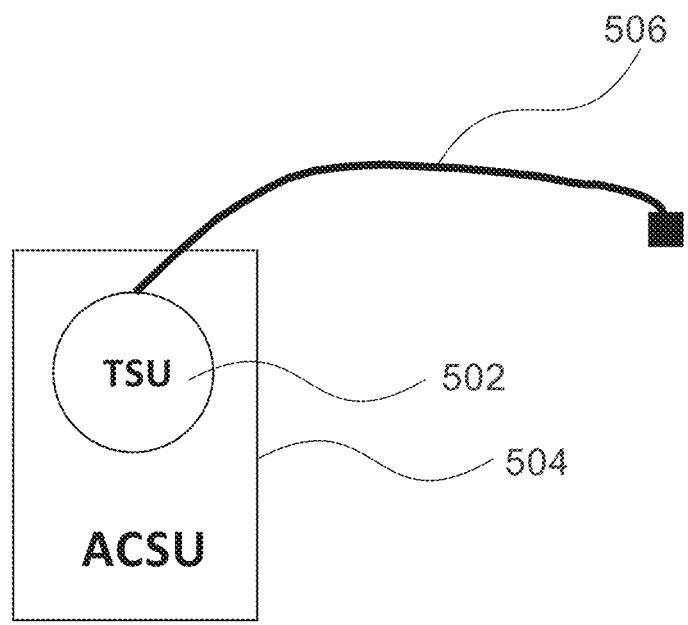
FIG. 5 is an exemplary transducer subunit containing a single transducer, according to come embodiments of the present invention.

Referring now to FIG. 5 showing an exemplary transducer subunit containing a single transducer. In some embodiments, the transducer 502 (in the FIG. 5—a round transducer), the ACSU 504 couples between the transducer 502 and the skin and a cable 506. In some embodiments, the cable is connected to an electrical signal subunit.

A Transducer Subunit Containing Two-Dimensional (2D) Array of Transducers

In some embodiments, each transducer in the 2D array of transducers transmits at a distinct time. A set of 3 transducers that are not arranged in a line is a minimal set of transducers to form a two-dimensional array. In some embodiments, only one electrical signal needs to be provided to the complete transducer subunit. In some embodiments, the transducer subunit directs the incoming electrical signal to the selected transducer by an addressing method that can be dynamic or pre-arranged. In some embodiments, each transducer has a number from 1 to $N_T$, $N_T$ being the number of transducers in the mat. The pulses arriving at the interface are transmitted one per transducer from 1 to $N_T$ and back to 1, ad infinitum, or until another scheme is selected. In some embodiments, the electrical pulse that is directed towards a transducer is accompanied by a digital communication signal, which encodes the index number of the selected transducer. In some embodiments, the encoded number can share the same electrical interface as the transmitted pulse, or use another line. In some embodiments, the distribution circuit shall direct the pulse to the proper transducer according to the decoded value as provided. In some embodiments, the same signal can be transmitted in some or all of transducers and/or at the discretion of the system, different signals can be transmitted from different transducers. In some embodiments, by adding to the electrical interface an encoded command that informs the distribution circuit which transducers should receive the signals, various schemes can be implemented, for example, single transducer selection, and group multiple transducer selection. In some embodiments, a transducer that is placed over a bone may be disabled, or may be programmed to send a different type of signal.

Figure 6:
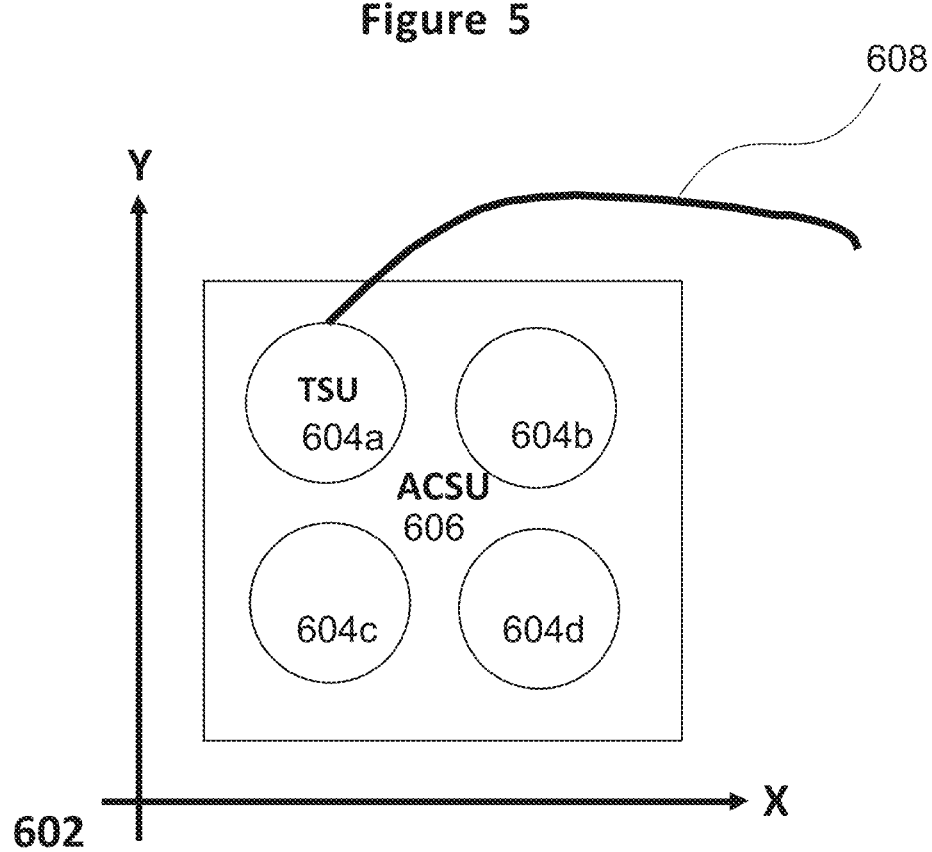
FIG. 6 is an exemplary transducer subunit with a 2D transducer set, according to come embodiments of the present invention.

Referring now to FIG. 6 showing an exemplary transducer subunit with a 2D transducer set. In some embodiments, the transducers are arranged in a 2D plane (X, Y) 602. In this example, there are four round transducers 604a-d. In some embodiments, the ACSU 606 couples between the transducers 604a-d and the skin and a cable 608 connects the whole module to the next subunit.

A Transducer Subunit Containing One or More Single Dimensional Arrays of Transducers In some embodiments, single dimensional array of transducers are a set of transducers that are arranged in a line. In some embodiments, the line is straight and is called a linear array. In some embodiments, the line is curved and is called curvi-linear. Linear arrays are very common in the diagnostic ultrasound industry. Many ultrasonic probes use linear and curvilinear transducer arrays. Thus, in some embodiments, the use of a technology that is commonly used may be advantageous in reducing the system manufacturing costs.

In some embodiments, in a type 1 system, the transducers along the one-dimensional transducer array are activated one at a time. In some embodiments, the sequence of transmission may be simple, e.g. every transducer transmits one pulse and the sequence starts in one end of the array and progresses towards the other end of the array: $T_1$, $T_2$, $T_3$, $T_4$ . . . $T_N$. In some embodiments, the sequence can be complex, with transducers firing multiple times and/or being hopped over. In some embodiments, the goal of the signal sequence is to ensure that the therapeutic signal reaches its destination in a balanced and effective spatial distribution.

In some embodiments, the transducer subunit may contain one or more linear transducer arrays. In some embodiments, the arrays may be parallel as is shown, for example, in FIG. 7, or have any other arrangement.

Figure 7:
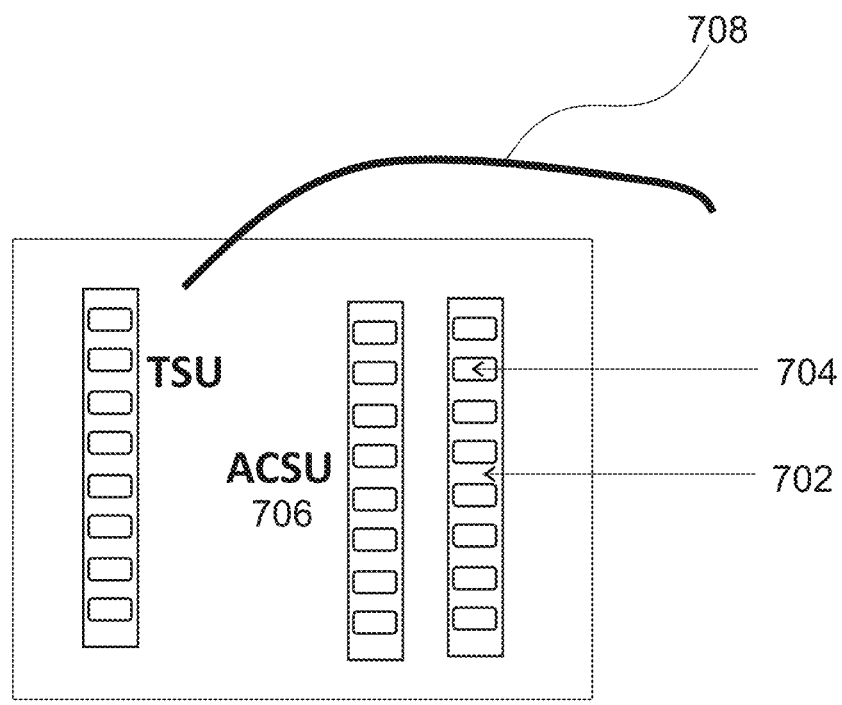
FIG. 7 is a schematic representation of an exemplary transducer subunit with one-dimensional arrays of transducers, according to come embodiments of the present invention.

Referring now to FIG. 7, showing a schematic representation of an exemplary transducer subunit with one-dimensional arrays of transducers. In some embodiments, the transducer arrays 702 are arranged vertically. In some embodiments, each transducer array contains individual transducers 704 arranged in a linear array. The ACSU 706 couples between the transducer arrays and the skin and a cable 708 connects the whole module to the next subunit.

A Transducer Subunit Containing an Annular Array of Transducers

In some embodiments, an annular array is capable to control the intensity of the ultrasonic signal along the axis perpendicular transducer plane. In some embodiments, this means that the depth where the ultrasonic signal amplitude is high is controlled. In some embodiments, this can be advantageous in assisting reducing ultrasonic signal intensity in the tissues between the transducer and the kidney (mostly skin, fat and muscle) and behind the kidney (mostly intestine).

Figure 8:
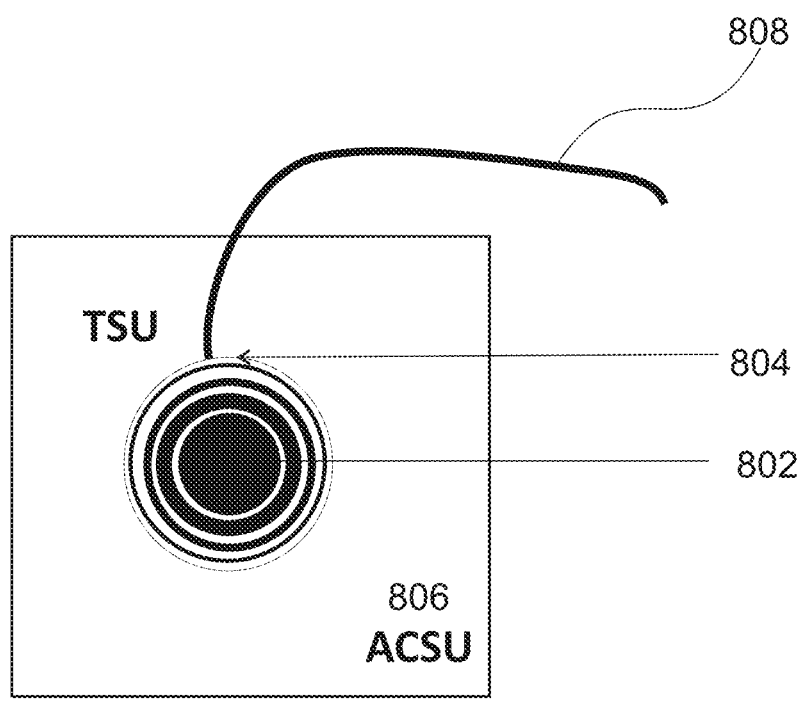
FIG. 8 is a schematic illustration of an annular array of transducers, according to come embodiments of the present invention.

Referring now to FIG. 8, showing a schematic illustration of an annular array of transducers. In some embodiments, the transducer unit contains one or more annular arrays. In some embodiments, the annular array has a center transducer 802 surrounded by concentric circular transducers 804. In some embodiments, the system delivers the electrical signal to the transducers with relative delays between each other and with amplitudes such to manipulate the intensity of the signal along the axis that is perpendicular to the array and goes through the center of all circles. In some embodiments, the ACSU 806 couples the array to the skin. The cable 808 connects the array to the electrical subunit.

A Transducer Subunit Containing a Combination of Arrays

In some embodiments, the transducer subunit may contain a combination of transducer arrangements as mentioned above (i.e. 2D arrays, annular arrays, one-dimensional arrays, individual transducers), and in various shapes and sizes.

Transducers Design for Near Field Tissue Exposure

In some embodiments, the goal of the transducer is to provide an ultrasonic pressure at the kidney from a location outside of the body. Prior art diagnostic systems are required to measure the acoustic properties of the tissue with high resolution—thus they need to make sure that the exposed volume is as small as possible in order to provide accurate information on small volumetric elements. In these examples, the transducer provides high-pressure amplitudes at one location and low-pressure amplitudes anywhere else. In other prior art systems, a therapeutic ultrasound system, such as High Intensity Focused Ultrasound (HIFU), needs also to focus the energy at a single location, which should be very small, and to reduce the amplitude everywhere else, so the therapeutic process (in this case—heating) shall be limited to a small volume only.

Contrary to the two prior art systems mentioned above, the system provides, in some embodiments, a signal on an organ that is relatively large—120 by 60 by 30 mm typical size. In some embodiments, this is achieved by providing also an unfocused beam where the kidney is exposed to the near field signal.

In some embodiments, the near filed of an acoustic transducer is characterized by rapid changes in amplitude over short distances at the order or magnitude of the transmitted wavelength. In some embodiments, certain tissue locations are exposed to high amplitude while adjacent locations are not exposed. For diagnostics and HIFU applications, this focus characteristic is crucial for the proper functionality of the device.

In prior art systems used for heating applications, some regions may be overheated while others may be under heated. Contrary to prior art systems, the system disclosed herein does not have such issues because, in some embodiments, the system designed not to expose the tissue to heating amplitudes. In some embodiments, there is no need to expose the whole kidney to the signal. In some embodiments, since the kidney is built from replications of the same nephron structure (about 1,000,000 copies in a healthy kidney), partial exposure means part of the nephrons are treated and this is enough, from the clinical point of view, to improve kidney performance. In some embodiments, the breathing motion moves the kidney relative to the transducer interface at the skin and thus the system averages out the signal over the breathing period.

An example for a design with near field exposure is provided:

Given the wavelength $\lambda$ and transducer diameter D, the near field range N for a round piston transducer is provided as $N=D^2/4\lambda$. For a wavelength of 0.28 mm (e.g. 5.5 MHz) and a diameter of 15 mm, we will have N=200 mm. In most patients, this distance allows for most of the kidney to be covered by near field range, if the underskin fat layer is not too thick.

The ultrasonic designs of diagnostic ultrasound systems and HIFU therapeutic ultrasound systems require investment in accurate design features in order to guarantee the required high resolution. Sometimes, this means knowledge in various technologies such as accurate layer thickness, homogeneity of size, acoustic impedance, absence of reflecting deformities, accurate feature sizes.

In some embodiments, where non-focused ultrasound is used, the designed system key requirements is to expose a large organ, and to use natural body movements to average out the exposure. The approach is statistical and allows for significantly relaxed material requirements that, in turn, enable production cost reduction.

Figure 9A:
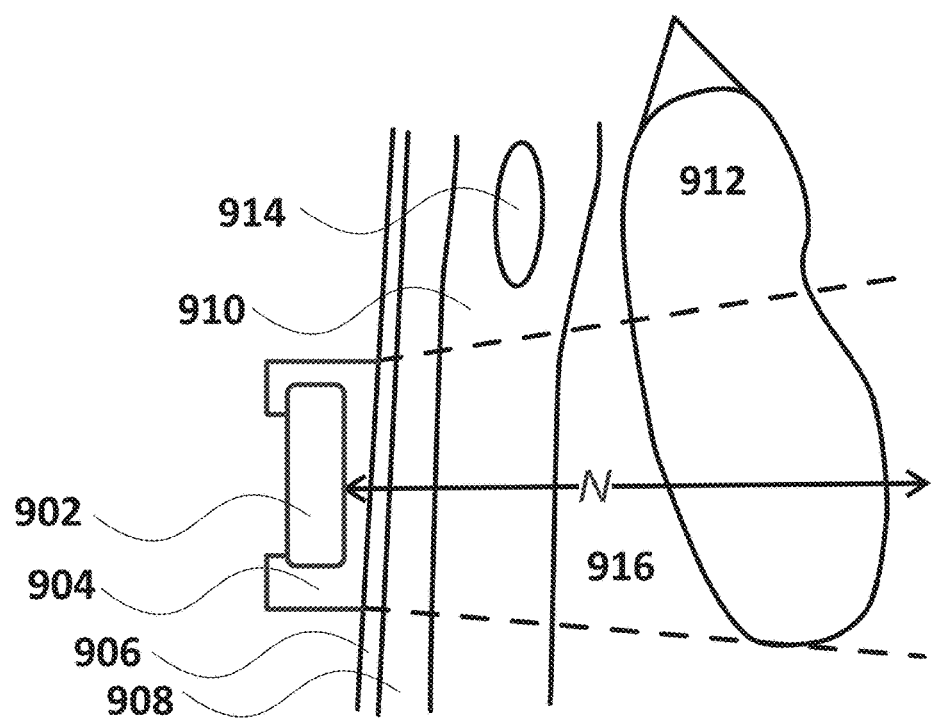
FIG. 9A is a schematic representation of a design with near field exposure, according to come embodiments of the present invention.

Referring now to FIG. 9A, showing a schematic representation of a design with near field exposure. In some embodiments, the transducer 902 is placed within an acoustic gel chamber 904, which is in touch with the skin 906. A layer of fat 908 and then a layer of muscle 910 are located between the skin 906 and the kidney 912. The rib 914 is above the transducer, not interfering with the ultrasonic signal. The distance N 916 of the near field, calculated before, describes the near field distance from the face of the transducer to the distal end of the kidney.

Sometimes, the kidney moves up and down, due to the movement of the diaphragm. In some embodiments, this movement averages out the changes in amplitude.

Averaging Out Near Field Waveform

As shown in section "Transducers design for Near Field tissue exposure", the near field zone (also called the Fresnel zone) is characterized by significant amplitude changes on distances in the order of magnitude of the wavelength. In some embodiments, most of the exposed volume, and particularly the kidneys, tend to move with the breathing cycle. This sometimes causes the tissue to be exposed to different intensities at different times, with a final result of a time average of the exposure. In some embodiments, this time average tends to smooth the overall exposure in a way that the spatial exposure difference between different volumetric zones (that are about the same distance from the transducer) is small.

In addition, in some embodiments, spatial averaging can be added by generating a relative movement between the transducer and the skin, at magnitudes of the wavelength. In these embodiments, even regions that tend not to move with the breathing cycle will be averaged out and positive and negative peaks will be smoothed.

In some embodiments, the movement is introduced as a slow mechanical movement between the transducer face 902 and the skin 906. In some embodiments, the distance between the transducer and the skin is modified by pumping additional gel into the gel chamber 904. In some embodiments, changes in width in the gel chamber are performed by changing the pressure in the chamber gel, by flowing gel in and out of the chamber. In some embodiments, the transducer is moved relative to the skin on the axis perpendicular to the transducer plane by means of a piston or a screw. In some embodiments, the volume of the gel chamber is modified by a movement of a rigid skeleton that is located inside the chamber. In some embodiments, the movement of the transducer is slow to allow the gel to flow without generating air bubbles.

Figure 9B:
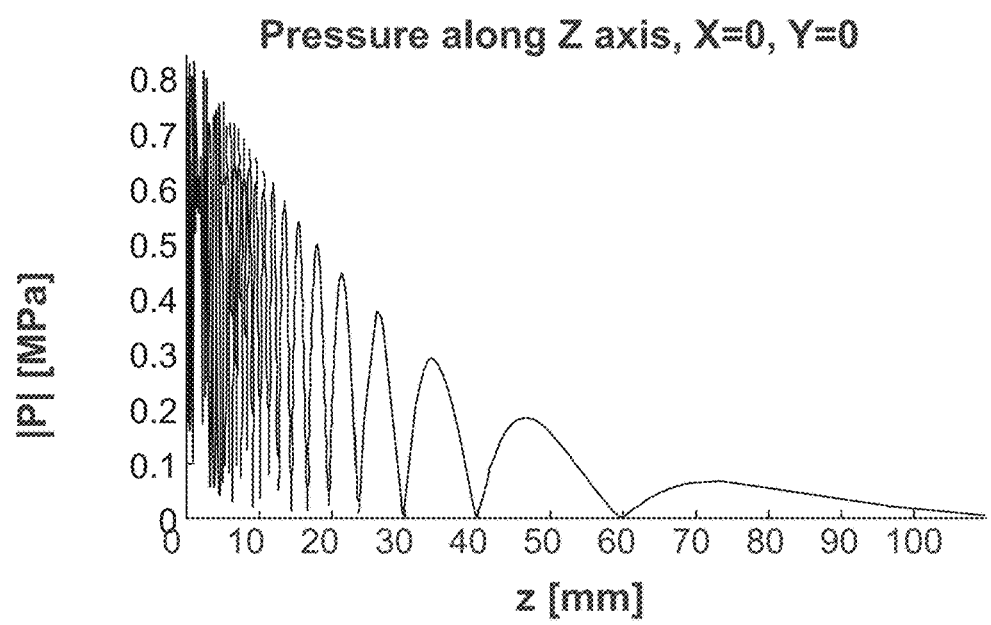
FIG. 9B shows the change of the ultrasonic pressure P (MPa) over the distance z (mm) from the center of the face of the transducer, according to come embodiments of the present invention.
Figure 9C:
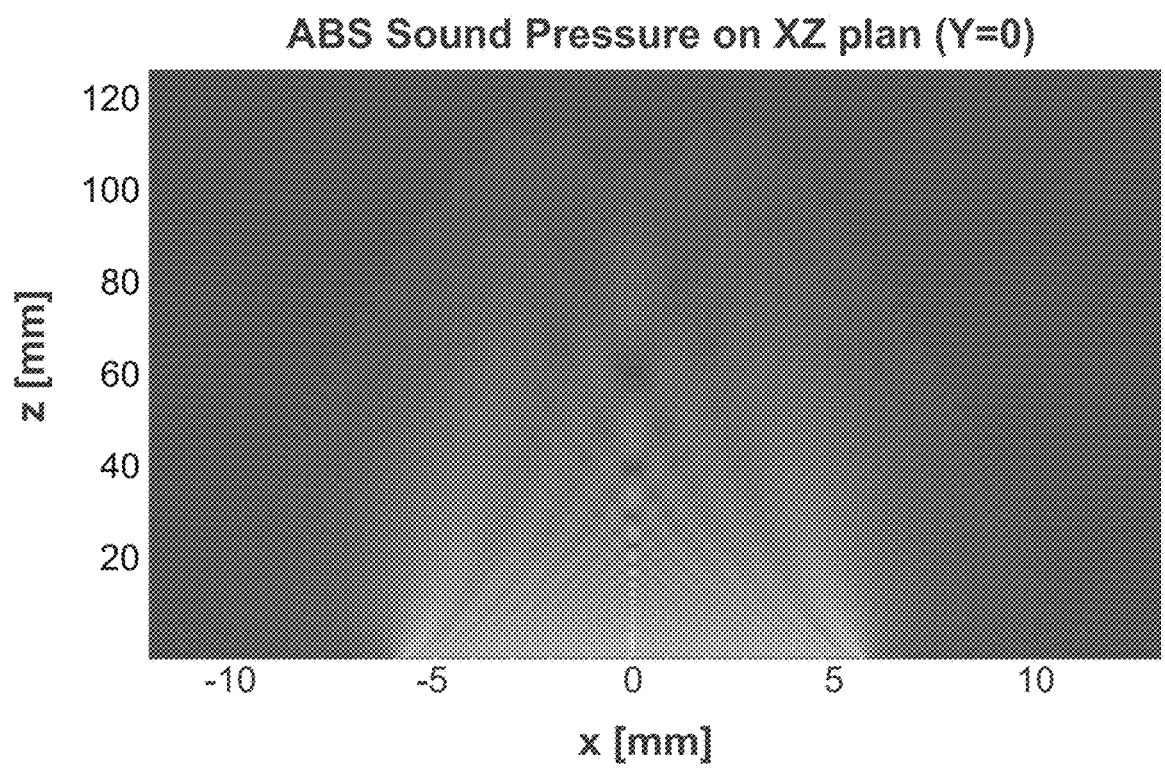
FIG. 9C shows the pressure on an XY plane perpendicular to the same transducer as in FIG. 9B, according to come embodiments of the present invention.

Referring now to FIG. 9B, shows the change of the ultrasonic pressure P (MPa) over the distance z (mm) from the center of the face of the transducer along the axis perpendicular to the transducer plane. In some embodiments, a round and flat transducer which is designed to operate in a high frequency of 10 MHz and a long near-field zone of 100 mm is used. The figure shows the reduction in pressure along the increasing distance, which is due to absorption of the ultrasonic signal in tissue, estimated as 0.3 dB/mm at 10 MHz. It can be seen that at the 10 mm near the surface of the transducer the pressure changes with distance. In some embodiments, this characterizes the Fresnel zone. In some embodiments, this characterizes the near field transducer design. It can also be seen that along lines parallel to the one shown in FIG. 9B, the graph changes. This is shown in FIG. 9C. FIG. 9C shows the pressure on an XY plane perpendicular to the same transducer as in FIG. 9B, where the center of the figure (x=0) is the same axis we showed in FIG. 9B. In some embodiments, the x axis is along the transducer, and the z axis is perpendicular to the transducer plane. In some embodiments, when such transducers transmit ultrasonic signal into the body, tangential movement of the organs relative to the transducer is expected. In some embodiments, the movement is due to the breathing cycle. In some embodiments, a few mm movement already provides significant smoothing and averaging of the pressure exposure experienced by any tissue volume element. In some embodiments, a near-field transducer design, together with natural tissue movement inside the body provide time and spatial average of the ultrasonic exposure. In some embodiments, a near-field transducer design, together with additional movement of the transducer location or orientation relative to the body provide time and spatial average of the ultrasonic exposure.

In some embodiments, the following parameters are used:

Usage of an ultrasound transducer with the following design characteristics: High power and low cost and/or Operating at the therapeutic frequency range and/or Designed to have a long near-field zone matching sum of the waveguide length and distance to kidneys.

Usage of a waveguide with the following design characteristics: Low absorption and/or Low cost and/or good match to the shape of the patient to ensure comfort and compliance and/or Diffraction of the ultrasonic waves towards the kidney through a window and/or Attenuation of the output ultrasonic signal to a clinically safe level.

Placement of the unit on the patient's body that enables relative movement of the internal organs relative to the window.

In some embodiments, the previous parameters are amended as follows:

Movement of the waveguide or parts of the waveguide (reflectors, gratings, lenses) to achieve the desired distribution of the ultrasonic beam over time.

In some embodiments, the use of the abovementioned parameters may prove advantageous in providing a low cost, safe and effective therapeutic system.

Figure 9D:
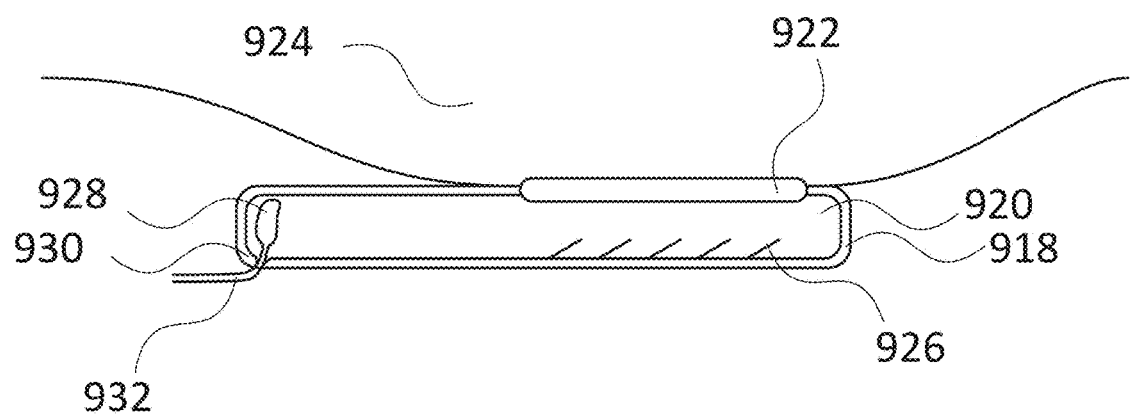
FIG. 9D is showing a schematic representation of a design with near field exposure, together with a use of an ultrasonic waveguide, according to come embodiments of the present invention.

Referring now to FIG. 9D, showing a schematic representation of a design with near field exposure, together with a use of an ultrasonic waveguide. In some embodiments, the body of the waveguide 918 is made out of an ultrasonic reflecting material. In some embodiments, the waveguide is filled with an ultrasonic transparent material 920 that minimizes propagation loss. In some embodiments, the only area where the ultrasonic signal may leave the waveguide is the window 922. In some embodiments, the window enables ultrasonic wave to leave the waveguide and enter the patient's body 924. In some embodiments, the window is made of a number of layers taking care of impedance matching between the ultrasonic transparent material 920 and the patient tissue 924. In some embodiments, the window also functions as an ultrasonic lens. In some embodiments, the window shape changes slowly over time. In some embodiments, reflectors 926 are placed opposite the window. In some embodiments, the purpose of the reflector is to redirect the acoustic waves towards the patient body through the window. In some embodiments, the transducer 928 is fixed in this structure. In some embodiments, the transducer can be inserted into the waveguide through a valve 930. In some embodiments, a cable 932 providing the input signal and power goes through the valve and connects the transducer to the electrical sub unit.

In some embodiments the transducer is designed for multiple use, multiple treatments, and multiple patients and the waveguide with all its parts is disposable.

In some embodiments, the transducer and waveguide are designed for multiple use, multiple treatments, and multiple patients, whereas the acoustically transparent window designed as a disposable element.

In some embodiments, the acoustically transparent window which is also a lens is disposable.

Figure 9E:
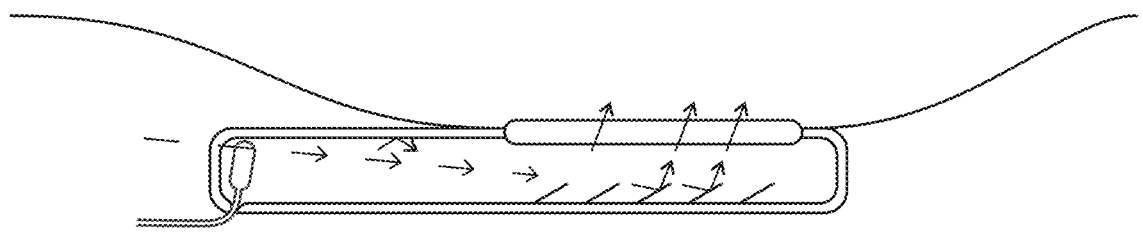
FIG. 9E is a schematic representation where arrows show the propagation path of the ultrasonic waves from the transducer to the patient, according to come embodiments of the present invention.

In some embodiments, the acoustically transparent window, which is also a lens that changes its acoustical transfer function over time is disposable Referring now to FIG. 9E, arrows show the propagation path of the ultrasonic waves from the transducer to the patient. In some embodiments, the waves may hit the wall of the unit, which is made of reflecting material and return. In some embodiments, when the ultrasonic waves hit the reflectors, they change their direction towards the window. In some embodiments, acoustic waves propagate from the window towards the patient skin and further towards the internal organs and kidneys.

In some embodiments, the waveguide is straight, as shown in FIG. 9D. In some embodiments, the waveguide is curved, to fit the patient's body. In some embodiments, the waveguide external material is made of metal, and is solid. In some embodiments, the reflecting material is soft and the waveguide may be flexible. In some embodiments, a flexible waveguide may be fitted to the curvature of the patient body.

In some embodiments, a waveguide may be fitted into furniture. In some embodiments, a flexible waveguide is fitted to a garment such as a belt or a corset.

In some embodiments, the reflectors are fixed, as shown for example, in FIG. 9E. In some embodiments, the reflectors are only partially fixed and may have some limited motion. In some embodiments, this motion causes the reflected ultrasonic signal to spread in various directions through the ultrasonic window. In some embodiments, movement of the waveguide induces the reflector movement. In some embodiments, the reflector movement is induced by changes in the pressure inside the waveguide. In some embodiments, a mechanical motor induces the reflector movement. In some embodiments, movement of the shell 918 of the waveguides induces the reflectors movement.

Figure 9F:
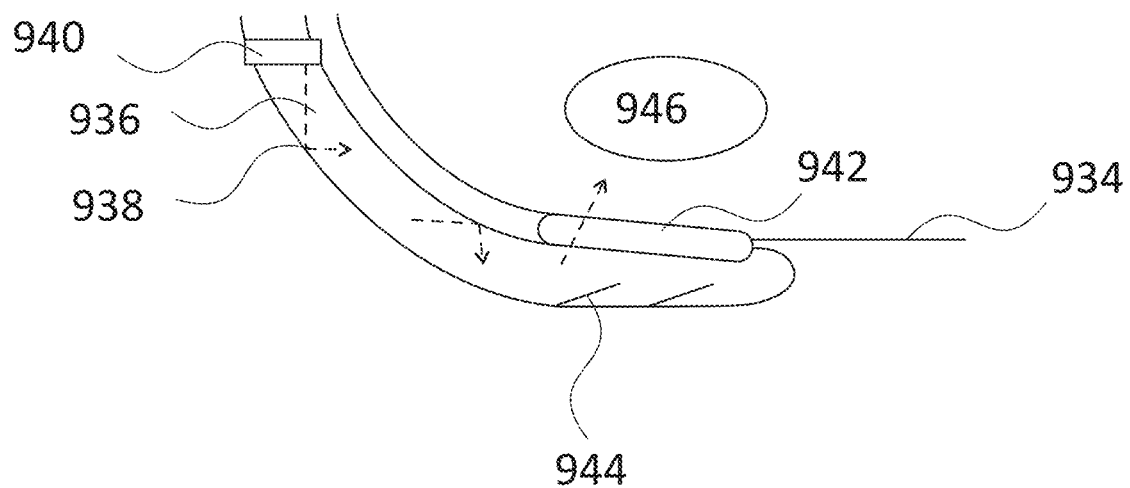
FIG. 9F is a schematic representation of a flexible waveguide that conforms to the patient body, according to come embodiments of the present invention.

Referring now to FIG. 9F, showing a flexible waveguide that conforms to the patient body 934. In some embodiments, the waveguide is made from acoustically transparent material 936 surrounded by a soft reflecting material 938. In some embodiments, a transducer 940 is placed at the edge of the waveguide, transmitting ultrasonic signal into the waveguide. In some embodiments, the ultrasonic waves are reflected from the walls as shown by the dashed arrows in the drawing. In some embodiments, at the other edge of the waveguide a window 942 is placed against the patient skin. In some embodiments, reflectors 944 are placed opposite the window. In some embodiments, the reflectors redirect the ultrasonic waves towards the kidney 946 through the window. In some embodiments, reflectors are built from structures that have a size of the order of the ultrasound wavelength. In some embodiments. In some embodiments, the reflectors are made of material with an acoustic impedance that is different than the acoustic transparent filling of the waveguide.

Figure 9G:
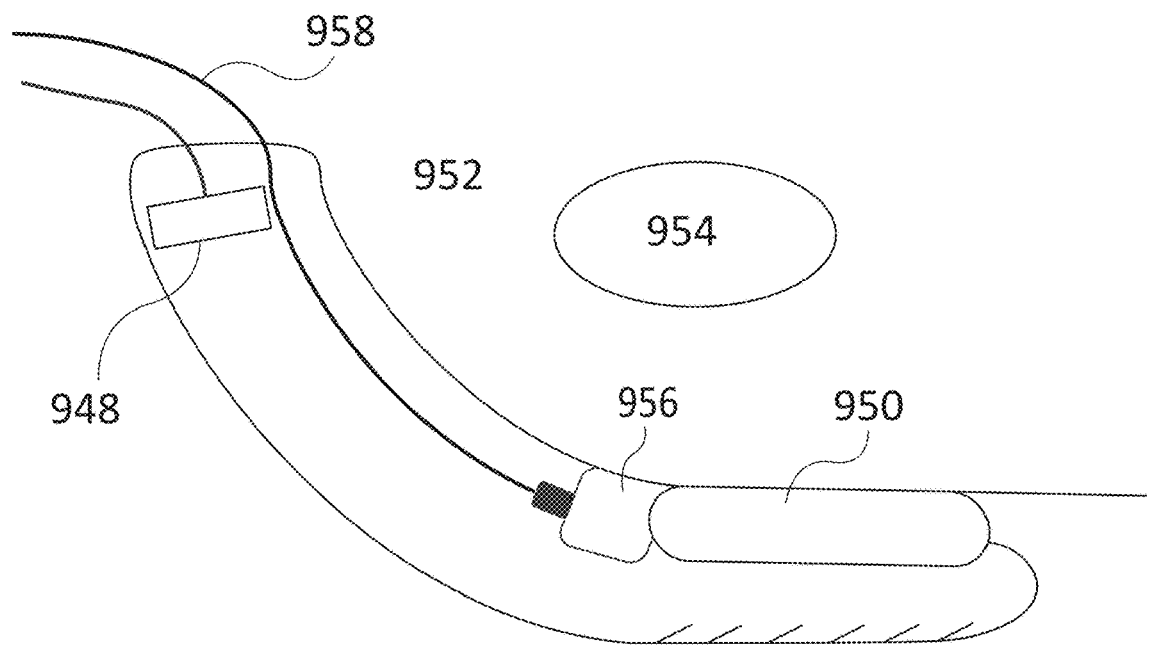
FIG. 9G is a schematic representation of a device where the waveguide and the transducer are part of the reusable TSU, while the acoustic window is disposable, according to come embodiments of the present invention.

Referring to FIG. 9G, in some embodiments, the waveguide and the transducer 964, 948 are part of the reusable TSU, while the acoustic window 950 is disposable. In some embodiments, the acoustic signal exits the unit through the window, enters the body 952 and reaches the kidney 954. In some embodiments, the waveguide is made of material that can be cleaned. In some embodiments, the apparatus includes a sensor 956. In some embodiments, the sensor needs to be in contact with the skin, for example, for measuring pulse, pressure, temperature, ultrasonic reflection. In some embodiments, the sensor is connected to a wire 958.

Figure 9H:
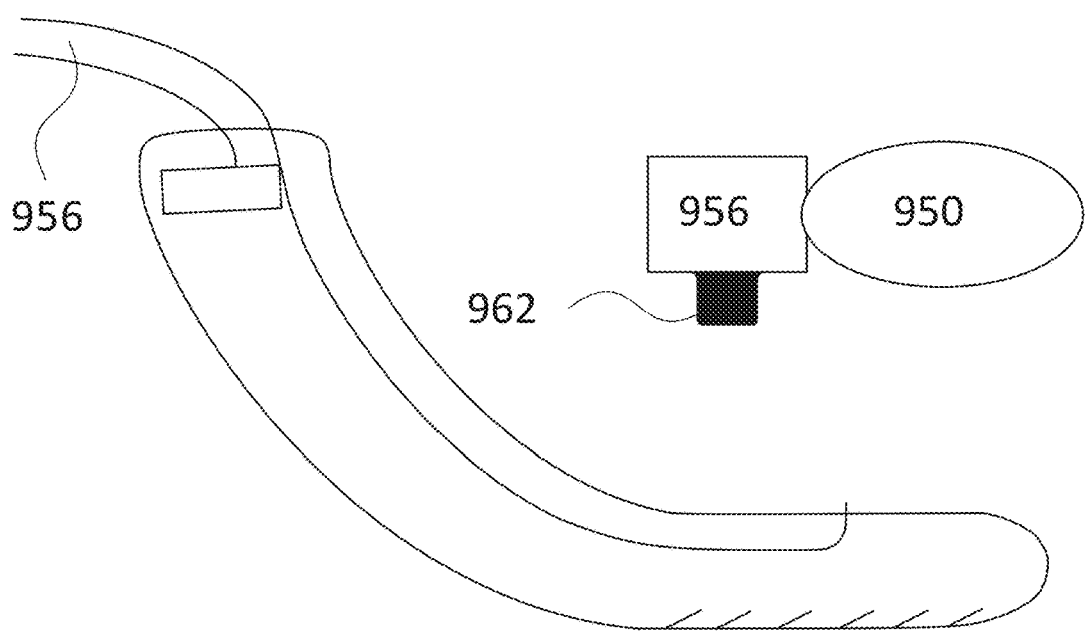
FIG. 9H is a schematic representation of a device where the waveguide and the transducer are connected to the acoustic window, according to come embodiments of the present invention.

Referring to FIG. 9H, the unit is as shown before (FIG. 9G) and the disposable window 950 is connected to the reusable waveguide. In some embodiments, the sensor 956 is part of the disposable unit. In some embodiments, the sensor 956 is connected to the reusable unit using a connector 962 that provides means for communication and power if necessary.

Figure 9I:
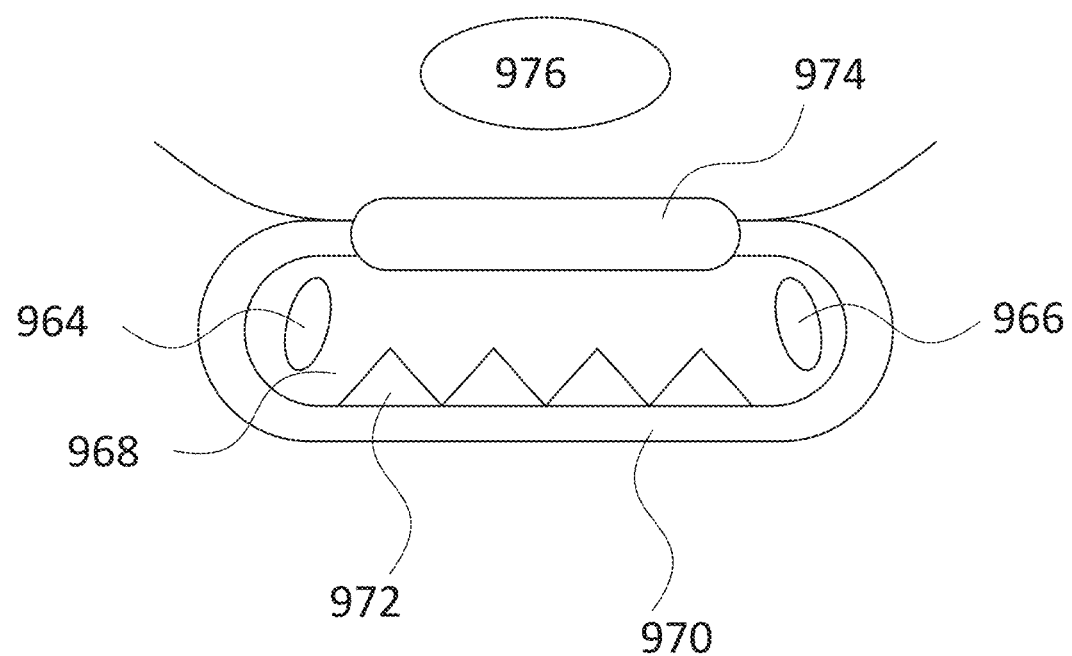
FIG. 9I is a schematic representation of a device where multiple transducers are placed in a unit; according to come embodiments of the present invention

Referring now to FIG. 9I, showing multiple transducers 964, 966 that are placed in the unit. In some embodiments, using multiple transducers reduces propagation loss inside the transparent media 968. In some embodiments, the waveguide body 970 reflects the ultrasound signal. In some embodiments, gratings or reflectors 972 are placed opposite the acoustic transparent window 974. In some embodiments, the reflectors have a conic shape. In some embodiments, the window lets the ultrasonic signal reach the kidney 976.

In some embodiments, the waveguide is placed on the skin inferior to the ribs. In this case the direction of the acoustic window is aligned with the skin, but the desired direction of the acoustic wave is not perpendicular to the window, but superior towards the upper lobe of the kidney.

In some embodiments, the reflectors opposite the window has a specific orientation to direct the ultrasonic signal to the superior direction. In some embodiments, direction of outgoing signal is marked on the waveguide. In some embodiments, the external marking of the waveguide indicates to the user how to place the waveguide on the skin, for example, with an arrow pointing superior towards the head.

Degassing of the Waveguide

In some embodiments, the waveguide and the transducer are separate. In this case, the transducer needs to be coupled to the acoustically transparent material of the waveguide. In some embodiments, the transducer enters the waveguide through a valve. In some embodiments, the design of the valve and the transducer are made to avoid inserting air bubbles into the waveguide.

Figure 9J:
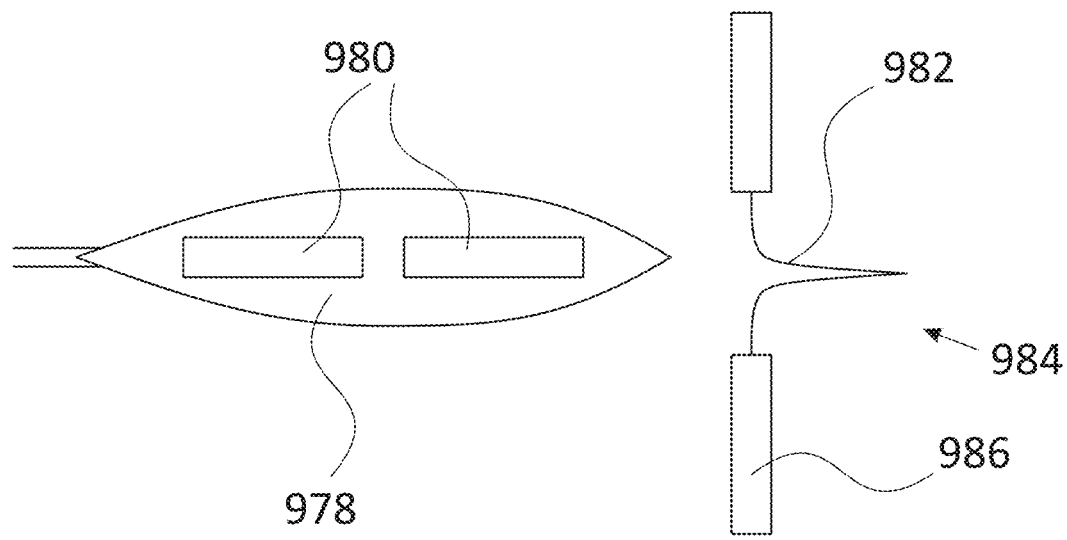
FIG. 9J is a schematic representation of a transducer unit that includes two transducers that is inserted into an ACSU through a valve, according to come embodiments of the present invention.

Referring now to FIG. 9J, showing a transducer unit 978 that includes two transducers 980 that is inserted into an ACSU through a valve 982, according to some embodiments of the invention. In some embodiments, the valve is designed to give way to the transducer unit and let it in without letting any air bubbles enter into the acoustically transparent gel 984. In some embodiments, the ACSU housing 986 is built from a waveform reflecting material.

In some embodiments, the transducer is part of the ACSU and is disposable. In this design, there is no need for gel degassing. In some embodiments, the transducer is part of the ACSU and has an electrical interface that only requires a connector providing metal conduction between the electronic subunit and the transducer.

In some embodiments, there is a need to eliminate gas bubbles inside the waveguide after the insertion of the transducer. In some embodiments, degassing is performed inside the waveguide by ultrasound. In some embodiments, the degassing is performed using the same transducers that are used for the therapeutic signal. In some embodiments, the electrical signal for degassing is distinct and different form the electrical signal applied for therapeutic ultrasound. In some embodiments, the degassing is performed using specialized degassing transducers. In some embodiments, a special degassing electrical signal is provided to the transducer to perform the degassing operation.

Anatomically Arranged Transducer Mats

In the art, there are multiple known options to access the kidney with an ultrasonic signal. These access methods are well known from the field of diagnostic examinations of the kidneys with diagnostic ultrasound. Other methods are also known from treatment of kidney with therapeutic ultrasound such as kidney denervation for hypertension, and ultrasonic shock wave lithotripsy.

Figure 10:
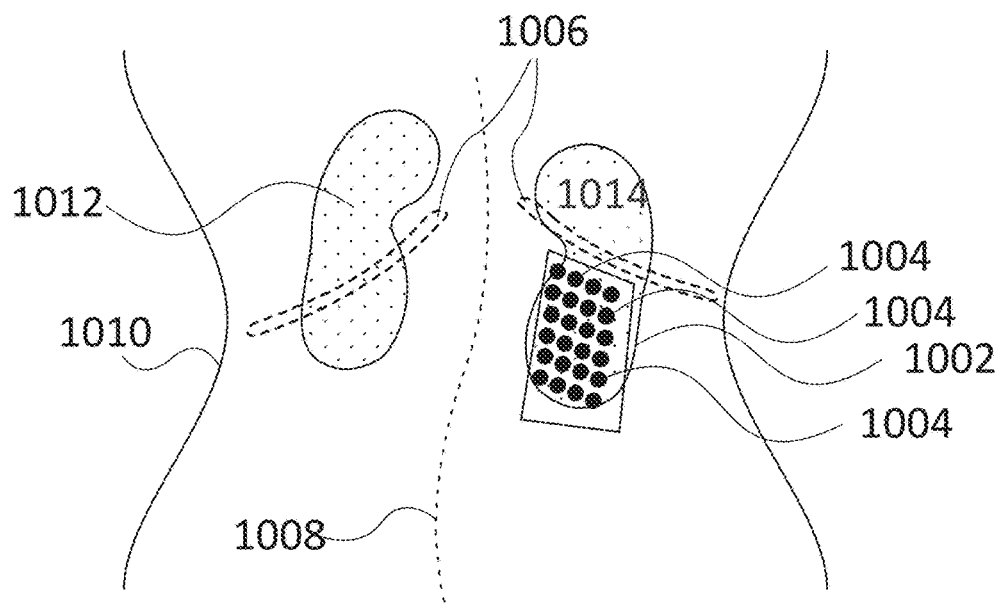
FIG. 10 is a schematic representation of a transducer mat, according to come embodiments of the present invention.

In some embodiments, optional transducer mats, which are optimal for the access zone, are prepared and used. For example, such a transducer mat is designed for back access. In some embodiments, all the transducers are arranged on both sides of the spine, below the lowest rib. In some embodiments, this would give a shape that may resemble a trapezoid. An example of such arrangement is provided, for example, in FIG. 10.

The transducer mat 1002 contains individual transducers 1004. In some embodiments, the mat comprises multiple transducers or multiple transducer arrays arranged in a two dimensional structure, as shown for example in FIG. 10. In some embodiments, the mat 1002 is anatomically placed below rib 12, which is depicted as a dashed line 1006 starting from the spine 1008 towards the waist 1010. The transducers in this design cover the lower lobe of the kidney. The left kidney 1012 and the right kidney 1014 are located in their relative positions. In the figure, only the right kidney is shown to be covered with a mat 1002 containing a 2-dimensional array of transducers. In some embodiments, all the transducers are placed with acoustic coupling to the skin.

In some embodiments, the transducers are placed over the lower thoracic back and the upper lumbar back, where the distance from the back to the kidney is the shortest. In some embodiments, the transducers cover the lower ribs (for example ribs 12 and 11 and optionally 10) as well as the spine. In some embodiments, by detecting the ribs and spine the system estimates which of the transducers is over the kidney and which of the transducers is away from the kidney, thus enabling the system to confirm the proper placement of the device on the patient's back, and dynamically adjust transducer activity and signaling parameters, when necessary.

Figure 11:
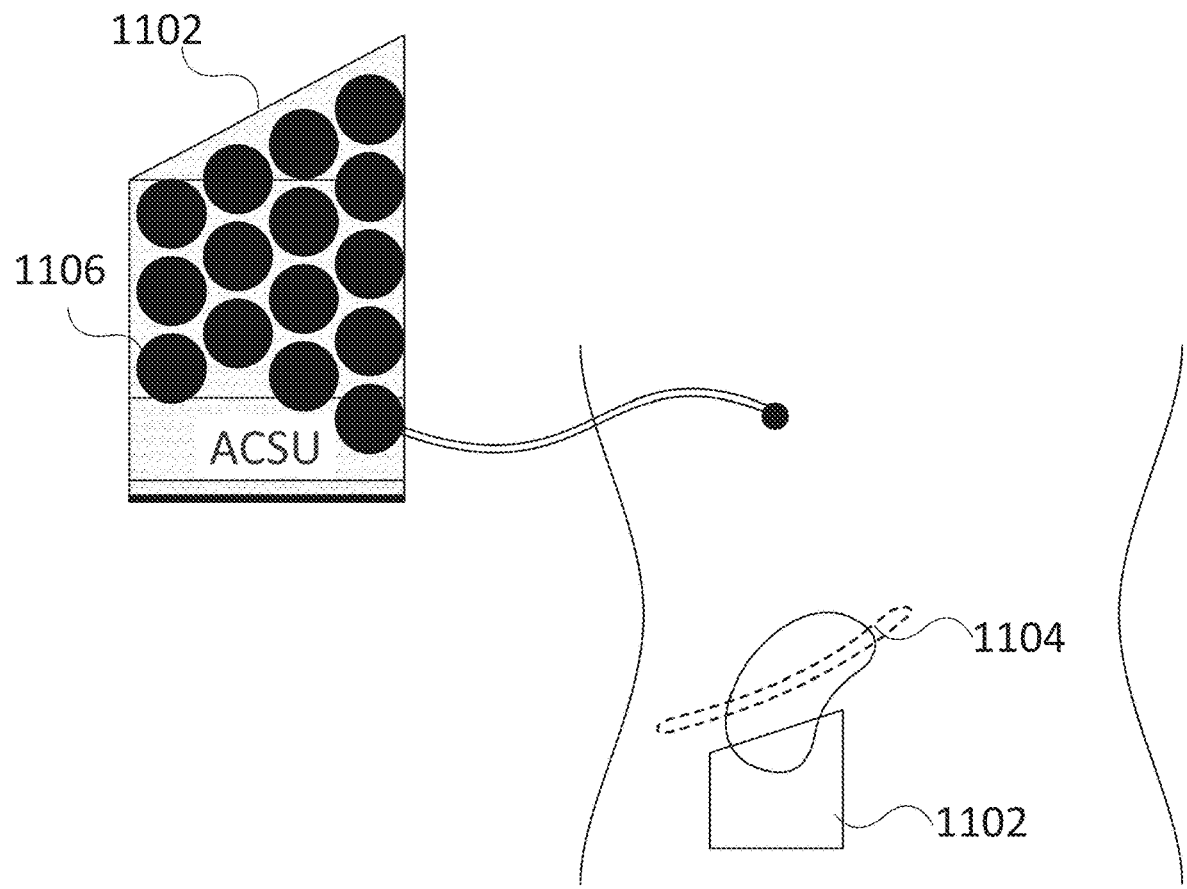
FIG. 11 is a schematic representation of a transducer mat that is design to fit the lower left back, according to come embodiments of the present invention.

Referring now to FIG. 11, showing a schematic representation of a transducer mat 1102 that is design to fit the lower left back, on the left of the spine and below left rib 12 1104. The mat is shown on the left hand side of the diagram, and its application on the body is shown on the right. Since the distal end of the rib (as in the figure) is inferior to the proximal edge near the spine, there are more transducers 1106 on the right hand side of the transducer map than on the left hand side. In some embodiments, the transducers are placed on the mat in a configuration to guarantee not to transmit onto a bone. In some embodiments, the configuration follows the anatomical place on which it will be placed.

Figure 12:
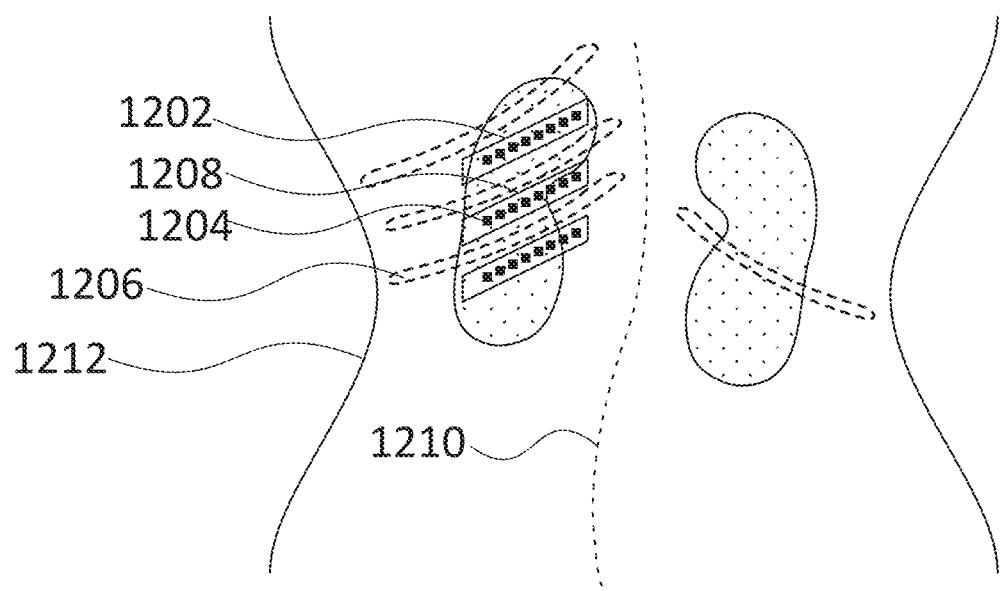
FIG. 12 is a schematic representation of a transducer mat, according to come embodiments of the present invention.

Referring now to FIG. 12, showing another schematic representation of a transducer mat. In some embodiments, the transducers are designed to be placed between the ribs. In some embodiments, the transducers are placed along the back ribs to directly face the kidney. In some embodiments, this design could be advantageous to alleviate a potential problem of ultrasonic transmission directly on a bone. In some embodiments, multiple mats are used. In the example shown in FIG. 12, three mats 1202 are shown. Each mat has a number of transducers 1204. Each transducer 1204 in the mat 1202 is designed to be able to transmit the ultrasonic signal though the space between the ribs 1206 towards the kidney 1208. The ribs 1206 are shown by dashed line between the spine 1210 and the waist 1212.

Figure 13:
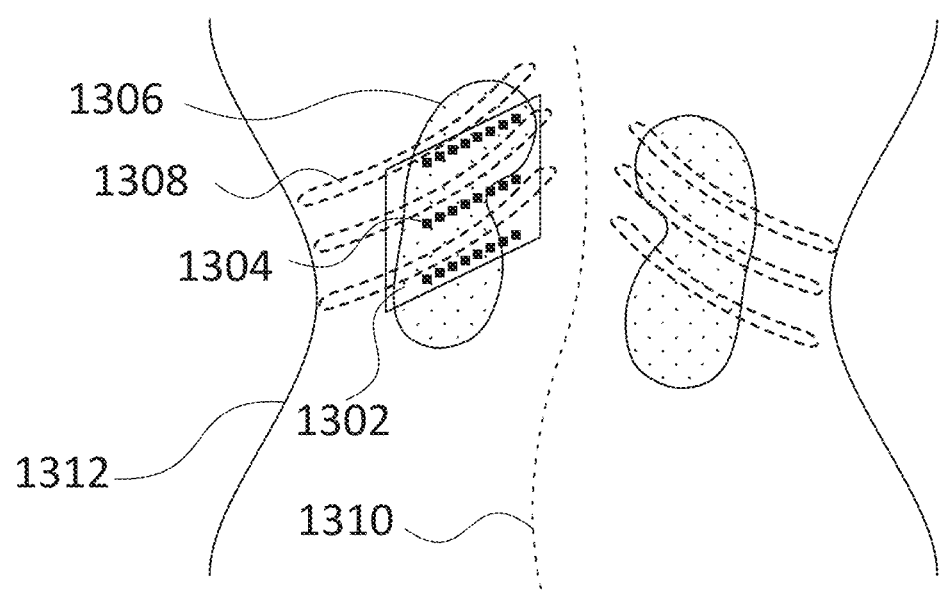
FIG. 13 is a schematic representation of a transducer mat, according to come embodiments of the present invention.

Referring now to FIG. 13, showing yet another schematic representation of a transducer mat. In some embodiments, the same result of transmitting between the ribs is achieved by using a single mat that is placed in such a way that the transducers end up between the ribs. In some embodiments, the advantage for this configuration is the built-in connectivity between the transducers, saving cables and connectors, which has an impact on the cost, reliability and complexity of the system. As mentioned above, in some embodiments, a single mat 1302 includes three rows of transducers, replacing the three mats of FIG. 12. Each transducer 1304 in the mat is designed to be able to transmit the ultrasonic signal though the space between the ribs towards the kidney 1306. The ribs are shown by dashed line 1308 between the spine 1310 and the waist 1312. Not shown in the figure is the single cable connecting the mat to the electrical signal subunit. In some embodiments, the connectivity of the transducers is embedded within the mat.

In some embodiments, since the distance between the ribs may be different between different patients, mats having different sizes, which incorporate varying distance between the rows, are used.

Figure 14:
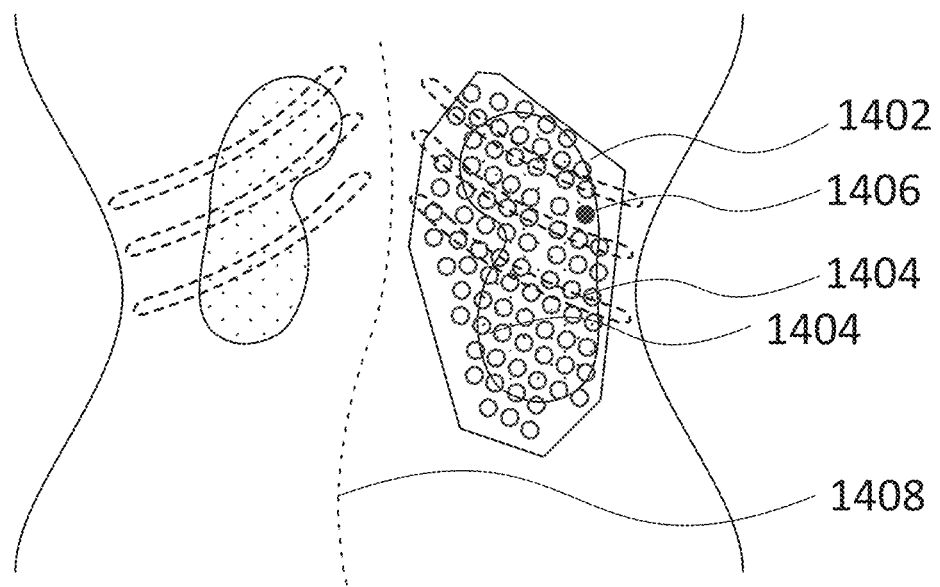
FIG. 14 is a schematic representation of a transducer mat having densely populated transducers, according to come embodiments of the present invention.

In some embodiments, a mat 1402 having densely populated transducers 1404 is placed over the ribs 1406, ignoring the anatomical details (e.g. the ribs 1406 and/or the spine 1408), as shown for example in FIG. 14. In some embodiments, the mat 1402 placed over the ribs 1406 may provide the desired functionality by a number of operational options listed below. In some embodiments, the operational modes evolve about the activation of individual transducers. In some embodiments, some exemplary operational options are:

1. All transducers are active, at a level that is safe and harmless to the body
2. Alternatively, some of the transducers may be shut down. The shutdown is performed by marking the specific transducers that are placed over the rib. In some embodiments, a medical practitioner does this. In some embodiments, the system will have a list of non-transmitting transducers that shall either not transmit any signal or transmit a signal with modified parameters.

Figure 15:
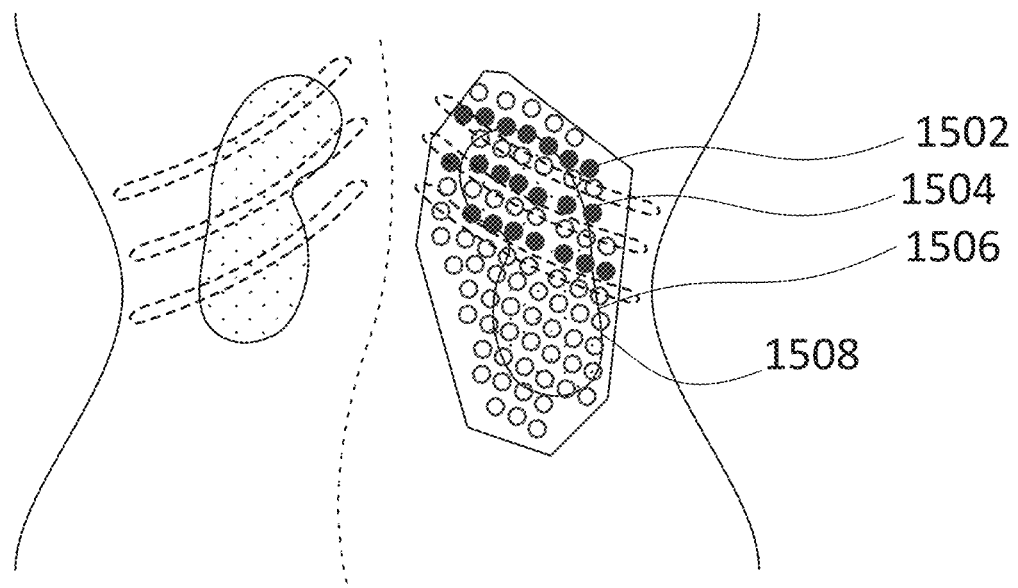
FIG. 15 shows the designated non-transmitting transducers marked in solid, according to come embodiments of the present invention.

Referring now to FIG. 15, showing the designated non-transmitting transducers marked in solid. For example, on the mat 1502 the transducer denoted by 1504 is over a rib and is thus operating at modified set of parameters compared to transducer 1506, which is not over a rib. In some embodiments, transducer 306 need not necessarily be over the kidney 1508. In some embodiments, transmission into the valid region is allowed without the necessity to know exactly where the kidney is.

Figure 16:
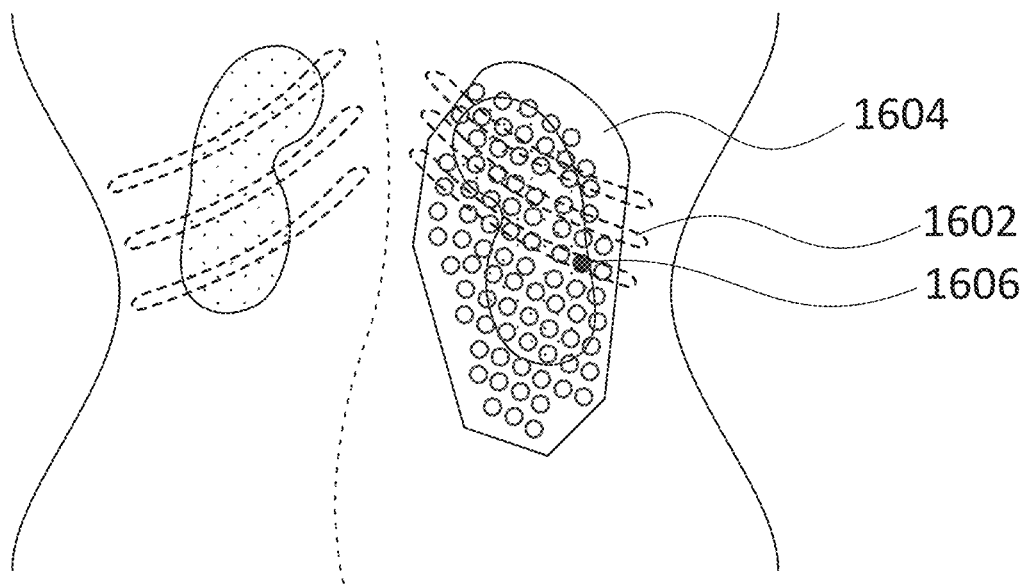
FIG. 16 is a schematic representation of a film, which may be implemented as a sticker, according to come embodiments of the present invention.

3. Another mechanism to mark the special transducers is by measuring the reflected ultrasonic signal at the transducer. In some embodiments, a transducer that transmits directly onto a tissue, such as bone, the ultrasonic signal reflected is strong. In some embodiments, this reflected signal level may be measured. In some embodiments, an automatic mechanism simplifies the application of the transducer mat onto the patient by using the reflected signal at the transducer.
4. In some embodiments, the system marks the specific transducers that measured a large reflection. In some embodiments, these transducers shall have a modified transmission parameter set. In some embodiments, the system provides a visual indication to the user with regard to these transducers, for example, by activating a small light emitting diode at the back of each transducer.
5. In some embodiments, the transducers are arranged in small transducer arrays. In some embodiments, the transducer arrays have the ability to change the direction of the ultrasonic beam by combining different signal amplitude, phase, delay synchronously to various transducers in the array, a method known as beam forming. In some embodiments, the beam forming is implemented by providing different waveforms to different transducers. In some embodiments, the beam forming is implemented by providing a similar signal but with differing parameters to the different transducers. In some embodiments, based on the reflected ultrasonic signal from each beam direction, an optimization of signal transmission is performed by transmitting more energy to beams that provide less reflection, optionally, also taking into account the transducer array location, the beam direction and the estimated kidney location.
6. Another mechanism to block the transmission of transducers that are placed over the ribs is to put an ultrasonic blocking film between the transducers and the skin. Referring now to FIG. 16, showing a film 1602, which may be implemented as a sticker. In some embodiments, a blocking material will be placed between the mat 1604 and the skin. In some embodiments, the film 1602 blocks or attenuates the undesired transmission towards the body areas that should be protected. As shown in FIG. 16, the transducer 1606, which is over a rib, will deliver significantly less ultrasonic signal to the tissue since its signal is attenuated.

In some embodiments, the same type of ultrasound protection can be aligned also for other points of irritation to the patient, such as skin rash or injury. In some embodiments, the solutions discussed for the back of the patient are also relevant to other kidney access zones. For example, side access via the ribs, frontal access via the liver, or access via the waist below the ribs.

Anatomic Mats Using Reflectors

In some embodiments, an alternative to the usage of transducer mats, is the use of transducers to generate the acoustic field, and the use of ultrasonic lenses and ultrasonic reflectors to change the direction of propagation of the ultrasonic wave In some embodiments, the wavelength λ for the ultrasonic wave can be calculated from the speed of propagation within tissue, which is approximately $c=1540$ meter second$^{-1}$ and the center frequency which may vary from 3 to 15 MHz. the wavelength range $$0.1\ mm \approx c/f_{max} < \lambda < c/f_{min} \approx 0.5\ mm$$

Figure 17:
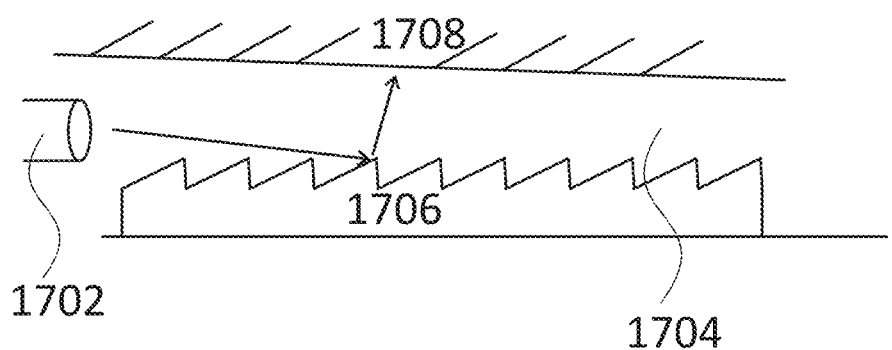
FIG. 17 is a schematic representation of reflective elements, according to come embodiments of the present invention.

Referring now to FIG. 17, showing a schematic representation of reflective elements. In some embodiments, a transducer 1702 transmits an ultrasonic signal at the aforementioned wavelength. In some embodiments, the signal traverses through an ultrasonically transparent medium 1704 and hits a reflective material 1706. In some embodiments, the reflected signal is redirected towards the patient 1708. In some embodiments, a relatively small cross section at the transducer interface 1702 is able to generate incoming ultrasonic signal towards the body.

The reflecting material 1706, in order to reflect the ultrasonic signal, has an impedance that is significantly different from the ultrasonic medium 1704. In some embodiments, it is hard, for example, is made of metal. In some embodiments, the reflective material is soft, for example, made out of polymer and contains gas or air.

Figure 18:
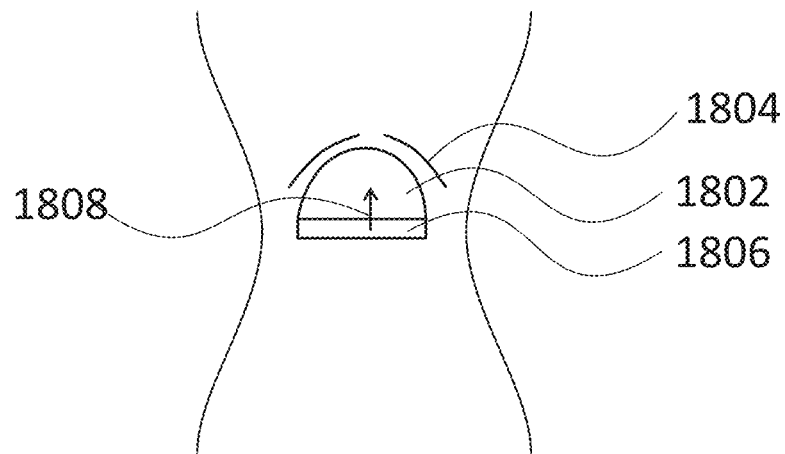
FIG. 18 is a schematic representation of a back view of the reflective mat, according to come embodiments of the present invention.

Referring now to FIG. 18, showing a schematic representation of a back view of the reflective mat. In some embodiments, a reflective mat 1802 is placed on the back of the patient. In some embodiments, the mat 1802 is placed below the bottom rib 1804. In some embodiments, a transducer array 1806 transmits the signal from a bottom interface of the mat. The direction of the ultrasonic signal into the mat is depicted by arrow 1808. In some embodiments, this signal is reflected towards the patient's skin.

Figure 19:
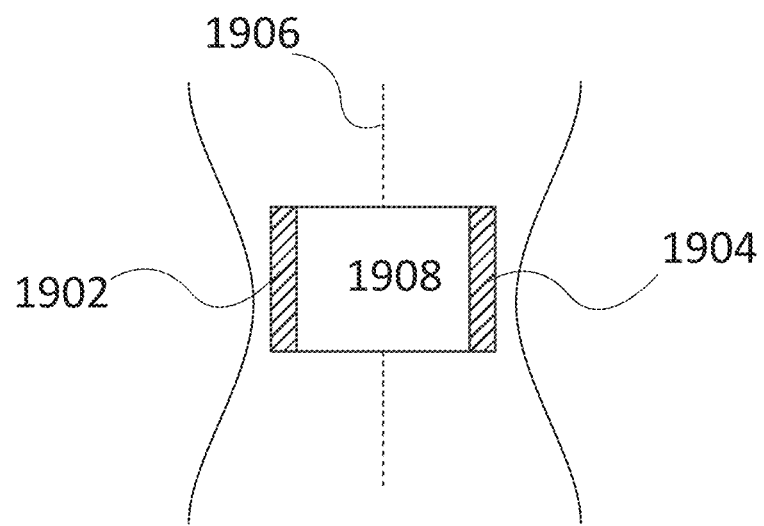
FIG. 19 is a schematic representation of a transducer mat, according to come embodiments of the present invention.

Referring now to FIG. 19, showing an alternative mat. In some embodiments, the mat is placed on the patient. In some embodiments, transducers are placed on the sides of the mat, one on the left side 1902 and one on the right 1904. The mat is symmetrically placed over the spine 1906, depicted in the Figure as the dotted line. In some embodiments, the signal enters the reflective mat 1908 and is redirected towards the skin. In some embodiments, this design separates between the reusable transducer interfaces 1902 and 1904 and between the disposable body interfaces 1908.

Figure 20:
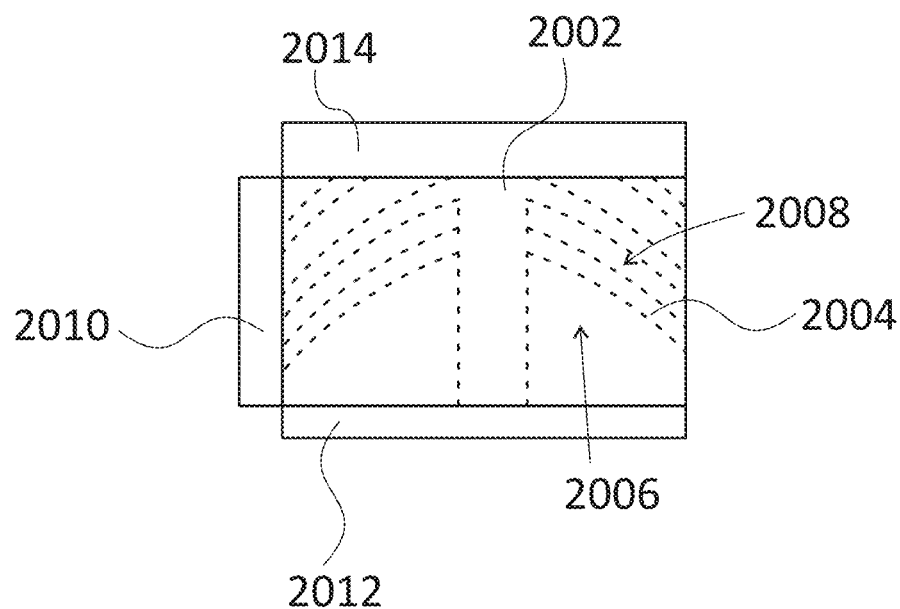
FIG. 20 is a schematic representation to a method to expose the body to ultrasonic signal, according to come embodiments of the present invention.

Referring now to FIG. 20, showing a schematic representation to a method to expose the body to ultrasonic signal at desired areas while avoiding others. In some embodiments, controlling the grating of the ultrasonic signal is used to avoid the signal to reach undesired zones, for example, the area near the spine 2002, the area near the right rib number 12 2004. In some embodiments, the areas where the signal should be redirected include, for example, the area below the rib on the right 2006 and the area between right rib 12 and right rib 11 2008. In some embodiments, the ultrasonic signal can arrive by a transducer array on the left hand side 2010, or at the bottom 2012 or from above 2014 or from the right (not shown), or a combination thereof.

In some embodiments, the areas of no reflection can be selected in advance, or can be manually selected when the device is applied to the patient, or dynamically adjusted by computer.

In some embodiments, the graphic user interface allows the user to mark the regions where reflection will be attenuated. In some embodiments, the unit indicates to the user the regions that were attenuated and the regions that were not attenuated, for example, by lighting a light emitting diode (LED) at the indicated regions. In some embodiments, the user interface screen will show which regions are active (reflecting into the body) and which regions are not. In some embodiments, the described user interface operates with a transducer mat, enabling the user to attenuate specific transducers. In some embodiments, when a transducer mat is used, each transducer or transducer group comprises a LED indication, providing feedback to the user to which areas are active and which are not.

Figure 21:
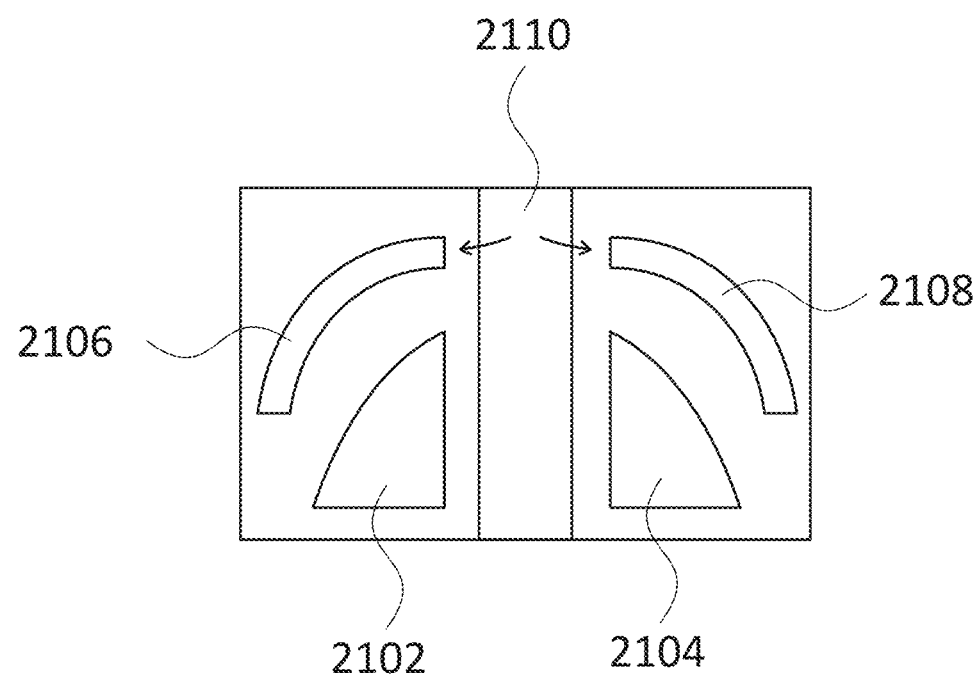
FIG. 21 is a schematic representation of treatment areas, according to come embodiments of the present invention.

Referring now to FIG. 21, showing a schematic representation of treatment areas. The zones below the ribs are denoted by 2102 and 2104. The zone above rib 12 and below rib 11 is denoted by 2106 and 2108. In some embodiments, the transducer interface is from the center of the transducer mat, over the spine—2110. In some embodiments, the ultrasound signal is transmitted from the center to the sides as denoted by the arrows, and reflected towards the patient's skin.

In some embodiments, the control of the areas where the ultrasound will be reflected depends on the acoustic impedance. Optionally, the acoustic impedance may be modified.

Figure 22:
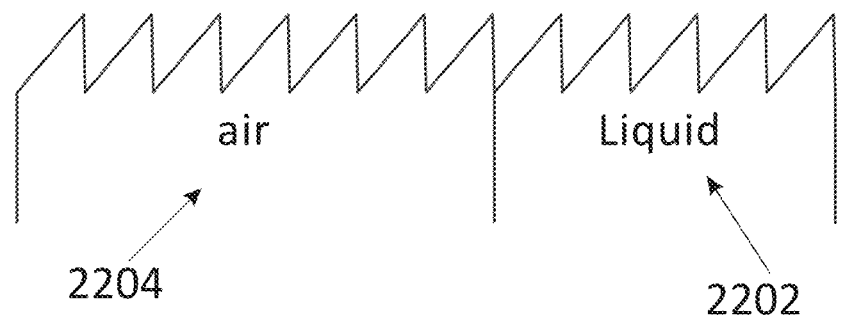
FIG. 22 is a schematic representation of the concept of modifying the acoustic impedance, according to come embodiments of the present invention.

The concept of modifying the acoustic impedance is shown schematically in FIG. 22. There is a grated structure, which is fluid filled. When filled with fluid 2202, there shall be no reflection since the impedance of the structure is close to the impedance of the circumventing gel. However, if the structure is filled with air as in 2204, the change of impedance would be significant and the structure shall turn into an ultrasonic mirror.

Figure 23:
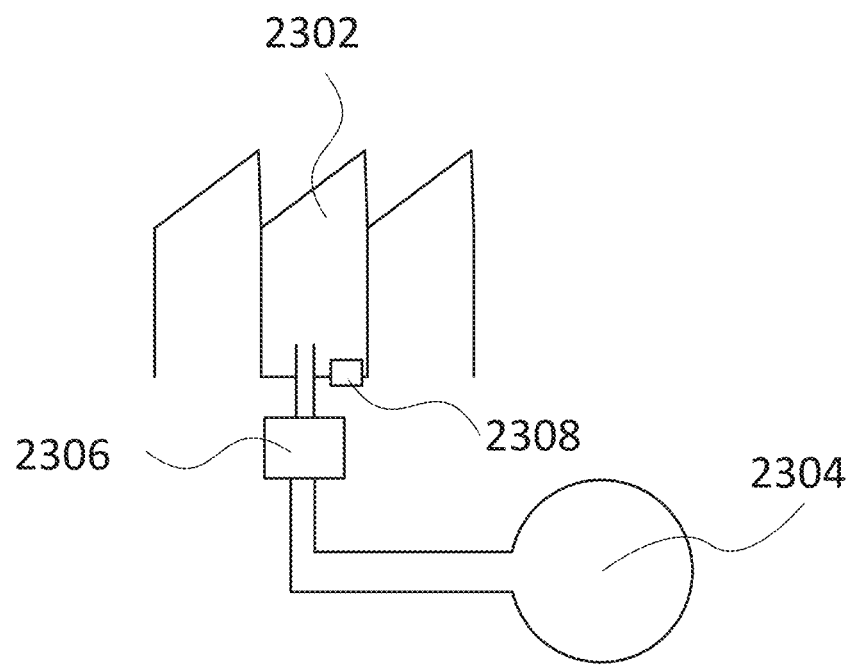
FIG. 23 is a schematic representation of a mechanism where a compartment, filled with liquid, is connected via a tube to a pressurized air chamber, according to come embodiments of the present invention.

In some embodiments, the make of the structure is set a priori, or dynamically changed, as detailed herein. FIG. 23 shows a mechanism where a compartment, filled with liquid 2302, is connected via a tube to a pressurized air chamber 2304. When the valve 2306 opens, air fills the compartment, and the fluid exits the chamber through a shunt 2308. In some embodiments, the content of the compartment 2302 changes from liquid to air and the top surface turns from non-mirror to mirror. In some embodiments, by marking an area to turn it to a mirror, a non-reflecting mat may turn to a partially reflecting mat according to the zones.

The above example showed a transition from liquid to air. In some embodiments, similar designs where the air vacates the compartment when pressurized fluid enters it under pressure can provide us with a bi directional control. In addition, it is also possible to use a compartment where the air and liquid are replaced upon command using the same mechanism. In some embodiments, the valve can be replaced by a one-time valve, opened using electrical control. In some embodiments, by using electrical current that flows through a high resistance metal cover of a valve, the cover is heated and subsequently opened. In some embodiments, the opening of the valve lets pressurized air displace the fluid. In some embodiments, this method could be advantageous in reducing the costs.

Anatomically Optimal Mats for Kidney Access—Side Access Example

Figure 24:
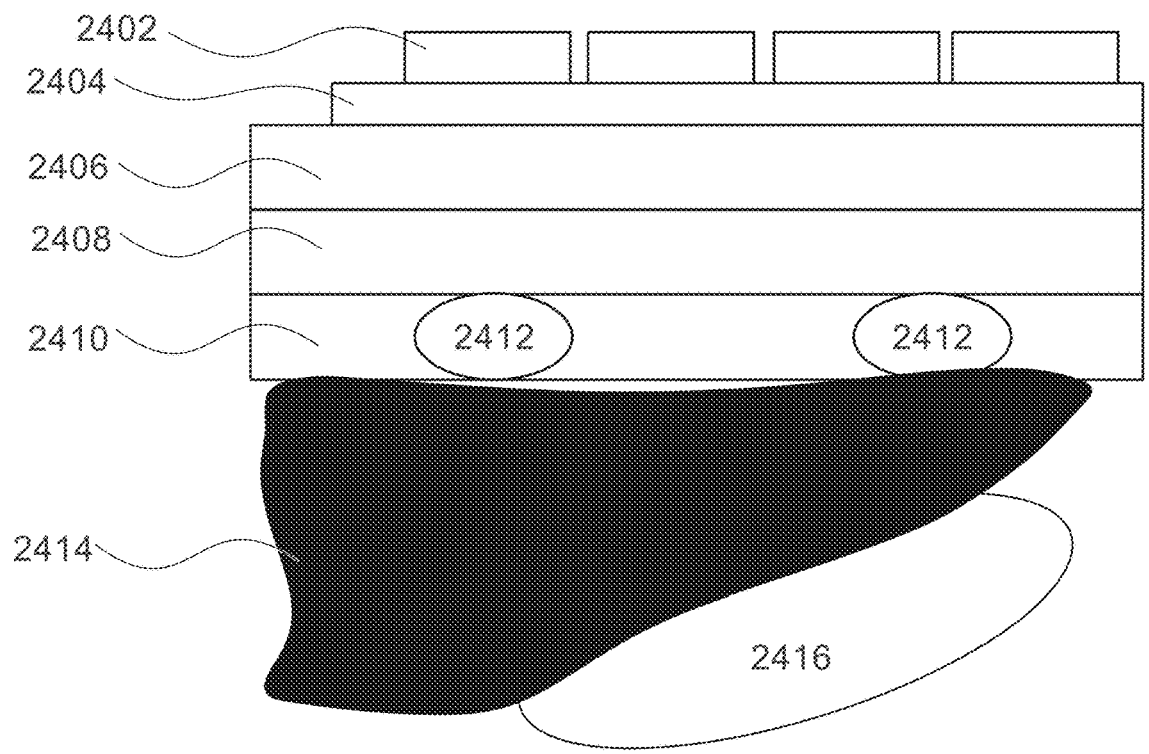
FIG. 24 is a schematic representation of the kidney side access via the ribs, according to come embodiments of the present invention.

In the FIG. 24 we show the kidney side access via the ribs.

In some embodiments, the transducers 2402 are placed on a hydrogel mat 2404 that provides acoustic coupling to the patient's skin 2406. Underneath the skin there is the under skin fat 2408 followed by the muscle 2410 and ribs 2412. Given side access to the right kidney—the liver 2414 will be seen. The kidney 2416 shall be viewed behind the liver. Specific transducers may be shut or activated according to need.

Figure 25:
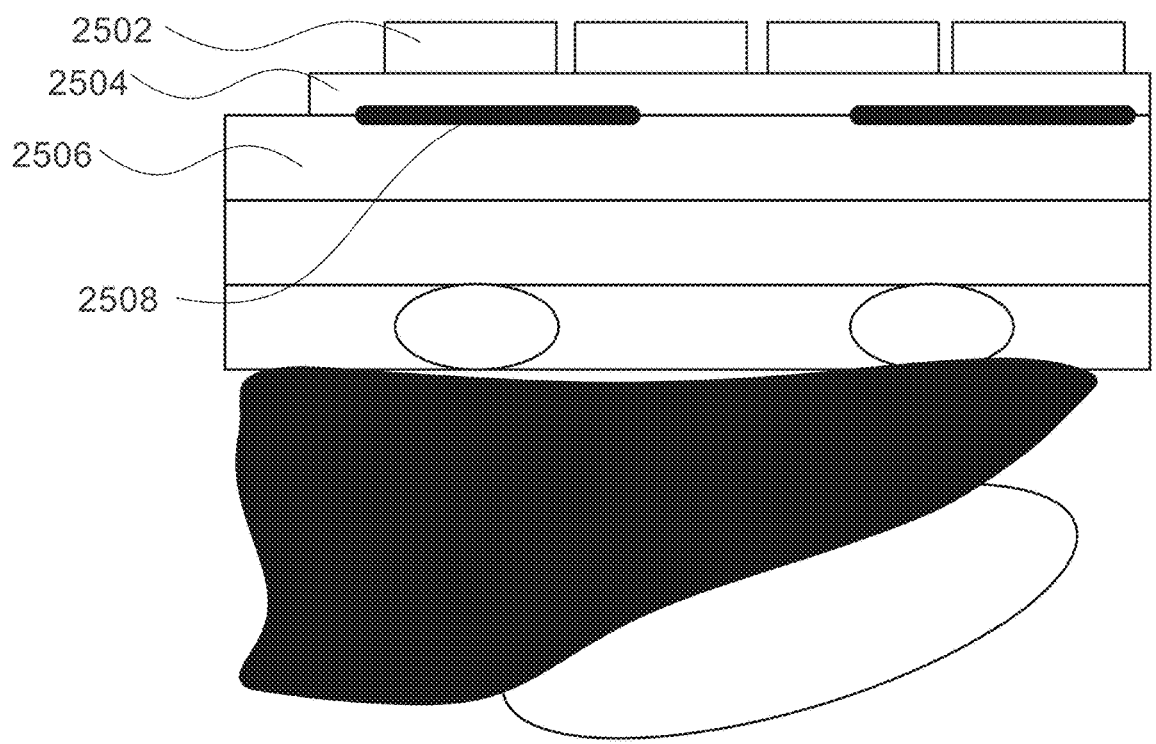
FIG. 25 is a schematic representation of a special film or sticker or other material that is inserted over the relevant area to block and/or attenuate the Ultrasound signal, according to come embodiments of the present invention.

In some embodiments, the ultrasound signal needs to be blocked and/or attenuated in a certain area. In some embodiments, a special film or sticker or other material is inserted over the relevant area to block and/or attenuate the Ultrasound signal as depicted in FIG. 25. As in FIG. 24, the ultrasound signal is generated by the transducers 2502, traverses through the hydrogel 2504 which is coupled to the skin 2506. The ultrasound blocking material 2508 may be placed over the rib locations to reduce ultrasound exposure there.

Figure 26:
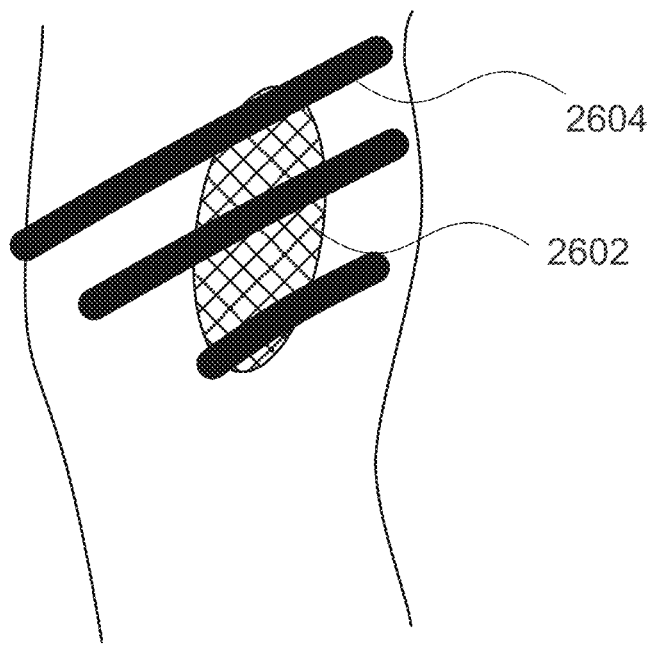
FIG. 26 is a schematic representation of how in the side access, a direct access with ultrasound to the kidney is hampered by the ribs, according to come embodiments of the present invention.

More examples are provided herein. In some embodiments, similarly to the back access, in the side access, a direct access with ultrasound to the kidney 2602 is hampered by the ribs 2604. This is depicted in FIG. 26. The figure shows an example of the projection of the 3 ribs (8, 9 and 10) as well as the kidney, on a sagittal plane. In some embodiments, the access can be achieved inferior to the ribs or between the ribs. In some embodiments, a transducer mat 2702 can be arranged with dense population of transducers 2704 over the ribs 2706, or by placing transducers between the ribs, or below then ribs, or any other method as described before.

Figure 27:
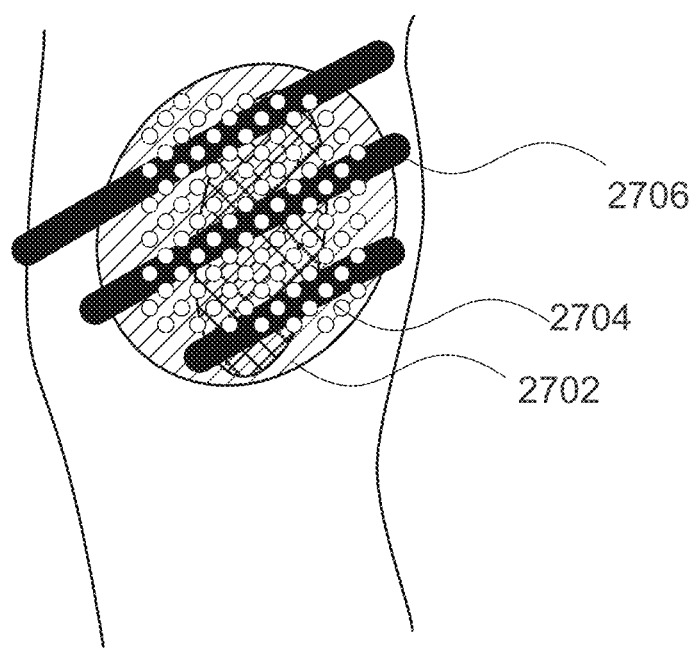
FIG. 27 is a schematic representation of a dense transducer mat, according to come embodiments of the present invention.

An example for a dense transducer mat is provided in FIG. 27.

In some embodiments, some of the transducers can be attenuated by means of mechanical ultrasound blocking (using an ultrasonic absorbing/reflecting material) or by software, or by other means. In some embodiments, transducers can also be applied to the waist, below the lowest rib, for access of the kidney. In some embodiments, waist is free of interference from the ribs but may require superior direction of the ultrasonic beam.

Examples of the Electrical Subunit

In some embodiments, the electrical subunit controls the operation of the system and provides an electrical signal to the transducers, which is converted to ultrasound at the transducer.

In some embodiments, the electrical subunit contains the following blocks:
System Control 2802
Signal generation 2804
Signal Distribution 2806

Figure 28:
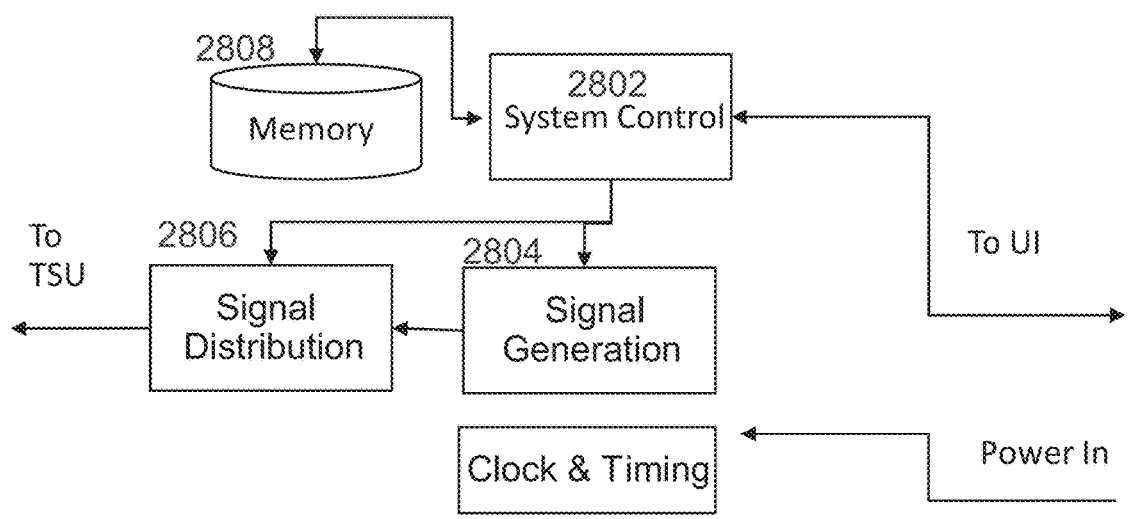
FIG. 28 is a block diagram of the electrical subunit, according to come embodiments of the present invention.

An example for the block diagram of the electrical subunit is provided in FIG. 28.

System Control Block 2802

In some embodiments, this block controls the operation of the whole system. In some embodiments, it is activated upon power up and checks the functionality of the system. In some embodiments, it then may activate the various other elements according to the configured operation mode and provide feedback to the user. It may also maintain time and log various operational parameters.

Memory Block 2808

In some embodiments, this block stores factory settings, and other settings that are learned or provided by the user. For example, a list of parameters that govern the transmission of every transducer may be part of the memory block.

In some embodiments, the memory block logs sensor information from the operational sessions, to be used by the control software or to be extracted later on.

Signal Generation Block 2804

In some embodiments, this block generates the electrical signal that is converted to the ultrasound. In some embodiments, this signal determines the following parameters:

Repetition rate—the length of time between subsequent pulses

Pulse amplitude—the electrical voltage of each pulse

Pulse duration—the exact time duration that a specific pulse is active. In some circumstances, the pulse duration is the inverse of the center frequency of the transmitted pulse Pulse Shape—a pulse may be bi polar, uni-polar positive or uni-polar negative In some embodiments, the actual shape (time domain shape) and frequency content (amount of energy transmitted at each ultrasonic frequency) are determined together by the electrical subunit and the transducer subunit—the transmitted ultrasonic signal is the result of the electrical signal being converted to an ultrasonic signal by the transducer.

| Parameter | value | |
| --- | --- | --- |
| Pulse repetition rate | 3-7 kHz | |
| Electrical Pulse Duration | 1 usec | May be transducer specific |
| Electrical Pulse shape | NRZ square wave | Non Return to Zero |
| Electrical Pulse amplitude | 300 V | Peak to Peak |

Figure 29:
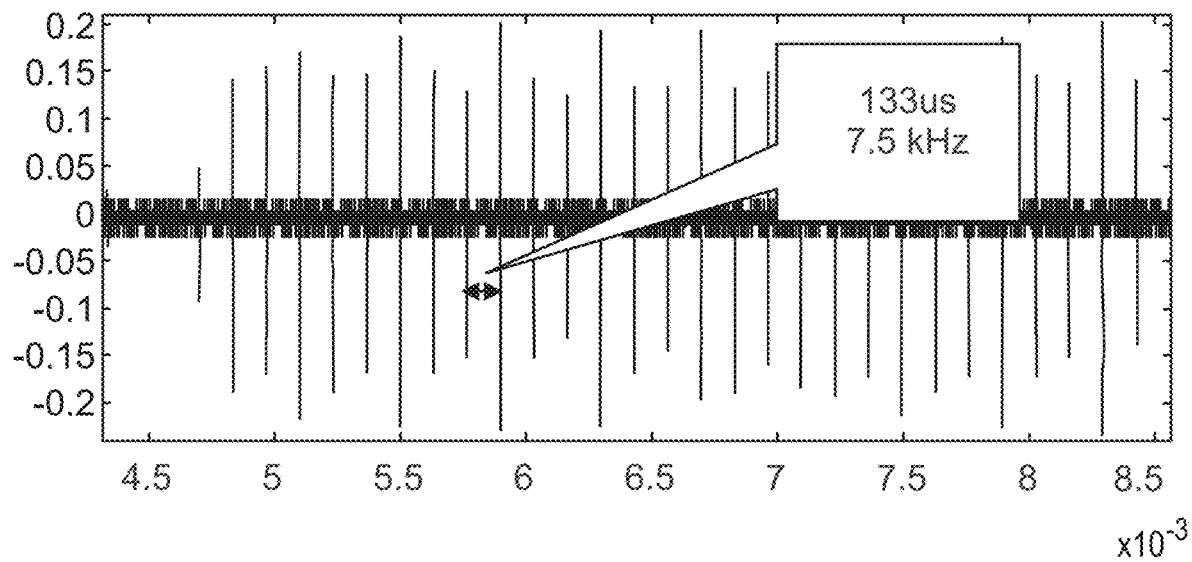
FIG. 29 is an example of how the electrical subunit operates at certain repetition rates, according to come embodiments of the present invention.

In some embodiments, the electrical subunit is able to operate at this repetition rate. An example is provided in FIG. 29 where multiple short ultrasonic pulses are transmitted separated by 133 microseconds between any two pulses.

In some embodiments, the signal generation block in the electrical signal subunit contains a few elements. In some embodiments, the basic pulse is typically generated by a fast return-to-zero (RTZ) damping Field-Effect Transistor (FET). In some embodiments, the reason for damping is to limit the duration of the pulse and shorten any "ringing" effect extending the duration of the transmitted pulse. In some embodiments, shortening the ringing is especially important in diagnostic Ultrasound systems, since the ringing tail of the ultrasound pulse may interfere with reflected echo signal returning from the tissue. In some embodiments, this is less important in designs when no signal reception is involved. In some embodiments, the only important reflected signal to be detected by the unit relates to signal reflection from air or bone; thus allowing for some level of ringing as long as the reflected received signal is stronger than the transmitted ringing signal, at all relevant depths. In some embodiments, the output stages operate at high voltage levels, in order to generate a high-pressure value. In some embodiments, level translators are used for the voltage shift. In some embodiments, for the output stage an AC-coupled Metal-Oxide Semiconductor Field-Effect Transistor (MOSFET) is used, with high-current P-channel and N-channel MOSFETs as output stages.

Figure 30:
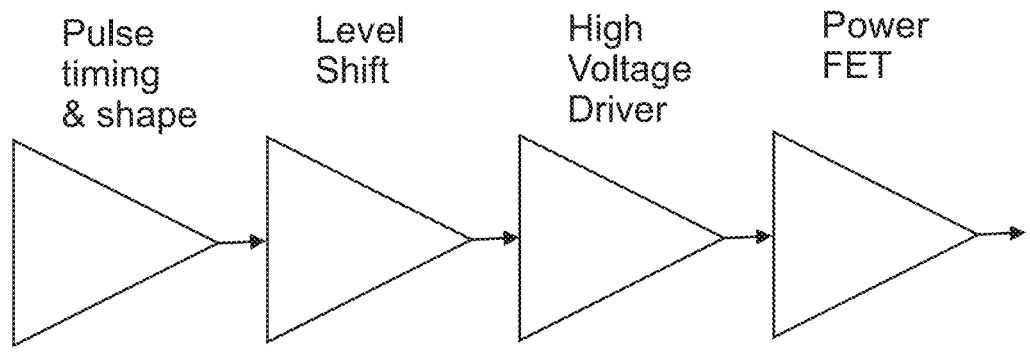
FIG. 30 is a block diagram of the signal generation block, according to come embodiments of the present invention.

A detailed outline of the signal generation block is provided in FIG. 30.

Figure 31:
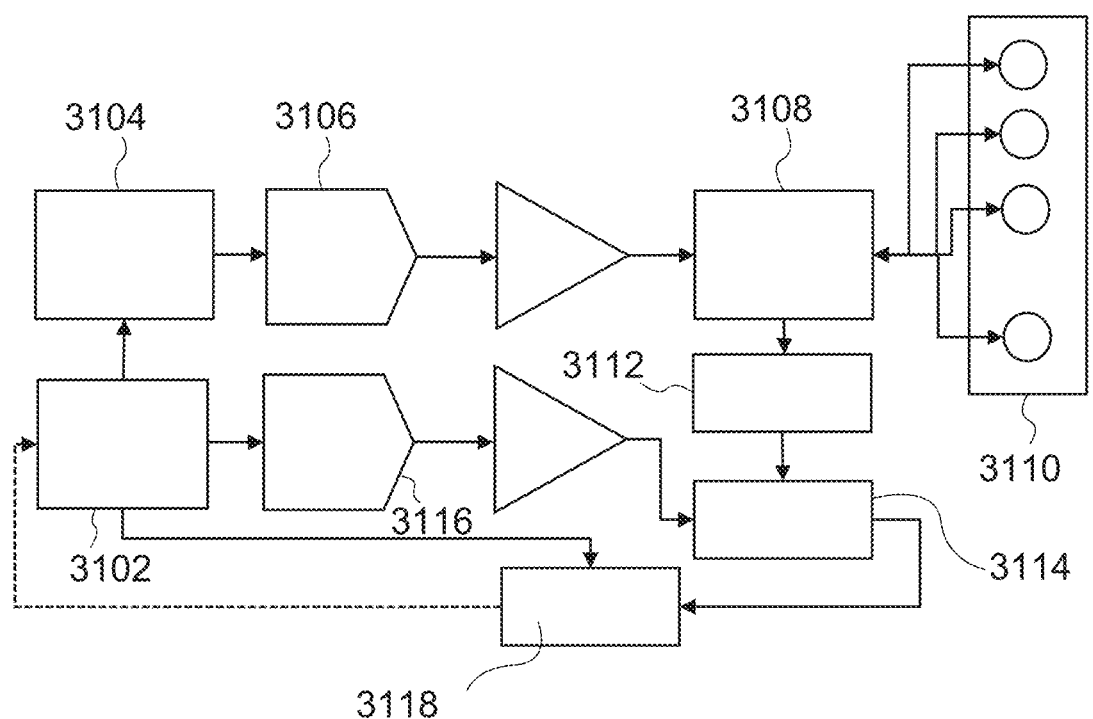
FIG. 31 is a schematic representation of a beam former unit, according to come embodiments of the present invention.

In some embodiments, the pulses are transmitted by preset schedule. Once the time for transmission of a pulse has arrived, the pulse is generated according to preset parameters. In some embodiments, the pulse is at low voltage, and thus requires amplification and conversion to the high voltage high current signal that would be driven to the transducer:

FIG. 31 shows an example of the beam former unit. In some embodiments, the beam-former control 3102 controls the block that generates the beam-former transmit signals—beam-former TX 3104. In some embodiments, the transmitted signal is converted to analog by transmit signal digital to analog converter (DAC) 3106. In some embodiments, the signal is amplified by an amplifier denoted by a triangle and reaches a multiplexer 3108, which controls the distribution of the signals to the acoustic transducer array 3110.

In FIG. 31, it is shown the treatment of an input ultrasonic signal. In some embodiments, this is optional since there is no input beam forming. In some embodiments, the input beam forming is performed for parameter estimation such as kidney location tracking. In some embodiments, when the reflected signal is used to verify the proper operation of the system or when an organ is tracked. In some embodiments, from the multiplexer 3108 the incoming signal goes via a TR (Transmit/Receive) switch 3112 to an analog front end (AFE) 3114. In some embodiments, the analog front end can also use internally generated receiver beamforming signals to control gain, and reduce echo signal. In some embodiments, these signals are generated by the beam-former controller 3102, converted to analog by the receive path DAC 3116 and amplified. In some embodiments, by using these signals at the analog front end (AFE) 3114 the dynamic range of the AFE can be kept small. In some embodiments, the input signals at the AFE are converted to digital by analog to digital converters (ADC) and processed at the receiver beam-former processor 3118. In some embodiments, the results of the processing of the input signal may influence the transmitted signal by the feedback signal, depicted in a dashed line, flowing from the receiver beam former to the beam former controller 3102.

Exemplary Electronic Functionality

In some embodiments, the electronic functionality must include
1. High voltage sources to support the generation of high pressure ultrasonic pulses
2. High voltage and Very Short duration (in the order of a few microseconds) signals that arrive at the transducers and produce high pressure and short duration peaks.

By high voltages in this discussion we refer to peak to peak voltage range of 100 to 400 Volts.

In some embodiments, the latter signals are converted at the transducers from electrical signal to acoustic signals. Since the transducers are physically located very close to the patient body, these signals must be present near the patient body. The presence of these signals near the patient body does not entail a safety problem by itself, since the duration of the signal is short.

In some embodiments, the high voltage sources are generated from DC power supplies, that can be fed from a low voltage source such as a battery, or from an AC powered (e.g. 110 VAC-240 VAC) power supply. These signals may be dangerous to the patient, if by means of one or more element failure the patient's skin is in contact with such an electrical signal.

For this reason, DC generating power supplies should be placed away from the patient body. The common solution to this design is to place the high voltage power supplies away from the patient, and use a cable to transfer the high voltage very short duration signals over a cable. Due to the signal loss over the lengthy cable, a low loss cable is needed, increasing the cost of the cable and ultrasonic probe.

In some embodiments, the solution is to use a third signal—High voltage and medium duration (in the order of a few hundreds of microseconds) electrical signals. These signals are safe and can traverse the cable near the patient. In some embodiments, these signals can be used to power the signal generation device, that generates the high voltage and very short duration signals needed for the transducers.

Figure 32:
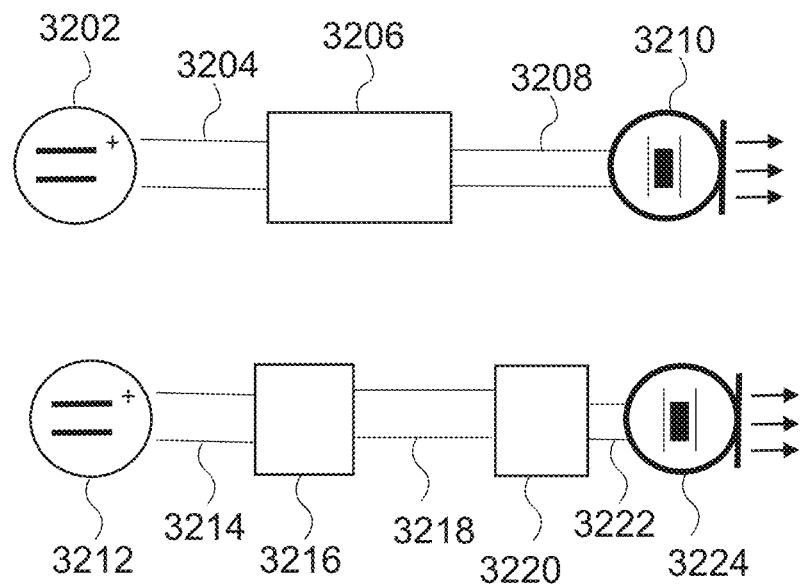
FIG. 32 is a schematic representation of a DC power supply, according to come embodiments of the present invention.

Referring to FIG. 32, The DC power supply 3202 is depicted on the left. This device and the voltages coming out of it should be kept away from the patient. Next is the pulse generator 3204 that requires the high voltage signals 3206 to generate the high voltage very short duration signals 3208. These signals arrive at the transducer 3210 that is placed next to the body. In order to keep the pulse generator away from the patient, the lines between the pulse generator and the transducer needs to be kept long.

In some embodiments, an innovative design of the DC power supply 3212 is depicted on the left. This device and the voltages coming out of it should be kept away from the patient, under all fault conditions. The output of the DC power supply is the DC high voltages 3214. These signals arrive at the power pulser circuit 3216 that converts the dc power supply to high voltage medium duration signals 3218. These high voltage medium duration signals arrive at the modified pulse generator module 3220 that generates the high voltage very short duration signals 3222. These high voltage very short duration signals 3222 arrive at the transducer 3224 that is placed next to the body. Now there is no need to keep the modified pulse generator 3220 away from the patient, since its incoming signals are not dangerous to the patient. This modification provides a significant advantage to a design that is used for prolonged ultrasound transmission that may be applied without a care taker. A block containing the units (3212, 3216) and the signals 3214 running between them can be built with proper isolation away from the patient, with safe signals 3216 emanating from the block.

Signal Distribution Block

Figure 33:
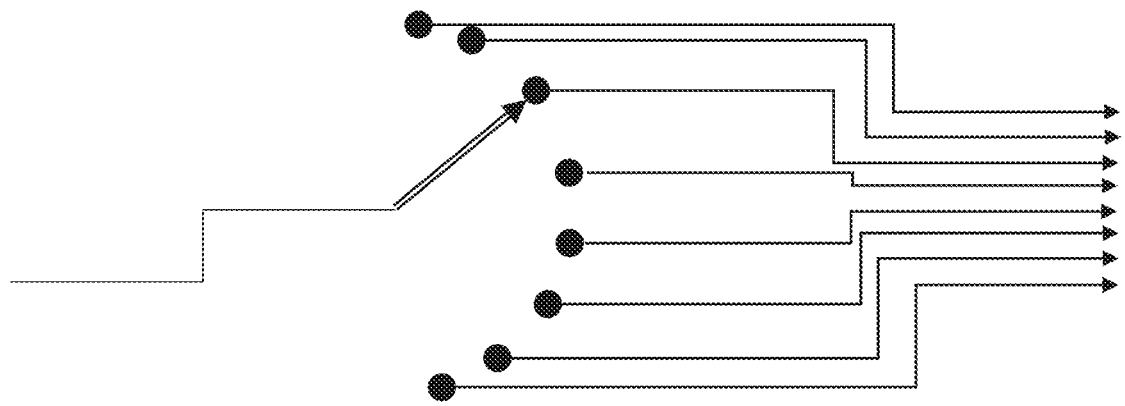
FIG. 33 is a schematic representation of a signal distribution block implemented as a switch, according to come embodiments of the present invention.

In some embodiments, there are various possible mechanisms to transmit an ultrasonic signal from an array of transducers. In some embodiments, in the case where only one transducer is active at any given time, the signal distribution block can be implemented as a switch (FIG. 33). In some embodiments, the incoming electrical signal is directed at any given time to the designated transducer. In some embodiments, when the transmitted signal needs to be sent to another transducer the switch directs the electrical signal towards that transducer.

In some embodiments, multiple transducers transmit at the same time. In some embodiments, there is a need to transfer multiple signals simultaneously. In some embodiments, this can be performed with a more complex switch, converting $M_s$ electrical signals to $N_T$ transducers. In some embodiments, a given $N_T$ outputs from the electrical signal module, a one-to-one connectivity can also be established.

In some embodiments, multiple signals can be multiplexed together on a small number of interfaces in order to save leads on a cable that may physically connect the electrical subunit to the transducer subunit.

Figure 34:
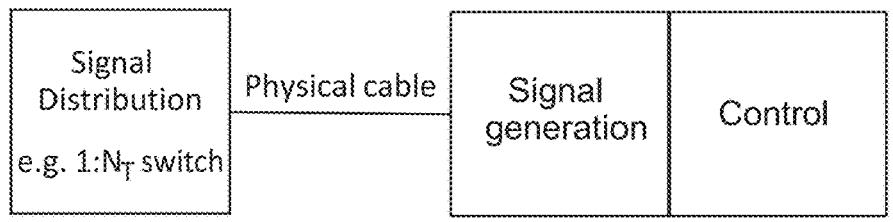
FIG. 34 is a schematic representation of a system where the physical cable needs to carry only a few signals since the switching is performed near the transducer, according to come embodiments of the present invention.
Figure 35:
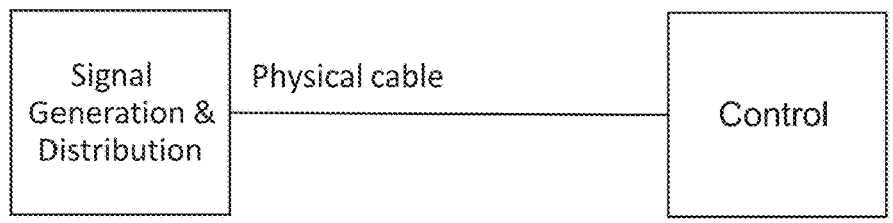
FIG. 35 is a schematic representation of a system where the physical cable carries control signals, according to come embodiments of the present invention.
Figure 36:
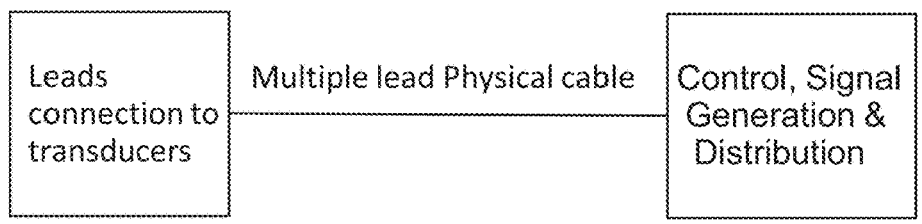
FIG. 36 is a schematic representation of a system where the physical cable carries multiple signals, according to come embodiments of the present invention.

FIG. 34 shows an example for a system where the physical cable needs to carry only a few signals since the switching (on the left hand side) is performed near the transducer FIG. 35 shows an example for a system where the physical cable carries control signals such as instructions and configuration parameters, since the signal generation (on the left hand side) is performed near the transducer FIG. 36 shows an example for a system where the physical cable carries multiple signals, since the signal generation and distribution are on the right hand side Clock Generation and Timing In some embodiments, this block is responsible for the generation of all clocks used internally that determine the accuracy of the transmission signal parameters Power Block In some embodiments, the power block handles the power storage for the system.

In some embodiments, one option would be to have the unit always connected to a standard AC power supply (e.g. 110-230 Volt AC supply). In some embodiments, another alternative would be to have a small battery enclosed in the unit. In some embodiments, the battery may be a primary non-rechargeable battery or a rechargeable battery.

In some embodiments, if batteries are used, the unit is equipped with commercially standard batteries that can be replaced by the user, or proprietary batteries that are part of the equipment, and only a power charging interface would be provided. In some embodiments, a power charging interface may be a proprietary one, using a charger (contact or non-contact charger) or an industry standard charging interface such as a USB interface, operating at 5 Volt DC. In some embodiments, in case a rechargeable battery is used, a charging circuit may be part of the power unit.

Figure 37:
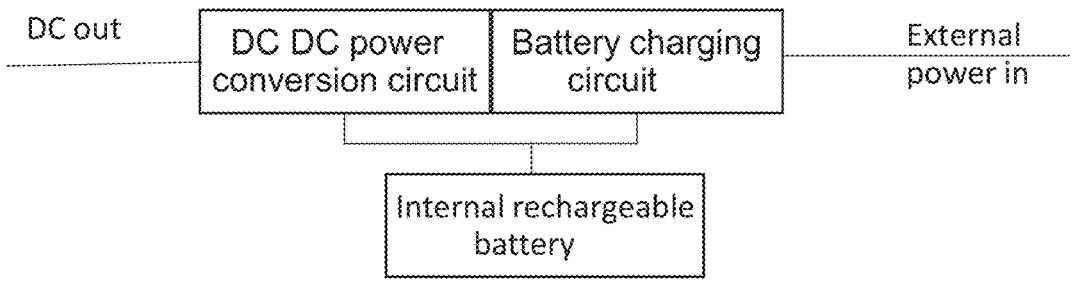
FIG. 37 is a block diagram of the power subunit, according to come embodiments of the present invention.

In some embodiments, the power functionality option tree is as below:

No Battery
  Standard grid AC (110-240V) power supply
Battery
Non-Rechargeable Battery:
  Non-rechargeable standard batteries and a mechanical mechanism to replace them (e.g. Door and screw)
Rechargeable Battery:
  Rechargeable standard batteries and a mechanism to replace them
  Rechargeable non-standard battery enclosed in a pack and a mechanism to replace packs. Also a battery pack charger
  Rechargeable battery and an external non-standard battery charger unit, with interface.
  Rechargeable battery, an internal charging circuit and a standard DC power interface (such as a standard micro-USB)
  Rechargeable battery, an internal charging circuit and a standard AC power interface A block diagram of the power subunit, assuming an internal rechargeable battery and an internal charger circuit is provided in FIG. 37.

Mechanical Structure

Integration into Beds and Furniture

In some embodiments, the type 1 unit is able to function when the patient uses one or more of the following components:

Pre-operation bed prior to entrance into a heart operation such as CABG or prior to Cath-Lab
  Operation room bed during a heart operation such as CABG
  Operation room bed in a Cath-lab
  Recovery room, while the patient is after an operation
  Regular ward bed, in all varieties of bed inclinations, up to "sitting" position
  Various couches, non-standard, as commonly used for hospitalized CHF patients
  Various couches, non-standard, as commonly used in patient's homes
  Other than these, there may be other cases such as:
  Special beds for treatment of pressure ulcers
  Dialysis couch In some embodiments, the type 1 unit enables simple transition from bed to bed when the patient is either conscious or sedated. For example, by using glue to attach the transducers to the patient's back.

Fixed and Disposable Division

In some embodiments, the type 1 unit has fixed components and disposable components. In some embodiments, the system is designed such that the removal and application of the disposable units are performed by a medical practitioner. Alternatively, this can be performed by an un-trained person e.g. the patient or a caretaker.

Division to Parts—Mechanical Structure

In some embodiments, there are a number of alternatives to divide the system to connected parts.

Figure 38A:
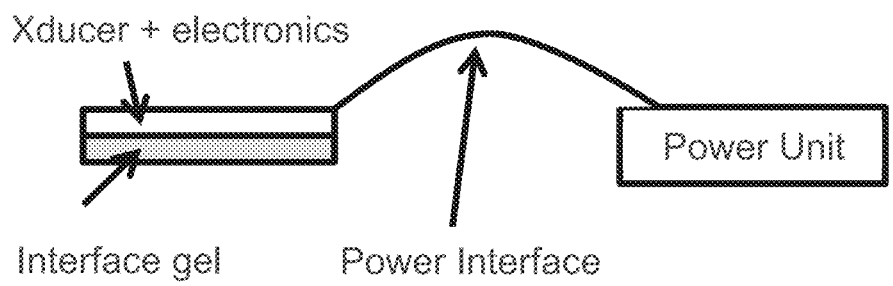
FIGS. 38A-C are schematic representations of embodiments of divided and non-divided systems, according to come embodiments of the present invention.
Figure 38B:
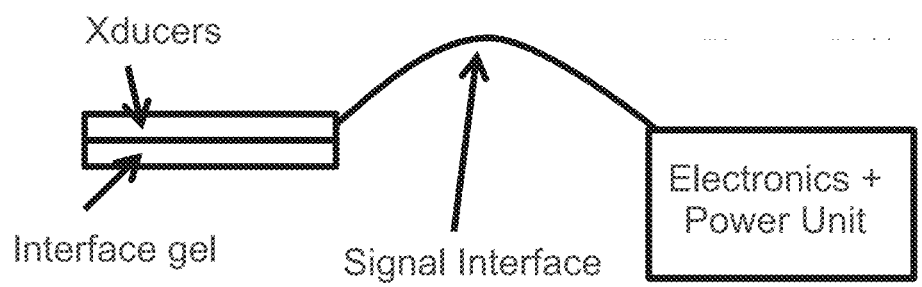

In some embodiments, the system is a two part package comprising: a bedside power unit providing power to a single unit control with an actuators box. In some embodiments, the boxes are connected with cable as in FIG. 38*a*; and a power and control bedside box with bed actuators connected with cable as in FIG. 38*b*.

Figure 38C:
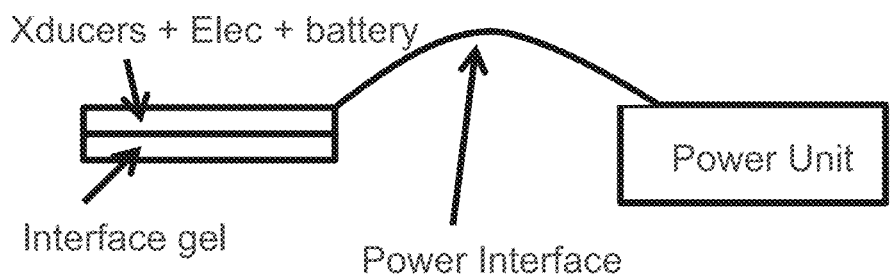

In some embodiments, the system is a single unit, which is battery powered, with an external battery charger, as in FIG. 38*c*.

In some embodiments, the system is a bed side unit with visual screen.

In some embodiments, the multi-use device is made of a combination of transducers (which are rigid) and connecting material between the transducers, which is flexible.

This design is innovative and different from most existing medical ultrasound devices.

Diagnostic ultrasound devices have multiple transducers (transducer arrays), but they must be all connected rigidly one to another to ensure a-priori known relationship between the transducer beams. The same rigid construction is mandatory for transducer arrays that are used in focused therapeutic ultrasound. Since the construction of the array is rigid—any adjustment to the human body contour needs to fill the space between the array and the skin. The filling needs to have a high density (such as the density of water 1 g cm$^{-3}$) and is thus heavy and inappropriate to become a wearable technology The prolonged low intensity ultrasound therapy uses an array of transducers that are connected with a flexible material, thus, it can adjust to the contour of the body and not imply heavy weight.

In order to support this architecture there is a need to embed the transducers in a material that has the following characteristics:

1. The material covering the transducers, located between the transducers and the skin needs to be with an acoustic impedance which is close to the acoustic impedance of the skin (about 1.7 10$^6$ Rayl)
2. The material covering the transducers, located between the transducers and the skin needs to be non-stretched in order to avoid the introduction of air bubbles between the material and the transducer face.
3. The material in the space between the transducers need to be flexible and stretchable in order to conform to the shape of the patient's skin The disposable material between the transducer mat and the skin has also to comply with the following:

4. The material covering the space between the transducers and the skin needs to be with an acoustic impedance which is close to the acoustic impedance of the skin (about $1.7 \cdot 10^6$ Rayl)
5. The material covering the space between the transducers and the skin needs to be non-stretched in order to avoid the introduction of air bubbles between the material and the transducer face.
6. The material in the space between the transducers need to be flexible and stretchable in order to conform to the shape of the patient's skin In some embodiments, this is achieved by using a single material (such as Silbione™ by Elkem). In some embodiments the areas near the transducers is hardened and made non flexible by means of controlling its thickness. In some embodiments the areas near the transducers is hardened and made non flexible by means of controlling its three dimensional structure, enabling different flexibility in various directions, for instance less flexibility in the top bottom direction (which translates to inferior-superior direction on the anatomic direction) vs. more flexibility on the distal proximal direction. In some embodiments the areas near the transducers is hardened and made non flexible by means of braiding—embedding non-stretchable material near the edges of the transducers in order to control the flexibility of the material.

In some embodiments, this is achieved by using a combination of multiple materials that have different chore value for instance a high shore near the transducer, and a low shore value between.

Type 2 System

Background

In some embodiments, the type 2 system has additional features compared to the type 1 system. In some embodiments, the key feature is in the extra complexity of the transducer subunits.

As shown above, in some embodiments, the type 1 transducers are attached to the human body. In some embodiments, the transducers can be attached by sticker, or a belt or any other mean that would generate some pressure of the transducer element that touches the human skin. In some embodiments, once this is achieved, no other means—mechanical means or electronic means—are used in order to guarantee that the ultrasonic signal reaches the desired destination.

In some embodiments, in a type 2 system, mechanical means are used to further spread the ultrasonic signals in order to increase the chances that all the desired tissue receive the proper amount to therapeutic ultrasound excitation.

Type 2 Key Parameters

In some embodiments, one or more transducers are attached to the body. In some embodiments, the attachment is done by sticker or belt or corset, with disposable acoustic gel pocket. In some embodiments, there is a power and signal sub-unit, which generates an electrical signal for the transducers. Optionally, one transducer at a time. In some embodiments, system controls and monitors the mechanical movement of transducer elements. In some embodiments, the system does not require sensing body internal organs to operate. In some embodiments, the System spreads ultrasound energy on the abdomen, covering target tissue as well as other tissues. In some embodiments, the control and monitor of the mechanical movements of the transducer elements is the parameter differentiating between type 2 system and type 1 system.

Transducer Subunit

In some embodiments, in order to enable a single transducer to expose different regions at different times, a moving mechanical element is used. In some embodiments, a single transducer may effectively cover a larger volume inside the body, making sure that no single volume is overexposed and/or no single volume is underexposed.

In some embodiments, there are a number of different ways to do this:

Exemplary Revolving Transducer with an Off Center Beam

Figure 39:
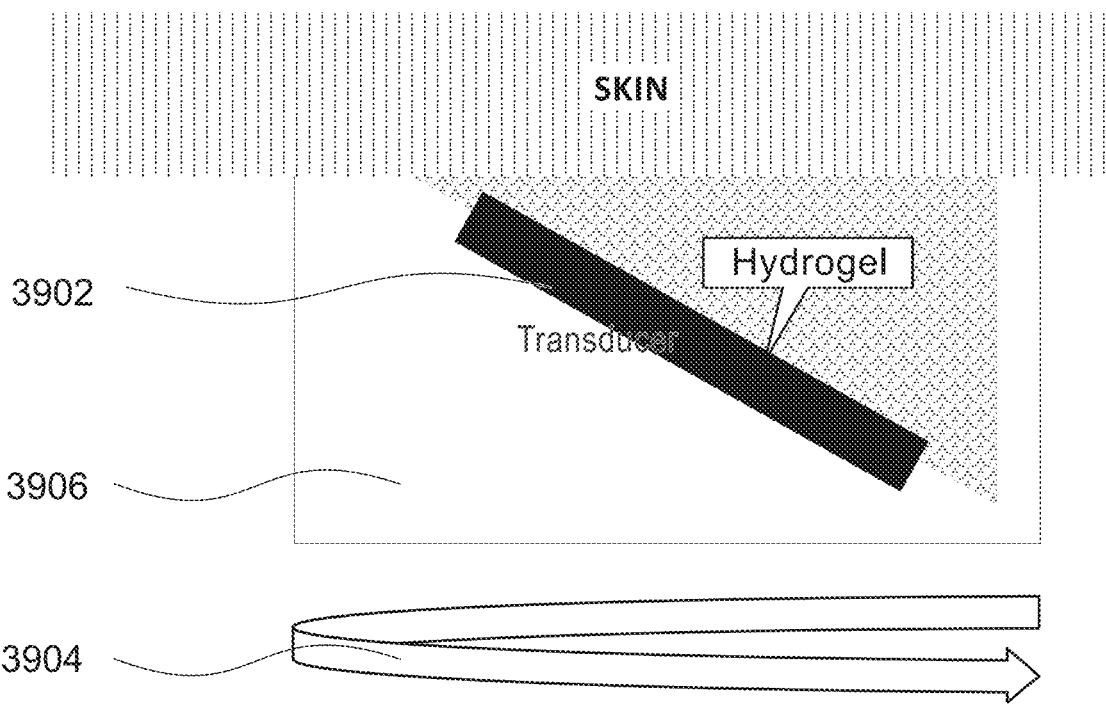
FIG. 39 is a schematic representation of a mechanism with an off center beam that revolves around an axis directed towards the body, according to come embodiments of the present invention.

Referring now to FIG. 39 showing a mechanism with an off center beam that revolves around an axis directed towards the body. In some embodiments, the off center beam is achieved by setting the transducer 3902 axis away from the axis of revolution 3904. In some embodiments, the whole transducer body 3906 revolves and since the transducer axis is off center, the ultrasound beam moves in space like a gyroscope precession.

Figure 40:
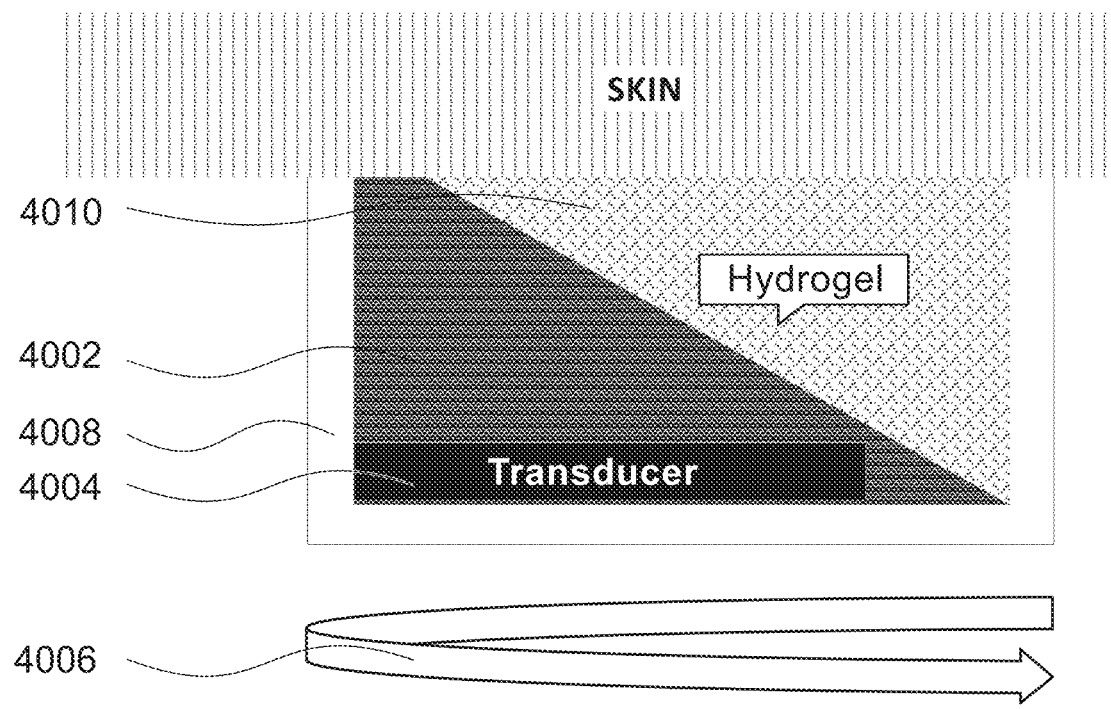
FIG. 40 is a schematic representation of a mechanism where the offset of the transducer beam is done by a wedge, according to come embodiments of the present invention.

In some embodiments, offset of the transducer beam is done by a wedge (depicted in FIG. 44) or by other known methods of transducer design. In FIG. 40, a wedge with a different acoustic impedance 4002 is placed over the transducer 4004 and both are turning around together around the axis of revolution 4006 inside the transducer housing 4008. In some embodiments, gel 4010 is used to couple the signal to the skin.

In some embodiments, there are a variety of ways to achieve the beam revolution. In some embodiments, an alternative to rotating the whole capsule including the transducer is by revolving a lens, which is located between the transducer and the gel. This is depicted, for example, in FIG. 41. In some embodiments, the lens 4102 is placed inside the gel 4104 between the transducer 4106 and the skin. In some embodiments, the lens alone rotates according to the rotation axis 4108. In some embodiments, the transducer housing 4110 does not rotate. In some embodiments, the lens axis is off from the rotation axis, achieving the off center beam rotation. In some embodiments, all elements are stationary except for the revolving lens.

Mechanical Movement of an Annular Array

In some embodiments, using an annular array, the distance to the focus of the ultrasound signal may be controlled by the signals coming to the annular array. In some embodiments, the pitch and yaw can be controlled by mechanical movement of the lens, or of the complete annular array. In some embodiments, the design can also use a reflector to move the focused ultrasound beam. In some embodiments, by combining distance pitch and yaw the exact location of the focus may be controlled.

An example with a lens is provided in FIG. 42. In some embodiments, a lens 4202 is placed above an annular transducer array 4204. In some embodiments, the turning of the lens 4202 with the wedge 4206 moves the beam azimuth according to the arrow depicted in 4208. In some embodiments, the control of the individual transducers in the array determines the amplitude of the signal along the axis as shown by arrow 4210. The focus area 4212 moves from location to location.

Mechanical Movement of a Linear Transducer Array

Figure 43:
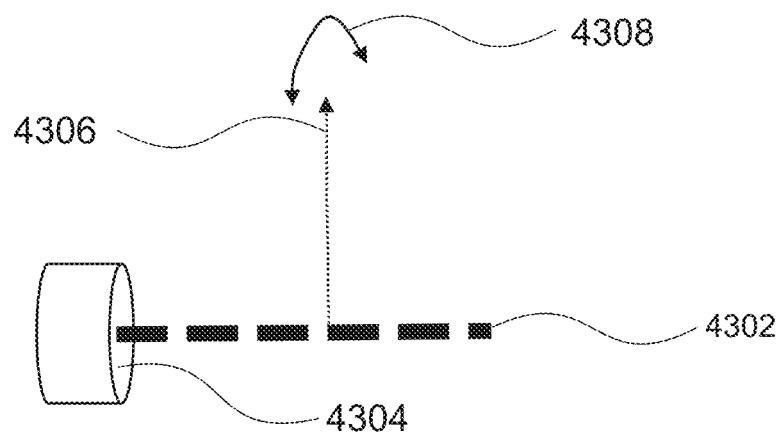
FIG. 43 is a schematic representation of a mechanism to twist a linear array, according to come embodiments of the present invention.

In the FIG. 43, it is shown a mechanism to twist a linear array (4302) around its transducer axis. In some embodiments, the mechanism to twist the array is depicted as an electrical rotor 4304, but can be implemented in various ways. In some embodiments, the direction of the beam denoted by 4306 changes and tracks the arrow depicted in

4308. Thus, in some embodiments, when the beam direction is moving, it enables the coverage of a larger volume over time.

Mechanical Displacement of Transducers

In some embodiments, another alternative to the usage of a large array of transducers is the use of a single transducer or a small array of transducers that is physically moving from place to place.

In some embodiments, a transducer can be moved at the plain that is parallel to the kidney plane, each time transmitting towards a different area. In some embodiments, by moving within the transducer mat the area of coverage can be determined. In some embodiments, one or more transducers may operate within the mat.

Figure 44:
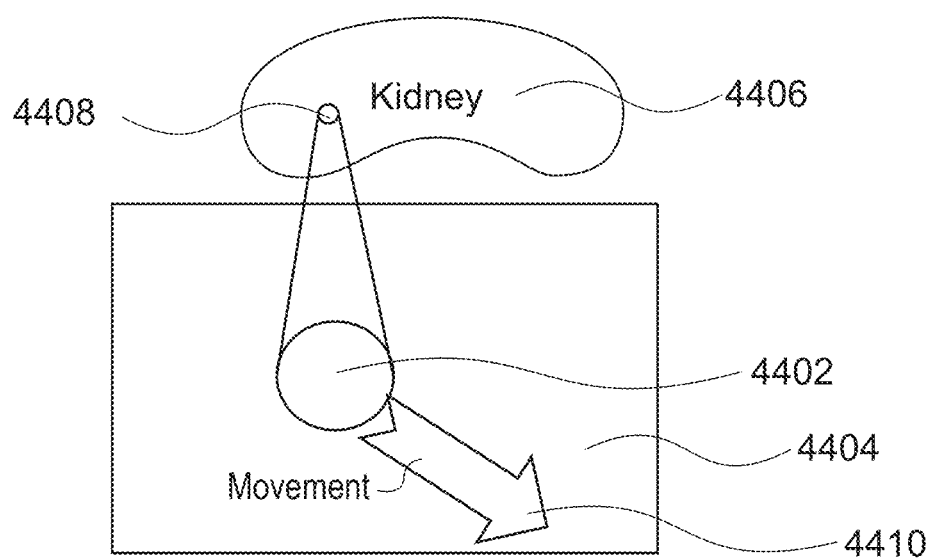
FIG. 44 is a schematic representation of an implementation with a single moving transducer, according to come embodiments of the present invention.

FIG. 44 shows an implementation with a single moving transducer. In the depicted example, a single transducer 4402 is placed in a mat 4404. In some embodiments, the transducer may move inside the mat, and is always coupled to the skin via the coupling mechanism of the mat. In some embodiments, the transducer emits ultrasonic signal that reaches the kidney 4406 and exposes part of the kidney to the signal, as shown in 4408 in the figure. In some embodiments, by moving the transducer itself 4410 the exposed area in the kidney changes accordingly.

In some embodiments, mechanical moving can be implemented as a translation movement or as an angle change (pitch and yaw) movement or a combination.

Type 3 System

Background

In some embodiments, the goal achieved by the type 2 system was to make sure that at different times the ultrasonic beam arrives at different locations within the body. In some embodiments, this is performed in order to guarantee that the therapeutic effect of the ultrasonic signal arrives at all desired target tissue.

In some embodiments, the time modulation of the beam was achieved mechanically. In some embodiments, it is also possible to achieve beam spreading electrically, by transmitting simultaneously from a number of transducers signals, which are adjusted in a way to achieve common beam modification. This is called "beam forming" in the literature, and requires that the original beams of the participating transducers have some common intersection.

In some embodiments, a reason to generate a beam from multiple transducers is in order to achieve ultrasound signal focus at a distance from the transducer. In some embodiments, the distance between the transducers and the kidney tissue is in the order of 3-10 cm, and may be more depending on the width of the under skin fat.

| Parameter | value | |
|---|---|---|
| Minimal distance to target tissue | 30 mm | Depends on access zone (back, waist, other) |
| Maximal distance to target tissue | 120 mm | Depends on access zone and under-skin fat |

In some embodiments, in a type 3 system, electrical mechanical means are used to further spread the ultrasonic signals in order to increase the chances that all the desired tissue receive the proper amount to therapeutic ultrasound excitation.

Type 3 Key Parameters

In some embodiments, type 3 system comprises multiple transducers attached to body. In some embodiments, attachment is done by sticker or belt or corset, with disposable acoustic gel pocket. In some embodiments, there is a power and signal sub-unit generating an electrical signal for the transducers. Optionally, multiple transducers may transmit simultaneously—the resulting ultrasonic beam is a moving ultrasonic beam. In some embodiments, the system does not require sensing body internal organs to operate. In some embodiments, the system spreads ultrasound energy on the abdomen, covering target tissue as well as other tissues. In some embodiments, the multiple transducers, the power and signal sub-unit generating an electrical signal for the transducers and the simultaneously transmission of multiple transducers are the parameters differentiating between type 3 system and type 1 system and/or type 2 system.

Block Diagram

Figure 45:
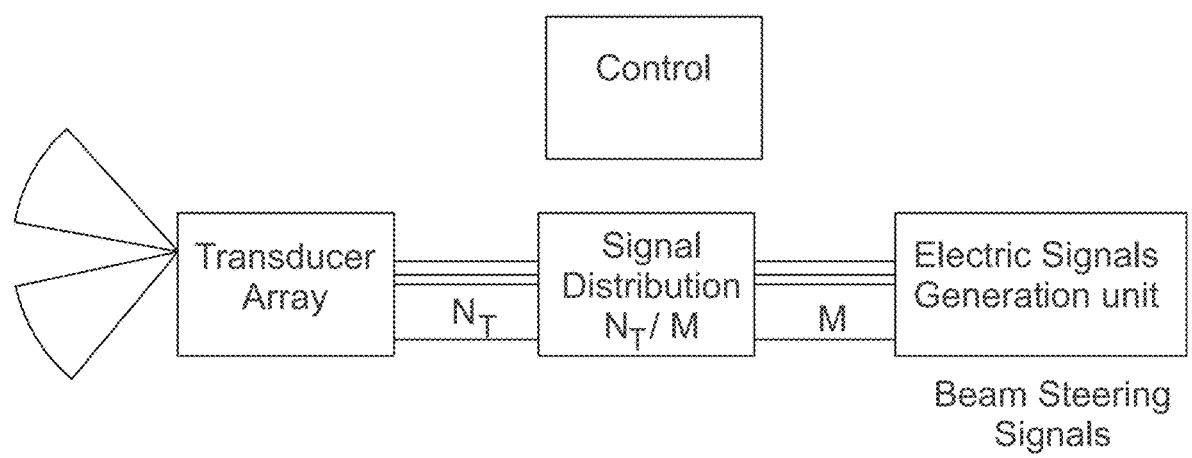
FIG. 45 is a block diagram of the system, according to come embodiments of the present invention.

In some embodiments, in order to enable a single transducer to expose different human regions at different times, electrical signals arrive simultaneously at a number of transducers. In some embodiments, this is achieved by modifications in both the transducer subunit and the electrical subunit, since multiple signals, not necessarily identical, arrive at the transducers. In some embodiments, this way, a single transducer array may effectively cover a larger volume inside the body, making sure that no single volume element is overexposed and/or no single volume element is underexposed. The block diagram of the system is depicted in FIG. 45.

Transducer Subunit

In some embodiments, an array of transducers operates simultaneously, where by providing the transducers with different signals, the intensity and direction of the ultrasonic beam. In some embodiments, one such known method is beamforming which uses varying signal phases in order to dynamically change the radiated ultrasonic beam. In some embodiments, beamforming can be fixed or time varying. In some embodiments, the optimal direction for the ultrasound signal will not be perpendicular to the transducer plane, due to various anatomical limitations. In some embodiments, for instance, when using back access one may elect to place all the transducers below the bottom rib. In some embodiments, the transducers will transmit upwards (in a superior direction) in order to cover the superior lobe of the kidney. In some embodiments, this would be possible with some sort of beam forming, or beam direction.

Using a Linear Array

Figure 46:
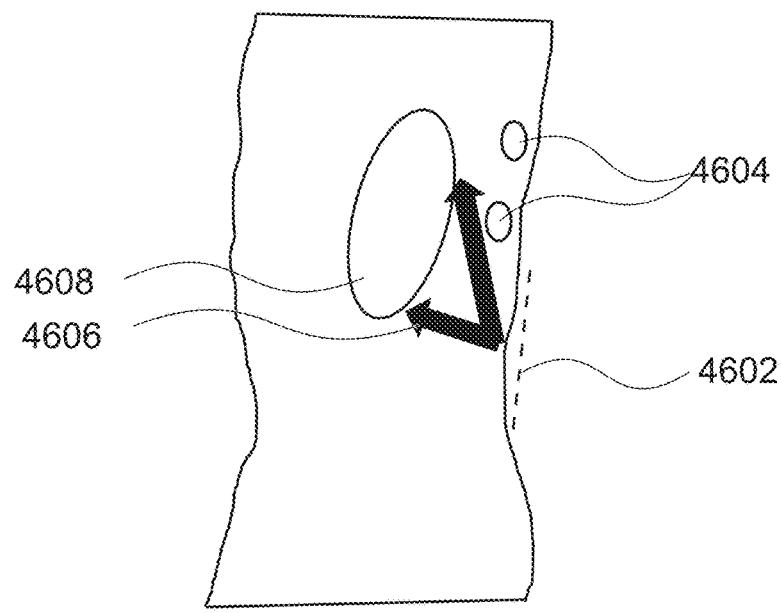
FIG. 46 is a schematic representation of an exemplary beam forming method, according to come embodiments of the present invention.

In some embodiments, by aligning a linear array along the major axis of the kidney, kidney coverage may be achieved with some form of beam forming along the major axis of the array, as shown in FIG. 46, where a sagittal plane is shown. In some embodiments, the transducer array 4602 is placed on the back below the ribs 4604. In some embodiments, the beam direction 4606 can be modified along the axis of the transducer array in the sagittal plane, reaching the kidney 4608 and exposing it to ultrasound signal at different locations.

In some embodiments, linear array of multiple transducers may be operated in many means. In some embodiments, a transducer may be shot one at a time, or beam forming may be used. When beam forming is used. In some embodiments, the angle of the beam in the plane defined by the array and the line perpendicular to the array is achieved.

Figure 47:
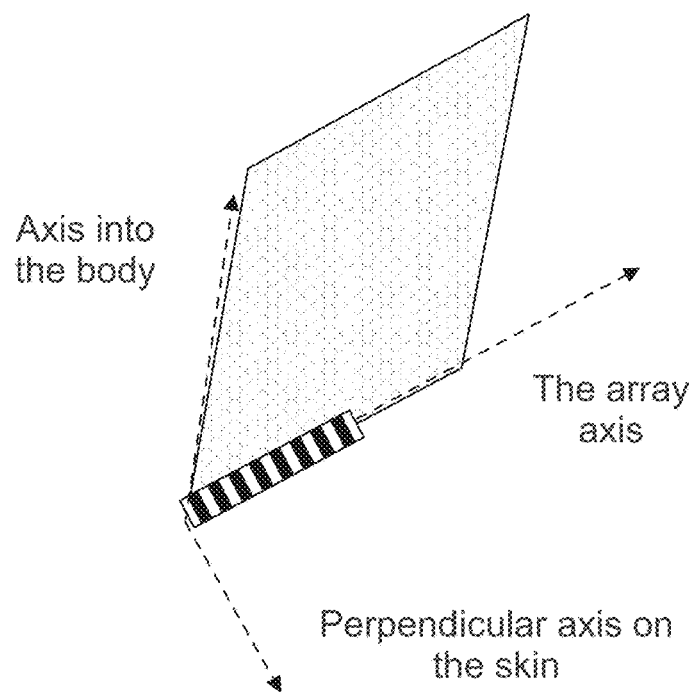
FIG. 47 is a schematic representation of the principal axis of the linear transducer array, according to come embodiments of the present invention.

In FIG. 47, it is shown the principal axis of the linear transducer array. In some embodiments, when the transducer array is placed on the skin facing into the body—the center of the ultrasonic beam is within the plane defined by the array axis and the axis perpendicular to it into the body. In some embodiments, electrical control of the signal at each transducer shall determine the angle of the beam within this plane. In some embodiments, in order to treat areas of the kidney not on this plane, we need to take into consideration the third axis, perpendicular to the two previously mentioned. In some embodiments, this would be typically tangential to the skin. In some embodiments, coverage of such off plane areas can be achieved, for example, but tilting the array along the array axis as shown in FIG. 43.

Figure 48:
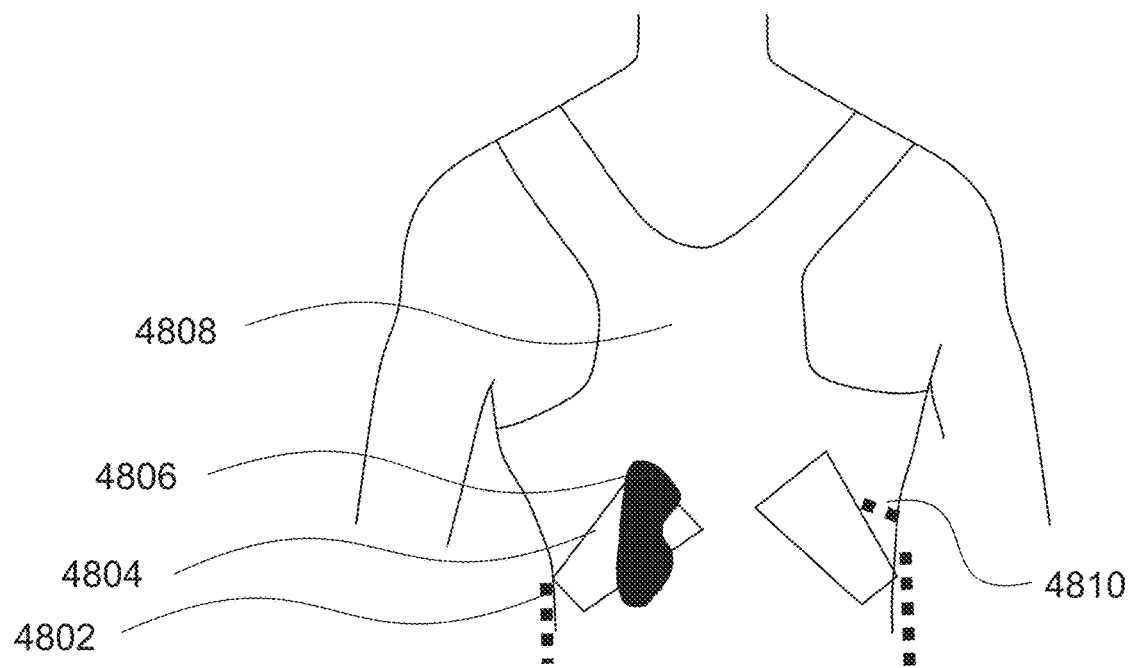
FIG. 48 is a schematic representation of the linear array placed at the waist, according to come embodiments of the present invention.

In some embodiments, the transducer subunit may contain one or more transducer arrays. In some embodiments, the arrays may be parallel or take any other arrangement. FIG. 48 shows the linear array 4802 is placed at the waist. In some embodiments, it generates a beam of ultrasonic signal 4804 that reaches the kidney location 4806. In some embodiments, the linear array is held in place by a wearable garment 4808. In some embodiments, an alternative location for the transducer array may be at the side between the ribs 4810.

In some embodiments, unlike the mechanical beam direction design, where each transducer operates on its own, and may be slightly disoriented compared to its neighboring transducers, when a transducer array beam forming is used typically all the transducers shall be aligned on a non-flexible mount, keeping the relative transducer to transducer distance and also transducer orientation constant.

Electrical Signal Subunit

Figure 49:
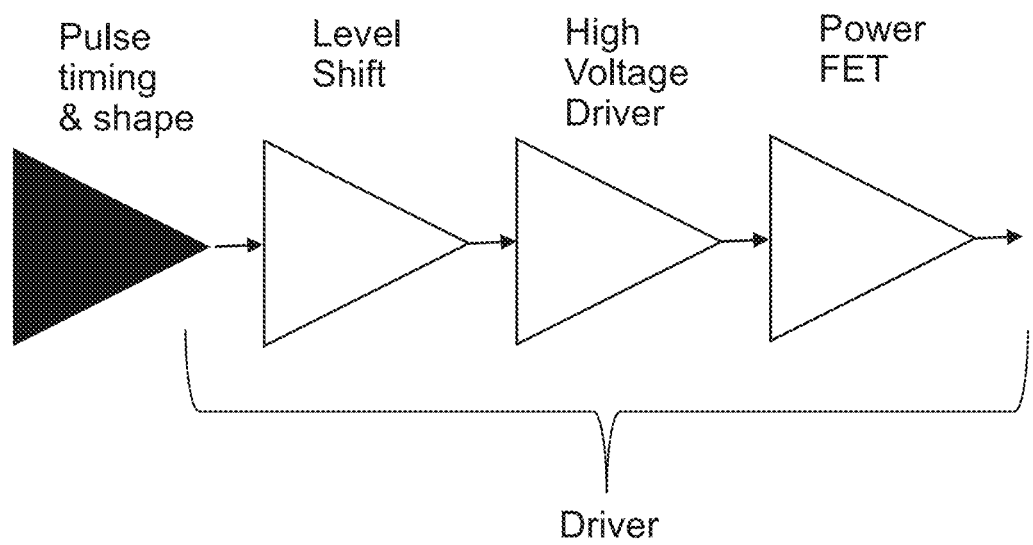
FIG. 49 is a block diagram of the electrical subunit, according to come embodiments of the present invention.
Figure 50:
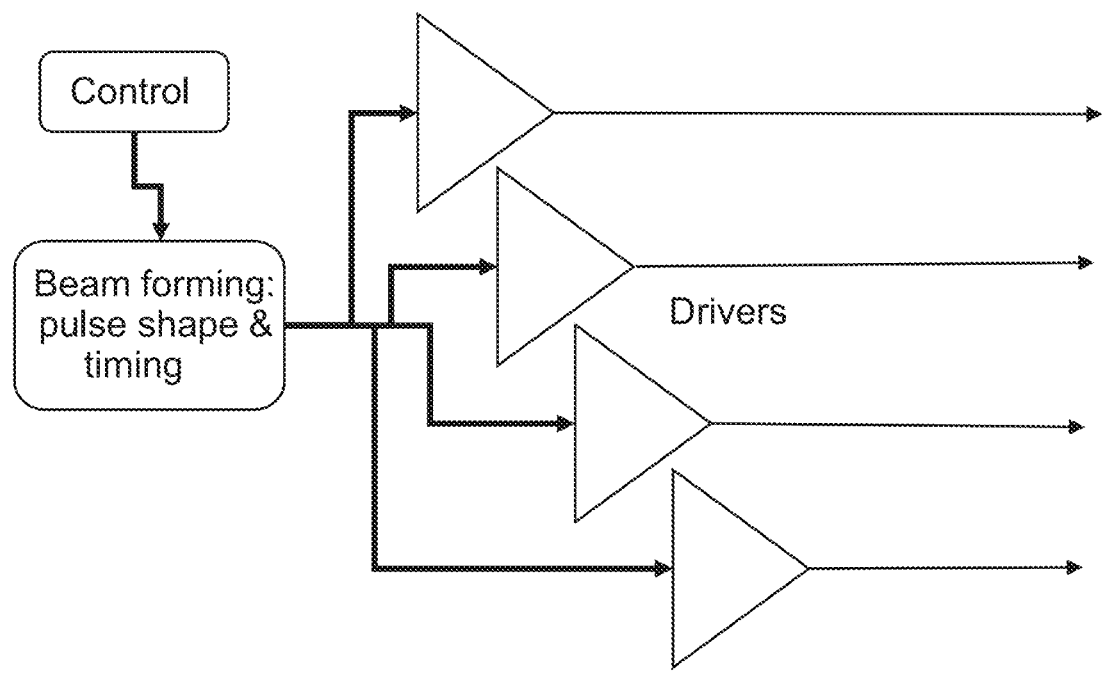
FIG. 50 is a schematic representation of the circuit, according to come embodiments of the present invention.
Figure 51:
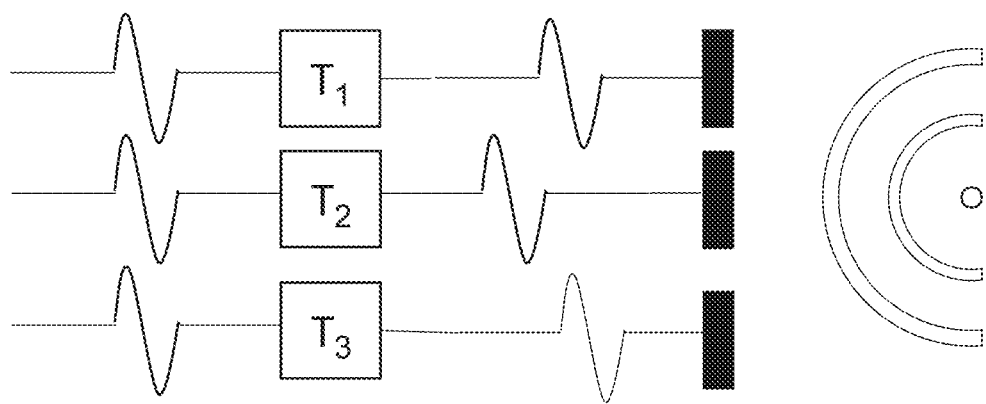
FIG. 51 is a schematic representation of the signals generated by the circuit in FIG. 50, according to come embodiments of the present invention.

A block diagram of the electrical subunit is provided in FIG. 49. In some embodiments, the electrical signal subunit is capable of generating signals in order to generate a bream former. In some embodiments, one way of implementing this is by generating a pulse train that arrives at different transducers with different delays. In some embodiments, the delay between one transducer and the next generates a phase shift that translates into a skewed beam. In some embodiments, the signals generated by the circuit depicted in FIG. 50 are provided in FIG. 51. Referring to FIG. 51, in some embodiments, by using three delays $T_1$, $T_2$ and $T_3$ the ultrasonic pulse from the different transducers are relatively delayed. In some embodiments, this brings the waveforms emitted from the transducers to constructively interfere at the target focus point.

Type 4 System

Background

In some embodiments, systems types 1 through 3 were systems where the attachment of the transducer subunit and the acoustic coupling sub unit was mainly via an adhesive patch, a belt or a corset. In this exemplary system we would elaborate more on various alternatives for this section of the system.

In some embodiments, the system is "wearable". In some embodiments, this mean that the patient can move from place to place while the system is still attached to the body. In some embodiments, the operation of the system while the patient is walking or performing various tasks is at the discretion of the patient or the system and can be determined.

In some embodiments, the system is "non-wearable". In some embodiments, it is placed on or is embedded in another piece of furniture such as a bed, sofa, couch, and chair. In some embodiments, when the patient leaves this furniture the system remains there and is not attached to the patient.

Type 4 Key Parameters

In some embodiments, the system comprises a disposable part that includes the system parts that are in touch with the human body. In some embodiments, the system comprises a transducer subunit that acoustically connect to the disposable part.

Block Diagram

Figure 52:
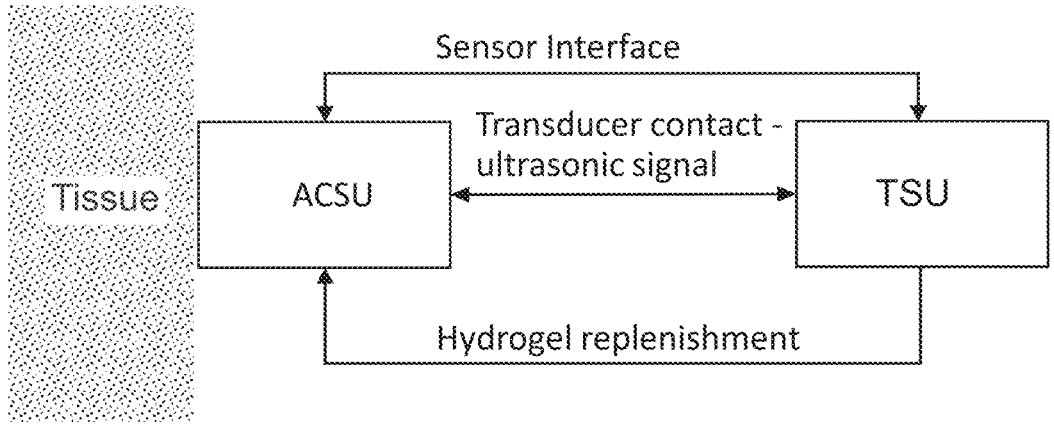
FIG. 52 is a block diagram of interfaces between the ACSU and the TSU, according to come embodiments of the present invention.

In some embodiments, there are possible a number of interfaces between the ACSU and the TSU. The ACSU has a number of characteristics: as shown, for example, in the block diagram in FIG. 52:

In some embodiments, the ACSU is acoustically transparent at the vicinity of the transducers. In some embodiments, the ACSU provides a boundary between the patient and the equipment. In some embodiments, the ACSU optionally comprises sensors that need human contact.

Embodiment for a Supine Treatment System

Figure 53:
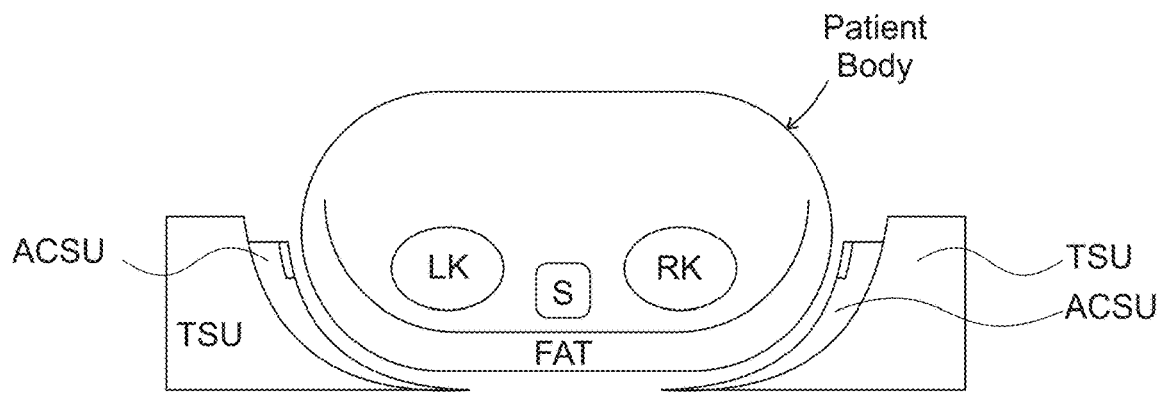
FIG. 53 is a schematic representation of a system for a patient in supine position, according to come embodiments of the present invention.

The system for a patient in supine position is described, for example, in FIG. 53.

This is a transverse view. A TSU on the right treats the right kidney (RK) and a TSU on the left treats the left kidney (LK). In some embodiments, between the TSU and the patient's skin there is an ACSU. The spine is marked with an S, near the back of the patient.

In some embodiments, the ACSU provides a sterile boundary between patient and equipment. In some embodiments, the equipment can be used many times for different patients. In some embodiments, patient fluids and wounds do not reach the treatment system.

In some embodiments, the ACSU provides a transparent acoustic window between the transducer that is located inside the TSU and the patient.

In some embodiments, the adjustment of the acoustic beam radiating from the TSU towards the kidney can be of various mechanisms according to other embodiments described in other chapters. For example: fixed mechanical adjustment; mechanical movement of the transducer inside the TSU to direct the beam to various directions; mechanical movement of the transducer element such as a lens or reflector inside the TSU to direct the beam to various directions; electrical steering of beam by using multiple transducers in an array; and movement of the kidneys themselves by an up down movement of the patient's diaphragm. In some embodiments, a combination of two or more of the above.

Design of the ACSU

Figure 54:
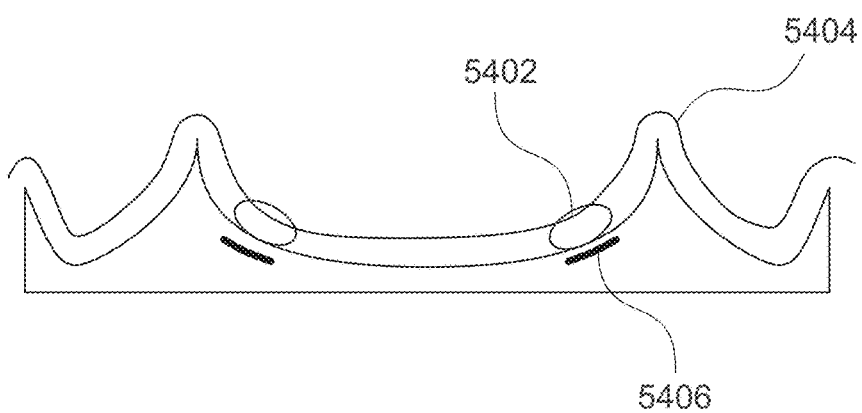
FIG. 54 is a schematic representation of an ACSU, according to come embodiments of the present invention.

In some embodiments, the ACSU needs to be acoustically transparent only near the transducers. However, the sterile separation function between the patient and the equipment may require significantly larger foils. In some embodiments, the two functions may be combined in a special foil that has two specially design acoustic windows at the desired locations marked 5402 in FIG. 54 and a non-acoustically transparent foil at all other locations. In some embodiments, the attachment of the window 5402 and non-window 5404 may be performed in advance or during the actual usage of the system. The window is positioned over the transducers 5406, which are embedded inside of the TSU. In some embodiments, the window 5402 may be covered during production with a thin cover, with stickers covering the hydrogel layer, or a silicone layer, in order to keep the acoustically transparent material when in stock.

Design of a Supine Position System

Figure 55A:
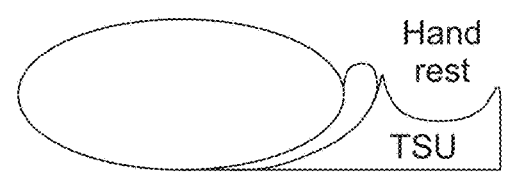
FIG. 55A is a schematic representation of the ACSU located between the patient and the TSU, according to come embodiments of the present invention.

In some embodiments, the human factor is key importance in the design of the devices. Since the system is used for an extended period of time, the patient should need to be comfortable. Usually, the patient hands are placed along the body on the mattress. In FIG. 55a, a special location to place the hand is provided on the side of the body, so the patient's hand shall not be too far and not to close to the body. In some embodiments, this distance allows for the placement of the transducers and electronics and power circuits.

In FIG. 55a, the ACSU is located between the patient and the TSU. In some embodiments, potentially better isolation of the patient from the equipment is achieved when the ACSU is placed behind the patient's back as well (FIG. 55c) or also on top of the TSU (FIG. 55E) to provide ample isolation.

Figure 55B:
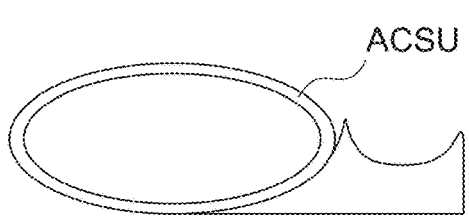
FIG. 55B is a schematic representation of the ACSU that circles the patient like a belt, according to come embodiments of the present invention.
Figure 55C:
FIG. 55C is a schematic representation of the ACSU placed behind the patient's back, according to come embodiments of the present invention.

FIG. 55b shows an embodiment where the ACSU circles the patient like a belt. In some embodiments, this allows the patient to move with the ACSU while attending to his/her needs at the treatment room, without the need to move the TSU around.

Figure 55D:
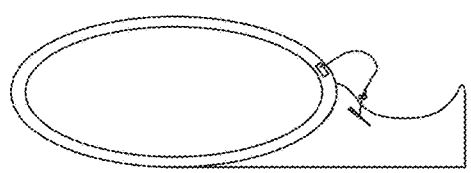
FIG. 55D is a schematic representation of the integration of sensors into the ACSU, according to come embodiments of the present invention.
Figure 55E:
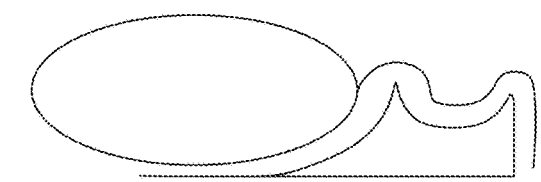
FIG. 55E is a schematic representation of the integration of sensors into the ACSU, according to come embodiments of the present invention.

FIG. 55d shows the integration of sensors into the ACSU. In some embodiments, the sensors are connected to the TSU (or any other subunit of the system) with a cable. In some embodiments, the sensors, which are in close proximity to the patient or in contact with the patient can be used to sense variable parameters relevant to the treatment and provided in further detail in other chapters. In some embodiments, the sensors may include: ECG sensors, sensors to track breathing (such as SpO2, microphone, EMG), Hemodynamic sensors (such as pulse and pulse rate), pressure sensors. Ultrasound Doppler Effect based hemodynamic sensor, infrared sensor, sensors that measure kidney functionality, chemicals sensors in urine (Urea, creatinine, proteins, Ca, Na, K, and Cl), under-skin chemical sensors, wearable chemicals sensors, oxygen levels in kidney sensors, catheter based chemical sensors, blood pressure, vascular stiffness and/or water intake.

Design of a Transducer Holder

In some embodiments, the transducer is placed close to the human skin. In some embodiments, the beam direction may be performed mechanically, electronically or both.

Figure 56A:
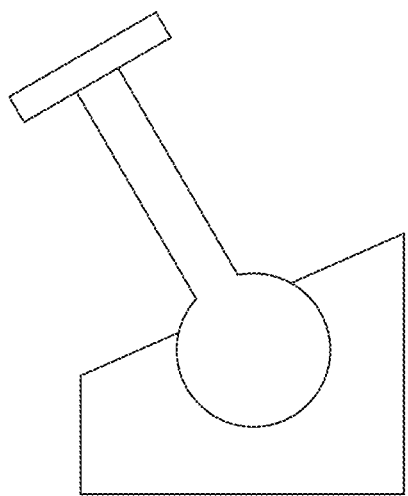
FIG. 56A is a schematic representation of a mechanism of a transducer holder with two degrees of freedom, according to come embodiments of the present invention.

In FIG. 56a, a mechanism with two degrees of freedom is shown, allowing the transducer to point at the desired location and desired angle at the patient's skin.

Figure 56B:
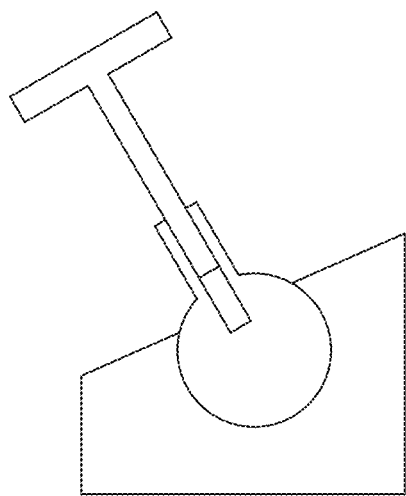
FIG. 56B is a schematic representation of a mechanism of a transducer holder with another degree of freedom, according to come embodiments of the present invention.

FIG. 56b adds yet another degree of freedom, allowing for extending the length of the rod connecting the fixture base with the transducer.

Figure 56C:
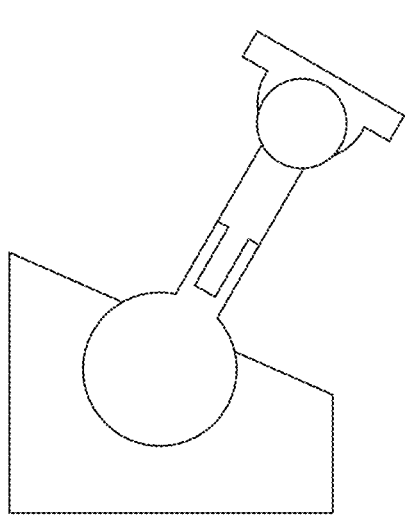
FIG. 56C is a schematic representation of a two-ball mechanism, according to come embodiments of the present invention.

FIG. 56c shows two-ball mechanism. In some embodiments, this allows to move the transducer to any radius elevation and azimuth angle, as well as to adapt to the angle of the skin. In some embodiments, this is useful when the transducer array needs to be parallel to the skin, and perform electronic steering. In some embodiments, the electronic steering can be in one dimension (such as the one perform in a linear phased array transducer array) or in two dimensions (such as when the transducer array is a matrix).

Figure 56D:
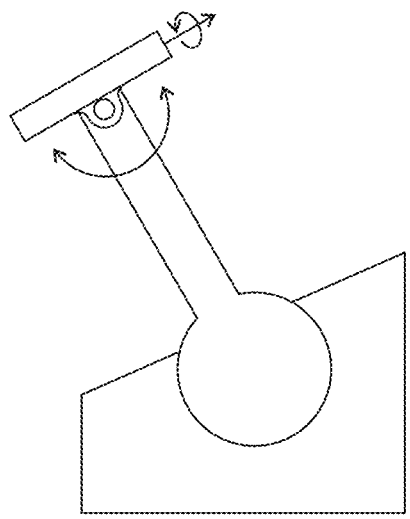
FIG. 56D is a schematic representation of an implementation with a linear 1 dimensional array, according to come embodiments of the present invention.
Figure 57:
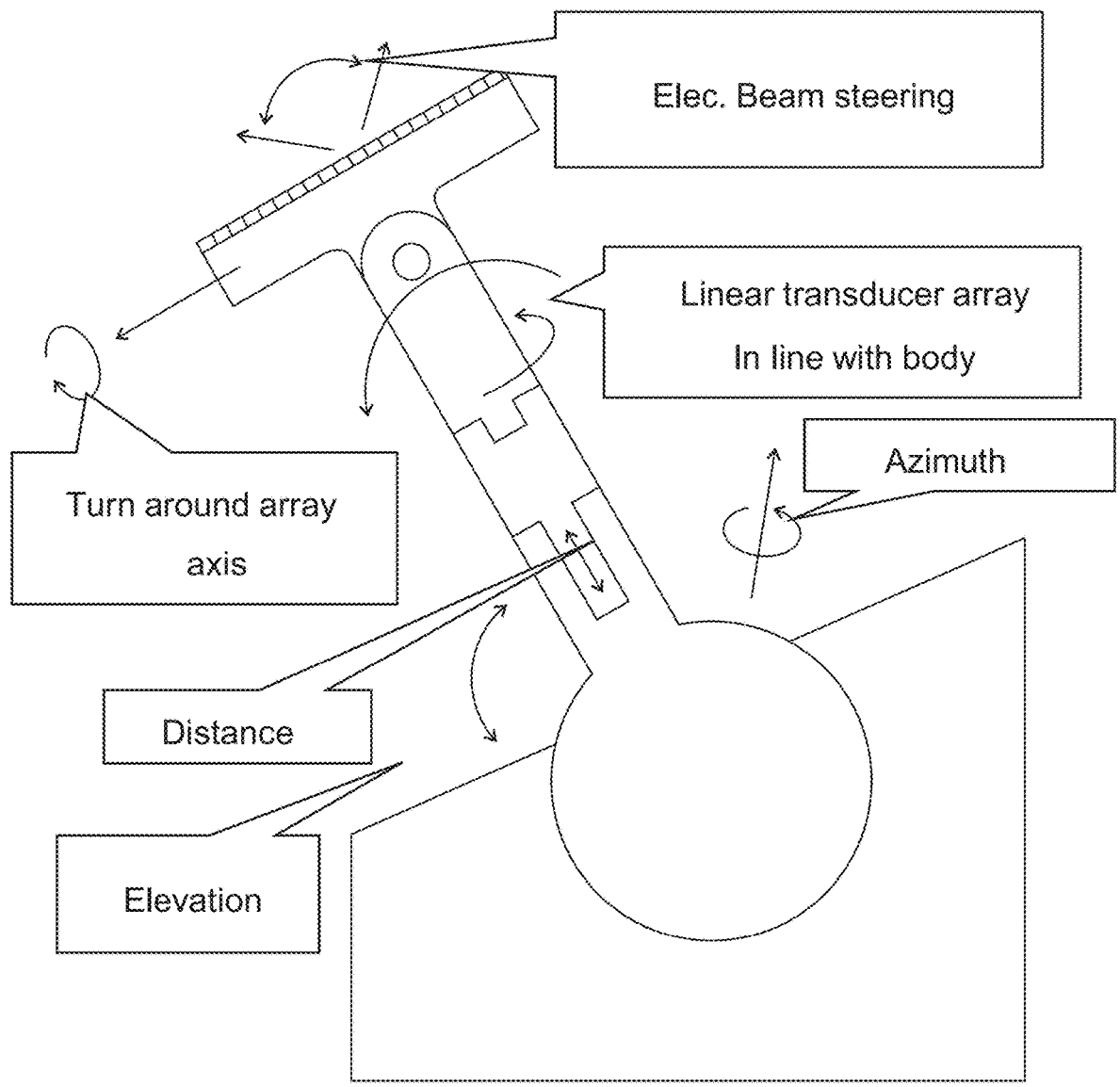
FIG. 57 is a schematic representation of a mechanism of a transducer holder with another degree of freedom, according to come embodiments of the present invention.

FIG. 56d shows an implementation with a linear 1 dimensional array. In some embodiments, the fixture provides close contact of the transducer array with the patient skin with 5 degrees of freedom (distance elevation and azimuth at the base, and two angles at the transducer). In some embodiments, the sixth degree of freedom is achieved by turning the linear transducer array along the major array axis. In some embodiments, the seventh degree of freedom is achieved by electronically steering the signal. This is also shown in FIG. 57.

Keeping the ACSU Wet

In some embodiments, the ACSU needs to provide acoustic transparency at all times. In some embodiments, acoustic gel that is used for ultrasonic diagnostic imaging devices tends to dissolve in the skin after some time, increasing the attenuation and reflection at the transducer-skin boundary.

In some embodiments, long-term transparency needs to be maintained for periods that are significantly longer than diagnostic imaging sessions, for instance for 6 hours, or for instance for 24 hours. In some embodiments, this can be done by a number of means, as will be explained below.

Figure 58A:
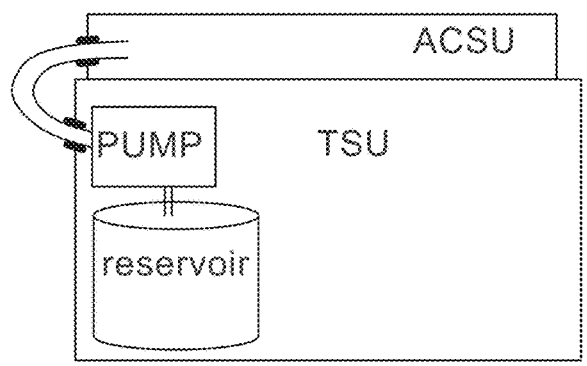
FIG. 58A is a schematic representation of a mechanism where the ACSU has a permeable membrane, according to come embodiments of the present invention.

In FIG. 58a, it is shown a mechanism where the ACSU has a permeable membrane. In some embodiments, the membrane allows for water to move across it along a pressure gradient. In some embodiments, as long as the pressure inside the ACSU is higher than the pressure outside, water molecules shall keep moving out and keep the transducer surface as well as the skin wet and acoustically transparent. In some embodiments, the extra pressure is achieved in the system depicted in FIG. 58a by pumping material into the ACSU. In some embodiments, the ACSU has a pump interface (that can be built as a shunt) that allows for a pressurized material entry.

In some embodiments, the TSU includes a pump and a reservoir, which are connected with a hose to the ACSU.

Figure 58B:
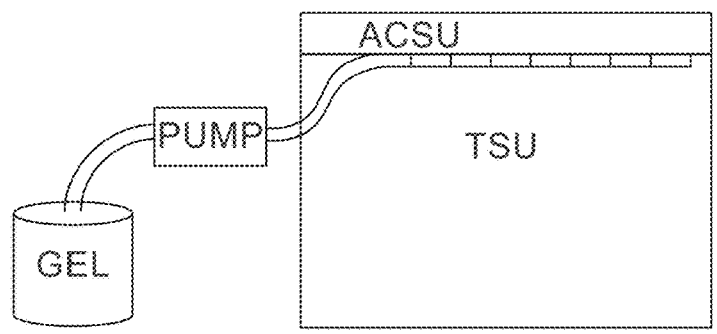
FIG. 58B is a schematic representation of a mechanism where multiple needles provide the extra pressure to the ACSU, according to come embodiments of the present invention.

In some embodiments, the interface to the ACSU can also be built with alternative design such as in FIG. 58b, where multiple needles provide the extra pressure to the ACSU, pumping acoustic transparent material (water, gel, saline, hydrogel) to the ACSU. The ACSU acoustically transparent part may be made from hydrogel. In some embodiments, the acoustically transparent window is made of hydrophilic silicone.

In some embodiments, the material in the ACSU needs to allow efficient ultrasonic energy transfer to the body. Thus, in some embodiments, the acoustic impedance of the material should be close to the skin impedance at $1.6 \; 10^6$ kg m$^{-2}$ sec$^{-1}$.

In some embodiments, other methods for keeping the ACSU at the desired impedance and the skin wet is to use a hydrophilic membrane, or to use a long lasting hydrogel material.

Figure 59:
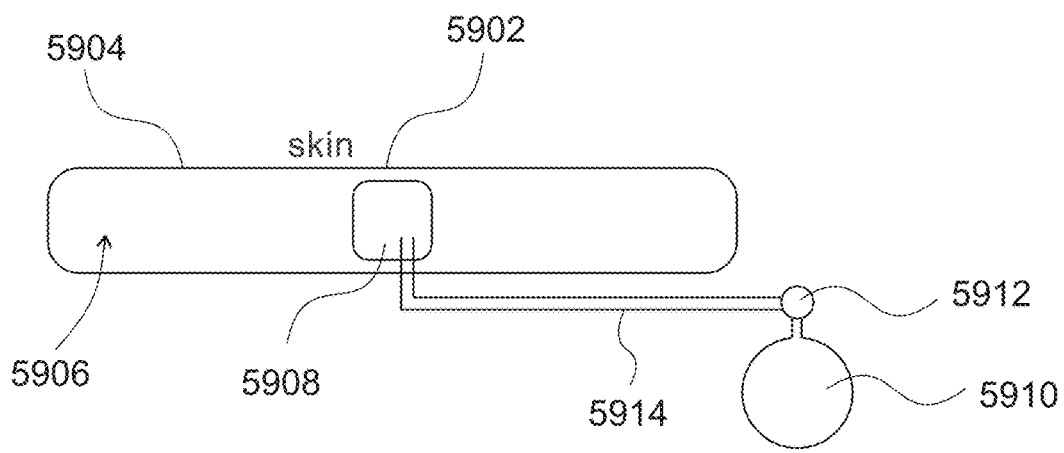
FIG. 59 is a schematic representation of an ACSU mechanism that is attached to the patient's skin, according to come embodiments of the present invention.

FIG. 59 shows an ACSU mechanism that is attached to the patient's skin 5902. In some embodiments, a porous membrane 5904 encloses gel 5906. In some embodiments, if the skin absorbs the water and dries out, water from the chamber 5908 may exit the membrane and replace the absorbed water. In some embodiments, the chamber 5908 should be pressurized for this.

An example of letting the chamber be pressurized mechanically is by having an internal gas chamber 5910 adjacent or inside the gel chamber. In some embodiments, the gas chamber is placed in this example in the center of the mat, where the ACSU is adjacent to the spine, so gel content is not important there. In some embodiments, an external mechanical air pump 5910 is connected via a uni-directional valve 5912 and a tube 5914 to the gas chamber 5908. In some embodiments, by filling extra air into the chamber, the pressure of the gel compartment is kept high, making sure that there is constant flow of water outside towards the skin.

Monitoring the ACSU

In some embodiments, in order to track the acoustic coupling to the skin the reflected power from the transducer can be measured. In some embodiments, another mechanism to track the acoustic energy that enters the body is by measuring from side to side. In some embodiments, the transmitter of the left kidney transmits while a transducer on the right side measures the incoming signal power. In some embodiments, the sensor enables the detection of decrease in ultrasonic power for any reason.

Figure 60:
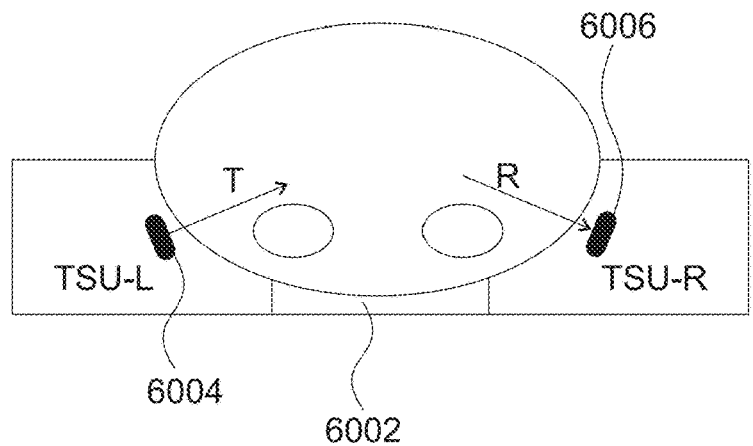
FIG. 60 is a schematic representation of a method for monitoring the ACSU, according to come embodiments of the present invention.

This scheme is shown in FIG. 60. In some embodiments, the unit includes an acoustic isolation material 6002 adapted to avoid direct acoustic coupling between the transmitter and receiver via the ACSU itself. In some embodiments, this guarantees that the measured signal is actually the signal that moved through the patient's body and not via another external path. The transmitting transducer 6004 transmits an ultrasonic signal in the direction marked by T. The signal or its reflections are picked up by the receiving transducer 6006 in a direction marked by R.

Figure 61:
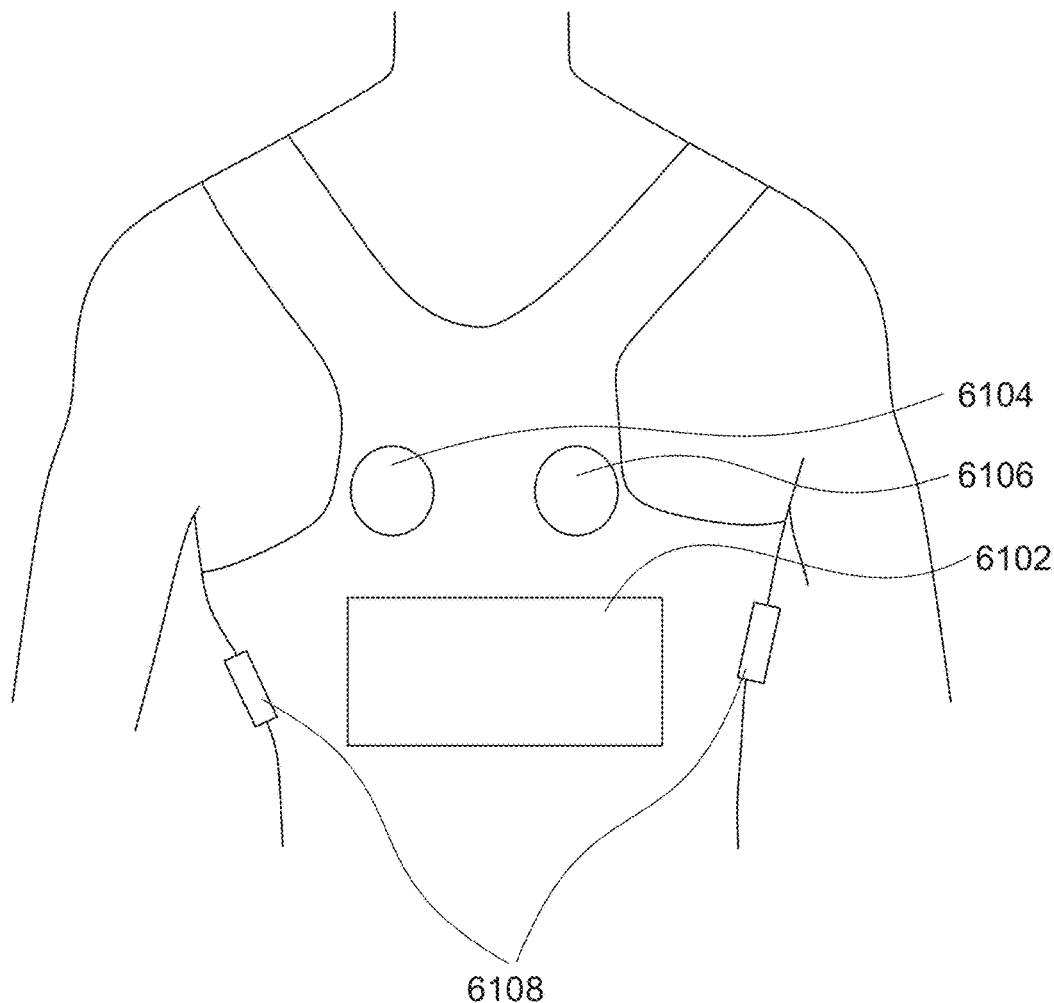
FIG. 61 is a schematic representation of a mechanism to monitor the absorption of the ultrasonic energy into the body, according to come embodiments of the present invention.

In some embodiments, another mechanism to monitor the absorption of the ultrasonic energy into the body is by placing receive monitoring transducers at selected locations. FIG. 61 shows 4 such locations, where the signal is transmitted to the kidney from the back 6102. In some embodiments, monitoring receive transducers are placed superior to the mat at locations 6104 and 6106. In some embodiments, these transducers measure the reflected energy that entered the body and was reflected by the intestine towards the upper back. In some embodiments, the transducers are placed inferior to the inferior lobe of the lung.

Alternatively, the received monitoring transducers can be placed at the right and left side of the rib cage above the waist 6108, picking up ultrasonic signal that came through the liver to the right distal side and through the spleen to the left distal side.

Figure 62:
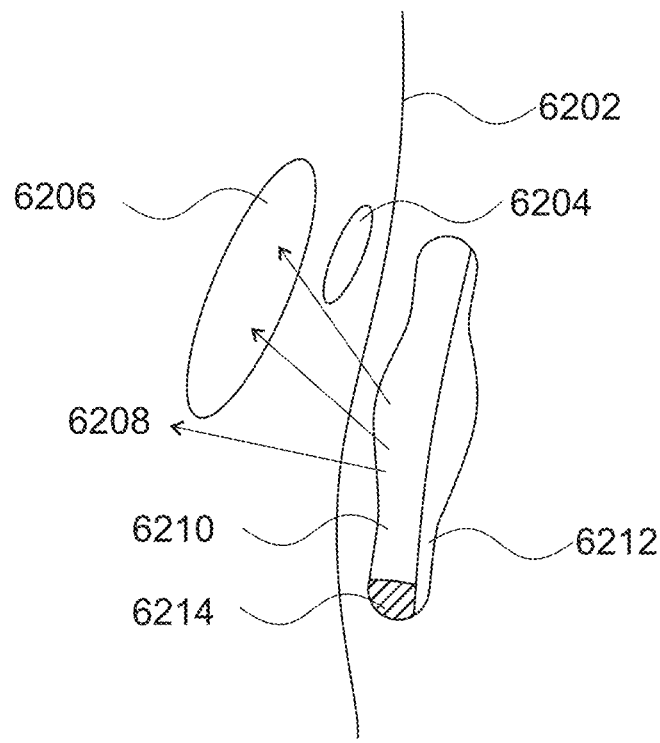
FIG. 62 is a schematic representation that summarizes the reflector manifold concept, according to come embodiments of the present invention.
Figure 63:
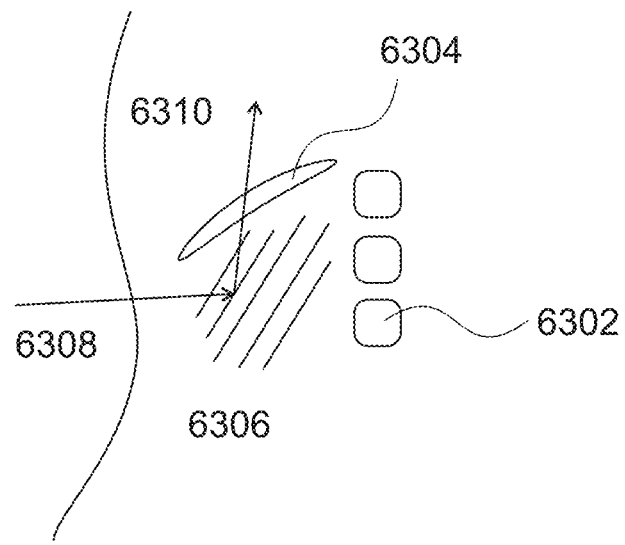
FIG. 63 is a schematic representation of a sagittal view of the reflector manifold concept, according to come embodiments of the present invention.

FIG. 62, summarizes the reflector manifold concept, in a side view. In some embodiments, an ACSU is attached to the patient's skin 6202, at the back, below the rib 6204. In some embodiments, the manifold reflects the incoming ultrasound signal towards the kidney 6206. In some embodiments, the ACSU includes a front porous membrane 6208 that allows water to exit the gel chamber 6210 and guarantee acoustic coupling to the skin. In some embodiments, the back side of the ACSU is the reflector 6212. In some embodiments, the reflector redirects the signal from its original direction (in this example a vertical direction) to a cone that is directed into the body and upwards towards the kidney portions 6206 that are above the rib 6204. In some embodiments, a pressurized chamber 6214 makes sure the gel compartment is always over pressurized A sagittal view is given in FIG. 63. In some embodiments, the spine 6302 and the rib 6304 confine the location of the manifold. In some embodiments, the grating 6306 of the manifold is shown in the direction to reflect the incoming ultrasound signal 6308 upwards 6310 and inside the body.

Figure 64:
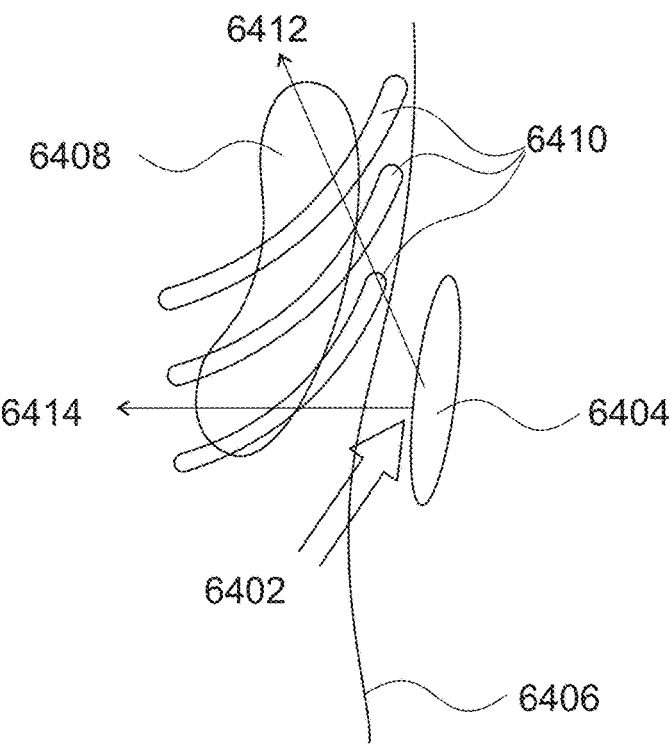
FIG. 64 is a schematic representation of an isometry view of the reflector manifold concept, according to come embodiments of the present invention.

The model is provided in isometry in FIG. 64. In some embodiments, the incoming ultrasonic signal comes from 6402 and is reflected by the manifold 6404. In some embodiments, the signal crosses the skin 6406 towards the kidney 6408 passing through the ribs 6410. In some embodiments, the deflected signal has both an upwards superior direction 6412 towards the superior lobe of the kidney and a horizontal direction 6414 towards the inferior lobe of the kidney, thus reaching maximal coverage of the kidney volume.

General Information Regarding the ACSU

In some embodiments, there are two main exemplary scenarios for the coupling component:

1. In some embodiments, the one or more transducer elements are semi-rigid, at least some of the elements having a dimeter of at least 3 mm, (optionally at least 5 mm, optionally at least 7 mm, optionally higher or lower values of mm) and located within a soft/flexible structure that conforms to the body curvatures. Therefore, in some embodiments, there is a coupling layer also to avoid pressure points in prolonged use. Also, in some embodiments, the coupling layer is not only for acoustic purposes but also for pressure distribution, and, in this case, it comprises some thickness and flexibility including compressibility (of the layer having viscous material, not compressibility of the material. For example, water is not compressible, but within a structure it can move and redistribute to allow one region to be thinner and another to be thicker), for example, with a thickness range of about 1 mm to about 1 cm, optionally higher or lower values of either mm or cm. In some embodiments, the layer does not comprise a material that is too elastic, or have an expansion limiter structure (e.g. a non-compliant film, or one or more welding points, or braiding or other structure) to control viscosity and avoid non-uniform deformations in some areas (e.g. the sides) when the patient is lying over it.

In some embodiments, the coupler comprises sensors and/or electrical measurement mechanisms along the body that faces the skin (superficially, e.g. by impedance and/or conductance and/or capacitance; e.g. every few seconds, which also requires the layer to be electrically conducting) within the coupling layer. In some embodiments, humidity measurement and/or evaluation of optical and/or acoustic transparency/absorbance/reflection is performed to determine, in real time, if there are any major deviation that require an alert/disposal-replacement-repositioning of the coupling layer/mode switch in the energy delivery/selection of active transducer elements.

In some embodiments, the layer may comprise a circuitry to evaluate the abovementioned measurements and/or timer, to indicate potential wear and tear and/or potential misalignment, and/or potential dislocation of the layer and/or or the wearable device.

2. In some embodiments, the transducer elements are by made of flexible material, e.g. PVFD (polymer), therefore, the transducer elements by themselves conform to body curvatures, and in some embodiments, the coupling layer may be made of flexible thin film, e.g. <1 mm thick.

In some embodiments, the measurement shall be of electrical continuity along the body facing the skin (superficially, e.g. by impedance and/or conductance and/or capacitance, which also require the layer to be electrically conducting), horizontal acoustic coupling, humidity measurement, or evaluation of optical and/or acoustic transparency/absorbance/reflection are performed to determine, in real time, if there are any major deviation that require an alert/disposal-replacement-repositioning of the coupling layer/mode switch in the energy delivery/selection of active transducer elements.

In some embodiments, the layer comprises a circuitry to evaluate the abovementioned measurement and/or timer, to indicate potential wear and tear and/or potential misalignment, and/or potential dislocation of the layer and/or or the wearable device.

Exemplary Design for a Supine System

In some embodiments, the supine system is relevant to a number of clinical applications, where supine position is prevalent. These clinical applications include but are not limited to:

1. Patients at risk of AKI that are after surgery. Such surgery includes cardio pulmonary bypass surgery.
2. Patients at risk of AKI due to shock, impact, burns or other conditions, that are hospitalized in an ICU and are anesthetized.
3. Patients during surgery.

Exemplary Characteristics of these Patients

In some embodiments, these patients are not expected to move. In some embodiments, covering the belly with a belt may be unattractive or risky for these patients, for instance, since they are after surgery.

In some embodiments, the treatment length may be limited by the time of their anesthesia, for example, one type of treatment and wearable component while anesthetized and then the treatment may be continued in a potentially other form suitable for an awake patient.

In some embodiments, the patients may be heavily monitored, and some measurements may be fed to the prolonged renal therapy device (as feedback and/or control), for example:

Respiration: rate—can affect ON/OFF decision, timing—e.g. can affect time of energy delivery ECG/PPG: HR/arrhythmia—can affect ON/OFF decision, or timing of systole/diastole—e.g. can affect time of energy delivery Blood electrolytes—may affect ON/OFF decision and/or protocol of energy delivery, for example, changes in K levels, Ca levels, Na levels Blood biomarkers—may affect ON/OFF decision and/or protocol of energy delivery, for example, Creatinine, Cystatin-C Urine electrolytes—may affect ON/OFF decision and/or protocol of energy delivery, for example, changes in K levels, Ca levels, Na levels Urine biomarkers—may affect ON/OFF decision and/or protocol of energy delivery, for example, Creatinine, Cystatin-C, KIM-1, NGAL, TIMP-2 and IGFBP-7

Urine output—may affect ON/OFF decision and/or protocol of energy delivery, for example, total urine output (e.g. cumulative over several hours), real time rate (e.g. changes in output over period of several minutes/less than an hour). These can be fed into the device manually, or using a urine output measurement system Bed/Chair sensors or telemetry, e.g. body weight It should be noted that it may be possible that the same patient will use the system and wearable throughout various "mobilization" stages, e.g. while anesthetized/immobile using one type of disposable coupling unit (e.g using a sticker, and/or energy delivered more from the sides), and while awake with another type of disposable coupling unit (e.g. using a wearable belt).

In another embodiment, for the clinical application of hospitalized patients that suffered heart failure, where improved renal function is desired, the length of the treatment may extend to 24 hours, or 48 hours or 72 hours, optionally higher or lower values of hours.

In some embodiments, these patients are mobile. Many such patients prefer to be in the supine position due to the pulmonary edema they may have.

For this application, the preferred configuration of the system is:

A lightweight system;

A wearable system, which enables treatment while the patient is reclining, or sitting, or optionally moving around;

A system that enables simple removal and re-application without a nurse intervention;

A system with internal sensors while avoiding wired connections to other monitoring systems;

A system that receive inputs (preferably wirelessly) from other monitoring systems;

A system that is not integrated into furniture;

A system comprising a disposable element in touch with the patient to allow simple transfer of the system from patient to patient in a clinic set-up, while maintaining proper hygiene and/or disinfection.

In some embodiments, the system is optimized for the clinical application of home use, by CKD patients. In this case, the unit is being used by a single patient.

In some embodiments, the disposable element is needed to guarantee ultrasonic acoustic transparency, while protecting the patient's skin from maceration, and irritation that can be caused by the lengthy treatment. It is preferable that the coupling component be used for up to several hours, e.g. up to 6, up to 12, up to 18 or up to 24 hours or up to 72 hours, and then replaced, whether immediately or after at least 3 hours, or after at least 6 hours. In an exemplary embodiment, the disposable coupling component is used during daytime, taken off during nighttime, and replaced on next day. In an exemplary embodiment, the disposable coupling component is used for about 12-18 hours and taken off for at least 6 hours, and then a replaced again for use in the next day.

The system should be lightweight.

In some embodiments, the system comprises the ability to identify the kidney location and the acoustical coupling to the patient's body, without the use of trained medical practitioners. In some embodiments, the system includes:

Garment: a belt/corset/vest like system. Possibility for self-application

Sensing: Ability to independently detect the kidneys orientation by utilizing back access, multiple transducers, ultrasonic detection of the ribs and spine, optionally Doppler detection of the renal artery, pressure and contact monitoring.

In some embodiments, the system is optimized for the clinical application of Ambulance use. In this application, some patients are at high risk for AKI. These include history of CKD, sepsis, shock, blood loss, cardiac failure, hypothermia, trauma, severe dehydration, use of contrast media, nephrotoxic materials, and more. In some embodiments, the duration of the treatment is limited to the time the patient travels from pick up site to the arrival at the medical center.

A system optimized for this application comprises:

Garment: Adhesive based. With the complexity of patient conditions in this setting, the device should have a minimal impact on other treatments that the patient may require.

Power: comprising a battery and/or connected to the local Ambulance power.

Disposable: the element in touch with the patient is disposable. Optionally, the complete system, including the transducers, may be disposables as well (due to the rough environment and potential cleaning and disinfection challenges).

Sensing: Minimal sensing required, where the main issue is the actual contact with the skin, to indicate if treatment is delivered to the patient or not.

In some embodiments, the system is optimized for Renal Replacement therapy RRT.

Garment: Belt based. The patients have limited mobility. Elements can also be integrated into the RRT furniture.

Power: battery power and/or local power.

Disposable: the element in touch with the patient is disposable. The system is shared among many different patients.

Sensing: feedback for the RRT device can assist in directing the duration and intensity of the prolonged ultrasound therapy Design for a Non-Supine System In another embodiment of the system, the patient is sitting. In some embodiments, the sitting posture is advantageous to various patients, especially since the treatment may be lengthy and take some hours. In some embodiments, patients, and especially congested-heart failure (CHF) patients, prefer the sitting position.

Figure 65A:
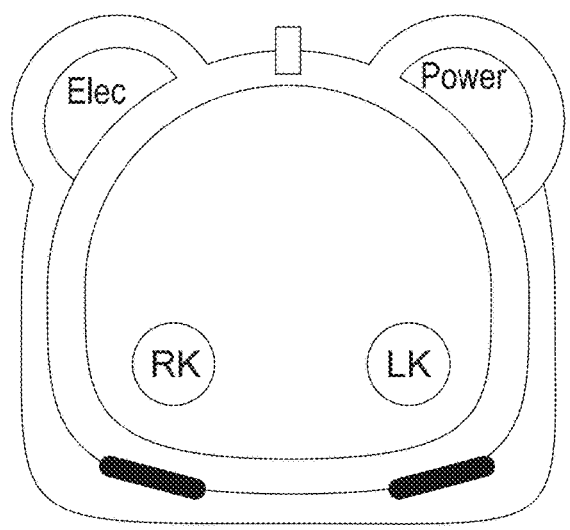
FIGS. 65A-B are respectively a transverse view and a general display of a patient in the sitting position, according to come embodiments of the present invention.

In FIG. 65a, a transverse view of the patient from above is shown. In some embodiments, the system is embedded into some type of corset. In some embodiments, the transducers are at the back, near the access points to the kidneys. In some embodiments, the electronics, and power are at the front. In some embodiments, by placing the electronic at the front one achieves a number of goals, for example, no interference with the sitting position from and back and the side, where typically a chair or sofa would not accommodate an extra system volume; a low thickness design of transducers; the unit shall not interfere with the patient's hands.

Figure 65B:
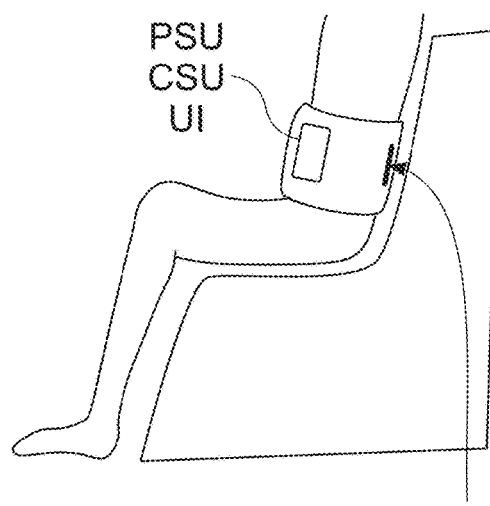

In some embodiments, the ACSU is placed round the corset on the inner side. In some embodiments, the corset closes in front, and provides the necessary pressure between the transducers and the patient's back. FIG. 65b shows a general display of how the system looks when the patient is sitting in the chair or sofa of his or her choice.

Figure 66:
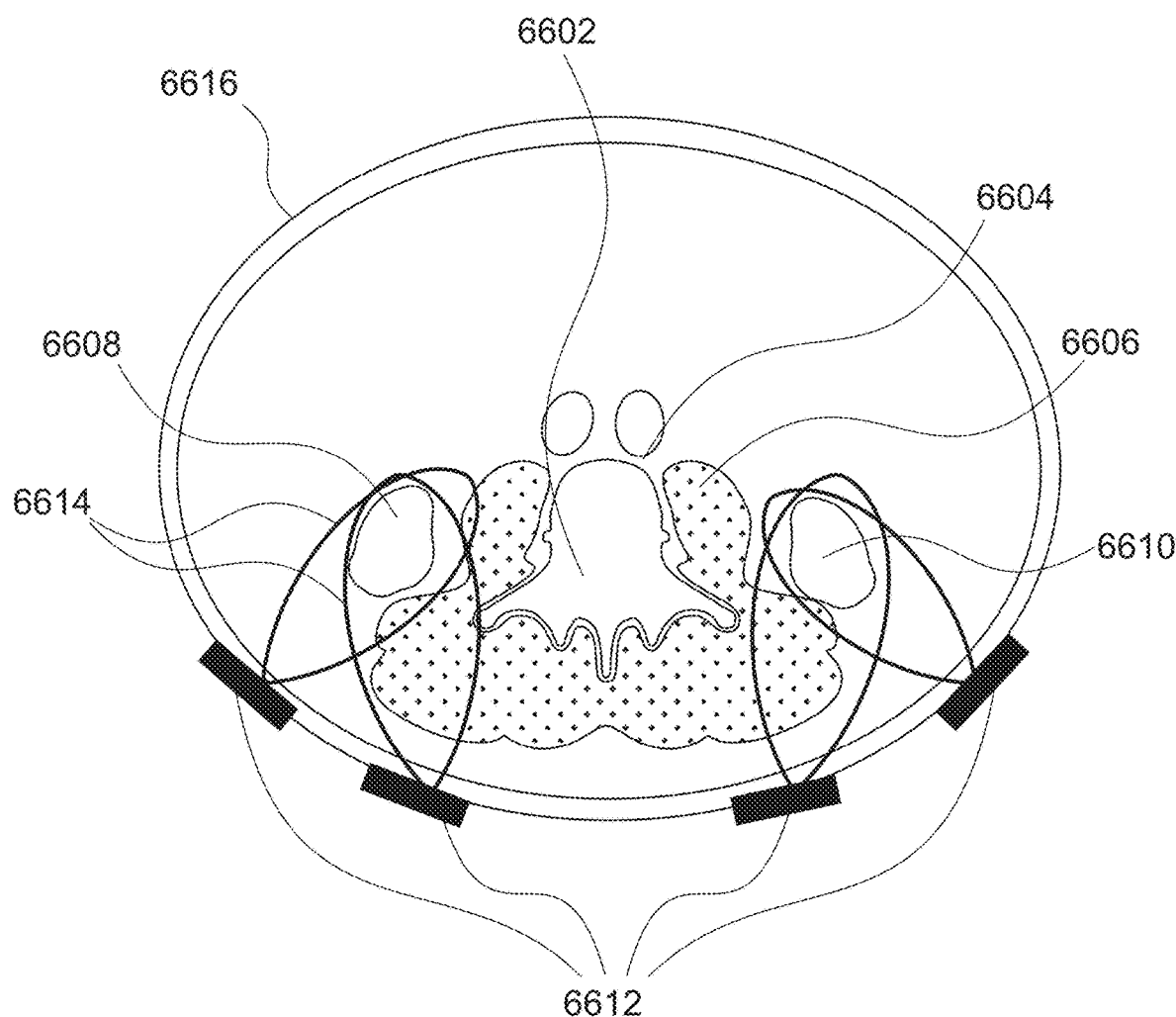
FIG. 66 is a schematic representation of an ACSU that closes round the patient's body, according to come embodiments of the present invention.

In FIG. 66, we provide another example for the ACSU that closes round the patient's body, providing this way the pressure needed to acoustically couple the transducers to the skin. In this transverse view, the spine 6602 and the abdominal aorta 6604 are shown. The spine is surrounded by the layer of muscle 6606. To the left and right of the muscle are the left kidney 6608 and right kidney 6610. The transducers 6612 connect to the ACSU at the back. The ACSU guarantees the acoustic coupling of the transducers to the skin. The ultrasonic lobes 6614 emitted from the transducers reach the kidneys. The ACSU 6616 surrounds the body, enabling quick garment putting on and off.

Ultrasonic Access Between the Ribs

Figure 67:
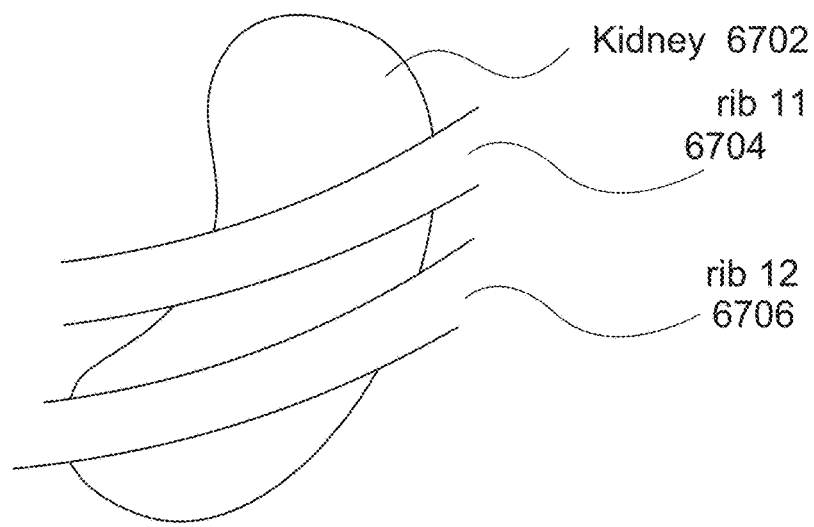
FIG. 67 is a schematic representation of a side view of the relationship of the ribs and the kidney, according to come embodiments of the present invention.

Ultrasonic access between the ribs, for therapeutic purposes is a new paradigm. There is a need to transfer energy to the soft tissue without exposing the ribs over a limit. From a side view the relationship of the ribs and the kidney look like in FIG. 67. This is a sagittal view. In the figure the kidney 6702 is shown behind rib 11 6704 and rib 12 6706. Rib 10 is not shown.

One exemplary system is designed to transfer energy between ribs 11 and 12. Transferring between any other pair of ribs is of course possible as well.

Figure 68:
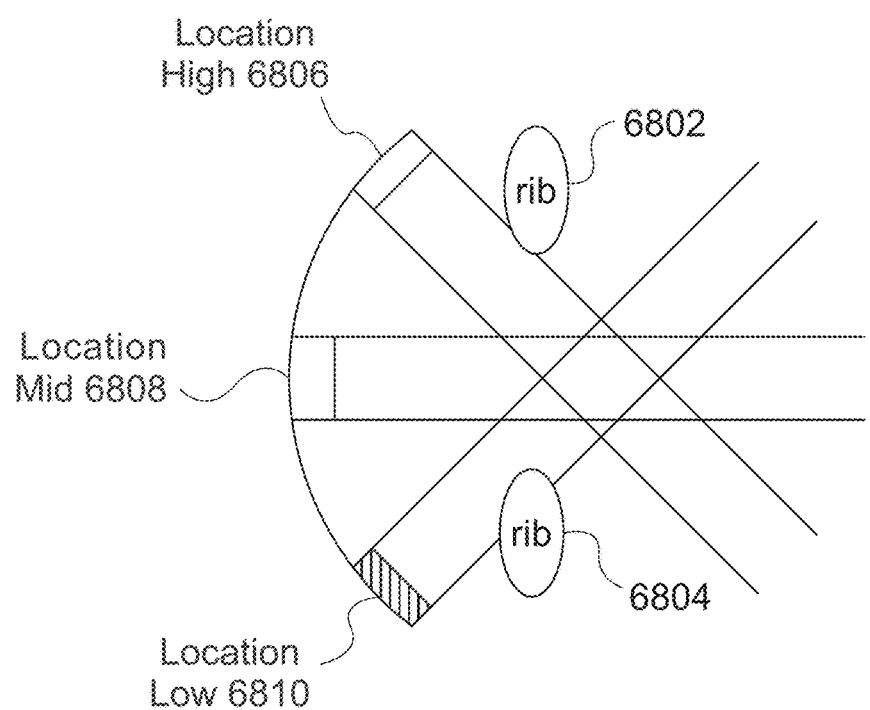
FIG. 68 is a schematic representation of a method of exposure of the kidney, according to come embodiments of the present invention.

In some embodiments, exposure of the kidney to the ultrasonic signal is achieved by a design as in FIG. 68. In some embodiments, a moving transducer (which may be implemented as a transducer array) is moving on a track. In some embodiments, the track enables the transducer to point the ultrasonic beam through the acoustic window between rib 11 6802 and rib 12 6804. In some embodiments, when the transducer is at the top position location high 6806 it can treat the lower part of the kidney. In some embodiments, when the transducer is at location mid 6808 the beam treats the middle section of the kidney and when the transducer is positioned in location low 6810 is can treat the top part of the kidney.

Figure 69:
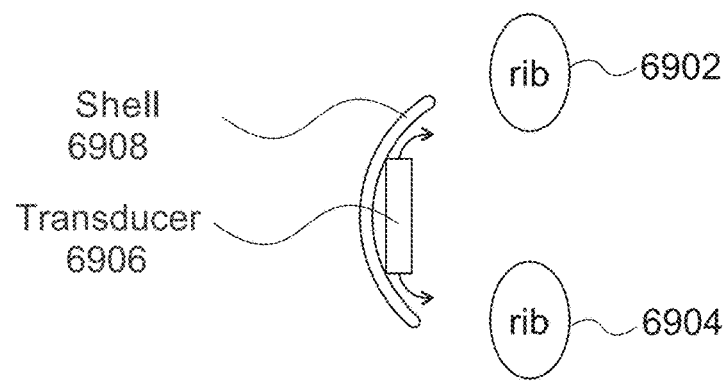
FIG. 69 is a schematic representation of a method of exposure of the kidney, according to come embodiments of the present invention.

In some embodiments, one example way to implement this system is by having the transducer move on a shell. In some embodiments, the shell form an arc, designed to have its focal point between the ribs. In some embodiments, when the ribs move, the shell needs to move with the ribs. In FIG. 69, rib 11 6902 and rib 12 6904 are shown. In some embodiments, the transducer 6906 is moving on a shell 6908 designed such that its circular center is between the ribs.

In some embodiments, for individual patients, the shell design may be different due to under-skin fat. This design can be fit to between the ribs operation from the back or from the side.

Figure 70:
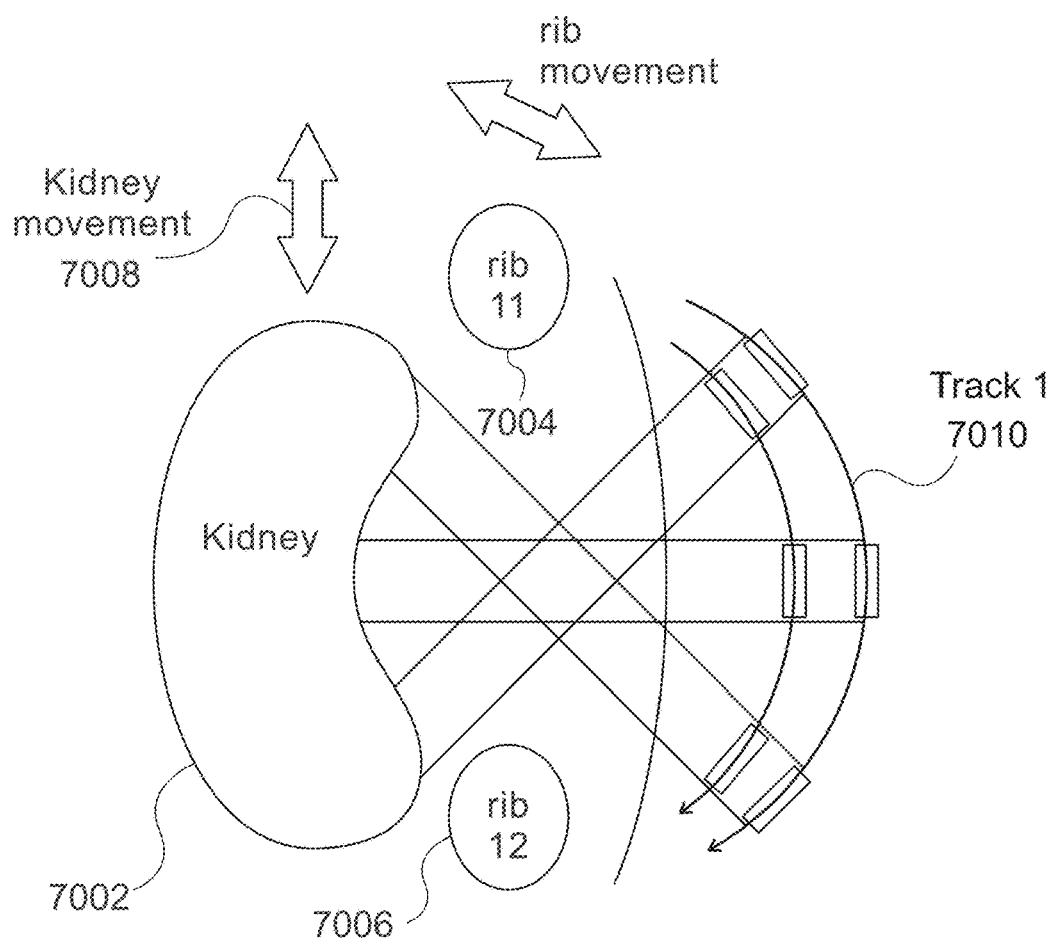
FIG. 70 is a schematic representation of an equipment to transfer ultrasound between the ribs, according to come embodiments of the present invention.

The equipment to transfer ultrasound between the ribs is described in FIG. 70. In this embodiment, we place the transducers at the side of the abdomen above the waist and this is a frontal view. The left kidney 7002 is shown medial to the rib 11 7004 and rib 12 7006. The kidney moves up and down 7008 with breathing due to diaphragm movement. The ribs move with the rest of the rib cage as shown in the figure.

To the right is the fixture that holds the transducer. In order to transmit between the ribs the transducer needs to move along a track, as shown in track 7010. There are a number of tracks that can allow such functionality.

In some embodiments, the devised system may mechanically adjust the track in order to guarantee efficient movement. In some embodiments, the transducer shall transmit a signal only when the beam is not reflected by the ribs. In some embodiments, at the optimal position the arc on which the transducer is moving has its center exactly between the ribs. In some embodiments, the arc can be modified according to the radius. In some embodiments, starting with a radius that is equal to the distance to the skin ($r_{skin}$) and increasing gradually the radius value, the system measures the length of the arc that transmits into the body with a low ultrasonic reflection. In some embodiments, the length of this arc is denoted as l(r) where r is the selected radius. As long as the beam enters between the ribs the reflection shall be small. In some embodiments, the selected radius $r_{ribs}$ is the distance providing maximum arc length, which is calculated as:

$$r_{ribs} = \underset{r>r_{skin}}{\operatorname{argmax}} \, l(r)$$

Figure 71:
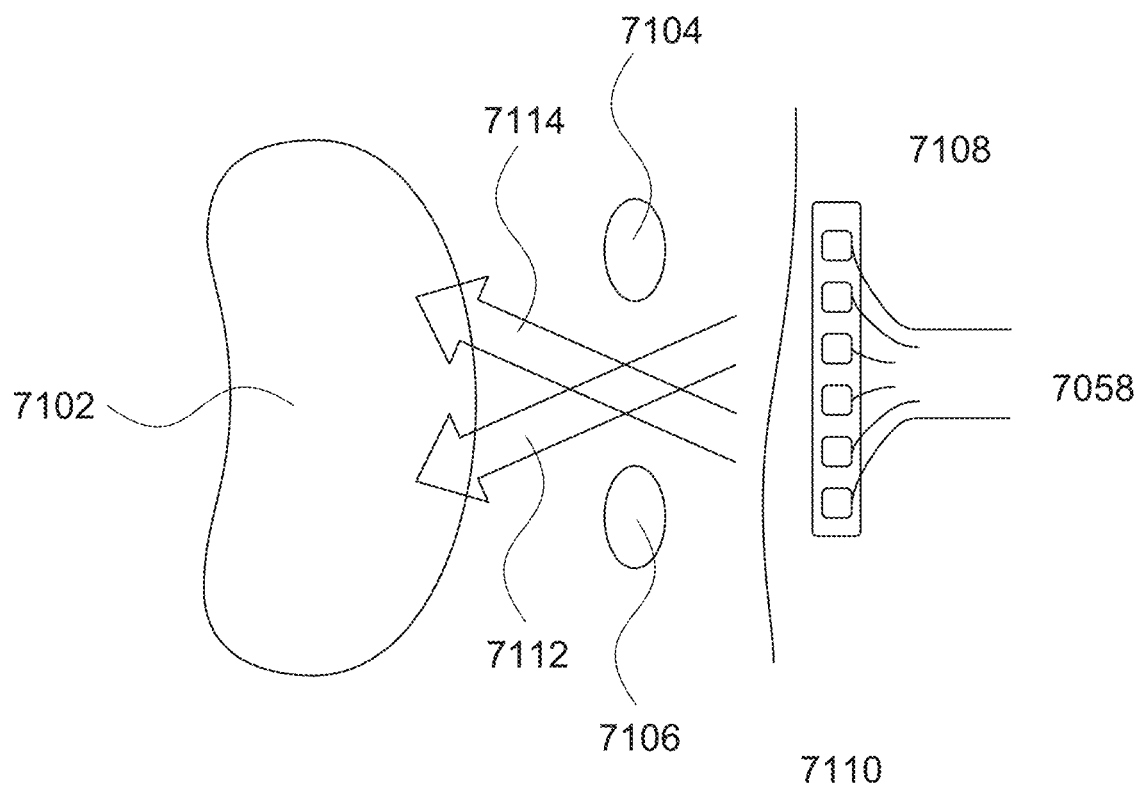
FIG. 71 is a schematic representation of a flatter design using a transducer array with bream forming, according to come embodiments of the present invention.

In some embodiments, the same design can be implemented much flatter design using a transducer array with bream forming, as in FIG. 71. In this figure, the kidney 7102 needs to be treated behind the ribs 7104 and 7106. The transducer array 7108—depicted here as a linear transducer array but may be 2 dimensional, or circular or any other design is placed on the skin 7110. By electronically steering the signal one can achieve a downward pointing beam 7112 or an upward pointing beam 7114 or any other one as required. The signals arrive at the transducers via cables or any other electrical signal lead 7116. In some embodiments, this requires more electronics, since there is a need to provide signals simultaneously to multiple transducers. However, this method may be more convenient to the patient due to its low height design that may allow the patient to lie supine, or recline on a chair.

Tracking and Avoiding Ultrasound Reflection from Bones (Ribs)

Background

In this design, a transducer mat placed over the ribs, in the general direction towards the kidney. In some embodiments, the goal is to transmit signal from individual transducers or from multiple transducers at time, avoiding the reflected signal from bone.

Problem Statement

Assuming transducers with marked index i, $0<i<=N_T$

In the simple case where one transducer transmits at any given time. Then we generate a table of discrete times $T_j$, j>0 and an index matrix $A_j$, where the transmitted signal is $$s(t) = \sum_{i,j} A_{i,j} * s_i(t - T_j)$$

$s_i(t)$ is a transmitted pulse from transducer i, and is positive only for $0<t<\Delta t$.

For any given index j, corresponding to time Tj, the Aij matrix is non zero for only one single i value, meaning only one transducer is transmitting.

The reflected signal is designated at r(t).

$$r(t) = \sum_{i,j} A_{i,j} * r_i(t - T_j)$$

In this example, the received signal is measured from exactly the same transducer that transmitted the signal. When this transducer receives a large reflection, this means that the ultrasound signal has hit a large reflector meaning either there is no good acoustic coupling (dry skin) or a bone reflected the signal. The goal of the adaptive algorithm is to adapt the Ai,j matrix and the Tj table in order to minimize $r^2(t)$.

In order to avoid the trivial solution of no transmission, the system would force a power metric for the transmitted signal $$\frac{1}{T}\int_T s^2(t)dt = P$$

Figure 72:
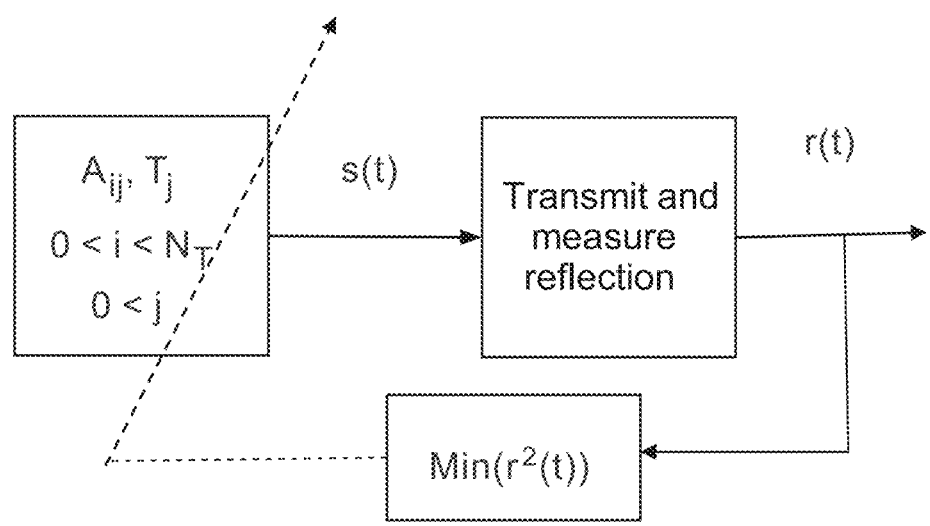
FIG. 72 is a block diagram of a system that would force a power metric for the transmitted signal, according to come embodiments of the present invention.

The block diagram of this system is shown in FIG. 72.

In case that beam steering is performed, then there are additional delays and Amplitudes involved, that allow to transmit from multiple transducers at a time.

$$s(t) = \sum_{i,j} A_{i,j} * s_i(t - T_j - \tau_{i,j})$$

Where $\tau_{(i,j)}$ are a set of delays (defining the steering) and the matrix $A_{(i,j)}$ can have multiple non zero values.

The cost function r(t) may be measured from one transducer or multiple transducers, and in general is some type of metric on $$r(t) = \sum_{i,j} B_{i,j} * r_i\left(t - T_j - \grave{\tau}_{i,j}\right)$$

Where the $B_{(i,j)}$ amplitude matrix together with the $\grave{\tau}_{(i,j)}$ delays describes the receiver beam steering.

The optimization may take the square of the r(t) or any other positive metric.

Other exemplary systems may have a designated receiver transducer or receiver transducer set, in order not to burden the whole transducer mat with reception quality equipment.

Other optimizations would try to avoid concentrating all the transmission from a single transducer. This can be achieved by trying to optimize the variance of the signal, for instance, by averaging over time the transmitter amplitude $\hat{A}_i$ and maximizing its variance.

$$\frac{1}{N_T}\sum_i (A_{i,j} - \hat{A}_i)^2$$

Figure 73:
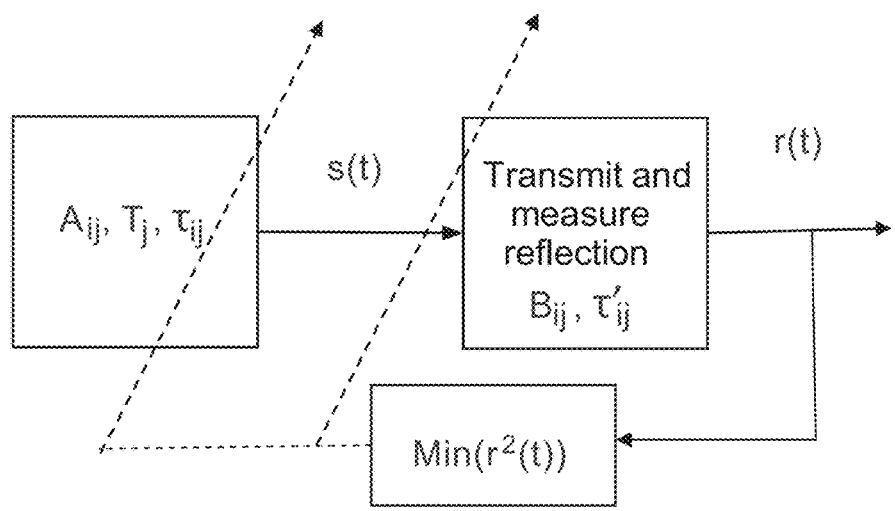
FIG. 73 is a block diagram of a system that avoids concentrating all the transmission from a single transducer, according to come embodiments of the present invention.

This system is depicted in FIG. 73.

Example

Let us assume that there is a relative movement between transducers and the bones. The key parameter determining the relative movement is the patient's breathing cycle.

If at a given point of time in the breathing cycle a specific transmission reflects from a bone, and if the breathing rhythm is tracked, the peak reflection from the bone at the next period may be avoided.

A transducer that always hits a bone independent of the breathing cycle shall not be used.

An array of transducers that can steer a beam and transmit to various directions shall transmit as much as possible in all directions except for the directions where a large reflection is received.

Increasing the signal variance has the implicit meaning of selecting multiple transducers over time, or multiple directions, which from the product point of view, means that the therapeutic ultrasound signal spreads in the target domain and gains the maximal therapeutic effect by covering evenly all reachable kidney tissue.

Figure 74:
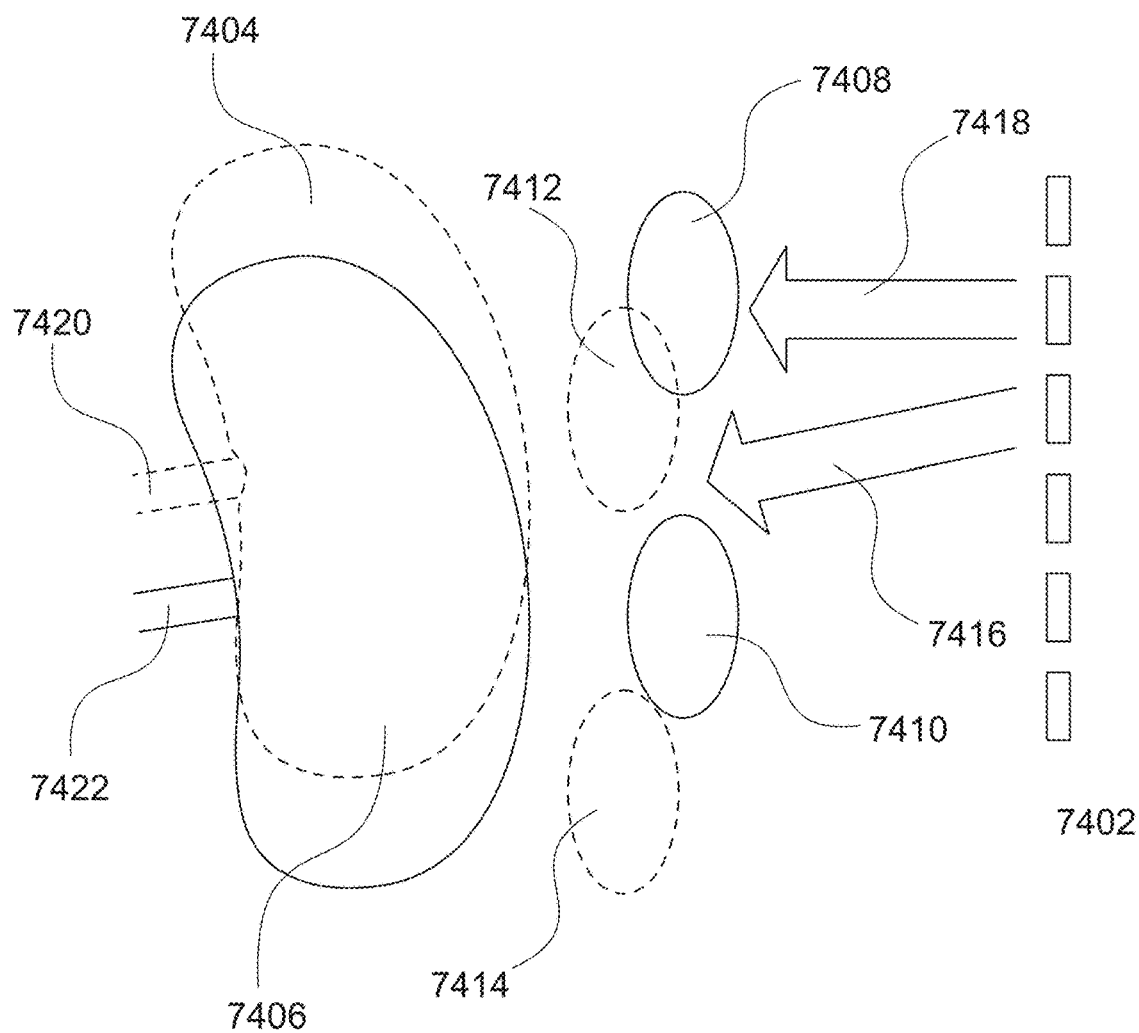
FIG. 74 is a schematic representation of the operating domain for the algorithm, according to come embodiments of the present invention.

FIG. 74 shows the operating domain for the algorithm. An array of transducers 7402 is lined on the skin, with the goal of transmitting ultrasonic signal towards the kidney. The kidney moves with the breathing cycle between a high position 7404 and a low position 7406, and can take of course any intermediate position as well. The ribs can be high 7408, 7410 or low 7412, 7414 depending on breathing. A transmission in the direction of 7416 would reach the kidney during the high state, but would be mostly blocked by the rib 7412 during the low state. The reverse happens in direction 7418—the signal would reach the top part of the kidney during the high state but would be blocked by the rib 7408 during the low position.

The renal artery can be tracked as well in this situation. The artery would move between locations 7420 and 7422 and thus measurement of Doppler shift from the artery flow can track these changes Low Height Transducer Design There are a number of options where a low height design for the transducer and the acoustic coupling would be beneficial for the system.

Here are some examples to name a few:

Transducer placed on the patient's back for back access when patient is in the supine position Transducer placed on the patient's back for back access when patient is reclining in a chair Transducer placed on the patient's waist or ribs. The patient may be uneasy with placing the hands comfortably Transducer placed on the patient's waist or ribs while the patient is reclining on a chair or narrow sofa.

A "wearable" situation where the patient moves around with the transducer attached using adhesive or belt or corset or special garment Connection of a Transducer to the Acoustic Coupling Subunit Using Plug-In Operation In some embodiments, the design of the TSU and the ACSU allow the reuse of the transducer in multiple treatments for the same patient, and also a reuse of the transducers for multiple patients.

In some embodiments, by limiting the usage of the ACSU to a single treatment the patient is protected from contamination, bacteria, fungus and other undesired materials that may be in contact with the unit during previous treatments of the same patient or previous treatments of other patients.

Figure 75:
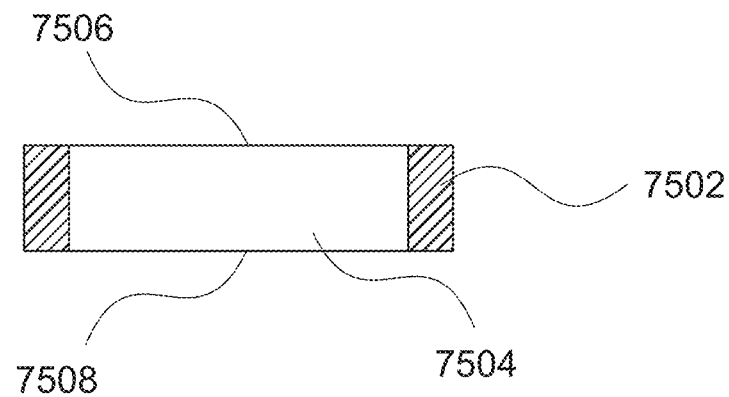
FIG. 75 is a schematic representation of a gel compartment, according to come embodiments of the present invention.
Figure 76:
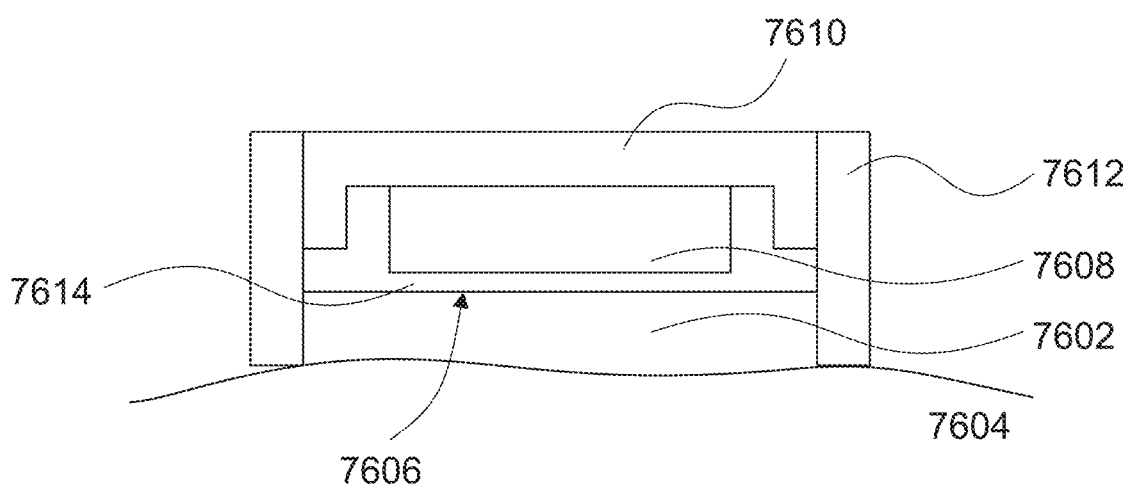
FIG. 76 is a schematic representation of the ACSU in use where the bottom is exposed by peeling off a shield/sticker and exposing the bottom compartment to the skin, according to come embodiments of the present invention.

In some embodiments, a gel compartment shall include (as shown for example in FIG. 75):
  A gel compartment with housing 7502 and gel 7504;
  An interface towards the TSU 7506;
  An interface towards the skin 7508.
In some embodiments, the gel compartment has two configurations:
  While in stock, where there is a need to keep the gel from being evaporated
  While In operation, where the gel has to be operative and not contain air bubbles
Here is an Exemplary Implementation Referring now to FIG. 76. In some embodiments, when the ACSU is in use, the bottom (skin interface) is exposed by peeling off a shield/sticker and exposing the bottom compartment 7602 to the skin 7604. In some embodiments, an optional blocking layer 7606 is between the transducer and the skin, allowing the transducer 7608 to remain clean. In some embodiments, the transducer is housed in its own housing 7610 that snaps or screws to the ACSU housing 7612. In some embodiments, when snapping the transducer into the ACSU the top membrane 7614 is either peeled off or perforates from the operation.

Figure 77:
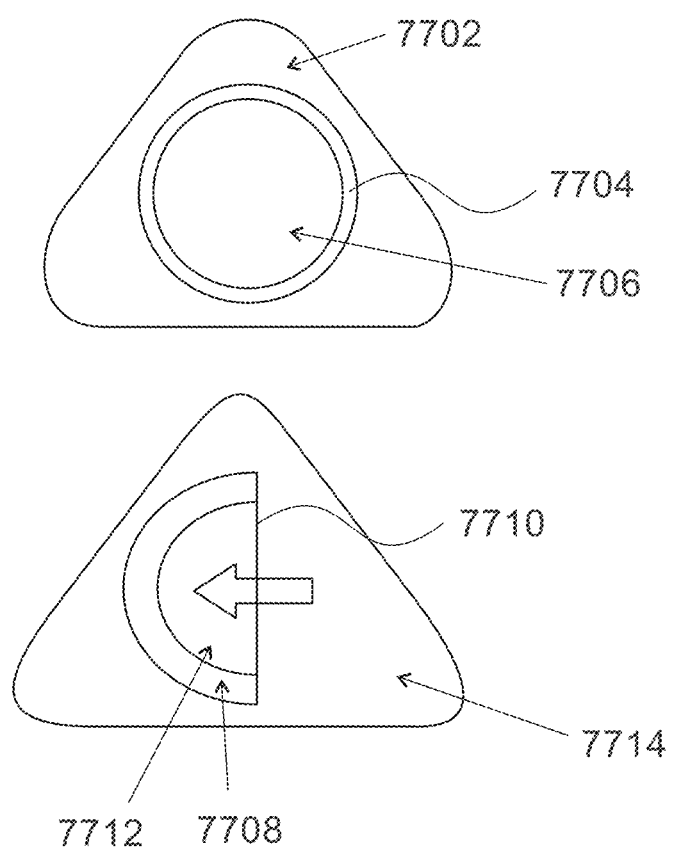
FIG. 77 is a schematic representation of the ACSU including extensions for connection to the patient's skin, according to come embodiments of the present invention.

Referring now to FIG. 77. In some embodiments, the ACSU includes extensions for connection to the patient's skin with an adhesive. In the top of the figure, and adhesive 7702 is placed on a patch surrounding the therapeutic ultrasound transparent zone. In some embodiments the adhesive may be pressure sensitive adhesive adapted to human skin. In some embodiments this may be silicon based human skin adhesive. In some embodiments this may be acrylic based human skin adhesive. In some embodiments it may be hydrocolloid adhesive. At the center of the adhesive patch the gel chamber is located. The compartment holds acoustically transparent material 7706. In the bottom figure, a side-sliding connection is shown. The transducer enters the gel compartment 7708 not from the top interface but through a side wall, fracturing a membrane 7710 that held the gel 7712 in the compartment. The sliding of the transducer into the gel is performed such that air bubbles shall not be introduced during this operation. The side sliding design saves total height. The external flaps 7714 stick to the patient's skin.

Using a Reflector for a Low Height Design

In some embodiments, an alternative to a forward facing transducer in a low height design is to have a reflector at about 45 degrees reflecting the ultrasonic beam towards the skin. An exemplary transducer array is shown at FIG. 78a, with multiple transducers facing to the right and cables connecting them further to an electronic circuit.

FIG. 78b shows a 45 degrees swiveling reflector 7802 made of metal, for instance) that may reflect the ultrasonic wave to the skin—at 90 degrees to the path of the original beam.

FIG. 78c shows a bottom view of the apparatus, where the transducer array 7804 is facing the swiveling reflector 7806, which moves within a gel 7808 that is filling a compartment. The compartment 7810 holds the gel in place and attached via adhesive or some sort of belt to the patient's skin. Signal arrives at this drawing via a cable 7812.

The Interface Between the Transducer Subunit and the Acoustic Coupling Subunit

This section describes the interface between the TSU and the ACSU.

In some embodiments, the interface has a number of requirements:

Enable acoustic coupling between the transducers (present in the TSU) and the coupling material: avoid air bubbles; avoid sputtering gel over the patient's cloths; optionally, allow more than one connect-disconnect cycles Enable a simple mechanical connection operation that can be performed by a medical practitioner and preferably by a patient Provide an electrical interface to sensor subunit embedded inside the ACSU Require minimal (preferably none) external equipment, such as a hydrogel bottle An exemplary interface is where the transducer slides into/enters a gel filled pocket or chamber. For this design:
  The transducer face is smooth and flat, in order to capture air bubbles.
  When the transducer enters the pocket, the processes does not draw air bubbles into the chamber
  There are no hard surfaces that are withdrawn one from another, generating a cavity that pulls air inside
  The edge of the transducer subunit is designed not to cause a cavity Embedding Transducers in Garments In order for the devices of this genre to work, the transducers need to be placed on specific locations on the body. One option is to use adhesives. However, adhesives have a number of disadvantages, such as irritation, pain when being taken off, need to take off during washing, skin allergy, etc. Another option might be the use of a belt, which might not bring the transducer to the right location. In addition, when covering the ribs, special care needs to be taken not to limit the breathing of the patients.

A number of medical grade garments were developed to help patients while keeping their comfort. In some embodiments, such designs are used for the placement of the ACSU for a long duration. In some embodiments, the garments may be adjusted to the patients Kidney Treatment with Implanted Devices Short Term Implants—Less than 30 Days In some embodiments, kidney treatment may be performed by an implanted transducer or transducer array. In some embodiments, the transducer is placed between the fat and the muscular tissue, or between the muscular tissue and the kidney.

Figure 79:
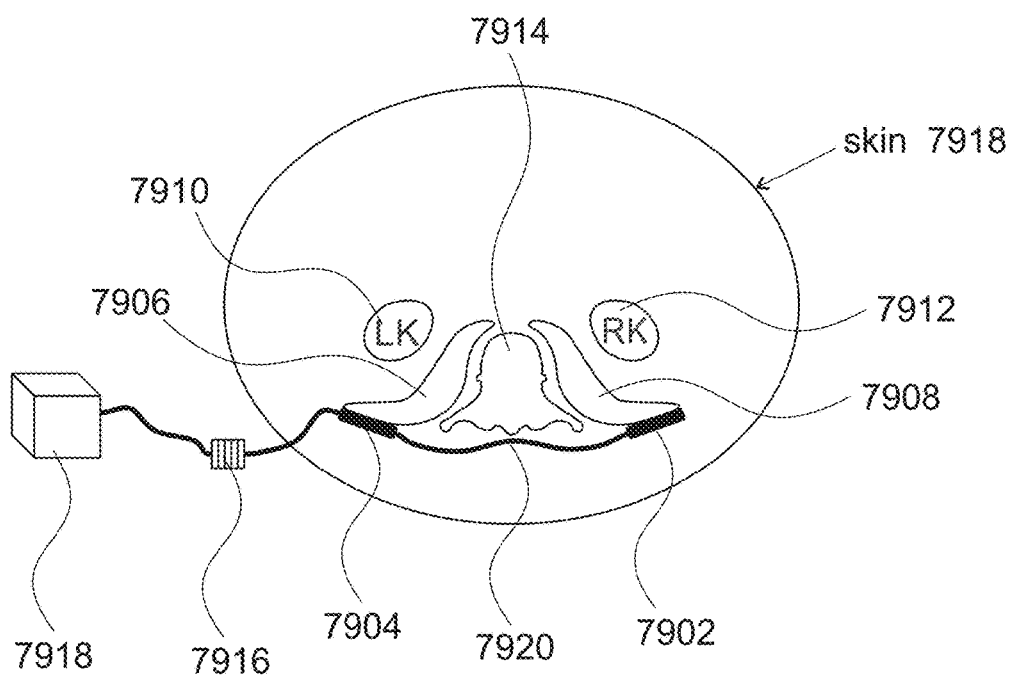
FIG. 79 is a schematic representation of two transducers placed under the fat, according to come embodiments of the present invention.

In FIG. 79, it is shown two transducers 7902 and 7904 that are placed under the fat. In some embodiments, the psoas major muscles on the left 7906 and on the right 7908 hold the transducers in place. In some embodiments, the distance of the transducers to the left kidney 7910 or to the right kidney 7912 is of the order of 10 to 70 mm the spine 7914 is also shown in the diagram. In some embodiments, a cable for signal and power connects the transducers to an external connector 7916. In some embodiments, the cable goes through the skin 7918. In some embodiments, a cable connects both transducers 7920. In some embodiments, an external unit that contains power, user interface and electronic circuits 7922 connects to the cable.

Figure 80:
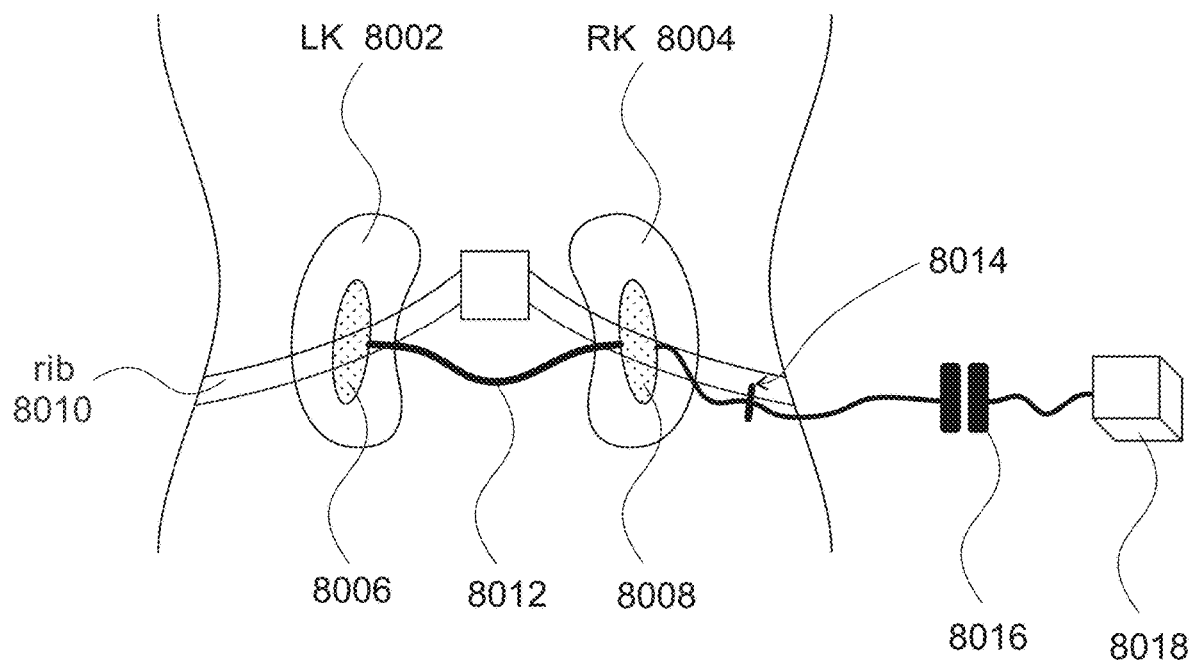
FIG. 80 is a schematic representation in back coronal view of two transducers placed under the fat, according to come embodiments of the present invention.

The same configuration is shown using a back coronal view in FIG. 80. The left kidney 8002 and the right kidney 8004 are shown. The ribs are present and the transducers 8006 and 8008 are implanted between the ribs 8010 and the muscle tissue. A cable 8012 carrying power and signal is connected between the two transducers. Another cable exits the patient body at point 8014 and connects using an external connector 8016 to the external electronics, power and control unit 8018.

In another example this cable can be replaced by having two cables exit the patient's body—one from the right transducer 8003 and one from the left 8008. This two cables would have two connectors and connect to the external power and control unit.

Permanent and Temporary (Up to 29 Days) Implants

In some embodiments, Kidney treatment may be performed by a permanently implanted complete system that provides the therapeutic signal to the kidney. The implant may be a permanent implant or a removable implant. Since the system is implanted, less transmission power is needed since the transducers are closer to the kidneys and the signal attenuation between the transducers and the kidneys is smaller.

The clinical application for such a system may be CKD and improved renal filtration, which can also be treated by non-implanted devices as described. When treated by external devices, the patient may be using the system a few hours per day, or a few sessions per week. When the unit is implanted the treatment schedule may be adapted to the capabilities of the implanted system.

Figure 81:
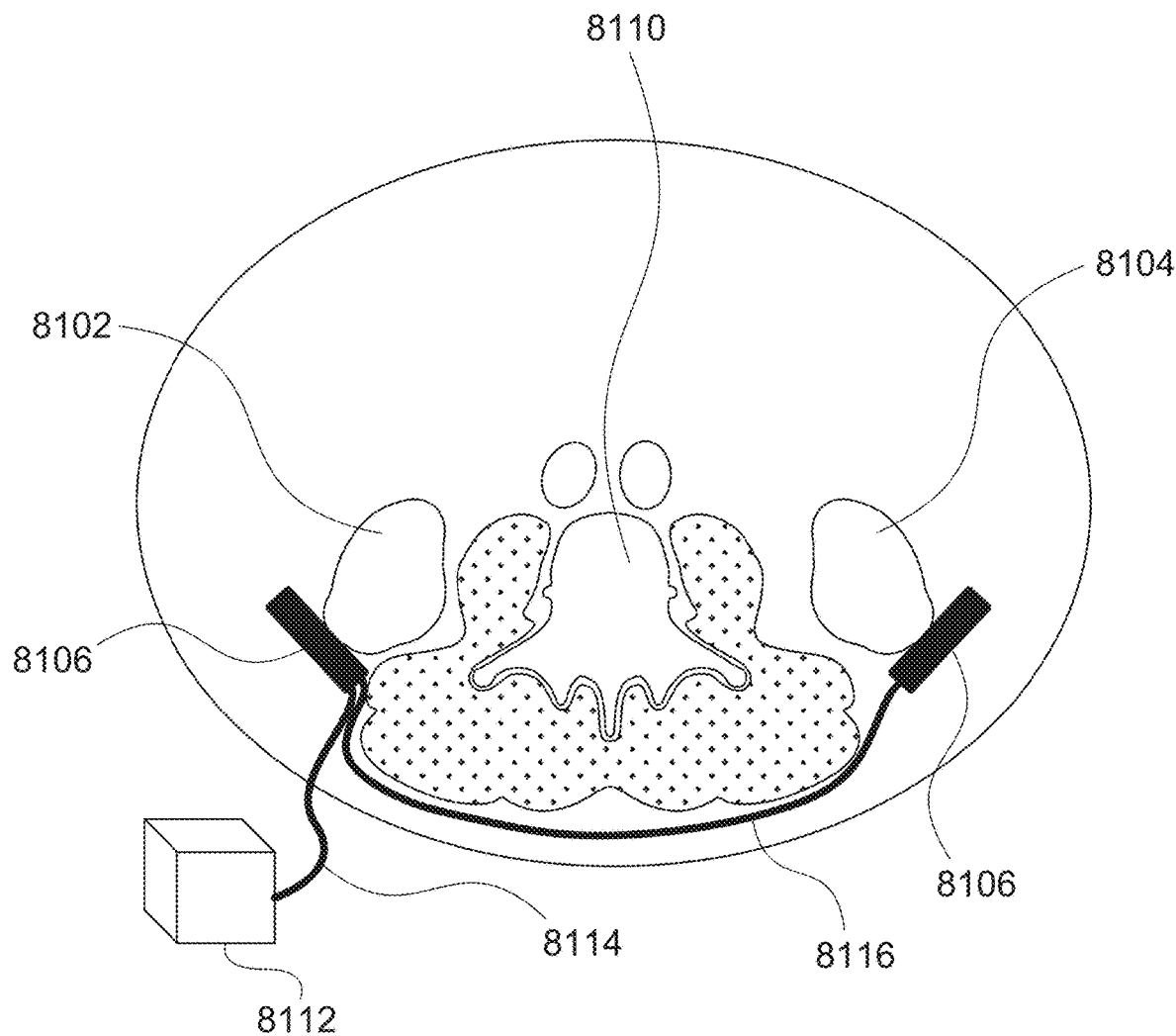
FIG. 81 is a schematic representation of a permanent implant system, according to come embodiments of the present invention.

In FIG. 81, a permanent implant system is depicted. The kidneys 8102 and 8104 are treated by two transducer units 8106 and 8108 that are placed between the kidneys and the back muscle. The transducer units are medial to the ribs. The spine 8110 is also shown. The left transducer unit 8106 connects to an external power and electronics box 8112 via a cable 8114. The right transducer unit 8108 connects to the left transducer unit also via a cable 8116. In some embodiments, there is no need to have any cable protrude through the body. In some embodiments, Power recharging can be performed via remote charging.

Placement of the Transducer Implant

In some embodiments, there are many alternative placements to the transducer mats, which may be beneficial. For instance, placing the transducer mat under the kidney may reduce the size of the mat. In some embodiments, alternative placements may be: Superior to the kidney near the diaphragm facing caudal; Inferior to the kidney facing cranial; Posterior to the kidney facing anterior; Anterior to the kidney between the kidney and the peritoneum facing posterior; Medial to the kidney facing lateral; Between the right kidney and the liver; Between the liver and the lateral ribs; Between the left kidney and the spleen; Between the spleen and the lateral ribs; Inside the renal vein; and Spherical transducer near the hilum.

Figure 82:
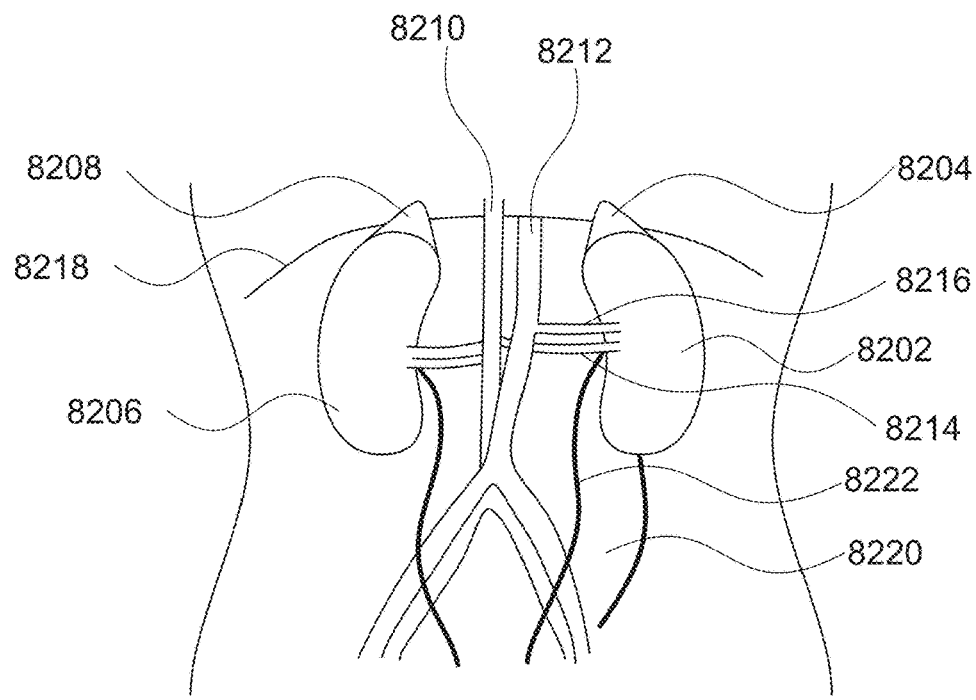
FIG. 82 is a schematic representation of locations of the transducer mats, according to come embodiments of the present invention.

The locations are shown in FIG. 82.

In this figure the left kidney 8202 and the left adrenal gland 8204 are shown on the right hand side of the image and the right kidney 8206 and the adrenal gland 8208 are on the left hand side. The inferior vena cava 8210 and the abdominal aorta 8212 are at the center. The left renal artery 8214 and the left renal vein 8216 connect the aorta and vena cava to the left kidney. The diaphragm 8218 is at the top and the psoas major muscle 8220 is shown below the kidney. The ureter 8222 connects the kidney to the bladder.

In some embodiments, the transducer mats may be designed as flat mats, linear arrays, transducers in a line (to enable implantation via a small hole), and/or a line of cylindrical transducers.

In some embodiments, the transducer may be designed to open inside the body to get a larger US coverage, and converge during implantation and extraction. In some embodiments, the implanted ultrasound is made of biocompatible material.

Non-Implanted Medium Term Unit

In some embodiments, the system is based on the same premise of the short term implanted therapeutic unit, only without the actual implanting. In some embodiments, the transducer mat is attached to the skin (for instance by an adhesive or belt). Technology similar to long term bandages used in treating ulcers or burns, may be used for this. In some embodiments, bandages may be used for periods of 1 day or a number of days to a week or two.

In some embodiments, the bandage comprises an interface to replenish it with acoustic gel. In some embodiments, the replenishment could be performed by the patient, and would not require a medical practitioner.

Figure 83:
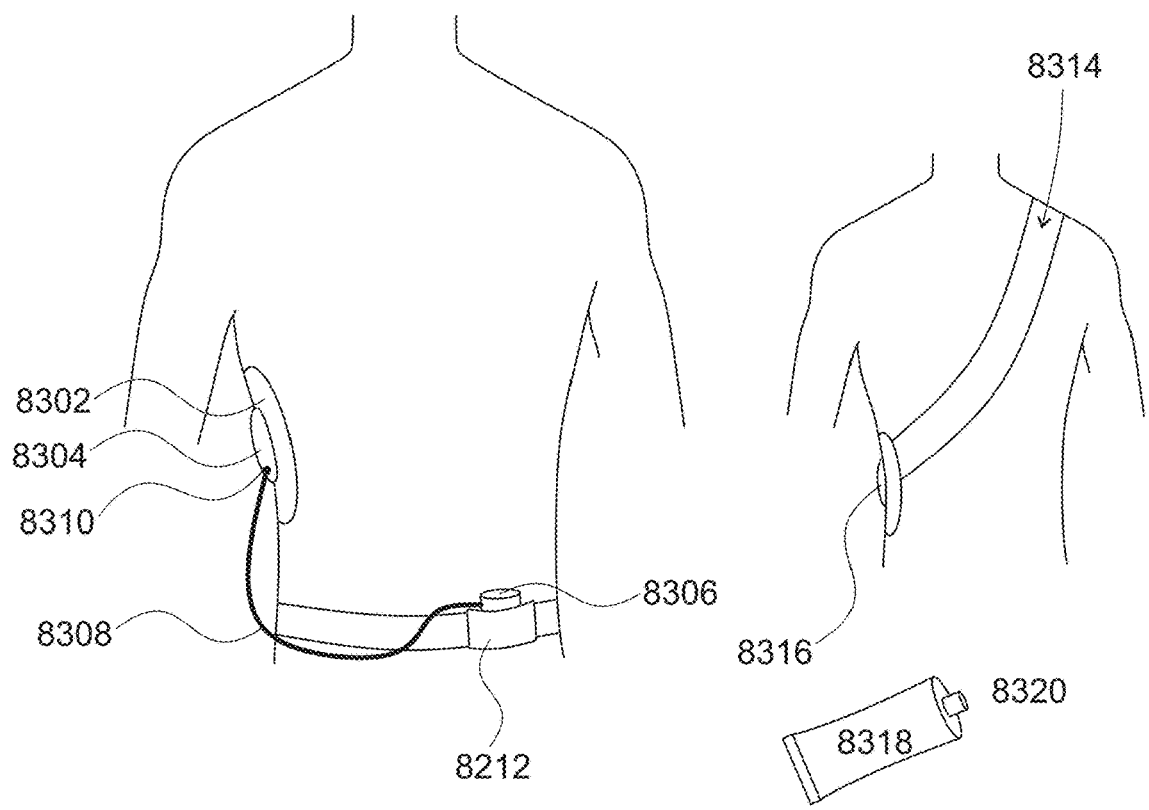
FIG. 83 is a schematic representation of the medium term device placed over the ribs at the right side of the patient, according to come embodiments of the present invention.

In FIG. 83, the medium term device is shown placed over the ribs at the right side of the patient. An adhesive bandage 8302 secures the device to the patient for a period of 1 to 60 days. The transducers are enclosed inside a housing 8304 facing the right kidney. A connector allows to connect an external power unit 8306 via a power and communication cable 8308 to the connector 8310. When in use, the external unit may be a bedside unit, or a carried unit as shown in the figure, placed in a pocket 8312 of a garment or a specially designed belt to carry it.

In some embodiments, a mechanical assistance 8314 may be used to secure the unit in place, to ease the requirements on the adhesive or replace it, ensuring acoustic coupling of the device to the therapeutic location. Since the treatment is long, an acoustic gel replenishment interface is provided 8316. In some embodiments, a sterile gel package 8318 with a matching head 8320 can be used to pump gel into the fixture via the special hose 8316. In some embodiments, the replenishment may be performed based on schedule or according to feedback received from the therapeutic system. In some embodiments the disposable ultrasound coupling layer shall be replaced every 24 hours.

In some embodiments, the therapeutic device is able to stop treatment if there is no acoustic contact between transducer and skin. In some embodiments, the therapeutic device is able to alert the patient if there is no acoustic contact between transducer and skin. In some embodiments, the therapeutic device shall be able to alert the caretaker if there is no acoustic contact between transducer and skin. In some embodiments, this requires an integration of the system to a remote patient monitoring system. In some embodiments, the integration only requires standard data interfaces.

Type 5 System

Background

Systems types 1 through 3 were systems where the transmitted signal was not controlled or adjusted by parameters that are sensed by the system. In some embodiments, there are various parameters that may be sensed, that may affect the transmitted signal, for example: Sensing the reflected ultrasound signal; Sensing the temperature; Sensing the patient's movement; Sensing the patient's breathing; Sensing the patient's hemodynamic parameters, for example cardiac output (e.g. from Swan Ganz catheter, or other non-invasive methods), saturation, Stroke Volume (SV0, stroke volume variance (SVV), Ejection Fraction (EF); Sensing the location of the kidney; Sensing the location other tissues or markers; Sensing the effectiveness of the treatment, for instance by measuring GFR eGFR, chemicals related to kidney function in urine, and/or urine quantity. Optionally including blood analysis including, for example Creatinine, Urea, BUN, BUN/Creatinine, hematocrit, blood count, Calc, Phos, Na, K, Chlor, Beta-2 microglobulin (Thymotaxin), Lysozyme. Optionally including urine analysis including, for example KIM-1, NGAL, Creatinine, Protein, Prot/Creat, Ca, Na, K, Cl, ACR, BUN, Beta-2 microglobulin (Thymotaxin, β2M), Lysozyme, urine color, urine transparency/opaqueness; Sensing heart arrhythmia (for example to monitor levels of K in the blood, which above or beyond certain levels may increase the level and types of arrhythmia); Fluids input (documentation of drinking or fluids in food intake, or documentation of IV infusion) and urine output (by volume or rate, either manually or by a sensor), as well as fluid accumulation in the body (e.g. by changes in body weight).

For each of these examples details on the rational and the mechanism to implement such system will be explained in the following paragraphs.

Type 5 Key Parameters

In some embodiments, the device comprises one or more transducers attached to body. In some embodiments, the device is adapted to sense and monitor internal organs of the body.

These parameters are the parameters differentiating between type 5 system and type 1 system and/or type 2 system and/or type 3 system.

Block Diagram

Figure 84:
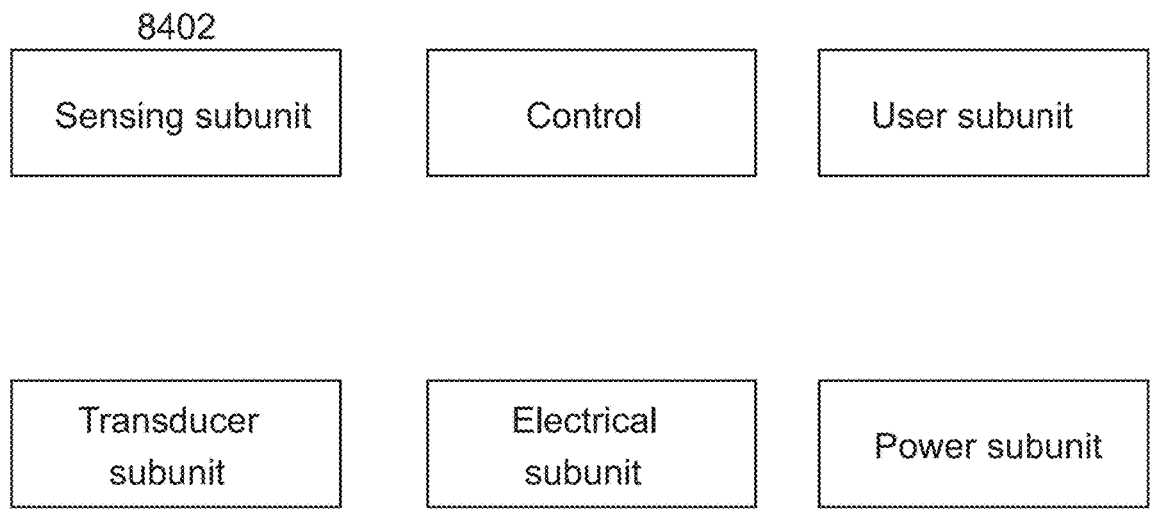
FIG. 84 is a block diagram of the system comprising a sensing module, according to come embodiments of the present invention.

In order to enable sensing, a sensing module 8402 is added, as shown in FIG. 84.

Sensing Modalities

Temperature Sensing

In some embodiments, transducer temperature may be monitored in order to make sure there in no risk for the patient's skin from overheating of the transducer. In some embodiments, a rise in transducer temperature over a certain threshold would stop the operation of the transducer. In some embodiments, probe temperature should not exceed 43 degrees Celsius (BMUS requirement).

Ultrasound Reflected Energy

In some embodiments, at any interface, part of the ultrasound signal traverse from one side of the interface to the other and part of it is reflected. In some embodiments, the proportions between the traverse and the reflected parts depend on the characteristics of the material at both sides of the interface. In some embodiments, the goal is to have as much of the signal enter the body, and thus we utilize impedance matching material and hydrogel at the interface between the transducers and the skin.

In some embodiments, lack of coupling material, or improper attachment of the transducers to the skin may cause a mismatch, reflecting much of the ultrasonic energy back towards the system. If this happens we would like to the system to measure this and either indicate the problem or fix it.

In some embodiments, a sensor measuring the reflected ultrasonic signal may provide a per-transducer factor that can be compared to thresholds and previous measurements Patient Movement In some embodiments, patient movement may interfere with the arrival of the therapeutic ultrasound signal to the kidney. In some embodiments, the system may react to some of the movements in a special way. For instance, breathing movements are continuous, but if a patient rises and starts to walk maybe the system would react differently.

In some embodiments, the location of the kidney relative to the transducer depends on a list of parameter:

Patient breathing, and specifically diaphragm movement
Patient position and posture (supine, face up or prone, sitting, reclining . . . )
Patient movement and activity
Abdominal muscle state
In some embodiments, these parameters can be monitored by a number of sensing modalities:

Position sensors—inertial measurement unit (IMU) using accelerometers, gyroscopes, magnetometers
Sensors to measure breathing—microphone, blood saturation and accelerometers and other motion sensors
Electromyography sensors (EMG)
Ultrasound—either by using the transmitted ultrasonic signal or using a different modality of ultrasound signal for this purpose In some embodiments, the motion sensor and/or accelerometer and/or orientation meter assist the system in determining which preferred mode of action to take. In some embodiments, the system identifies from these sensors the positional status of the patient: whether the patient is supine, semi-supine, stand still, sitting, reclining, moving, walking, in bed facing side-ways, in bed facing up, in bed facing down and other possible postures and movement characteristics. In some embodiments, these parameters affect the signal transmission.

In some embodiments, posture affects the expected distance between kidney and transducers, which may be reflected in transmission amplitude and repetition rate.

In some embodiments, patient movements affect the relative movement of kidneys and transducers, affecting the averaging out of treatment over kidney volume, in changing the distribution of signal between transducers.

In some embodiments, posture affects the optimal pressure applied between the disposable unit and the skin, changing the thresholds used by the system in order to start, stop and modify transmission parameters according to measured disposable-skin pressure.

In some embodiments, posture affects the target goals of the active mechanism that changes the pressure between the disposable and the skin (described elsewhere in the patent).

In some embodiments, posture such as laying on the side, affects the selection of active transducers within the session.

In some embodiments, posture change that would stop treatment would also generate a patient alert, or care taker alert to indicate treatment pause.

Figure 85:
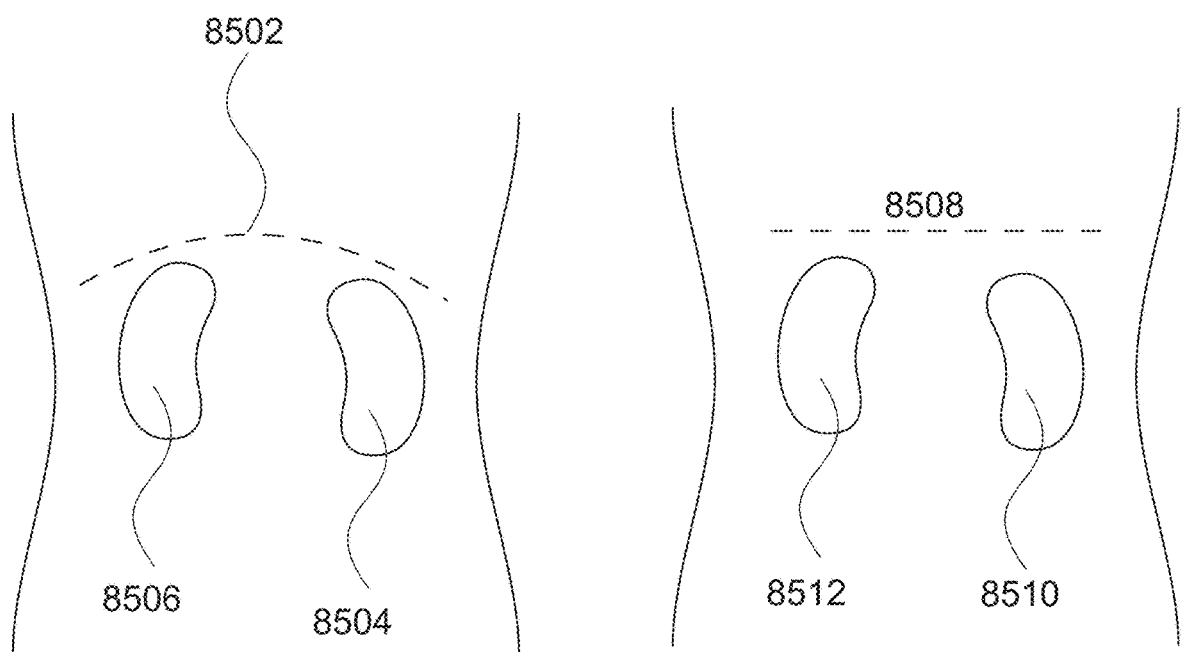
FIG. 85 is a schematic representation of the effect of breathing on the location of the kidneys, according to come embodiments of the present invention.

In some embodiments, the effect of breathing on the location of the kidneys is by moving them up and down in the body This is shown in FIG. 85. On the left at the peak of the exhalation the diaphragm 8502 is curved upwards and the right kidney 8504 and left kidney 8506 are superiorly pulled. When the body is at the peak of inhalation, the diaphragm 8508 straightens and right kidney 8510 and the left kidney 8512 move in the inferior direction.

In some embodiments, the system that tracks the patient's breathing can adjust the parameters of the transmission accordingly. For instance:

In some embodiments, the system may transmit towards the kidneys only when the patient inhales and the kidney are lower. In some embodiments, the system may transmit towards the kidneys only when the patient exhales and the kidney are higher. In some embodiments, the system may direct the signal upward when the patient inhales and the kidney are pushed down, and downward when the patient exhales, or vice versa, depending on the exact transducer position and direction.

Figure 86:
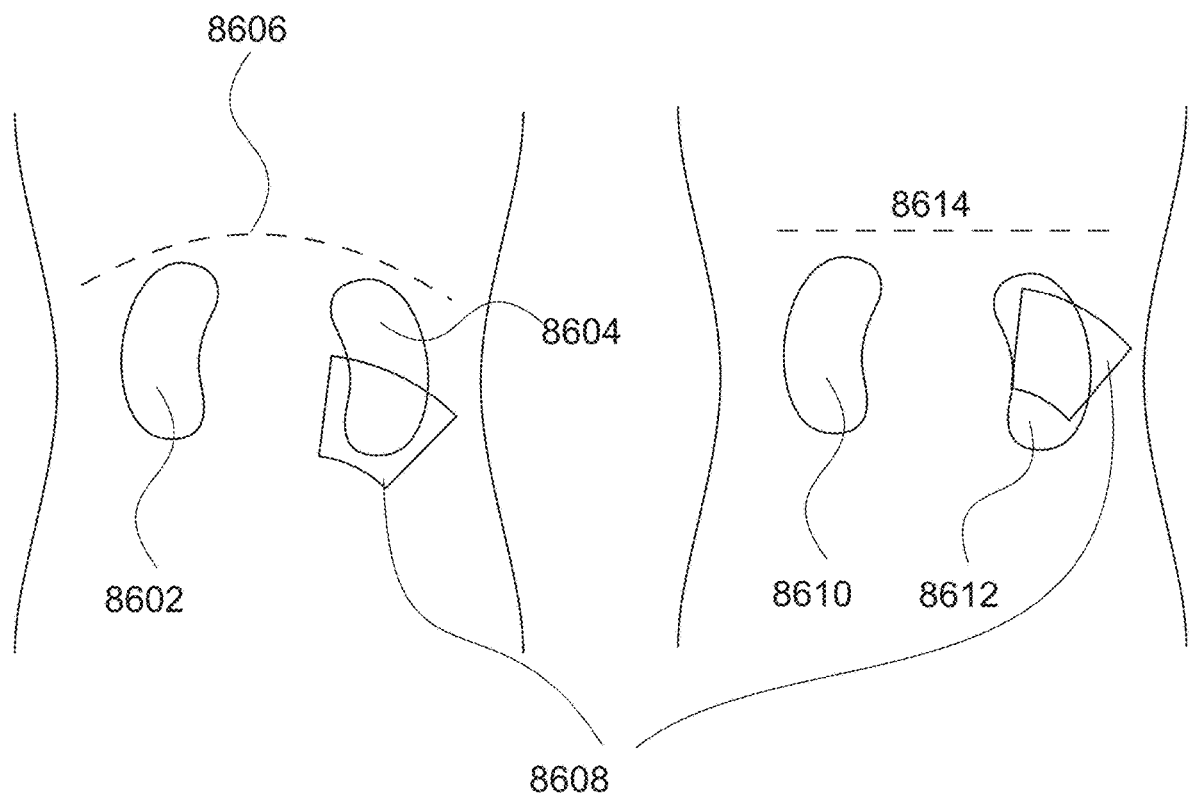
FIG. 86 is a schematic representation of the effect of breathing on the location of the kidneys, according to come embodiments of the present invention.

In FIG. 86, on the left we show the kidneys 8602 and 8604 during exaltation, when the diaphragm 8606 is up. An array of transducers is shown treating the lower lobe of the right kidney 8608. In FIG. 86, on the right we show the kidneys 8602 and 8604 during inhalation, when the diaphragm 8606 is up. An array of transducers is shown treating the lower lobe of the right kidney 8608. On the right we show the kidneys 8610 and 8612 during exaltation, when the diaphragm 8614 is pushed down. The same array of transducers 8608 is shown treating now the middle section of the right kidney 8612.

In some embodiments, the adjustment of the transmission according to the patient's movement may be significant to achieve wide and uniform desirable coverage of the kidney with the therapeutic ultrasonic signal An example for such a system would use a movement sensor to track the patient's breathing cycle. The signal would be fed to a tracking algorithm (such as a Kaltman filter) that would track the kidney's location. The location of the kidney changes with time and is mark as θ(t). This estimation is fed to the electrical signal generating block that optimizes the transmitted signals according to some cost function. Let us denote the true location of the kidney by θ(t). Thus, the estimated location as derived by the algorithm is $\widehat{\theta(t)}$.

In some embodiments, the transmitted signal depends on the estimation of the location, and is changing with time. We denote is by $S_i(t, \widehat{\theta(t)})$ where the $i^{th}$ index is the index of the transducer i. CU is some volume coverage function that we define that provides uniform coverage of the kidney, and this uniform coverage is our maximization goal as depicted below $$\max_{i,t}\{C_U(S_i(t, \widehat{\theta(t)}), \theta(t))\}$$

Figure 87:
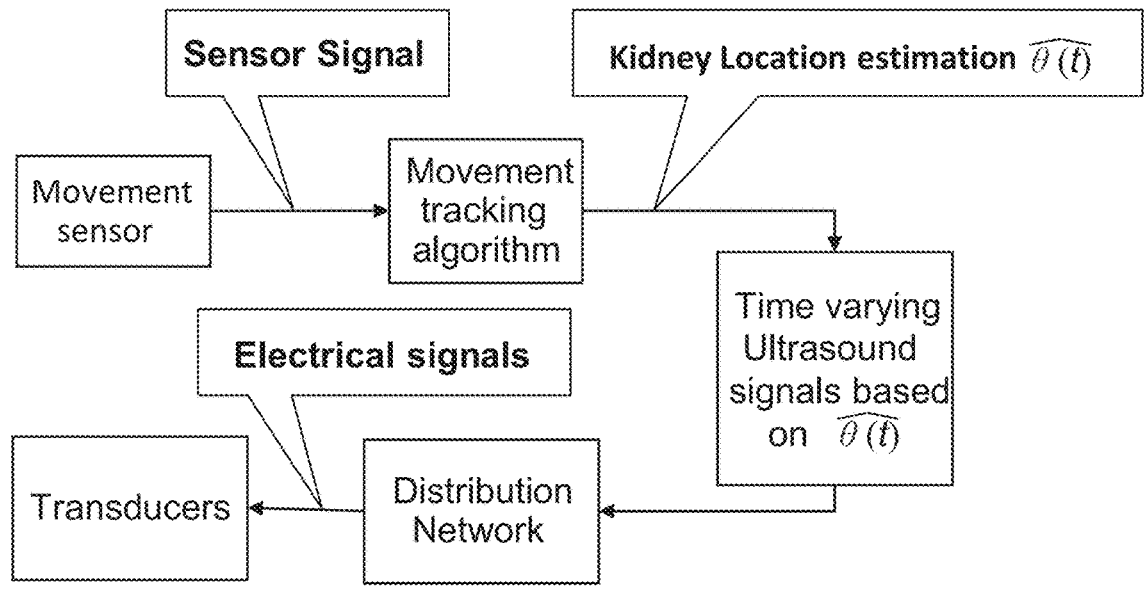
FIG. 87 is a block diagram of a system, according to come embodiments of the present invention.

The block diagram to implement this would look like the system depicted in FIG. 87. Alternatively, the optimization can be performed in one block, based on the raw sensor measurement input.

Patient Hemodynamics

In some embodiments, the blood pressure inside the kidney is a close function of the hemodynamics of the patient. All pressure gradients at the various kidney modules are time variant and depend on the specific hemodynamic cycle—the shape, rate, and specific parameters such as the systolic pressure and diastolic pressure with their rates of change. In some embodiments, the sensing modalities for hemodynamics may be:

Dedicated sensing that are local in the vicinity of the transducers

Dedicated sensing that are placed at another location of the patient's body—e.g. ECG, pulse oximeter. The sensor may be connected to the transducer patch or to another part of the system (such as a bed side box)

Connection to 3rd party off the shelf equipment via a standard or proprietary interface Usage of existing Ultrasound sensors for local measurement, for instance, the actual flow speed at the renal artery using tracking of the renal artery location and local Doppler measurements In some embodiments, the effectiveness of the kidney treatment may well depend on the exact timing of the application through the hemodynamic cycle. For this reason, the transmitted signal may depend on the hemodynamic timing as well as on the actual pressure parameters.

Figure 88:
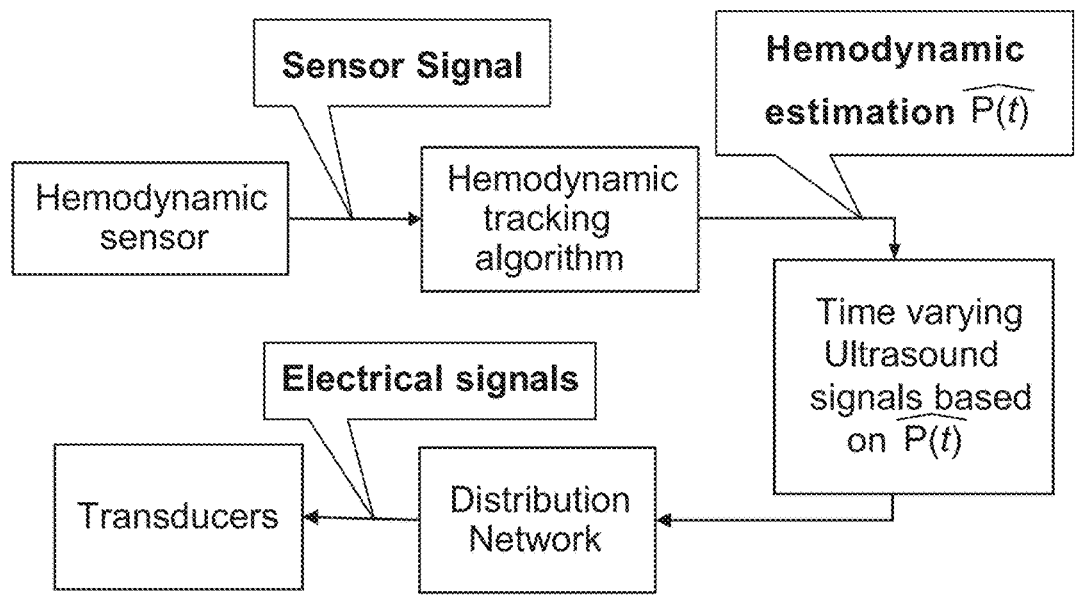
FIG. 88 is a block diagram of a system, according to come embodiments of the present invention.

An example for such a system is depicted in FIG. 88. In some embodiments, the system includes a hemodynamic sensor. In some embodiments, the sensor signal would be fed to a tracking algorithm estimating the various important parameters of the hemodynamic cycle such as the rate, time of systole, time of diastole, peak values and others that may be important for the kidney function. This estimation is fed to the electrical signal generating block that optimizes the transmitted signals according to some cost function. Let us denote the true pressure parameter set by P(t). Thus, the estimated parameter set would be $\widehat{P(t)}$.

In some embodiments, the transmitted signal depends on the estimation of the location, and is changing with time. We denote is by $S_i(t, \widehat{P(t)})$ where the $i^{th}$ index is the index of the transducer i.

Let us assume that the therapeutic signal is most efficient at the time of peak pressure gradient over the kidney glomerular membrane. If the time estimate for this peak happens once per hemodynamic cycle at times $T_G^1, T_G^2, T_G^3, T_G^4, T_G^5, T_G^6, T_G^7 \ldots$ then the transmitted signal S for transducer i at hemodynamic cycle j, would be $$S_i(t=T_G^j, \widehat{P(t)})$$

Which take into account the difference of the hemodynamics between the point of measurement and the kidney itself. The hemodynamics may be measured and estimated by Electro Cardiograph (ECG), by pressure measurement, by reflected ultrasound signal and others means.

Alternatively, the optimization can be performed in one block, based on the raw hemodynamic sensor measurements input.

Figure 89:
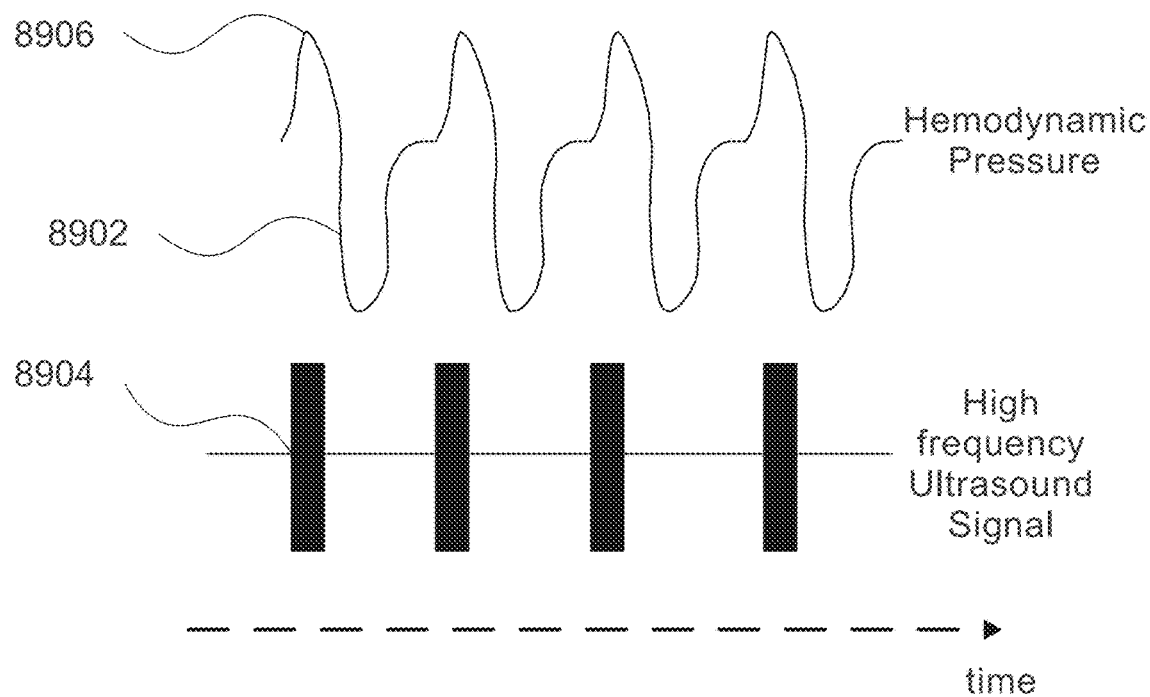
FIG. 89 is an example for an ultrasonic signal that only transmits during the peak of the systolic pressure, according to come embodiments of the present invention.

An example for an ultrasonic signal that only transmits during the peak of the systolic pressure is provided in FIG. 89. In the figure, we show on top the hemodynamic pressure 8902, as measured directly or as estimated by using an indirect sensor. Below is the transmitted ultrasonic signal 8904 that is timed exactly to the peak of the pressure 8906. In a specific example, the hemodynamic pressure may be the estimation of the pressure within the glomerular cavity and the ultrasonic signal is designed to be transmitted when the pressure difference on the glomerular membrane is maximal.

Hemodynamic Estimation Using Ultrasound

In some embodiments, implementation of hemodynamic modulated therapeutic ultrasound, is performed by using ultrasound sensors for the estimation of the hemodynamic parameters. In some embodiments, by using the same transducers that apply the therapeutic ultrasound for sensing, there is no need to use another sensing modality. In some embodiments, the transducers are already available and coupled to the skin using gel. In some embodiments, by efficient implementation of a receive circuit for the transducers, hemodynamics may be estimated.

In some embodiments, the hemodynamics can be estimated using dedicated transducers that are optimized for hemodynamic estimation. The optimization may be in placing special transducers at a location that would improve hemodynamic estimation, and/or in the use of transducers that by size, frequency and shape shall be optimized to estimating hemodynamic parameters.

Alternatively, the same transducers at their regular location near the kidney may be used for the estimation of the hemodynamic parameter.

Figure 90:
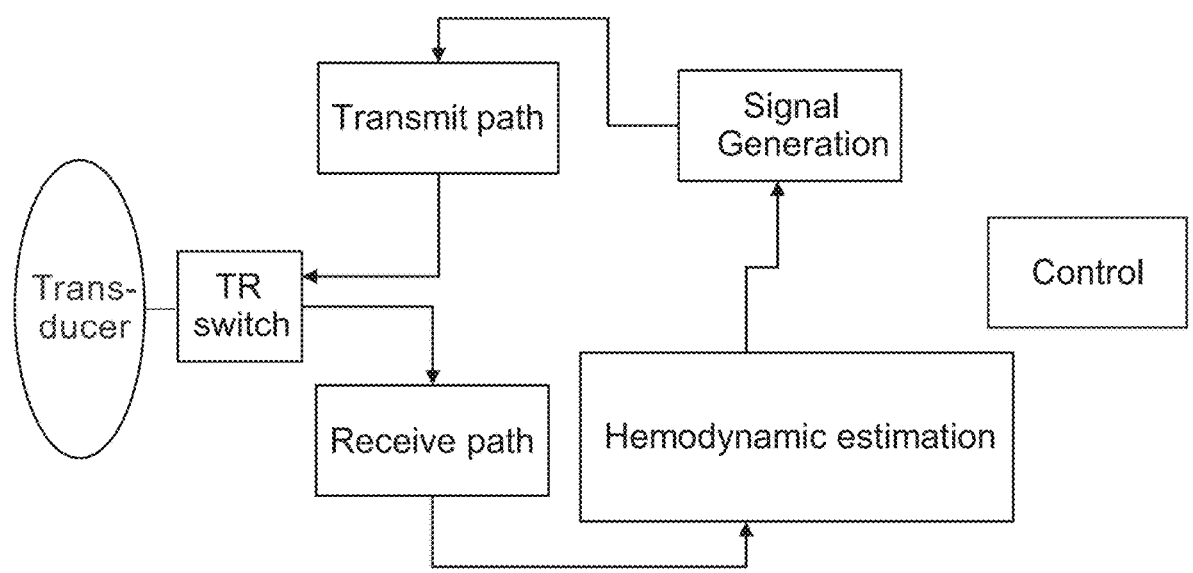
FIG. 90 is a schematic representation of an implementation of a circuit using a single transducer, according to come embodiments of the present invention.

In some embodiments, the sensing may be performed from a group of sensors that are adapted to receiving signal as well as transmitting signals, or as a default were all transducers in the system can provide an input signal. FIG. 90 shows the implementation of such a circuit using a single transducer. In some embodiments, this may be repeated to all transducers or implemented to a selected few. In order to receive an ultrasound signal the electrical circuit implements a TR switch (for transmit receive switch)

In some embodiments, the main source for hemodynamic information in the vicinity of the kidney is the renal artery and the various arteries within the kidney. The flow of the blood through the renal artery may be estimated and used for tracking the timing of the hemodynamic cycle.

Figure 91:
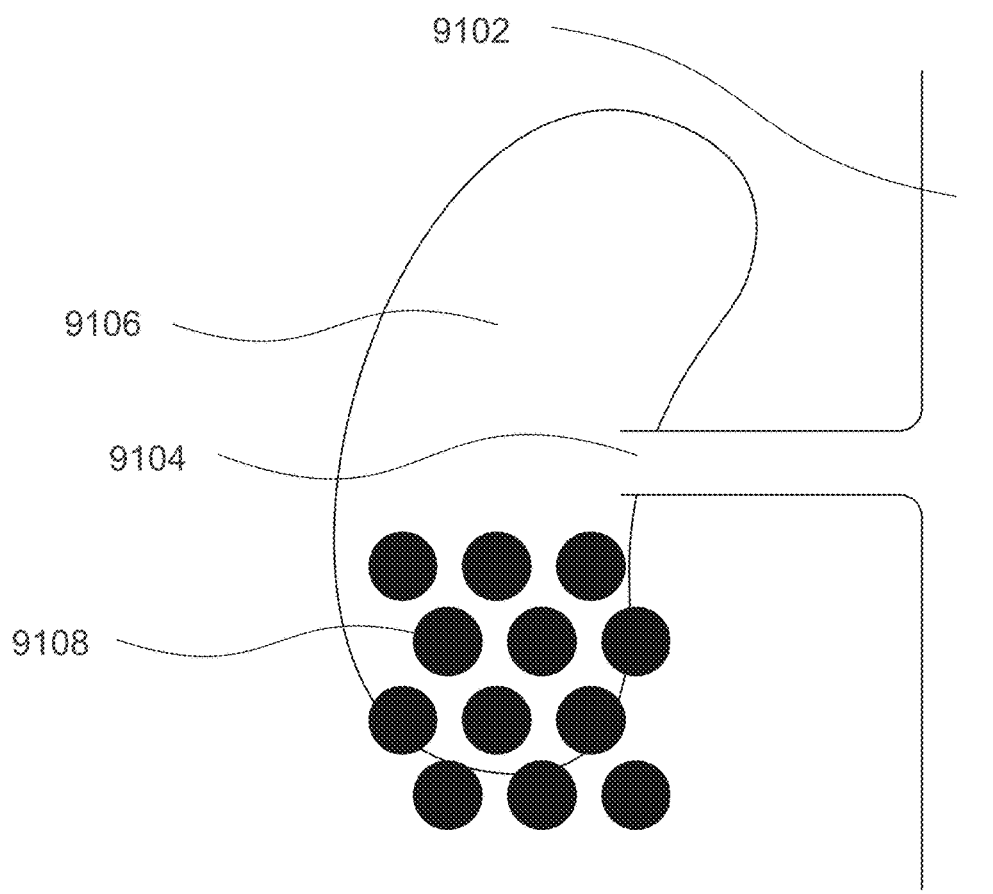
FIG. 91 is a schematic representation of a side view of the relationship between the transducer array and the kidney and renal artery, according to come embodiments of the present invention.
Figure 92:
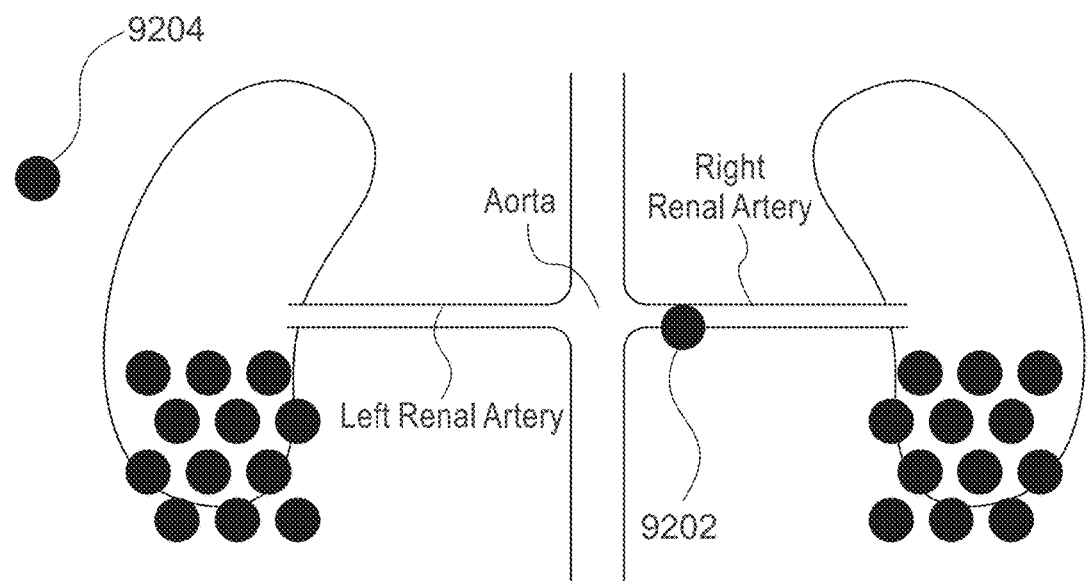
FIG. 92 is a schematic representation of an example of the relative position of the transducers when placed on the back of the patient, according to come embodiments of the present invention.

From a side view, the relationship between the transducer array and the kidney and renal artery would be like in FIG. 91. The abdominal aorta 9102 carries the blood and responds to the hemodynamic cycle. The renal aorta 9104 carries the blood to the kidney 9106. The transducers 9108 in this example cover the bottom lobe of the kidney. In this example the transducers are placed on the back of the patient, the relative position as shown in FIG. 92.

In some embodiments, the transducers occupy the lower portion of the kidneys. In some embodiments, by selecting the transducer that covers the renal artery, or by using beam forming, the ultrasonic beam can be directed towards the renal artery. In some embodiments, the returning signal would be modulated by the hemodynamic flow due to the Doppler Effect.

Alternatively, a dedicated transducer 9202 can be placed pointing at the renal artery or the abdominal aorta. It can be placed on the back, or placed on the side 9204 facing the renal artery, and thus receiving a maximal signal since the direction of the blood flow in the renal artery would be radial for this transducer.

If we model the outgoing signal as a short duration sine wave $A(t)*\sin(2\pi ft+\psi)$ where $A(t)$ is the signal amplitude, f is the frequency and $\psi$ is the phase, the returning signal By estimating the central frequency shift of the returning signal the radial velocity of the blood may be measured at different times. The time of maximal velocity would enable to estimate the hemodynamic timing $$f_d = f_R - f_T = \frac{2v f_T \cos\vartheta}{c}$$

Where $f_d$ is the Doppler frequency, $f_T$ is the transmit frequency, and $f_R$ is the received frequency. The velocity v is the blood velocity, which is actually the value we would like to estimate. The speed of ultrasound signal in the blood is denoted as c, which is approximately 1570 m/second, for the estimation of blood flow typically lower central frequencies are used.

The angle between the direction of flow and the direction of the ultrasonic signal is provided as $\vartheta$. This angle will be relatively small when we place the transducer at the waist but can be close to 90 degrees when we access the kidney from the back. For this reason some tuning of the beam towards the renal artery is advantageous in order not to hit the renal artery from a perpendicular angle, which would reduce the value of $\cos\vartheta$ to be close to zero. The right renal artery typically is longer than the left renal artery and has a distinct arc that makes it easier to find and get a good measurement, since along this arc there would be a number of preferable directions to measure The renal artery itself moves with the movement of the kidney during the breathing cycle. Some tracking of the artery location may help in getting a good estimate of the hemodynamic parameters The Doppler estimation of the blood velocity can be performed with various transmitted signal. The three main options are: Continuous Wave Signal; Pulsed wave; and Color Doppler.

Figure 93:
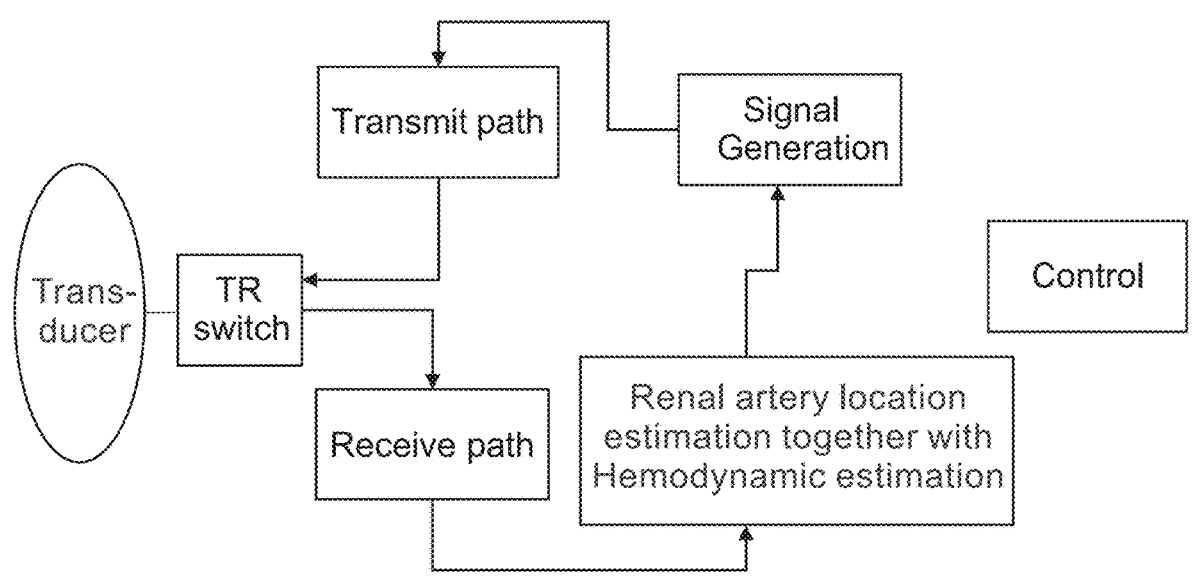
FIG. 93 is a schematic representation of an exemplary method of tracking the location of the renal artery, according to come embodiments of the present invention.

In order to get a good signal with flow, the location of the renal artery may be tracked. This is a combination of location tracking and Doppler tracking, since the location of the artery is not achieved by the ultrasonic 2D structure necessarily but by the significant Doppler characteristics of the signal at that location. This can be done as shown in FIG. 93 or from the back access as well.

Kidney Location Estimation Using Ultrasound

In some embodiments, a combination of sensing and therapeutic ultrasound is performed by using ultrasound signaling to track the location of the kidney. In some embodiments, by utilizing this configuration, special transducers can be used to track the kidney location, or the same transducers may be used.

In some embodiments, the advantages of kidney location tracking might be that the system can avoid as much as possible the exposure of non-kidney tissue to ultrasound, and/or the power efficiency of the system is improved since the signal is directed at the target organ.

The architecture of the system may be as described in FIG. 94.

Location estimation algorithms are known in the art, and hereby few of them are presented as examples.

Complete kidney location estimation based on the location of the renal artery and hilum The renal hilum is a relatively distinct region to estimate, due to the large blood vessels that arrive from a known location and angle. The renal artery and renal vein have distinct features. By tracking the hilum, a relatively accurate location of the complete kidney is possible.

Complete kidney location estimation based on the special structure of the kidney. This algorithm is reminiscent of the operation that a human would do for kidney tracking based on its unique shape. The borders of the kidney with the surrounding tissue shall be registered, as well as some internal structure within the kidney. The registered marks shall be continuously tracked to generate a detailed model of kidney location FIG. 95 shows the transducer array at the waist, and 4 identified markers over the left kidney. The markers are the hilum, the top and bottom edges of the kidney and the kidney cortex surface that is closest to the transducer array In some embodiments, the kidney tracking algorithm continuously tracks the 4 markers and provides the changing locations of the markers to the signal generation algorithm module. The transmission module, using beamforming generates a signal that achieves the desired coverage. The time varying marker locations are provided as $$\vec{\gamma}_i(t)|_{i=1,2,3,4}$$

Where i is the index of the marker, and the location $\vec{\gamma}$ is a three dimensional vector for the location of the kidney The location is provided in a relative coordinate system of the transducer. In this case, the transducer would use beam forming to direct the therapeutic ultrasound signal not higher than the top mark and not lower than the bottom mark.

$$S_j(t) = S(\vec{L}_j, \vec{\gamma}_i(t))|_{i=1,2,3,4}$$

The transmitted pulse signal $S_j(t)$ per transducer j depends on the location of the marker and on the location $\vec{L}_j$ of the jth transducer.

Tracking Methods

In some embodiments, tracking techniques used are, for example, unsupervised and untrained organ tracking. Tracking that is initialized by a trained practitioner. The trained practitioner may provide landmarks on an ultrasound image to be followed. The trained practitioner may OK an autonomously generated estimation. The trained practitioner may mark (using an ellipse marker) the general location of the kidney to be followed.

In some embodiments, special cases such as horseshoe kidney are excluded or treated differently.

Kidney Classification

In some embodiments, there are special pathologies for kidneys where an automatic algorithm may find harder to track, for example, horseshoe kidney (ren arcuatus, 1:600), renal ectopia (1:900, misplaced kidney), crossed (fused) renal ectopia (both on one side), fused pelvic kidney, and/or autosomal Dominant PKD (1:1000).

Some pathologies would be non-congenital such as various Kidney diseases, tumors and others. In some embodiments, for automated kidney tracking these pathologies may be excluded. In some embodiments, further testing would be required to identify algorithm refinement for such pathologies. In some embodiments, reference transducers are used to improve location tracking.

In some embodiments, in order to improve location estimation a reference transducer that is not part of the transducer array may be used to receive the transmitted pulses and calibrate. In some embodiments, by transmitting ultrasonic signal from the transducer array and receiving the signal at a known location $\vec{L}_R$ of the reference design, many of the inaccuracies of the system may be calibrated. The beam forming algorithm for focusing the signal at location $\vec{L}_R$ would be used, and verified. Later adjustments would be made to the relative delays in order to direct the ultrasonic signal from the transducer array towards the kidney tissue location. A system with a reference transducer is provided in FIG. 96. In some embodiments, however, the location of the reference transducer, shown in the figure to be close to the spine, may be optimized. In some embodiments, for low frequency ultrasound signals this may be even one of the transducers at the other waist, e.g. transmission from the left waist to the right waist and vice versa.

Detection of Cavitation

In some embodiments, the unit optionally includes a detection of cavitation events. In some embodiments, counting cavitation events is used to modify treatment parameters Sensing the Effectiveness of the Treatment, for Instance by Estimating GFR, Chemicals in Urine, Chemicals in Blood, Urine Quantity In some embodiments, the system may be connected to a sensor that measures treatment effectiveness.

Examples for such measurements are: measurement of quantity of urine, measurement of chemicals in urine such as:
  Chemicals sensors in urine (Urea, creatinine, proteins, Ca, Na, K, Cl)
  Chemicals sensors in blood
  Under-skin (interstitial fluid) chemical sensors
  Wearable chemicals sensors
  Oxygen levels in kidney
  Catheter based chemical sensors In some embodiments, the system shall be able to stop treatment when wellness threshold is exceeded.

Type 6 System

System where the Transducers Focus the Ultrasound Signal to Kidney Sub-Elements

Type 6 systems are similar to the previous systems but with the addition of the focus of the ultrasound signals to kidney sub-elements.

Background

The idea to focus the Ultrasound signal at specific locations is attractive for two reasons: getting a maximal effect on the target tissue with minimal energy resources, and/or reducing unknown risks associated with Ultrasound exposure of other tissues.

In some embodiments, ultrasound focus is achieved by the usage of a number of non-focused transducers and flexible control of the electronic signal arriving at each and every transducer. Alternatively, this can be achieved by moving a transducer array with a fixed focus, or a combination of both.

In some embodiments, Highly Focused treatment systems direct a very accurate signal to a specific volume deep inside the body. In some embodiments, this requires knowledge of the 3 dimensional structure of the patient's body, and the ability to identify the desired locations based on sensed data. In some embodiments, in a breathing patient, the kidney may be constantly moving with the breathing cycle. Thus, real time location tracking is needed if specific zones in the kidney are targeted. In some embodiments, the 3 dimensional structure of the body, and specifically the location of the kidney is provided to the system from a previous imaging measurements such as an MRI or similar. In some embodiments, the system is connected to an imaging ultrasound system that is able to identify the kidney based on the reflected ultrasonic signals.

A System to Therapeutically Treat Inter-Kidney Organs

In some embodiments, the ultrasound signal is applied to the renal cortex alone, where the renal corpuscles are located. In some embodiments, this is done since there is a clinical need (and goal) to increase the clearance of contrast medium from the blood, and this is performed only in this location.

In some embodiments, there is a need to clear other molecules through the renal corpuscles and the system operation is similar to the one described herein clearing contrast media.

Figure 97:
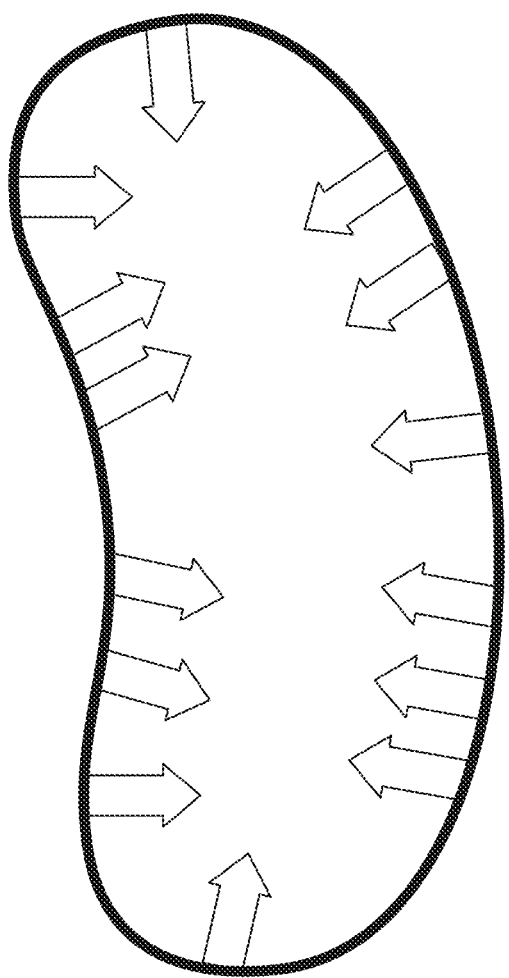
FIG. 97 is a schematic representation of an exemplary method for opening blockage of nephrons and improve GFR, according to come embodiments of the present invention.

In some embodiments, the system applies ultrasound on the renal medullas only. In some embodiments, this is done to achieve clinical goals such as to increase GFR, or to increase urine excretion for CHF patients. Referring to FIG. 97, in some embodiments, moving the ultrasound signal along the arrows, in the direction of renal cortex to renal core is effective in opening blockage of nephrons and improve GFR.

Avoiding the Kidney Exterior

In some embodiments, due to a need to avoid exposure of specific other organs to the ultrasonic signal, the design that identifies the kidney boundaries and avoids exposure of other tissues is used as described.

Implanted Kidney

In some embodiments, there is a need to treat an implanted kidney. In some embodiments, this requires the attachment of the unit at another location, fitting the anatomical location of the implanted kidney.

Type 7

In some embodiments, system type 7 is similar to types 1-6 with the addition of visual feedback to the user.

System with Visual Feedback

In some embodiments, this type of system provides visual feedback to the user on the proper functionality. In some embodiments, the visual feedback also assists in setting up the treatment. In some embodiments, the system is used also as a diagnostic ultrasound prior to the application of the system. In some embodiments, prior to the application of the unit, visual inspection, if needed, is performed using a visualization system which is an off the shelf standard equipment, part of the hospital's regular equipment.

In some embodiments, the goal of the check may be to validate the location of the kidneys—position and depth. Measurements output may be:
  Approximate location of each kidney
  Approximate size of each kidney
  Kidney depth—minimum, maximum and average
  Kidney markers, as needed for tracking algorithm
  Location of kidney artery
  Other kidney functional information such as blood flow estimation In some embodiments, this information is provided to the system by a data interface or by a user interface.

In some embodiments, the information from the ultrasound visual inspection may be used for:
  Verification of treatment parameters (making sure the kidney location is within unit treatment guidelines)
  Adjustable parameter (kidney depth may affect treatment parameters, for instance signal intensity)
  Guideline regarding the placement of the system transducers
  Guideline regarding the placement of the system transducers sensors (if any, e.g. hemodynamic sensor)

Exemplary System Type 8

In some embodiments, system type 8 is similar to types 1-7 with the addition of multiple independent transducers/transducer arrays.

System with Multiple Independent Transducers/Transducer Arrays

Figure 98:
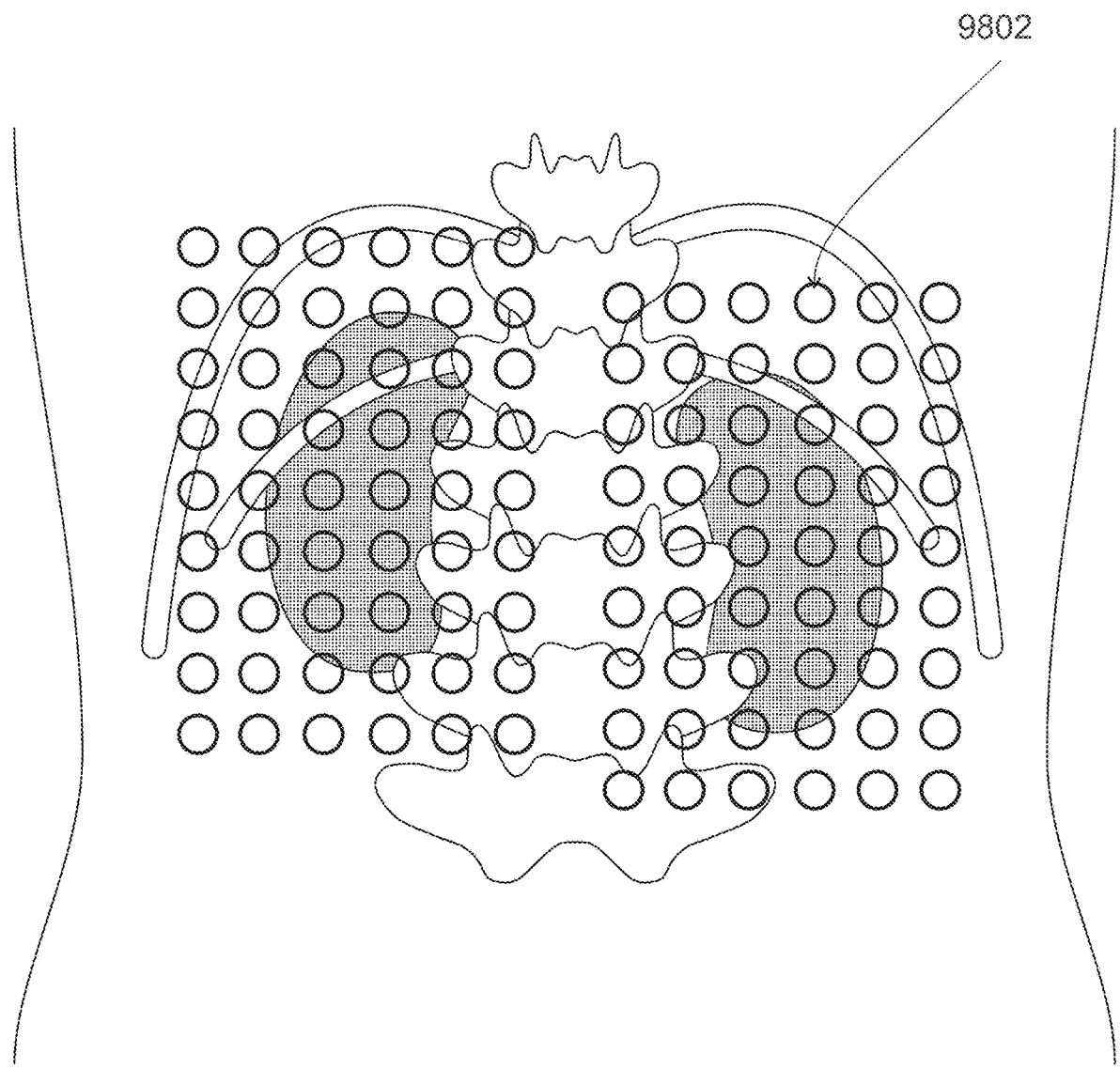
FIG. 98 is a schematic representation of how transducers cover the back, according to come embodiments of the present invention.

In some embodiments, this type of system provides coverage of the lower thoracic and upper lumbar back using multiple transducers or transducer arrays. In some embodiments, the transducers 9802 cover the back area as shown in FIG. 98 and are intended to be placed over the spine and ribs number 12, 11 and potentially 10 as well. In some embodiments, some of the transducers may be placed over the spine as well Anatomical Orientation In some embodiments, the transducers that are placed over the back, the ribs and parts of the spine, transmit ultrasonic signals and measure the parameters of the reflection such as amplitude and delay. In some embodiments, strong reflections are correlated with reflection of the ultrasound signals for bones, such as the ribs and the spine. In some embodiments, strong reflections are correlated with reflection of the ultrasound signals from the air present in the lungs in the superior part of the transducer mat. In some embodiments, based on the measured reflections, the system builds a reflection map of the tissues facing the transducers. In some embodiments, based on the map, the system can identify the location of the ribs, spine, kidneys, kidney arteries, and other organs that have a known area distribution. In some embodiments, the algorithm for estimating the kidney location is based on anatomical information, optionally information recovered a priori. In some embodiments, the algorithm for estimating the kidney location is based on calibration performed on subjects while using other imaging information such as CT, MRI, and Ultrasound. In some embodiments, the kidney location is accurately estimated without measuring any signal that is reflected from the kidney itself, but rather based on the known distribution of kidney location and other distinct anatomical markers such as ribs and spine.

In some embodiments, the result of the orientation measurement is used as an automated verification tool for the system to ensure that the system was applied correctly to the patient. In some embodiments, the result of the orientation measurement provides a feedback to the user, in case the system accidentally moves. In some embodiments, the result of the orientation measurement provides accurate direction and orientation instructions to the user, in case the system moves. In some embodiments, the result of the orientation measurement provides a treatment map, enabling ultrasonic transmission for only the transducers that are likely to affect the target tissue. In some embodiments, a potential advantage of the use of an accurate ultrasonic transmission map is the reduction of power consumption, reduction of system weight and reduction of overall costs, and increased time between battery replacements.

Figure 99:
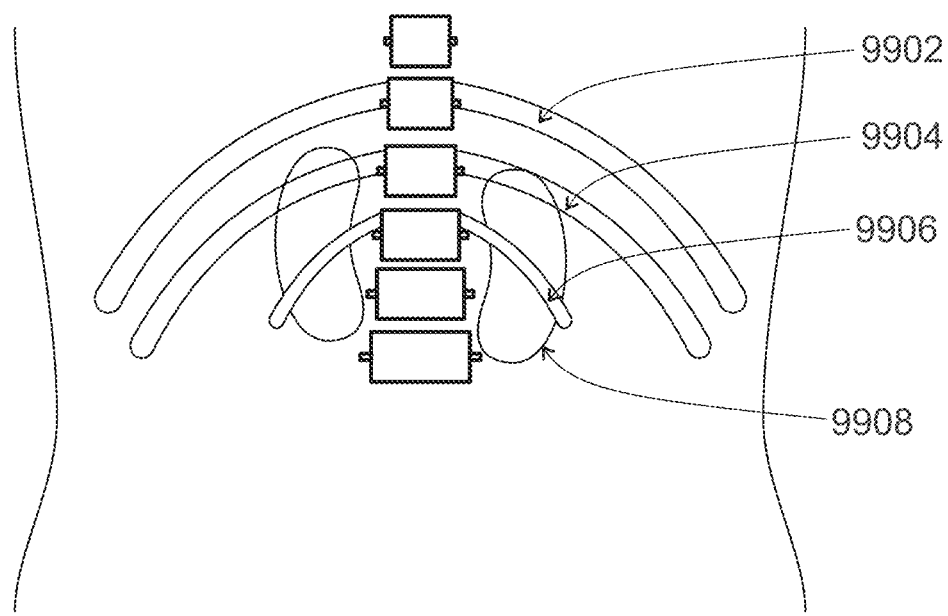
FIG. 99 is a schematic representation of the ribs and the spine, according to come embodiments of the present invention.

Referring now to FIG. 99, showing rib 10 9902, rib 11 9904 and rib 12 9906 from both sides of the spine. In this example, rib 12 is posterior to the kidney, while rib 11 may or may not be posterior to the kidney. Rib 10 would typically be superior to the kidney. In some embodiments, by identifying the very unique structure of the lower ribs, via ultrasound reflection, the location of the kidney 9908 is estimated even without detecting any unique characteristic of the ultrasound as reflected from the kidney.

Figure 100:
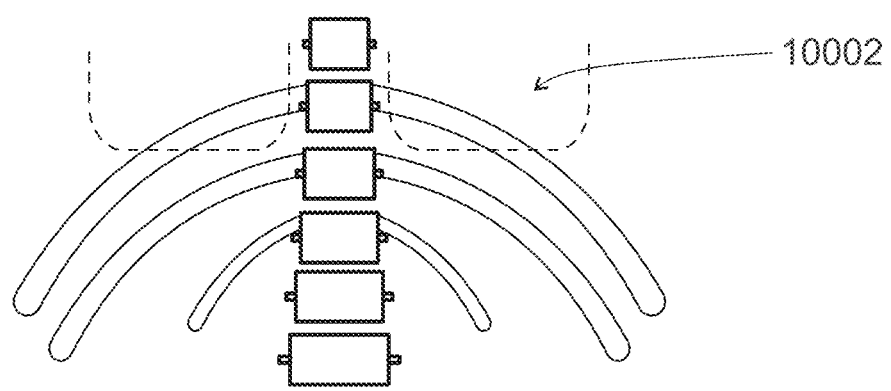
FIG. 100 is a schematic representation of the ultrasound reflection that is measured from the multiple transducers, according to come embodiments of the present invention.

In some embodiments, the ultrasound reflection that is measured from the multiple transducers shall resemble what is shown in FIG. 100. The superior zone of the ultrasound reflection map would be marked by high reflections from the lungs (10002).

Independent Transducer Arrays

In some embodiments, transducer array beamforming is applicable when the relative orientation and position of the transducers are known. In some embodiments, transducer arrays that include a number of transducers that are connected together to a solid frame from the basis in the transducer mat. In some embodiments, for each kidney, one or more transducer arrays may be placed over the back. In some embodiments, in order to fit anatomically with the back curvature, the total diameter of a transducer array should be up to about 25 mm, optionally larger or smaller diameters can be used. In some embodiments, individual transducers within the transducer array receive the same signal. In some embodiments, individual transducers within the transducer array receive the same signal with varying amplitudes and/or varying phases and/or varying delay. In some embodiments, individual transducers within the transducer array receive different signals. In some embodiments, the fact that transducers within an array share signal characteristics, they may also use the same signal cables connecting to the signal generator unit. In some embodiments, a potential advantage of saving cables is the reduction of the system size, weight and cost. In some embodiments, by using signals directed to multiple adjacent transducers, the ultrasonic beam is optimized, avoiding highly reflecting tissue such as bone, and enabling more ultrasonic signal delivery to the target tissue.

Figure 101:
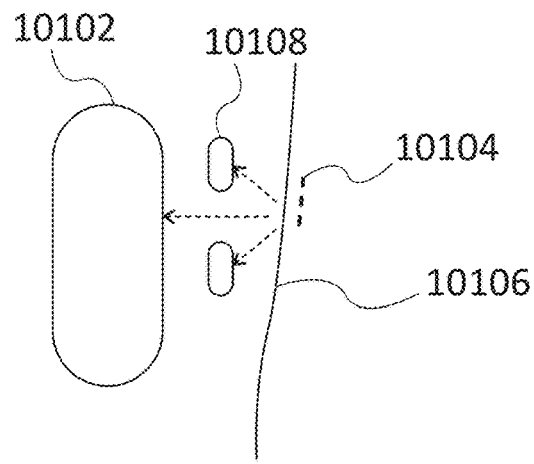
FIG. 101 is a schematic representation of how the kidney is exposed to ultrasound signals arriving from an ultrasonic array that is placed on the back, according to come embodiments of the present invention.

FIG. 101 shows how the kidney 10102 is exposed to ultrasound signals arriving from an ultrasonic array 10104 that is placed on the back 10106. As can be seen in the figure, rib 11 10108 and rib 12 10110 interfere with the signal. In the figure is also shown that there are three options for beam direction, as shown by the arrows 10112, two of them would generate strong reflection from the ribs, while the middle option would generate milder reflection from the ribs, with more ultrasonic energy reaching the kidney. In some embodiments, the system may record the reflections from the ribs and employ more time generating signals that are not strongly reflected.

Exemplary System Type 9

In some embodiments, system type 9 is similar to types 1-8 with the addition of decubitus ulcer reduction and ultrasound transmission.

System with Combined Decubitus Ulcer Reduction and Ultrasound Transmission

In some embodiments, in order to provide the most efficient therapeutic effect the transducers should be in contact with the skin. In some embodiments, under some circumstances, the very same contact may be the source of unpleasant feeling, pain, skin irritation and skin injury. In some embodiments, decubitus ulcers is one of such injuries, with increased prevalence when there is an increase in contact pressure, an increase in duration of the contact, a decrease in skin blood perfusion and an increase in water content at the contact area. In some embodiments, the system changes the pressure distribution of skin and transducers in order to reduce risk of skin irritation and damage. This is performed by building into the system a mechanism that allows for better control of the pressure applied to the skin, from simple pressure equalization techniques, to elaborate mechanisms that modify contact pressure independently over location and/or time.

In some embodiments, the system tries to passively equalize the pressure along all locations, for instance by using a fluid interface substance between all the transducers and the skin. This implementation spreads the hydrostatic pressure evenly. By spreading the pressure over a large body area, large local pressure peaks average out with areas of lower pressure, providing an even pressure distribution, and reducing the probability that a high pressure peak pressure at one specific location may injure the skin.

In some embodiments, the system tries to passively equalize the pressure along all locations, for instance by using an air filled chambers that spreads the aerostatic pressure evenly. Since air is not an ultrasonic transparent material, the air chambers should not be between the transducer and the skin, but rather the transducers should be between the air chambers and the skin. In order to spread the pressure evenly the transducers, that are located between the gas/air/liquid filled chamber and the skin, should be connected with a highly flexible material, in order not to add any additional pressure to the skin, that is caused not by the pressure from the chamber but rather due to the pressure from the elasticity of the material connecting the transducers.

In some embodiments, the pressure applied on the skin by each transducer or transducer array or group of transducers is measured, and may be dynamically modified. In some embodiments, pressure modification is achieved by mechanical movement of motors. In some embodiments, pressure modification is achieved by moving gas or liquid or gel from pressurized chambers to less pressurized chambers, via valves. In some embodiments, pressure modification is achieved by controlling valves that let gas or liquid or gel move from place to place.

In some embodiments, the rules for pressure modification take into consideration the actual dosage of ultrasound signal applied to the tissue, the required dosage of ultrasound signal, the pressure history applied to the skin, and the characteristics of the skin. In some embodiments, the blood perfusion is measured using light or infrared light. In some embodiments, the skin, which is pressed between a rib and a transducer, is detected using the reflected ultrasound signal from that zone.

System with Pressurized Chambers, Contact Sensors and Transducers

In some embodiments, in order to achieve good acoustically transparent contact between the transducers cover and the patient's skin, there is a need to apply pressure on individual transducers or transducer groups or transducer arrays. In some embodiments, the pressure decreases the remaining volume between the transducers and the skin, and allows for the acoustically transparent material within this volume to fill it and enable low reflection and high transmissivity of the ultrasonic signal from the transducer to the skin.

Due to the three-dimensional shape of the patient's skin, which is different for each individual patient, the shape of the transducer mat needs to be adjusted to match the shape of the patient. In some embodiments, the exact shape is achieved by patient's 3D measurement and production of patient specific structure. In some cases, preparing a patient specific structure is impractical and expensive. In some embodiments, pressurized chambers are placed behind the transducers, pushing the transducers towards the patient's skin. In some embodiments, at least one pressurized chamber is used. In some embodiments, multiple pressurized chambers all with the same pressure are used. In some embodiments, multiple independent pressurized chambers, with varying pressure are used for this function. In some embodiments, the pressure of individual chambers or group of chambers are controlled using a controlled valve and valves.

Figure 102:
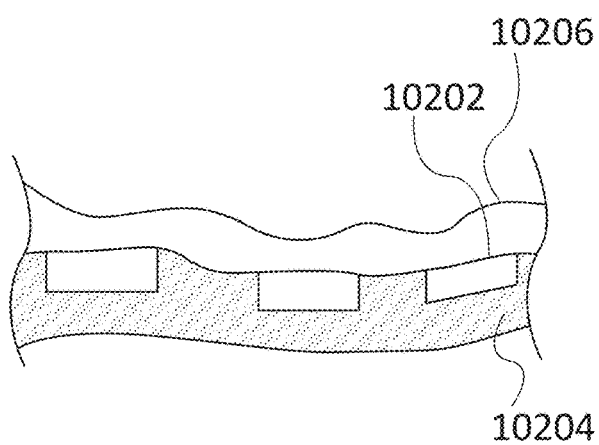

An embodiment of a transducer mat is shown in FIG. 102. In some embodiments, the transducers 10202 are embedded within a flexible layer 10204 allowing the transducer mat to adjust to the shape of the patient's skin 10206, even though each transducer is made of non-flexible piezo-electric material. In some embodiments, the remaining volume that remains between the skin 10206 and the transducers 10202 in the transducer mat is filled with the disposable acoustically transparent material.

Figure 103:
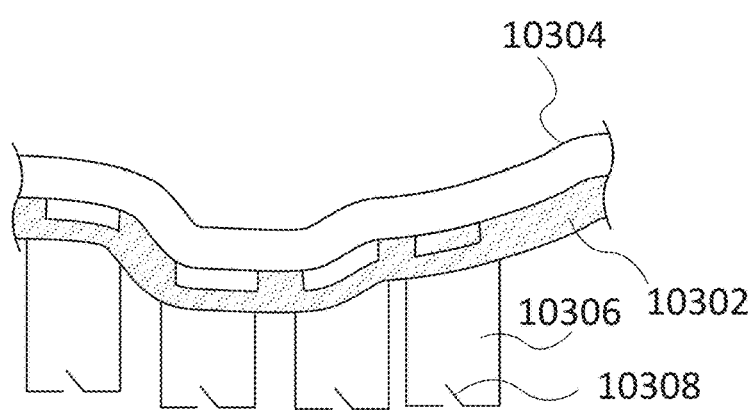

Another embodiment of a transducer mat is shown in FIG. 103. In some embodiments, the transducer mat 10302, which is built from transducers and a flexible material, is facing the patient's skin 10304. In some embodiments, the flexible material is made of silicone. In some embodiments, the flexible material is made of polyurethane. In some embodiments, the flexible material is made of foam. In some embodiments, in order to achieve contact with the skin, pressure is applied on the bottom part of the transducer mat. In some embodiments, this pressure is generated from flexible chambers 10306 that can be filled via valves 10308. In some embodiments, the pressurized chambers may be filled with gas, liquid or gel.

In some embodiments, there is an inflatable chamber under each transducer or transducer array. In some embodiments, there is an independently controlled inflatable chamber under each transducer or transducer array. In some embodiments, using valves, such chambers can be under-inflated or over-inflated relative to adjacent chambers.

In some embodiments, there is a contact sensor for each transducer that provides feedback to the control unit on the quality of the coupling. In some embodiments, the contact sensor is implemented using pressure sensor. In some embodiments, the contact sensor is implemented using an electrical sensor, measuring the conductivity of electric current to the skin. In some embodiments, the contact sensor is implemented using an electric sensor, measuring the impedance circuit that changes according to the mechanical impedance. In some embodiments, the contact sensor is implemented using an ultrasonic sensor, measuring the reflected signal from the body. In some embodiments, the contact sensor is implemented using a strain sensor, measuring the strain in the disposable element that changes with skin contact. In some embodiments, the contact sensor is implemented using a magnetic sensor, measuring the signal affected by miniature magnets embedded in the disposable unit.

In some embodiments, the blood perfusion is measured in the skin using infrared sensors. In some embodiments, pressure on the skin may change blood perfusion in the skin, which is under pressure from the transducer.

In some embodiments, temperature sensors measure indirectly the blood perfusion in the skin.

In some embodiments, water sensors detect water content at the skin interface. In some embodiments, excess water and sweat are important for monitoring patient wellness, skin damage and therapy effectiveness.

In some embodiments, sensors measure tear in the disposable material or the multi-use device. In some embodiments, the integrity of the device is measured using resistance of wires, electrical resistance, strain, ultrasonic vibration and other mechanisms to monitor material continuity.

In some embodiments, accelerometers or magnetic sensors measure the angle of the device, for instance, angle to the horizon. In some applications, for instance, an AKI application where the patient is supine on a bed, the angle of the device may indicate that the patient and or the device are out of the approved operating angles for the treatment.

Exemplary System Type 10

System that optimizes the structure of the disposable unit in order to maximize the transmission of ultrasonic signal into the body even when the patient performs movements, small to large, by utilizing acoustic windows, skin adhesives, and sensors In this exemplary system we show:
1. Designs that have different material in areas between transducer and skin, compared to areas between transducers
2. Designs that have unique skin adhesive patterns depending on location of transducers, anatomy and other design parameters that shall be elaborated
3. Designs that have different locations of various sensors, and in particular strain sensors and pressure sensors, depending on location of transducers, anatomy and other design parameters that shall be elaborated The designs take into consideration
1. Patient movement—the types of movements' patients are taking at different clinical applications.
2. The Interaction of such movements with the transducer mat.
3. Ultrasonic beam direction and beam direction changes, as well as the probability that a beam covers the kidney when the patient moves.
4. Pain and irritability that the patient may feel depending on the disposable structure.
5. Treatment duration.
6. Need of skin for water and oxygen exchange.
7. The disposable material reaction to movements (tear, stretch, air bubble intake) in response to patient movement.

In some embodiments, the disposable acoustic window material lies between a transducer and the skin, which have significantly different mechanical characteristics: the transducer is relatively rigid (high young modulus) compared to the skin that is much more flexible and stretchable. These relative rigidity differences are problematic when relative movement between the two are present. Relative movements can take place due to patient movement small and large. Such movements can cause the disposable material to tear, form vacuum micro-cavities, disconnect form the skin and allow air to enter the volume.

The common practice in the medical ultrasound domain with regard to this problem is to fill the void between the transducer and the skin with medium viscosity gel. Air bubbles that form when the gel is applied between the transducer and skin are usually manually moved away by the ultrasound technician. This solution is inappropriate for a device that has one or more of the following
1. Use for prolonged periods of time, up to 24 hours at a time
2. Has a large contact area with the skin
3. Is applied without visual feedback on an imaging ultrasound device
4. May be applied without a trained medical practitioner at site
5. Needs to be light weight and wearable Other practiced solutions to this problem is in the use of hydrogel pads and cavities of gel that are compressed to the skin. The ideal material for this function would have the acoustic impedance of the skin, together with lower attenuation at the relevant frequencies (4-15 MHz) and the viscosity to allow for the change of shape when there is a relative movement between the skin and transducer.

In some embodiments the design goal is achieved by a combination of two materials with different characteristics. The acoustic transparent window between the transducer and the skin has limited stretchability compared to the material filling the void between the transducers that is highly stretchable, but does not need to be acoustically transparent.

In some embodiments, the design of the disposable may be adapted to the clinical situation, and the expected patient movements. For instance, a post-operative patient under anesthesia is less likely to move compared to a heart failure patient treated for increased fluid secretion, who would be typically awake. The types of movements—amount of twist, stretch and bend the patient performs also depends on the clinical outset.

In some embodiments, this difference in the reaction of the material to stretch is achieved by adding other materials or structures to the material in various locations. In some embodiments, braided material is placed on the boundary of the acoustic windows (the material in front of the transducers) and the connective volume (all the other volume that is not part of the acoustic windows residing between the transducer mat and the skin). The braiding limits the movement of the window, thus controlling the shape and the pressure that it may experience.

Figure 104:
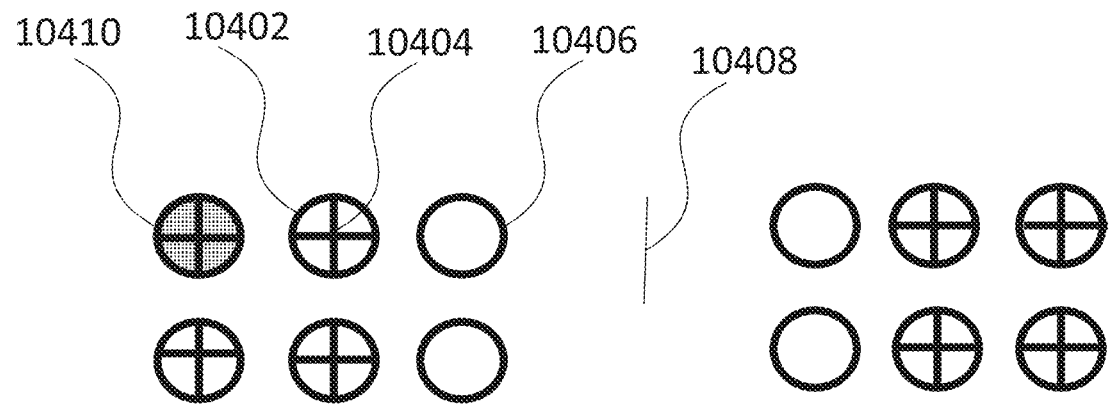

An example of such braiding can be shown in FIG. 104. The disposable material is prepared with additive braiding material during production, where the braiding material 10402 encircles the acoustic window, which is in front of the transducer. In addition, two diagonals 10404 limit the stretching of the acoustic window material in two directions. Not all transducers need to have the same protection. For instance, in the figure the transducer closest to the spine 10406 does not have the diagonal material added since skin stretching near the spine is limited. Braiding can also be added in areas, which are not part of the acoustic windows. In the figure, for instance, along the spine 10408. On the left top corner, the shadow of the transducer 10410 is shown in grey In some embodiments, this difference in the reaction of the material to stretch is achieved by adding a skeleton to the material in various locations. Skeleton material within the acoustic window may limit the minimum volume it may reach.

In some embodiments, the acoustically transparent material is made of an adhesive to the skin, to allow it to stretch together with the skin. In some embodiments this stretching is limited by a layer or carrier material (such as thermoplastic elastomer—TPE) with higher rigidity than the adhesive.

In some embodiments, the acoustically transparent material is made out of a silicon adhesive that is spread on a thermoplastic elastomer (TPE) such as 3M Medical Silicone Tape 2477P, where a silicone adhesive is facing the patient skin and an acrylate adhesive is facing the transducer.

In some embodiments, the acoustically transparent material is made out of a polyurethane membrane coated with silicone gel such as Scarfix by Safran Coating (Lyon, France). In some embodiments, the silicone gel ensures the ultrasonic characteristics of the material. In some embodiments, it may be further doped with elements such as ZnO in order to increase its acoustic impedance in order to move it closer to the acoustic impedance of the skin, at about 1.6 to $2 \times 10^6$ Rayl. In some embodiments the rigidity of the polyurethane membrane is modified to allow for limited stretchability, mimicking the stretchability of the skin. This is done to increase patient comfort. In some embodiments the rigidity of the polyurethane membrane is modified by means of perforations in the membrane. In some embodiments other membranes are used to carry the low viscosity silicone gel.

In some embodiments, the acoustically transparent material is made out of Silbione™—a soft skin adhesive (by Elkem/BlueStar) with low skin adhesion, and yet high MVTR and breathable. In some embodiments, the carrier layer of the disposable unit is modified to support increased level of MVTR.

In some embodiments, the acoustically transparent material is made out of silicone gel with low to medium viscosity such as NuSil (by Avantor Inc.) for example models MED 6360 or MED 6350 or variations of them with adjusted acoustic impedance, matching the impedance of the skin.

In some embodiments, skin adhesive does not cover the whole area of the acoustically transparent material, but only a small fraction of the area. In some embodiments, this provides a potential advantage since it allows for simpler and lower pain peeling, because the total area of skin with adherence to the device is lower. In some embodiments, this allows for the use of low cost adhesives such as biocompatible acrylate adhesives. In some embodiments, the disposable device may be constructed from a one or more materials, with some adhesive patches between the disposable and the skin. The exact location of the skin adhesive patches on the disposable unit must correspond to the locations of transducers in order to enable the following characteristics that are important to the functionality of the device Limited adhesive area in order to reduce peel pain
Limited adhesive area in order to reduce pain when the patient skin moves and stretches
Controlled and limited stretching of the disposable material in the acoustically transparent areas
High flexibility of the disposable material in the connective zones not functioning as acoustically transparent areas, to allow the device to track the patient's 3 dimensional body structure.

Figure 105:
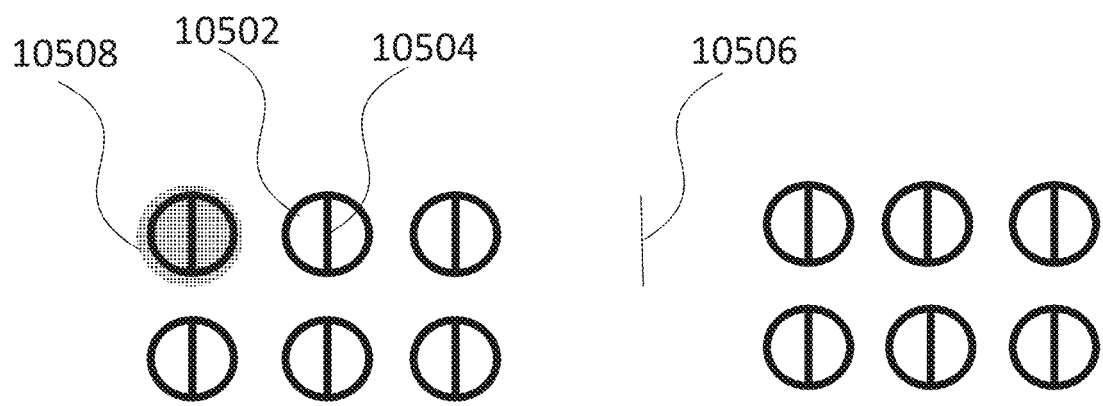

An example of an adhesive patch on the disposable material is provided in FIG. 105, where in front of every transducer, there is an adhesive patch that is constructed form a circle 10502 with diameter 85% of the transducer diameter, and one diagonal 10504 that limit the stretchability of the acoustic window in the inferior-superior direction, allowing some patient twisting but limited front bending. At the center, some vertical line adhesive over the spine is shown 10506, assisting in securing the device to the body. On the left top corner, the shadow of the transducer 10508 is shown in grey. It is clear from the description, that the exact shape of the adhesive patches on the disposable unit, which takes into consideration the locations of the transducers, the patient's anatomy and possible patient movement and its implications to the direction of the ultrasonic beams is unique to the device.

The construction of adhesive patches on a disposable unit may be performed by adding adhesive to specific locations, or by removing adhesive from specific locations, or any combination herein.

In some embodiments, sensing is required at the skin boundary to detect various operation parameters. One of the most important parameters, is the contact between the disposable material and the skin, which ensures the proper transfer of ultrasonic signal from the transducers to the kidney. The lack of contact can cause loss of therapeutic effect. By sensing the proper contact of the disposable acoustic windows to the skin, the device can then perform one or more of the following for example Alert the user that there is a need to improve the contact
Stop or pause to treatment
Perform device adjustments, such as stopping the transmission of signal from specific transducers
Perform beam forming device adjustments according to the movements of the transducers
Perform mechanical adjustments of the transducers, such as pumping air into inflatable chambers pushing the transducers towards the skin, described elsewhere in the patent.

Figure 106:
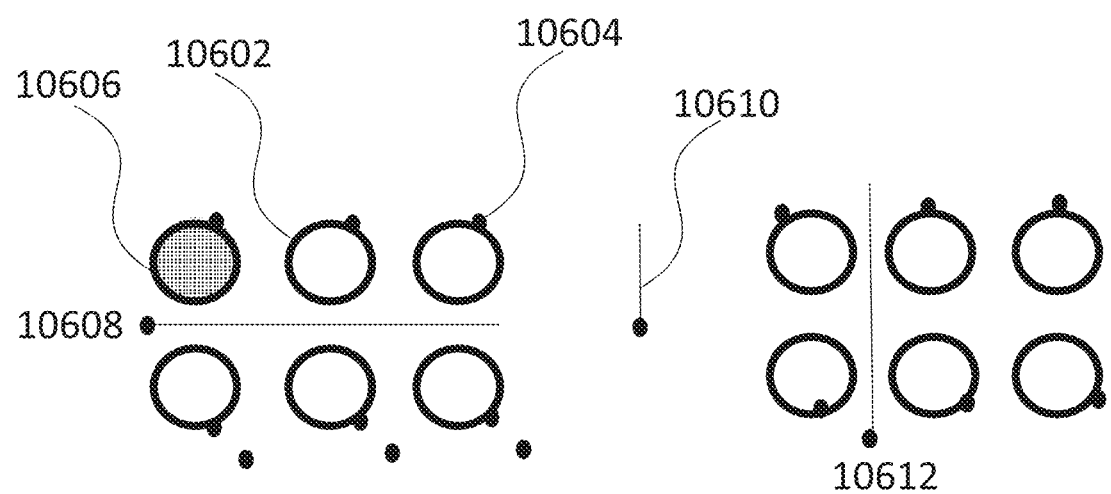

There are various ways to introduce sensors into the disposable unit. In FIG. 106, we show a mechanism that uses strain sensors. Strain sensors are low cost and provide information on the strain. By calibrating strain on the circumference of the transducer the event of inferior contact can be detected. One such sensor aligned with the circumference of a transducer is shown 10602. The sensor needs to be connected to the electronics of the multi-use transducer mat. This is performed for example by a connector 10604 at the edge of the transducer. Electrical contact between leads of the strain sensors and designated leads near the transducer provide for the transfer of the signal from the disposable unit to the electrical unit. On the left top corner, the shadow of the transducer 10606 is shown in grey. Strain sensors can also provide information on the 3 dimensional structure of the transducer mat, for instance by measuring along the horizontal line between transducers 10608 or vertically along the spine 10610 or vertically between transducer tows 10612. This information can provide indications to the device with regard the size and shape of the patient. For instance, a small sized patient will have more curvature along the horizontal line 10608. For this patient, there is probably no need to activate the distal most transducers that would already be near the patient's waist and away from the kidneys. This information would allow the system to shut down some transducers, and thus save on unnecessary transmission, and reduce power consumption and generated heat.

It is clear from the description, that the exact shape of the strain sensors on the disposable unit, which takes into consideration the locations of the transducers, the patient's anatomy and possible patient movement and its implications to the direction of the ultrasonic beams is unique to the device.

Figure 107:
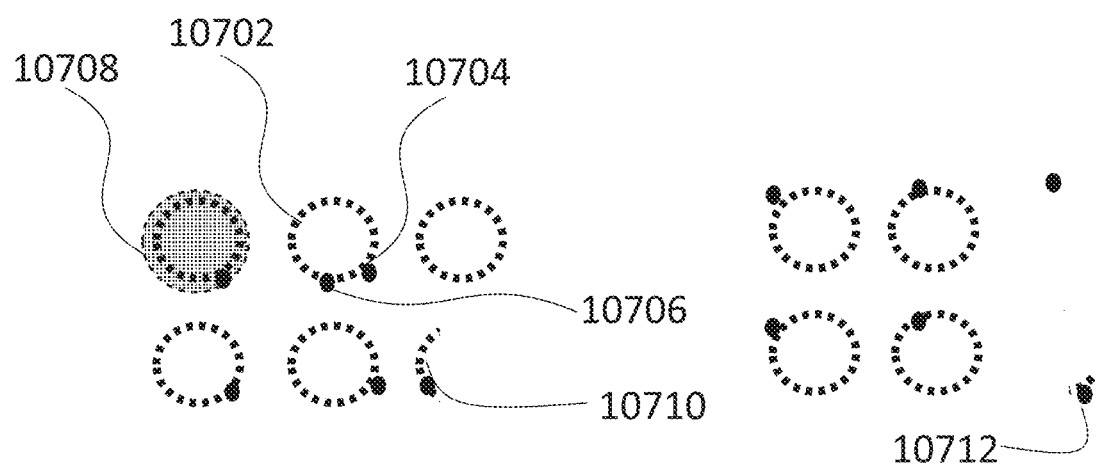

In some embodiments, pressure sensors are used to directly measure pressure between the patient's skin and the disposable unit. In FIG. 107, we show a mechanism that uses pressure sensors. On each transducer circumference, the minimal pressure sensor should be detected. A line of pressure sensors is connected 10702. They can be individually connected to a wire pair via a connector 10704, or combined with other sensors. The important aspect is the ability to detect at high probability the event of miss-contact, which would affect the loss of therapeutic function of the specific transducer under question. Thus, one or more connectors may be allocated to one transducer as shown in 10706. On the left top corner, the shadow of the transducer 10708 is shown in grey. The anatomical constraints mean than a disconnection of a transducer from the skin may happen at certain locations before others. This can help us significantly in reducing the number of pressure sensors and reduce overall system and disposable cost. A transducer near the spine 10710 will more likely disconnect from the skin on its distal part, thus sensors shall be allocated only in the distal part of the sensor. This way, with clean modeling of the human anatomy and the mechanical constraints of the transducer mat different allocations of sensors 10712 can be set.

It is clear from the description, that the exact number and location of the pressure sensors on the disposable unit, which takes into consideration the locations of the transducers, the patient's anatomy and possible patient movement and its implications to the direction of the ultrasonic beams is unique to the device.

Air bubbles that are trapped between the transducers and skin, when the system is applied to the patient's skin, may interfere with the proper function of the system. When compared to the transducers and the skin, the air has a significantly lower acoustic impedance. Thus, ultrasonic waves reaching the air bubbles waves are reflected, thus not reaching the desired destination. Common degassing practices are impractical in this situation, due to the high viscosity of the material.

In some embodiments, the disposable unit is mechanically and functionally split to areas that are acoustically transparent and areas that are not acoustically transparent. The acoustically transparent zones are positioned in front of the transducers and other zones that fill the area and volume between the acoustically transparent zones.

In some embodiments, the stretchability of the system in the non-acoustically transparent zones is threefold to enable the stretching and relative movement of the transducers, to enable the transducer mat to adjust to the 3 dimensional shape of the patient's skin surface, to absorb gel, liquid and air bubbles that are displaced from the volume between the transducer and the skin and to provide some adhesiveness to the skin to facilitate the operation.

In some embodiments, the non-acoustically transparent zone in the device comprises foam, thereby enabling the absorption of gel, liquid and gas. In some embodiments, the non-acoustically transparent zone in the device contains gas-absorbing material such as powdered activated carbon.

In some embodiments, vacuum is used to assist in the absorption of gas and liquid into the non-acoustically transparent material in the device.

In some embodiments, new gel and liquid are replenished between the transducer and the skin, pushing the old gel and liquid (which may also contain air bubbles) away from the acoustically transparent zone and into the zone located between transducer chambers.

Figure 108:
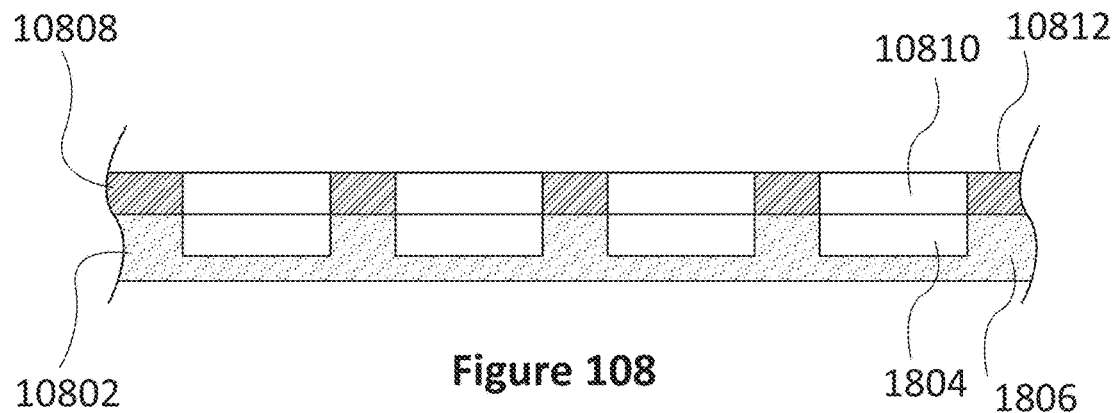

An example of the system is provided in shown in FIG. 108. The lower layer 10802 is the transducer mat that is built from transducers 10804 and flexible material between the transducers 10806. The disposable material 10808 matches the transducer mat—in front of every transducer there is a section of acoustically transparent material 10810 while in front of the flexible filler material there is an absorbing flexible material 10812. In some embodiments, this material allows excess gel or oil or air-bubbles to be absorbed into it. In some embodiments, there is no requirement for acoustic transparency for this material, since the ultrasonic signal does not pass through it.

In some embodiments, the acoustically transparent material has to be aligned with the transducers to guarantee the proper functionality of the device.

In some embodiments, the acoustically transparent material is in front of the transducers and a flexible material is in front of the flexible material between the transducers.

Figure 109:
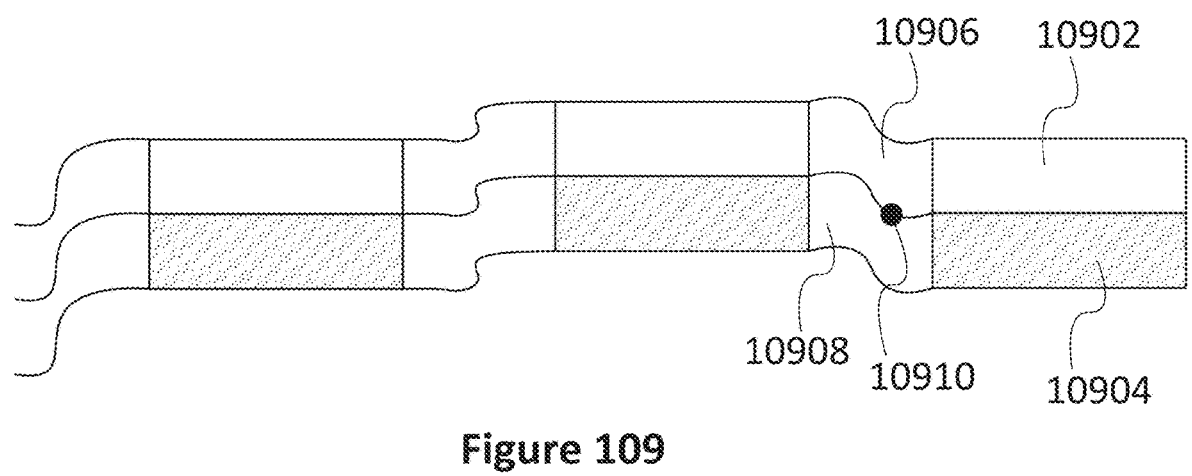

In some embodiments, the transducer is shaped in a way to push the air bubbles and extra acoustically transparent material away from the transducer center into the inter-transducer area. In FIG. 109 is shown that the transducer 10902, which is part of the multi-usage device, is matched with the acoustically transparent material 10904, while the flexible material between transducers 10906 is matched with the flexible material between acoustically transparent zones in the disposable 10908 part. In some embodiments, air bubbles 10910 may be trapped between those materials.

In some embodiments, the acoustically transparent material 10904 is made out of a silicon adhesive that is spread on a thermoplastic elastomer (TPE) such as 3M Medical Silicone Tape 2477P, where a silicone adhesive is facing the patient skin and an Acrylate adhesive is facing the transducer 10902.

In some embodiments, the acoustically transparent material 10904 is made out of a polyurethane membrane coated with silicone gel such as Scarfix by Safran Coating (Lyon, France). In some embodiments, the silicone gel ensures the ultrasonic characteristics of the material. In some embodiments, it may be further doped with elements such as ZnO in order to increase its acoustic impedance in order to make it closer to the acoustic impedance of the skin, at about 1.6 to $2 \times 10^6$ Rayl.

In some embodiments, the acoustically transparent material 10904 is made out of Silbione™—a soft skin adhesive (Elkem a BlueStar Company) with low skin adhesion, and yet high MVTR and breathable.

In some embodiments, the acoustically transparent material 10904 is made out of silicone gel with low to medium viscosity such as NuSil (Avantor Inc., US) for example models MED 6360 or MED 6350 or variations of them with adjusted acoustic impedance, matching the impedance of the skin.

In some embodiments, skin adhesive does not cover the whole area of the acoustically transparent material 10904, but only a small fraction of the area. In some embodiments, this provides a potential advantage since it allows for simpler and lower pain peeling, because the total area of skin with adherence to the device is lower. In some embodiments, this allows for the use of low cost adhesives such as biocompatible acrylate adhesives.

Figure 110:
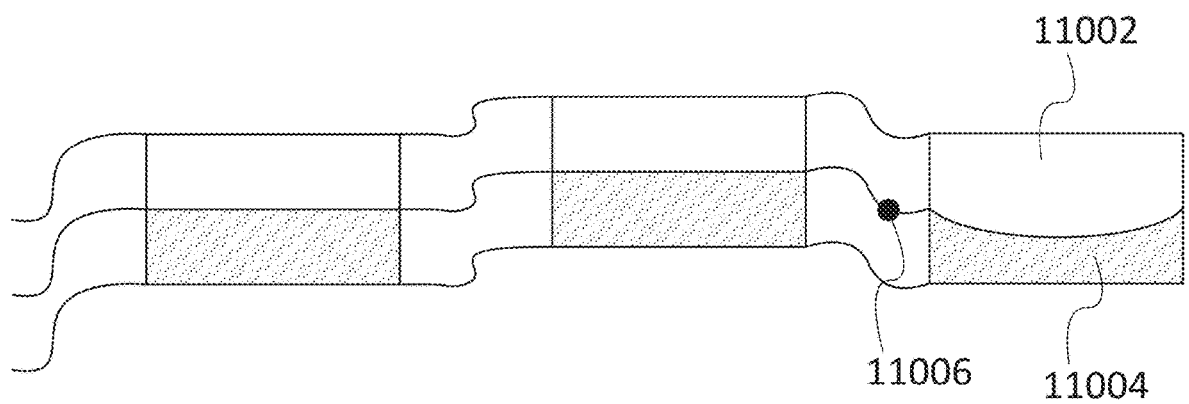

In some embodiments, the transducer is shaped spherically to push the air bubbles and extra acoustically transparent material away from the transducer center to the inter-transducer area. In FIG. 110, the transducer 11002, which is part of the multi-usage device, has a shape that is spherical facing the patient. In some embodiments, this shape assists in displacing the air-bubbles away from the center towards the sides of the transducers. In some embodiments, the transducer material is stiff and the acoustically transparent material 11004 is flexible. In some embodiments, the transducer face layer and the acoustically transparent face layer are made of hydrophilic materials in order to assist in displacing the air-bubbles.

In some embodiments, the face of the flexible material between the acoustically transparent windows, which are between the transducers and the flexible material, has a high affinity to the air bubbles, so air bubbles trapped in that space 11006 would not tend to migrate back to the ultrasound high transmissivity zone.

Figure 111:
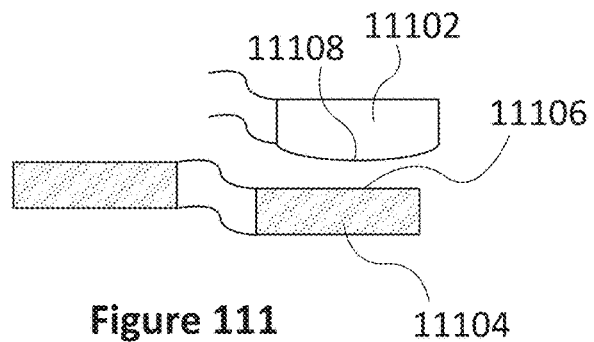

In some embodiments, before connecting the transducer 11102 to the acoustically transparent window 11104 water is added to the face 11106(903) of the acoustically transparent window 11104, as shown for example in FIG. 111. This water displaces the air from the surface of the acoustically transparent material. In some embodiments, the transducer is pushed towards the acoustically transparent window, with the most extended part of the transducer 11108 touching first the window.

Referring now to FIGS. 112*a* and 112*b*, in some embodiments, the transducer and the window are connected using an adhesive. In some embodiments, the transducer 11202 and the window 11204 are connected using a mechanical apparatus 11206 that guides the transducer to face exactly the window. The bottom part is a female connector, with conic cut, which is protruding from the surface and is guiding the male acoustically transparent window into place. In some embodiments, the apparatus resembles a cylinder protruding from the window. In some embodiments, the transducer 11202 and the window 11204 are connected using a mechanical apparatus 11206 that resembles a female tube at the bottom leading the window with the curved interface into exact location. The movement of the transducer is shown by the arrow 11208. In some embodiments, the volume between the transducer 11202 and the window 11204 is filled with water 11210 (or degassed water) to push away the air bubbles.

In some embodiments the material of the prism 11206 allows air bubbles 11212 and excess fluid to pass it to the space 11214 between the transducers and windows, which is not transparent to ultrasound.

In some embodiments, the spherical shape of the transducer makes it a collimating transducer, increasing the coverage of the system to kidney volume, since the total emitting area of the transducer mat is smaller than the area of the mat. In some embodiments, the spherical shape of the transducer makes it a collimating transducer, increasing the probability that the nephrons shall get equal coverage. In some embodiments, the spherical shape of the transducer makes it a collimating transducer, reducing the probability that some nephrons shall not be treated.

In some embodiments the combination of the transducer and the disposable acoustically transparent window ensure the right shape of the beam.

In some embodiments the combination of the transducer and the disposable acoustically transparent window ensure the pushing of air-bubbles away from the ultrasonic beam.

Exemplary System Type 11
A System Optimized for a Supine Patient, with a Risk of AKI, Possibly Anesthetized, Possibly within an Intensive Care Unit In some embodiments, the system is built from a multi-use device that includes the transducer mat that is connected to a control unit, and a disposable bag that comprises all the interface hardware with the human body.

An embodiment, of a multi-use device is shown in FIG. 113, and it comprises:
1. A transducer mat 11302 holding an array of transducers, as well as sensors that monitor the effectiveness and safety of the operation. In some embodiments, the transducer mat has multiple transducers 11304 or small independent transducer arrays 11304.
2. A control unit 11306 that includes the user interface—buttons, LEDs and a screen. The control unit also holds a rechargeable battery, providing the necessary power.
3. A mechanical connection interface 11308, to accurately connect the disposable unit to the transducer mat.
4. A connection strip connecting the control unit to the transducer mat. In some embodiments, there is no connector on either side of the strip. In some embodiments, the strip passes all the electrical signals from the electronic board inside the control unit to the transducers and sensors.
5. The center of the transducer is the spinal zone—the area facing the patient's spine. This area has an alignment transparent "window" to allow the visualization of the exact placement of the mat on the patient 11310. In some embodiments, this section may be implemented in various forms, and optionally it may be not-implemented if other aligning mechanisms are provided.

In some embodiments, the disposable interface completely encloses the multi-use device to provide an isolation and a clean interface to the patient. In some embodiments, the disposable unit includes the following:
1. Two acoustically transparent zones 11312, which are aligned in front of the transducers. In some embodiments, they enable the US signal to efficiently cross from the transducer to the skin and ensure that the skin shall be in good ultrasonically transmissivity contact with the patient's skin. In some embodiments, the acoustically transparent zones are made of some type of silicone, with an acoustic impedance, which is similar to the skin.
2. Mechanical connection buttons 11314 to accurately connect the disposable unit to the transducer mat. In some embodiments, one of these mechanical connectors also connects a sensor in the disposable film to the transducer mat, and through it to the control unit.
3. A shaped inflatable pad located at the other side of the bag that encloses the transducer mat. In some embodiments, the function of this pad is to push the transducers towards the patient's skin and spread the pressure evenly all over the contact area to ensure good contact and patient's comfort.
4. An air hose 11316 for inflating and deflating the shaped inflatable pad. In some embodiments, it may be connected to a manual pump or to an electrical compressor built into the control unit.
5. A sleeve 11318 that covers the strip and allows for a simple placement of the transducer mat into the disposable unit.
6. A cover over the control unit located at the edge of the sleeve that allows easy activation of the control unit buttons and observing the LEDs and screen.

7. A spinal zone 11320 comprising an alignment window 11322 at the center that allows accurate placement of the device over the vertebrae (for example the L1 vertebrae). In some embodiments, along the spinal zone there is an adhesive interface to assist in accurate placement of the device on the patient's back.

Visual Interface Provided as Part of the System

In some embodiments, the visualization system may be a supplement for the IF system. For instance for any N treatment units, one visualization unit shall be provided. In some embodiments, the probe of the visualization system may be identical to the treatment probe or different from the treatment probe. In some embodiments, the visualization system may hook (by connector) to the treatment system or be completely independent, as shown in FIG. 114.

In some embodiments, the goal of a visual interface is to verify the location, size and depth of the kidney. In some embodiments, the caretaker requires some feedback but does not require a 2D high resolution screen. For this reason, the type 6 unit has a low-end interface that provides the relevant information In some embodiments, for instance, an interface that shall instruct the care-taker with regard to the proper placement of the transducer mat, but would use a simple interface such as an arrow, or colored LEDs indicating a direction of movement, or just indicating that the kidney was detected and is covered. In some embodiments, this can be provided with a screen, or other dedicated hardware.

Mechanical Division of Subunits

In some embodiments, the procedure for placing the Ultrasound transducers on the patient's body can have of a number of alternatives. In some embodiments, placing a transducer unit that is able to cover a large area, highly likely to include the kidneys. In some embodiments, a big portion of the abdomen is exposed to ultrasound as shown in FIG. 115. In some embodiments, the pressure is spread over an area of 150 mm by 200 mm, optionally over an area of 250 mm by 300 mm, optionally over an area of 350 mm by 500 mm. In some embodiments, the pressure applied to a single area is higher than an area of a circle having 50 mm diameter, optionally a circle having 75 mm diameter, optionally a circle having 100 mm diameter.

In some embodiments, using a third party Ultrasound visualization system to locate the kidneys, as shown in FIG. 116. In some embodiments, generating instructions to the medical practitioner on how to place the transducer mat subunit In some embodiments, the System has the ability to process Ultrasound visual signals and direct the practitioner where to place the transducer units. In some embodiments, simple interface with arrows, colored LEDs would efficiently direct the practitioner with the placement as shown in FIG. 117.

In some embodiments, the system has the ability to show visual interface and let the practitioner place the transducer at a better location, up to real time display as shown in FIG. 118.

Exemplary Built-in Systems in Furniture

Referring to image 119A, an exemplary embodiment of the present invention where the device is built for back access and is embedded in a bed mattress.

Referring to image 119B, an exemplary embodiment of the present invention where the device is built for side access, designed as a bed top.

Referring to image 119C, an exemplary embodiment of the present invention where the device is built for back access, embedded in a chair.

Feature—Logging

In some embodiments, the System shall log exposure time and enable to display exposure time per day. The interface will enable to reset the logging, for instance when the unit is provided per patient Patient Logging In some embodiments, a system comprises a software and hardware version to include integration with the caretakers IT system, logging the patient ID, and updating the care taker about the usage online. In some embodiments, if logging of patient ID is required, the system shall have an interface for receiving a patient ID. In some embodiments, the system confirms to patient data storage requirements, data security and privacy. In some embodiments, the system includes procedures for erasing data, correcting data, interfaces, maintenance, and loading of data.

No Logging

In some embodiments, the system has a version where no logging is part of the unit. It is designed as a tool, oblivious to patient ID, with some configuration parameters, and not part of a patient treatment logging system.

Treatment Logging

In some embodiments, logging by treatment days may assist in motivating the patient to comply with the treatment by providing accurate information of treatment hours per day and setting goals.

Data Access

In some embodiments, information derived from logging devices, if available to the company, is used, for example, to: improve the product, assist is post deployment support of ongoing research, and/or generate new IP, applications and product versions.

Feature—Support of Patient Size (Pediatric, Obese)

In some embodiments, the System shall support (using the same infrastructure) pediatric and obese patients—with limitations. In some embodiments, this is enabled by dedicated hardware and software, for instance transducer mats for special populations. Sometimes, kidney depth may be too large for the system for some obese patients. In some embodiments, both types of patients require changes in kidney detection, classification and tracking algorithms.

Exemplary Patient Selection Criteria

In some embodiments, the aforementioned systems and their related methods are indicated for use in the treatment of patients who are characterized by at least one of the following exemplary criteria:

Acute or chronic heart failure (HF): patient with HF who is refractory to diuretics, patient with HF who is already treated with diuretics at dose equivalent to at least 50 mg of furosemide, patient with HF who is already treated with diuretics at dose equivalent to at least 70 mg of furosemide, patient with HF who has renal dysfunction, patient with HF and reduced GFR with ACR<=30 mg/mmol, patient with HF and reduced GFR with ACR<=0.4 mg/mg, patient with HF and reduced GFR without proteinuria or hematuria, patient with HF without any of abnormal kidney anatomy, abnormal kidney location, abnormal kidney orientation, one kidney only, kidney tumor, or transplanted kidney.

Patient with suspected or diagnosed Renal Dysfunction: patient with suspected or known renal dysfunction with HF, patient with suspected or known renal dysfunction with acute MI, patient with suspected or known renal dysfunction with cardiogenic shock, patient with suspected or known renal dysfunction with sepsis, patient with suspected or known renal dysfunction with hemorrhagic shock, patient with suspected or known renal dysfunction with substantial reduction in blood pressure, patient with suspected or known renal dysfunction with substantial reduction in cardiac output, patient with suspected or known renal dysfunction with substantial reduced left ventricular ejection fraction (less than 50%, or for example, less than 30%), patient with suspected or known renal dysfunction with substantial reduction in blood volume, patient with suspected or known renal dysfunction with substantial reduction in renal artery flow, patient with suspected or known renal dysfunction with abnormal blood osmolarity, patient with suspected or known renal dysfunction with abnormal blood osmolality, patient with suspected or known renal dysfunction with abnormal blood pH, patient with suspected or known renal dysfunction with abnormal elevation in blood Na concentration, patient with suspected or known renal dysfunction with abnormal level of blood K concentration, patient with suspected or known renal dysfunction with substantial reduction in blood volume, patient with suspected or known renal dysfunction with hemorrhagic shock, patient with suspected or known renal dysfunction that undergoes chemotherapy, patient with suspected or known renal dysfunction that received medication that has known nephrotoxic side effect, patient that receives high dose medication of ACE-inhibitors, Entresto or similar compounds, patient with chronic kidney disorder (CKD), patient with end-stage renal dysfunction (ESRD), patient with reduced GFR with ACR<=30 mg/mmol, patient with reduced GFR with ACR<=0.4 mg/mg, patient with reduced GFR without proteinuria or hematuria, optionally a patient on acute dialysis treatment, optionally a patient on chronic dialysis treatment, a patient without any of abnormal kidney anatomy, abnormal kidney location, abnormal kidney orientation, one kidney only, kidney tumor, or transplanted kidney.

In some embodiments, patient suffering from heart failure or symptoms related to heart failure, are treated and an positive effect may potentially be mediated by reducing kidney stress (e.g. by the hypothesis of improved local pressure gradients in the kidney thanks to this energy) and therefore, potentially reduce the angiotensin level, which is exactly a treatment target in HF), it is a common treatment to HF the use of ACE inhibitors that tell the heart to "ignore" the stress applied by the kidney).

Patient who is contraindicated for or cannot tolerate or are refractory to further diuretics: patient with reduced GFR with ACR<=30 mg/mmol, patient with reduced GFR with ACR<=0.4 mg/mg, patient with reduced GFR without proteinuria or hematuria, a patient without any of abnormal kidney anatomy, abnormal kidney location, abnormal kidney orientation, one kidney only, kidney tumor, or transplanted kidney.

A patient suspected and/or at risk of developing of and/or detected with Contrast Induced Nephropathy (CIN): patient that is expected to undergo a radiological procedure and/or cardiac catheterization with contrast media, patient following a radiological and/or catheterization procedure with contrast media has elevated blood creatinine values of more than 50% relative to the value before the procedure, patient following a radiological and/or catheterization procedure with contrast media has elevated blood creatinine values of more than 50% relative to the value before the procedure, patients with history of renal dysfunction (e.g. blood Creatinine>1.1) that receive contrast media, patient that is expected to be and/or was given contrast media (e.g. iodine, or iohexol) of more than 50 cc, patient that is expected to be and/or was given contrast media (e.g. iodine, or iohexol) of more than 150 cc, patient that is expected to be and/or was given contrast media (e.g. iodine, or iohexol) of more than 200 cc, patient that is expected to be and/or was given contrast media (e.g. iodine, or iohexol) of more than 250 cc, patient with reduced GFR with ACR<=30 mg/mmol, patient with reduced GFR with ACR<=0.4 mg/mg, patient with reduced GFR without proteinuria or hematuria, a patient without any of abnormal kidney anatomy, abnormal kidney location, abnormal kidney orientation, one kidney only, kidney tumor, or transplanted kidney.

Suspected and/or at risk of developing of and/or detected with Acute Tubular Necrosis (ATN) and/or Acute Kidney Injury (AKI): patient with suspected or known or chronic or acute HF, patient with suspected or diagnosed acute MI, patient with cardiogenic shock, patient with sepsis, patient with hemorrhagic shock, patient with substantial reduction in blood pressure, patient with substantial reduction in cardiac output, patient with substantial reduced left ventricular ejection fraction (less than 50%, or for example, less than 30%), patient with substantial reduction in blood volume, patient with substantial reduction in renal artery flow, patient with abnormal blood osmolarity, patient with abnormal blood osmolality, patient with abnormal blood pH, patient with abnormal elevation in blood Na concentration, patient with abnormal level of blood K concentration, patient with substantial reduction in blood volume, patient with chronic kidney disorder (CKD), patient that undergoes chemotherapy, patient that receives medication that has known nephrotoxic side effect, patient that receives high dose medication of ACE-inhibitors, Entresto or similar compounds, patient that is expected to undergo or had a cardiac catheterization, patient that is expected to undergo or had a cardiac catheterization due to suspected acute MI, patient that is expected to undergo or had a cardiac catheterization for coronary intervention, patient that is expected to undergo or had a cardiac catheterization for valvular intervention, patient that is expected to undergo or had a cardiac surgery (for example, aortic valve surgery, mitral valve surgery, tricuspid valve surgery, coronary artery bypass grafting, or combination of these procedures), patient that is expected to undergo or had a cardiac surgery with cardio-pulmonary bypass machine (for example, aortic valve surgery, mitral valve surgery, tricuspid valve surgery, coronary artery bypass grafting, or combination of these procedures), patient that has a cardiac assist device or artificial heart pump that may cause cell destruction, patient with detected elevation (for example, of at least 50%) in blood concentration of creatinine, patient with detected elevation (for example, of at least 50%) in blood concentration of urea, patient with detected elevation (for example, of at least 50%) in blood concentration of BUN, patient with detected elevation (for example, of at least 50%) in blood concentration of NGAL, patient with detected elevation (for example, of at least 50%) in blood concentration of KIM-1, patient with detected elevation (for example, of at least 50%) in blood concentration of Beta-2 microglobulin (Thymotaxin), patient with detected elevation (for example, of at least 50%) in blood concentration of Lysozyme, patient with detected elevation (for example, of at least 50%) in blood concentration of TIMP-2, patient with detected elevation (for example, of at least 50%) in blood concentration of IGFBP-7, patient with detected elevation (for example, of at least 50%) in urine concentration of NGAL, patient with detected elevation (for example, of at least 50%) in urine concentration of KIM-1, patient with detected elevation (for example, of at least 50%) in urine concentration of Beta-2 microglobulin (Thymotaxin), patient with detected elevation (for example, of at least 50%) in urine concentration of TIMP-2, patient with detected elevation (for example, of at least 50%) in urine concentration of IGFBP-7, patient with detected elevation (for example, of at least 50%) in urine concentration of Lysozyme, patient with mild to severe chronic kidney dysfunction, patients with 20<eGFR<6O ml/min/1.73m2, or for example patients with 30<eGFR<6O ml/min/1.73m2, or for example patients with 20<eGFR<45 ml/min/1.73m2, patient with reduced GFR with ACR<=30 mg/mmol, patient with reduced GFR with ACR<=0.4 mg/mg, patient with reduced GFR without proteinuria or hematuria, a patient without any of abnormal kidney anatomy, abnormal kidney location, abnormal kidney orientation, one kidney only, kidney tumor or transplanted kidney, patient with blood Creatinine level greater than 1.1 mg/dl, patient with blood Creatinine level greater than 1.3 mg/dl, and patient with blood Creatinine level greater than 1.1 mg/dl and less than 2.5 mg/dl.

Patient Selection for Ultrasound Radiation Treatment:
1. The treatment shall be indicated for treatment of diagnosed AKI (AKI is already developed). Detected AKI shall mean, for example:
   ≥0.3-mg/dl increase or 50% increase over baseline within 48 h or 100% increase over baseline or ≥200% increase over baseline or 0.5-mg/dl increase to at least 4.0 mg/dl; or 1.2<serum creatinine level≤2.5
   Substantial reduction in urine output as defined by <0.5 mL<kg/hr*6 hours (risk), <0.5 mL/kg/hr*12 hours (injury), <03 mL/kg/hr*24 AKI as clinically determined or anuria for >12 (failure)
   Baseline shall be either historical medical record before hospitalization, level at admission, level prior to insult caused during admission (e.g. prior to surgery, sepsis development, contrast media insertion in catheterization, etc.), or level immediately post insult (e.g. post-surgery, at admission to ICU=intensive care unit)
2. The treatment shall be indicated for prevention of AKI development in patients at risk. Patients at risk shall mean, for example:
   Patient admitted to ICU due to sepsis
   Patient in ICU who develop sepsis
   Patient undergoing cardio surgery
   Patient undergoing cardiac catheterization
   Patient with cardiogenic shock
   Patient with sepsis shock
   Patient with hypovolemic shock
   Patient with a serious blood loss
   Patient with dehydration
   Patient undergoing chemotherapy
   Patient with trauma (kinetic trauma—being hit cause muscle protein release, which might cause damage to the kidney)
   Patient that has dialysis and is in danger to have AKI
   Patient with diabetes
   Patient that has low cardiac output
   Vasculitis
   Systemic diseases that hurt the kidneys
   Anemia
   Cleveland Clinic Dialysis After Cardiac Surgery Risk Score≥6 and ≤8 or
   Cleveland Clinic Dialysis After Cardiac Surgery Risk Score≥6
   History of chronic kidney disease stage III, as indicated by 30<eGFR<6O ml/min/1.73 m² (as calculated by chronic kidney disease Epidemiology Collaboration (CKD-EPI) formula), and 1.2<serum creatinine level≤2.5 mg/dL from medical records within 30 days prior to the surgery.
3. CIN–, for example, undergoing cardiac catheterization or interventional procedure, or imaging procedure involving contrast media
   Patient that is expected to undergo a cardiac catheterization due to acute MI
   History of mild to severe chronic kidney dysfunction as indicated by 30<eGFR<6O ml/min/1.73 m² (as calculated by chronic kidney disease Epidemiology Collaboration (CKD-EPI) formula), and 1.1<Blood Creatinine<2 mg/dl from medical records within 30 days prior to the procedure
4. CKD, for example, defined as abnormalities of kidney structure or function, present for >3 months, with implications for health with one or more of the following markers:
   Albuminuria (AER>=30 mg/24 hours; ACR>=30 mg/g [>=3 mg/mmol]
   Urine sediment abnormalities
   Electrolyte and other abnormalities due to tubular disorders
   Abnormalities detected by histology
   Structural abnormalities detected by imaging
   History of kidney transplantation
   GFR<60 ml/min/1.73 m²
5. Diuretic resistant
6. Heart failure with acute decompensation (need for diuresis), for example:
   Gained weight over 1 Kg per day in recent week, or over 2 Kg/day in recent week, or over 3 Kg in recent week, or over 5 Kg in recent week, or over 10 Kg in recent week; or, for example:
   diuretic resistant
   Functional class NYHA II or III
   LV ejection fraction between 20 and 45%.
   Chronic kidney dysfunction as indicated by 20<eGFR<45 ml/min/1.73 m² (as calculated by chronic kidney disease Epidemiology Collaboration (CKD-EPI) formula) and serum creatinine between 1.1 and 2.5 mg/dl.
   Patient is hospitalized for acute decompensation with signs of volume overload including 2 of the following: dyspnea, peripheral edema, jugular venous distention, and jugular venous pressure greater than 10 cm of water, pulmonary edema or pleural effusion on chest radiography.

Diuretic Resistance

For example, diuretic resistance is defined as a failure to achieve the therapeutically desired reduction in edema despite a full dose of diuretic The causes of diuretic resistance include poor adherence to drug therapy or dietary sodium restriction, pharmacokinetic issues, and compensatory increases in sodium reabsorption in nephron sites that are not blocked by the diuretic.
   breastfeeding women that needs diuretics
   Chronic HF—for daily/weekly/hourly/continuous/intermittent home treatment
   Portable, wearable—for home and outdoors use Use at home or at dialysis center together with RRT (renal replacement therapy):
   Intermittently (between RRT sessions)
   Before RRT session
   After RRT session
   Simultaneously with RRT in the same session
   Operated by the patient at home
   Operated by an operator at a dialysis center or a clinic The treatment may be potentially contraindicated in a patient exhibiting one or more of the following exemplary indications:

urine ACR (Albumin to Creatinine Ratio) above 30 or above 20, or above 40

Patient with (or undergoing a procedure for) VAD or heart transplant documented, or observed in ultrasound by an ultrasound specialist, abnormal kidney anatomy, abnormal location, abnormal orientation, kidney stones, kidney tumor or significant cysts polycystic kidney, one kidney only, transplanted kidney, or fatty liver disease Patient whose kidneys are not clearly visualized using the test ultrasound device (due to e.g., fatty liver, high BMI, etc.), or with documented BMI>35 Kg/m$^2$ Patient whose distance from the skin to the center of the kidneys is more than 200 mm, or more than 250 mm or more than 300 mm or more than 350 mm or more than 400 mm Ejection fraction of <25% prior based on medical record from within 6 past months Has ongoing sepsis or documented history of sepsis in the last 2 weeks Severe Proteinuria or hematuria.

Patient that has documented allergies to the ultrasound gel components.

Patient that has a wound or cut (or a risk of having a wound or a cut, e.g. due to decubitus) at the area to be covered by the device (for example bilateral posterolateral sides of the body) or has a risk of skin tear due to pressure applied during use of the device.

Patient with documented diagnosis of coagulation abnormalities (e.g. hemophilia)

Severe proteinuria as indicated by a urine albumin-to-creatinine ratio (ACR)>30 mg/mmol (>0.4 mg/mg) during the current hospitalization.

Serum potassium level greater than 5.5 mEq/L

Patient with VAD or heart transplant.

Exemplary Methods

In some embodiments, the therapy applied over a therapeutic session of at least 30 minutes, optionally at least an hour, optionally at least 2 hours, optionally at least 3 hours, optionally at least 5 hours, optionally at least 12 hours, or optionally at least a day.

In some embodiments, the therapy session is applied repeatedly for at least once in 30 minutes, optionally at least once in an hour, optionally at least once in 2 hours, optionally once in at least 3 hours, optionally at least once in 5 hours, optionally at least once in 12 hours, optionally at least once a day, or optionally at least once a week.

In some embodiments, the therapeutic session has intermittent breaks of at least 30 seconds, optionally at least 1 minute, optionally at least 3 minutes, optionally at least 5 minutes, optionally at least 30 minutes, optionally at least 1 hour, optionally at least 3 hours, or optionally at least a day.

In some embodiments, the therapeutic session has intermittent breaks in according to a sensor input.

In some embodiments, the therapeutic session has intermittent breaks in according to an input of at least one of patient input, temperature sensor, pressure sensor, heart rate sensor, cavitation detector, indication of patient discomfort, indication of patient sensation or pain, indication of a change in the patient clinical condition beyond a threshold, and an indication of a change at least one of in urine output, urine content, a concentration of a compound in the urine, a concentration of a compound in the blood beyond a certain upper and/or lower threshold.

In some embodiments, the therapeutic session includes variations in one or more frequency components of the applied energy.

In some embodiments, the therapeutic session includes variations in one or more frequency components of the applied energy with at least alternation between 2 or more frequencies that each is considered safe and effective.

In some embodiments, said frequencies are above 3 MHz, optionally above 4 MHz, optionally above 5 MHz.

In some embodiments, the therapeutic session includes variations in one or more amplitude components of the applied energy.

In some embodiments, the therapeutic session includes variations in one or more amplitude components of the applied energy with at least alternation between 2 or more amplitudes that each is considered safe and effective.

In some embodiments, the therapeutic session includes variations in one or more pulse durations of the applied energy.

In some embodiments, the therapeutic session includes variations in one or more pulse durations of the applied energy with at least alternation between 2 or more pulse duration that each is considered safe and effective.

In some embodiments, the therapeutic session includes variations in one or more pulse repetition rates of the applied energy.

In some embodiments, the therapeutic session includes variations in one or more pulse repetition rates of the applied energy with at least alternation between 2 or more pulse repetition rates that each is considered safe and effective.

In some embodiments, the therapeutic session includes variations in one or more pulse properties of the applied energy.

In some embodiments, the therapeutic session includes variations in one or more pulse properties of the applied energy with at least alternation between 2 or more pulse properties that each is considered safe and effective.

In some embodiments, the device is configured to deliver therapy to/therapy is applied to one kidney.

In some embodiments, the device is configured to deliver therapy to/therapy is applied to both kidneys.

In some embodiments, the device is configured to deliver therapy to/therapy is applied to both kidneys simultaneously.

In some embodiments, the device is configured to deliver therapy to/therapy is applied to both kidneys while alternating the therapy between the kidneys, alternating every about 1 minute, alternating every about 2 minutes, alternating every about 5 minutes, alternating every about 7 minutes, alternating every about 15 minutes, alternating every about 20 minutes, alternating every about 30 minutes, alternating every about 1 hour or more.

In some embodiments, the therapeutic energy is safe:

In some embodiments, said applies energy is configured not to cause tissue heating In some embodiments, said applies energy is configured not to cause tissue heating over 1 deg C. In some embodiments, said applies energy is configured not to cause tissue heating over 2 deg C.

In some embodiments, said applied energy is configured to generate TIS<0. In some embodiments, said applied energy is configured not to cause cavitation in the tissue.

In some embodiments, said applied acoustic pressure is configured to generate MI<1.

In some embodiments, the therapy/device is applied from the patient's abdomen orientation.

In some embodiments, the therapy/device is applied from the patient's side.

In some embodiments, the therapy/device is applied from the patient's back side.

In some embodiments, the device component that is in contact with the patient is slim, it has width of no more than 3 cm, optionally no more than 2 cm, optionally no more than 1 cm.

In some embodiments, the device is attached to the body.

In some embodiments, the device is portable and/or body mounted.

In some embodiments, the device is configured to avoid wounds contact.

In some embodiments, the device is body mounted, belt mounted, chair mounted, bed top unit, incorporated into bed/mattress structure, and/or hand held.

In some embodiments, the treatment duration is at least 1 hour, optionally at least 2 or 3 hours, optionally at least 4 hours, optionally at least 6 hours.

In some embodiments, the treatment duration is at least 2 hours per day for at least 2 days, optionally at least 6 hours per day for at least 2 days.

In some embodiments, the treatment it is applied for at least a day, optionally for at least 3 days, optionally for at least a week, optionally for at least a month, optionally for at least 2 months.

In some embodiments, the treatment is applied continuously for up to 1 week.

In some embodiments, the treatment is applied intermittently for up to 1 week, optionally intermittently for up to 2 weeks.

In some embodiments, the treatment is applied intermittently for repetitive periods of at least 5 minutes each, optionally intermittently for repetitive periods of at least 10 minutes each, optionally intermittently for repetitive periods of at least 15 minutes each, optionally intermittently for repetitive periods of at least 20 minutes each.

In some embodiments, the intermittent application comprises off-period of at least 5 minutes, optionally comprises off-period of at least 10 minutes.

In some embodiments, the application comprises switching sides of treatment between the kidneys. In some embodiments, the application comprises switching direction of treatment by selection among transducer elements. In some embodiments, the application comprises switching direction of treatment by changing beam forming using the transducer elements. In some embodiments, the application comprises changing modes of energy delivery.

In some embodiments, the change of modes of energy delivery comprises changes in at least one of frequency, bandwidth, beam forming, amplitudes, pulse shape, pulse duration, pulse repetition rate, pulse duty cycle.

In some embodiments, the treatment is applied at pre-scheduled hours of the day. In some embodiments, the treatment is applied during night time. In some embodiments, the treatment is applied during daytime.

In some embodiments, the treatment is applied when the patient is not moving. In some embodiments, by means of a at least one sensor, for example motion sensor, accelerometer, orientation meter, the treatment mode is changed to a preferred mode according to the state of the patient, for example when posture is supine, semi-supine, stand still, sitting, moving, walking, in bed facing side-ways, in bed facing up, in bed facing down. In some embodiments, during treatment the heart rate and/or breathing rate are monitored and the treatment mode is activated, deactivated, changed accordingly.

In some embodiments, the treatment is intermitted when the patient is not moving. In some embodiments, the treatment is continuous if the patient is moving. In some embodiments, the treatment is applied (or ON or OFF mode is selected) by some of the transducer elements only when the patient body weight is applied onto the transducer elements (e.g. when sleeping on the right side, then the right side is treated). In some embodiments, the treatment is applied (or ON or OFF mode is selected) by some of the transducer elements only when the patient body weight is not applied onto the transducer elements (e.g. when sleeping on the right side, then the left side is treated).

In some embodiments, the system comprises sensors and alerts and mode switch for improper pressure distribution, sensors and alert for and mode switch improper contact, sensors and alerts and mode switch for change in humidity (the device wet), sensors and alerts and mode switch for change in skin temperature, sensors and alerts and mode switch for change in device temperature humidity.

In some embodiments, the treatment is applied during night time. In some embodiments, the treatment is applied during night time. In some embodiments, application comprises switching sides of treatment between the kidneys. In some embodiments, the treatment comprises an off-period of at least 5 minutes.

Exemplary Preferred Methods:

For AKI treatment or prevention, it may be preferred to apply it continuously for at least 2 hours, preferably for at least 4 hours, preferably for at least 6 hours, preferably for at least 12 hours. It is further preferred to repeat treatment multiple times during the day. It is further preferred to repeat the treatment over several days, e.g. for at least 2 or 3 or 4 days. In some cases, the treatment should begin pre-surgery, or during surgery, or immediately post-surgery, or pre-catheterization procedure, of during catheterization procedure, or immediately post-catherization procedure, or upon admission to hospital or upon determination of an elevated risk factor for developing AKI, or upon detection of developing AKI. Risk factors include, for example sepsis, cardiogenic shock, hemorrhagic shock, prolonged surgery, use of contrast agent in a procedure, dehydration, acute heart decompensation of heart failure. In some preferred embodiments, the treatment shall be applied every day, during daytime. In some embodiments, the treatment shall be applied every day, during night time.

For acute heart failure treatment or for insufficient diuresis treatment, it may be applied continuously or intermittently for at least 6 hours, preferably for at least 12 hours per day, preferably for at least 18 hours per day hours. Preferably continuously. It is further preferred to repeat the treatment over at least several days, e.g. for at least 2 or 3 or 4 days. It is further preferred to repeat the daily treatment over at least a week. It is further preferred to repeat the daily treatment over at least 2 weeks. It is further preferred to repeat the daily treatment until at least half of the excess body fluids that need diuresis as were observed upon hospital admission have been cleared. In some preferred embodiments, the treatment shall be applied every day, during daytime. In some embodiments, the treatment shall be applied every day, during night time.

For chronic CKD treatment or Heart Failure treatment (at home), it may be applied continuously or intermittently for at least 3 hours, preferably for at least 6 hours, preferably for at least 12 hours per day, preferably for at least 18 hours per day hours. Preferably continuously. It is further preferred to deliver the treatment upon need over at least several days, e.g. for at least 2 or 3 or 4 days. It is further preferred to repeat the daily treatment over a at least week. It is further preferred to repeat the daily treatment over at least 2 weeks.

It is possible to repeat the treatment only during alternating days. It is further preferred to repeat the daily treatment until at least half of the excess body fluids that need diuresis as were observed upon hospital admission have been cleared. In some preferred embodiments, the treatment shall be applied every day, during daytime. In some preferred embodiments, the treatment shall be applied every day, during night time.

In all cases, most preferably is to treat several hours. In AKI it is at least 3 hours, preferably at least 6 hours, for at least the first day, preferably repeated daily for 2-4 days. In HF and reduced diuresis, several hours shall mean at least 6 hours, preferably more than 12, and even better more than 18 hours per day, preferably repeated for at least 2-4 days, in some cases for at least a week.

Exemplary Use Methods
1. Prepare the device
   a. Take the disposable out of its package
   b. Attach disposable to multi-use device such that no air is introduced between transducers and acoustically transparent regions, and all acoustic windows and transducers are aligned
   c. Remove protective covers if needed
2. Prepare the patient
   a. Turn the patient by 90 degrees on the bed.
   b. Mark the L1 Trachea on the patient back. The nurse may use some custom measurement tool to better locate location
3. Apply the device
   a. Use the alignment window method to align device to Trachea L1 or other marker.
   b. Attach the device to the back—if the face of the disposable unit has adhesive zones—press these areas to secure the device to the back
   c. Turn the patient back by 90 degrees until the patient is back in the supine position, and the device is under the lower thoracic and upper lumbar back
   d. To improve contact of the device and the patient, in some embodiments there is a need to inflate a pressure bag that pushes the transducers towards the skin. This can be done with a manual pump or an electric pump
4. Activate the device
   a. Let the device perform pre-treatment test, identifying the kidney location
   b. Activate the device for the desired treatment duration.

Description of an Exemplary Application Procedure
Preparing the Patient

The multi-use device is inserted into the disposable bag. All mechanical connectors are attached. The patient is brought on the treatment bed. FIG. 120 shows the first part of the procedure. The patient is turned by 90 degrees to a right lateral recumbent position, and his or her back is exposed 12002. A practitioner identifies based on anatomical landmarks the location of the L1 vertebrae and marks this location on the skin 12004. This would be used to align the alignment window of the product to the patient.

Preparing the Patient and the Unit

The unit 12006 is placed on the bed perpendicular to the patient. Any protective cover used in storage (if exists) is removed prior to applying the device to the patient's skin.

Applying the Device to the Patient—Back Cushion Version—FIG. 121

The spinal zone is adjusted over the patient's spine. The alignment window is placed over the L1 mark 12102. The control unit 12104 is placed on the front side of the patient temporarily in order not to interfere with the alignment action. The air hose 12106 also follows the control unit. Once the alignment window is in place, and the spine markers are aligned with the patient's spine 12108, the rest of the transducer mat falls naturally in place. Some adhesive along the spine zone in the disposable section helps in the proper placement of the central spinal zone over the patient's skin covering the over spine. The back of the disposable unit 12110 that includes the inflatable bag now faces the mattress.

Placing the Patient in the Supine Position—FIG. 122

The patient is turned to the supine position, with the transducer mat 12202 between the patient 12204 and the mattress 12206, which is a side view of the patient prior to inflating the inflatable bag, which is part of the disposable. Due to natural curvature of the back, only part of the transducers are in good contact with the patient's back. The air hose 12208 is fitted to the control unit, where the air pump resides. The air-hose is shown in a top view of the patient in the supine position on bed. The control unit 12210 includes an air pump.

Inflating the Airbag and Starting the Treatment

The control unit 12210 is powered up.

The control unit, upon command, inflates the air bag via the hose 12208 to the exact pressure. Since the air-bag is between the mattress and the transducer mat, by inflating the air bag the transducers are pushed upwards towards the patient's skin. This is shown in the side view of the patient after the inflation of the air bag. This allows for the product to accurately adjust to the patient's contour, and to apply equal pressure on the patient's back, relieving tension and increasing comfort.

In some embodiments, a manual air pump may be used instead of an electrical air pump. The treatment parameters are adjusted (e.g. treatment time) and the activation button is pressed. The treatment commences.

In some embodiments, the system shall detect misplacement and alert the user upon such occurrence. For instance, the system shall detect the US reflection from the ribs to verify that it has been deployed over the lower part of the posterior rib cage.

For a belt type of patient interface
5. Prepare the device
   a. Take the disposable out of its package
   b. Open the transducer mat chamber at the back of the belt and place the transducer mat in place, aligned in such a way to make sure that acoustically transparent windows are facing the transducer locations.
   c. Close the chamber so that the device is completely covered.
   d. Remove protective covers if needed
6. Prepare the patient
   a. Turn the patient by 90 degrees on the bed.
   b. Mark the L1 Trachea on the patient back. The nurse may use some custom measurement tool to better locate location
7. Apply the device
   a. Use the alignment window method to align device to Trachea L1 or other marker.
   b. Attach the device to the back—if the face of the disposable unit has adhesive zones—press these areas to secure the device to the back
   c. Tack the bottom part of the belt under the patient's lower waist, in a way that the edge of the belt will be accessible when the patient is supine again d. Turn the patient back by 90 degrees until the patient is back in the supine position, and the device is under the lower thoracic and upper lumbar back
e. Pull the belt edge from under the patient and close both part of the belt to apply pressure between the belt and the patient.
f. To improve contact of the device and the patient, in some embodiments there would be a need to inflate a pressure bag that pushes the transducers towards the skin. This can be done with a manual pump or an electric pump
8. Activate the device
   a. Let the device perform pre-treatment test, identifying the kidney location
   b. Activate the device for the desired treatment duration.

Description of the Application Procedure—Back Belt Version—FIG. 123
Preparation of the Device The disposable belt is shown on a table (or any work platform available in the ward)

The belt is shown from the external side 12302, the side that is not facing the patient. Multi-use device is inserted on a work table into the disposable bag. The belt has a flap 12304 that can be opened in ordered to place inside the transducer mat. At the center of the flap there is the transparent alignment window 12306, assisting in aligning the device to the location of the L1 vertebrae.

In order to place the multi-use transducer mat inside the single use belt, the flap is opened 12308. In some embodiments, this flap is also an inflatable air bag. An air hose connected to the inflatable parts of the flap enable pressurized air to flow into the flap and press the transducer mat towards the patient's back.

This exposes the cavity where the transducer map shall be placed. The bottom part of the cavity is the special acoustically transparent zone 12310 that shall couple the patient's skin to the transducers The transducer mat 12312 is placed in the cavity, aligning the alignment window and spine markers of the belt and the transducer mat. The control unit that is connected to the transducer mat 12314 is placed to the side, over the disposable belt 12316. The transducer mat is connected to the disposable unit using mechanical fasteners. In some embodiments, this also enables electrical connections of the wires in the transducer mat to sensors embedded inside the disposable belt.

The flap is closed while making sure the alignment window 12318 is aligned and transparent. In some embodiments, the control unit 12320 may be connected to the air hose.

The device is flipped to the other side. Now the side facing the patient 12322 is at the top, and the side that is not facing the patient is at the bottom. On this side one can observe the acoustically transparent window 12324. This window is covered with a protection cover that needs to be removed prior to applying the device to the patient.

The protective cover is removed and the alignment window 12326 and the transducers in the transducer mat 12328A are exposed, under the acoustically transparent layer. The device is ready to be applied to the patient back.
Preparing the Patient—FIGS. 124*a-b*

The patient is supine on the treatment bed. In FIG. 124*a* the first part of the procedure is shown. The patient is turned by 90 degrees to a right lateral recumbent position, and his or her back is exposed 12402. A practitioner identifies based on anatomical landmarks the location of the L1 vertebrae and marks this location on the skin 12404. This would be used to align the alignment window of the product to the patient.

The unit 12406 is placed on the bed perpendicular to the patient. Any protective cover used in storage (if exists) is removed and the transducers are seen 12408.

The part of the belt that is supposed to cross under the patient's right waist is tucked under the waist 12410. When the patient shall be supine again this part shall be pulled from the other side.

Referring to FIG. 124*b*, after placing the unit on the spine, with the alignment window over the L1 mark, the patient turned to be supine again 12412. The flaps of the belt are connected 12414. The air hose, which is part of the belt 12416 is connected to the control unit 12418. This way the electric pump inside the control unit can pump air into the pressurized bag.

The control unit can be placed for convenience inside a dedicated pocket 12420 on the belt 12422.
Further Information In some embodiments, Non-heating means that does not generate heating in the tissue of >2 deg C., preferably not above 1 deg C., and TIS<), low mechanical index (MI<1, preferably MI<0.7), prolonged (>1 hour, for example >2 h, for example >3 h) high frequency (>3 MHz, preferably >4 MHz, preferably >5 MHz, Preferably >6 MHz) ultrasound delivery for safe treatment of kidney disorder or prevention (or reducing the buildup) of kidney disorder, without delivering micro-bubbles to the target tissue.

In some embodiments, emitting is without focusing the ultrasound beam to deliver the majority of energy to a spot smaller than 2 cm in diameter.

In some embodiments, emitting is using an ultrasound beam having a geometrical form with a spot size that delivers the majority of the energy to a volume of the kidney greater than 2 cm in diameter.

In some embodiments, emitting is using an ultrasound beam having a geometrical form with a spot size that delivers the majority of the energy at a distance of 4-8 cm, to a cross section greater than 2 cm in diameter.

In some embodiments, the sensors can be analyzed by the system and the system can provide alarms to the operator and to the patient, if a certain criteria is reached.

In some embodiments, a patient provides input, for example, an ON/OFF button, alert button, immediate stop button, reduction of amplitude or pressure if there is any discomfort.

It is expected that during the life of a patent maturing from this application many relevant irradiation techniques and transducers will be developed; the scope of the term irradiation is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for modifying renal function, comprising:
   a. selecting a patient requiring an increment in renal function;
   b. emitting a quantity of ultrasound radiation, enough to provide an increment in renal function, to at least one part of a kidney for a treatment period of time from about 1 hour to about 30 days;
   c. monitoring temperature at skin or tissue, said monitoring is at multiple interface locations to manage ultrasound power distribution;
   wherein said ultrasound radiation is characterized by having a pulse frequency from about 3 MHz to about 15 MHz and a duration from about 0.2 µsec to about 10 µsec; and
   wherein said emitting comprises achieving renal function modification while avoiding inducing thermal adverse effects.

2. The method according to claim 1, wherein said ultrasound radiation is characterized by individual emission pulses having an amplitude of less than 2 MPa.

3. The method according to claim 1, wherein said ultrasound radiation is characterized by a pulse repetition rate from about 0.1 kHz to about 30 kHz.

4. The method according to claim 1, wherein said emitting ultrasound radiation comprises emitting said ultrasound radiation between ribs.

5. The method according to claim 1, wherein said emitting ultrasound radiation comprises emitting said ultrasound radiation over an area of skin.

6. The method according to claim 1, further comprising positioning an ultrasound emission device in one or more locations selected from the group consisting of back, sides, under thorax and over thorax.

7. The method according to claim 1, wherein said ultrasound radiation is characterized by having high frequency higher than 3 MHz and a duration from 0.2 µsec to 10 µsec.

8. The method according to claim 1, further comprising achieving renal function modification while avoiding inducing cavitation adverse effects.

9. The method according to claim 1, further comprising not using ultrasound contrast agent or any other injected material that, when exposed to ultrasonic radiations, a characteristic of said contrast agent or any other injected material is modified.

10. The method according to claim 1, wherein said emitting is repeated for a period of time selected from the group consisting of at least a day, at least 3 days, at least a week, at least a month and at least 2 months.

11. The method according to claim 1, wherein said emitting is applied intermittently for repetitive periods of time selected from a group consisting of: at least 5 minutes each, at least 10 minutes each, at least 15 minutes each and at least 20 minutes each.

12. The method according to claim 1, wherein said emitting further comprises emitting for preventing acute kidney dysfunction.

13. The method according to claim 1, wherein said emitting further comprises emitting for treating symptoms of heart failure in said patient.

14. The method according to claim 1, wherein said emitting comprises not to cause cavitation in the tissue.

15. The method according to claim 1, further comprising monitoring cavitation at skin or tissue, said monitoring is at multiple interface locations to manage ultrasound power distribution.

16. The method according to claim 1, further comprising monitoring mechanical index at skin or tissue to be lower than 1.

17. A system for modifying renal function, comprising:
  a. a plurality of transducer elements;
  b. circuitry comprising instructions for:
    i. emitting a quantity of ultrasound radiation, enough to provide an increment in renal function, to at least one part of a kidney for a treatment period of time from about 1 hour to about 30 days;
    ii. monitoring temperature at skin or tissue, said monitoring is at multiple interface locations to manage ultrasound power distribution;
  wherein said ultrasound radiation is characterized by having a pulse frequency from about 3 MHz to about 15 MHz and a duration from about 0.2 μsec to about 10 μsec; and
  wherein said emitting comprises achieving renal function modification while avoiding inducing thermal adverse effects.

* * * * *